US012760029B2

(12) United States Patent
Fink et al.

(10) Patent No.: US 12,760,029 B2
(45) Date of Patent: Oct. 13, 2026

(54) KRAS G12D INHIBITORS

(71) Applicant: Bristol-Myers Squibb Company, Princeton, NJ (US)

(72) Inventors: Brian Edward Fink, Yardley, PA (US); Robert Joseph Cherney, Princeton, NJ (US); Khehyong Ngu, Pennington, NJ (US); Upender Velaparthi, Princeton, NJ (US); Wayne David Vaccaro, Princeton, NJ (US); Zheming Ruan, Princeton, NJ (US); Lan-Ying Qin, Princeton, NJ (US); Pravin S. Shirude, Bangalore (IN); Hasibur Rahaman, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 348 days.

(21) Appl. No.: 18/550,234

(22) PCT Filed: Mar. 14, 2022

(86) PCT No.: PCT/US2022/020239

§ 371 (c)(1),
(2) Date: Sep. 12, 2023

(87) PCT Pub. No.: WO2022/192794

PCT Pub. Date: Sep. 15, 2022

(65) Prior Publication Data

US 2024/0317769 A1 Sep. 26, 2024

Related U.S. Application Data

(60) Provisional application No. 63/236,497, filed on Aug. 24, 2021, provisional application No. 63/220,386, filed on Jul. 9, 2021, provisional application No. 63/173,021, filed on Apr. 9, 2021, provisional application No. 63/160,431, filed on Mar. 12, 2021.

(51) Int. Cl.

*C07D 487/08* (2006.01)
*A61K 31/517* (2006.01)
*C07D 471/08* (2006.01)
*C07D 519/00* (2006.01)

(52) U.S. Cl.

CPC .......... *C07D 487/08* (2013.01); *A61K 31/517* (2013.01); *C07D 471/08* (2013.01); *C07D 519/00* (2013.01)

(58) Field of Classification Search

CPC .. C07D 487/08; C07D 471/08; C07D 519/00; A61K 31/517

See application file for complete search history.

(56) References Cited

U.S. PATENT DOCUMENTS

| | | | |
|---|---|---|---|
| 10,011,600 | B2 | 7/2018 | Li et al. |
| 11,999,753 | B2 | 6/2024 | Wang et al. |
| 2023/0072276 | A1 | 3/2023 | Wang et al. |
| 2023/0081426 | A1* | 3/2023 | Zhang et al. |
| 2023/0242544 | A1* | 8/2023 | Dai et al. |
| 2024/0025907 | A1 | 1/2024 | Wang et al. |
| 2024/0067662 | A1 | 2/2024 | Condakes et al. |
| 2024/0199584 | A1 | 6/2024 | Fink et al. |
| 2024/0217982 | A1 | 7/2024 | Fink et al. |
| 2024/0376127 | A1 | 11/2024 | Wang et al. |

FOREIGN PATENT DOCUMENTS

| | | | |
|---|---|---|---|
| CN | 114436976 | A | 5/2022 |
| CN | 115141215 | A | 10/2022 |
| CN | 115181106 | A | 10/2022 |
| CN | 115197245 | A | 10/2022 |
| CN | 115260214 | A | 11/2022 |
| CN | 115368381 | A | 11/2022 |
| CN | 115368382 | A | 11/2022 |
| CN | 115368383 | A | 11/2022 |
| CN | 115385938 | A | 11/2022 |
| CN | 115417868 | A | 12/2022 |
| CN | 115466272 | A | 12/2022 |
| CN | 115490699 | A | 12/2022 |
| CN | 115490709 | A | 12/2022 |
| CN | 115611923 | A | 1/2023 |
| CN | 115677601 | A | 2/2023 |
| CN | 115850267 | A | 3/2023 |
| CN | 115960105 | A | 4/2023 |
| CN | 116143708 | A | 5/2023 |
| CN | 116162099 | A | 5/2023 |
| CN | 116217591 | A | 6/2023 |
| CN | 116262759 | A | 6/2023 |
| CN | 116554208 | A | 8/2023 |
| CN | 116731045 | A | 9/2023 |
| CN | 116813646 | A | 9/2023 |
| CN | 117462688 | A | 1/2024 |

(Continued)

OTHER PUBLICATIONS

Abbott, J.R., et al., "Discovery of Quinazolines That Activate SOS1-Mediated Nucleotide Exchange on RAS," ACS Medicinal Chemistry Letters 9(9):941-946, American Chemical Society, United States (Aug. 2018).

Cheng, H., et al., "Structure-Based Design and Synthesis of Potent and Selective KRAS G12D Inhibitors," ACS Medicinal Chemistry Letters 14(10):1351-1357, American Chemical Society, United States (Sep. 2023).

Co-pending Application, U.S. Appl. No. 18/759,708, inventors Fink, B.E., et al., filed Jun. 28, 2024 (Not yet Published).

Co-pending Application, U.S. Appl. No. 18/759,719, inventors Fink, B.E., et al., filed Jun. 28, 2024 (Not yet Published).

(Continued)

*Primary Examiner* — Brandon J Fetterolf
(74) *Attorney, Agent, or Firm* — STERNE, KESSLER, GOLDSTEIN & FOX P.L.L.C

(57) ABSTRACT

The present disclosure relates to KRAS inhibitors. Methods of treating cancers using the compounds are also provided.

10 Claims, No Drawings

(56) References Cited

FOREIGN PATENT DOCUMENTS

| | | | | |
|---|---|---|---|---|
| CN | 117586280 | A | | 2/2024 |
| CN | 117624190 | A | | 3/2024 |
| CN | 117624194 | A | | 3/2024 |
| JP | 2024520791 | A | | 5/2024 |
| WO | WO-2017172979 | A1 | | 10/2017 |
| WO | WO-2018218070 | A2 | | 10/2017 |
| WO | WO-2018212774 | A1 | | 11/2018 |
| WO | WO-2021031952 | A1 | | 2/2021 |
| WO | WO-2021041671 | A1 | | 3/2021 |
| WO | WO-2021106231 | A1 | | 6/2021 |
| WO | WO2021107160 | A1 | * | 6/2021 |
| WO | WO-2022002102 | A1 | | 1/2022 |
| WO | WO-2022015375 | A1 | | 1/2022 |
| WO | WO-2022031678 | A1 | | 2/2022 |
| WO | WO-2022042630 | A1 | | 3/2022 |
| WO | WO-2022061251 | A1 | | 3/2022 |
| WO | WO-2022066646 | A1 | | 3/2022 |
| WO | WO-2022098625 | A1 | | 5/2022 |
| WO | WO-2022105855 | A1 | | 5/2022 |
| WO | WO-2022105857 | A1 | | 5/2022 |
| WO | WO-2022105859 | A1 | | 5/2022 |
| WO | WO-2022148421 | A1 | | 7/2022 |
| WO | WO-2022148422 | A1 | | 7/2022 |
| WO | WO-2022170802 | A1 | | 8/2022 |
| WO | WO-2022170999 | A1 | | 8/2022 |
| WO | WO-2022171118 | A1 | | 8/2022 |
| WO | WO-2022171143 | A1 | | 8/2022 |
| WO | WO-2022171147 | A1 | | 8/2022 |
| WO | WO-2022173032 | A1 | | 8/2022 |
| WO | WO-2022173033 | A1 | | 8/2022 |
| WO | WO-2022173678 | A1 | | 8/2022 |
| WO | WO-2022173870 | A1 | | 8/2022 |
| WO | WO-2022177917 | A2 | | 8/2022 |
| WO | WO-2022184178 | A1 | | 9/2022 |
| WO | WO-2022187528 | A1 | | 9/2022 |
| WO | WO-2022188729 | A1 | | 9/2022 |
| WO | WO-2022192790 | A1 | | 9/2022 |
| WO | WO-2022193871 | A1 | | 9/2022 |
| WO | WO-2022194066 | A1 | | 9/2022 |
| WO | WO-2022194191 | A1 | | 9/2022 |
| WO | WO-2022194192 | A1 | | 9/2022 |
| WO | WO-2022194245 | A1 | | 9/2022 |
| WO | WO-2022199586 | A1 | | 9/2022 |
| WO | WO-2022199587 | A1 | | 9/2022 |
| WO | WO-2022206723 | A1 | | 10/2022 |
| WO | WO-2022206724 | A1 | | 10/2022 |
| WO | WO-2022214102 | A1 | | 10/2022 |
| WO | WO-2022221386 | A1 | | 10/2022 |
| WO | WO-2022221739 | A1 | | 10/2022 |
| WO | WO-2022223020 | A1 | | 10/2022 |
| WO | WO-2022227987 | A1 | | 11/2022 |
| WO | WO-2022228568 | A1 | | 11/2022 |
| WO | WO-2022228576 | A1 | | 11/2022 |
| WO | WO-2022232331 | A1 | | 11/2022 |
| WO | WO-2022232332 | A1 | | 11/2022 |
| WO | WO-2022235866 | A1 | | 11/2022 |
| WO | WO-2022236578 | A1 | | 11/2022 |
| WO | WO-2022237649 | A1 | | 11/2022 |
| WO | WO-2022246092 | A1 | | 11/2022 |
| WO | WO-2022247757 | A1 | | 12/2022 |
| WO | WO-2022247760 | A1 | | 12/2022 |
| WO | WO-2022256459 | A1 | | 12/2022 |
| WO | WO-2022258057 | A1 | | 12/2022 |
| WO | WO-2022261154 | A1 | | 12/2022 |
| WO | WO-2022262686 | A1 | | 12/2022 |
| WO | WO-2022262838 | A1 | | 12/2022 |
| WO | WO-2022266069 | A1 | | 12/2022 |
| WO | WO-2022266206 | A1 | | 12/2022 |
| WO | WO-2022268051 | A1 | | 12/2022 |
| WO | WO-2022268209 | A1 | | 12/2022 |
| WO | WO-2023001141 | A1 | | 1/2023 |
| WO | WO-2023274383 | A1 | | 1/2023 |
| WO | WO-2023278600 | A1 | | 1/2023 |
| WO | WO-2023280026 | A1 | | 1/2023 |
| WO | WO-2023280280 | A1 | | 1/2023 |
| WO | WO-2023283933 | A1 | | 1/2023 |
| WO | WO-2023284730 | A1 | | 1/2023 |
| WO | WO-2023284881 | A1 | | 1/2023 |
| WO | WO-2023018699 | A1 | | 2/2023 |
| WO | WO-2023020347 | A1 | | 2/2023 |
| WO | WO-2023025116 | A1 | | 3/2023 |
| WO | WO-2023030385 | A1 | | 3/2023 |
| WO | WO-2023030495 | A1 | | 3/2023 |
| WO | WO-2023046198 | A1 | | 3/2023 |
| WO | WO-2023051586 | A1 | | 4/2023 |
| WO | WO-2023072188 | A1 | | 5/2023 |
| WO | WO-2023081476 | A1 | | 5/2023 |
| WO | WO-2023101928 | A1 | | 6/2023 |
| WO | WO-2023103523 | A1 | | 6/2023 |
| WO | WO-2023103906 | A1 | | 6/2023 |
| WO | WO-2023104018 | A1 | | 6/2023 |
| WO | WO-2023116934 | A1 | | 6/2023 |
| WO | WO-2023125627 | A1 | | 7/2023 |
| WO | WO-2023138524 | A1 | | 7/2023 |
| WO | WO-2023138662 | A1 | | 7/2023 |
| WO | WO-2023151621 | A1 | | 8/2023 |
| WO | WO-2023171781 | A1 | | 9/2023 |
| WO | WO-2023179629 | A1 | | 9/2023 |
| WO | WO-2023185864 | A1 | | 10/2023 |
| WO | WO-2023193085 | A1 | | 10/2023 |
| WO | WO-2023197984 | A1 | | 10/2023 |
| WO | WO-2023198078 | A1 | | 10/2023 |
| WO | WO-2023198191 | A1 | | 10/2023 |
| WO | WO-2023205719 | A1 | | 10/2023 |
| WO | WO-2023213269 | A1 | | 11/2023 |
| WO | WO-2023215906 | A1 | | 11/2023 |
| WO | WO-2023244713 | A1 | | 12/2023 |
| WO | WO-2023246903 | A1 | | 12/2023 |
| WO | WO-2024001839 | A1 | | 1/2024 |
| WO | WO-2024008178 | A1 | | 1/2024 |
| WO | WO-2024008179 | A1 | | 1/2024 |
| WO | WO-2024012456 | A1 | | 1/2024 |
| WO | WO-2024017392 | A1 | | 1/2024 |
| WO | WO-2024019103 | A1 | | 1/2024 |
| WO | WO-2024022507 | A1 | | 2/2024 |
| WO | WO-2024027814 | A1 | | 2/2024 |
| WO | WO-2024040080 | A1 | | 2/2024 |
| WO | WO-2024041573 | A1 | | 2/2024 |
| WO | WO-2024044334 | A2 | | 2/2024 |
| WO | WO-2024045066 | A1 | | 3/2024 |
| WO | WO-2024046406 | A1 | | 3/2024 |
| WO | WO-2024051721 | A1 | | 3/2024 |
| WO | WO-2024051852 | A1 | | 3/2024 |
| WO | WO-2024054647 | A1 | | 3/2024 |
| WO | WO-2024055112 | A1 | | 3/2024 |
| WO | WO-2024061370 | A1 | | 3/2024 |
| WO | WO-2024063576 | A1 | | 3/2024 |
| WO | WO-2024063578 | A1 | | 3/2024 |

OTHER PUBLICATIONS

Engel, J., et al., "Structure-guided Development of Covalent and Mutant-selective Pyrazolopyrimidines to Target T790m Drug Resistance in Epidermal Growth Factor Receptor," Journal of Medicinal Chemistry 60(18):7725-7744, American Chemical Society, United States (Sep. 2017).

Gaurav, A., et al., "An Overview on Synthetic Methodologies and Biological Activities of Pyrazoloquinolines," Mini Reviews in Medicinal Chemistry 10(13):1194-1210, Bentham Science Publishers, Netherlands (Nov. 2010).

Gordon, D.E., et al., "A SARS-CoV-2 Protein Interaction Map Reveals Targets for Drug Repurposing," Nature 583(7816):459-468, Nature Publishing Group, United Kingdom (Jul. 2020).

Li, L., et al., "Discovery of Thieno[2,3-d]pyrimidine-based KRAS G12D Inhibitors as Potential Anticancer Agents via Combinatorial Virtual Screening," European Journal of Medicinal Chemistry 233:114243, 10 pages, Editions Scientifiques Elsevier, France (Apr. 2022).

Wang, X., et al., "Identification of MRTX1133, a Noncovalent, Potent, and Selective KRASG12D Inhibitor," Journal of Medicinal Chemistry 65(4):3123-3133, American Chemical Society, United States (Feb. 2022).

(56) References Cited

OTHER PUBLICATIONS

Wang, Y., et al., "Discovery of Potent and Noncovalent KRASG12D Inhibitors: Structure-based Virtual Screening and Biological Evaluation," Frontiers in Pharmacology 13:1094887, 11 pages, Frontiers Media, Switzerland (Dec. 2022).

Xiao, X., et al., "Design, Synthesis, and Pharmacological Evaluation of Multisubstituted Pyrido[4,3-d]pyrimidine Analogues Bearing Deuterated Methylene Linkers as Potent KRASG12D Inhibitors," Journal of Medicinal Chemistry 66(22):15524-15549, American Chemical Society, United States (Nov. 2023).

Yang, J., et al., "Structural Optimization and Structure-activity Relationships of N2-(4-(4-Methylpiperazin-1-yl)phenyl)-N8-phenyl-9H-purine-2,8-diamine Derivatives, a New Class of Reversible Kinase Inhibitors Targeting Both Egfr-activating and Resistance Mutations," Journal of Medicinal Chemistry 55(23):10685-10699, American Chemical Society, United States (Dec. 2012).

Co-pending Application, U.S. Appl. No. 19/109,443, inventors Fink, B.E., et al., filed Sep. 7, 2023 (Not yet Published).

Co-pending Application, U.S. Appl. No. 18/873,229, inventors Fink, B.E., et al., filed Jun. 8, 2023 (Not yet Published).

Co-pending Application, U.S. Appl. No. 19/103,040, inventors Condakes, M.L., et al., filed Aug. 10, 2023 (Not yet Published).

Co-pending Application, U.S. Appl. No. 19/072,656, inventors Fink, B.E., et al., filed Mar. 6, 2025 (Not yet Published).

Co-pending Application, U.S. Appl. No. 18/875,573, inventors Kulyk. S., et al., filed Jun. 13, 2023 (Not yet Published).

Co-pending Application, U.S. Appl. No. 18/875,574, inventors Marx, M.A., et al., filed Jun. 13, 2023 (Not yet Published).

Co-pending Application, U.S. Appl. No. 18/875,603, inventors Wang, X.., et al., filed Jun. 13, 2023 (Not yet Published).

Co-pending Application, U.S. Appl. No. 18/875,610, inventors Wang, X.., et al., filed Jun. 13, 2023 (Not yet Published).

International Search Report and Written Opinion for International Application No. PCT/US2022/020229, European Patent Office, Netherlands, mailed on Aug. 8, 2022, 10 pages.

* cited by examiner

KRAS G12D INHIBITORS

CROSS REFERENCE TO RELATED APPLICATIONS

This application claims priority to U.S. Provisional Application No. 63/160,431, filed on Mar. 12, 2021; U.S. Provisional Application No. 63/173,021, filed on Apr. 9, 2021; U.S. Provisional Application No. 63/220,386, filed Jul. 9, 2021; and U.S. Provisional Application No. 63/236,497, filed Aug. 24, 2021, which are each incorporated by reference in their entirety.

FIELD

The present disclosure provides KRAS inhibitors. Methods of treating cancers using the inhibitors are also provided.

BACKGROUND

The KRAS oncogene is a member of the Ras family of GTPases that are involved in numerous cellular signaling processes. KRAS mutations are gain-of-function mutations that are present in up to 30% of all tumors, including as many as 90% of pancreatic cancers. KRAS G12D mutation is present in 28% of all pancreatic ductal adenocarcinoma patients, 13% of all colorectal carcinoma patients, 4% of all non-small cell lung carcinoma patients and 3% of all gastric carcinoma patients (e.g., see https://www.mycancergenome.org/content/alteration/kras-g12d/). Due to the clinical significance of this protein, many attempts have been made to develop Ras inhibitors, but such attempts have been mostly unsuccessful. This is largely due to the difficulty in outcompeting GTP for the KRAS binding pocket in cells, and the lack of known allosteric regulatory sites. Accordingly, agents that inhibit KRAS G12D are desired.

SUMMARY

In a first aspect, the present disclosure provides a compound of formula (I):

(I)

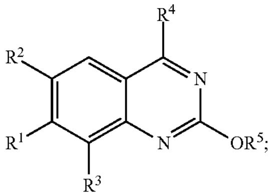

or a pharmaceutically acceptable salt thereof; wherein:

$R^1$ is aryl or heteroaryl, wherein the aryl and the heteroaryl are optionally substituted with one, two, three, four, or five substituents independently selected from $C_1$-$C_3$alkyl, $C_2$-$C_4$alkenyl, $C_2$-$C_4$alkynyl, amino, amino$C_1$-$C_3$alkyl, $C_3$-$C_4$cycloalkyl, halo, halo$C_1$-$C_3$alkyl, hydroxy, and hydroxy$C_1$-$C_3$alkyl;

$R^2$ and $R^3$ are independently selected from hydrogen, $C_1$-$C_3$alkoxy, $C_1$-$C_3$alkyl, cyano, halo, halo$C_1$-$C_3$alkyl, and hydroxy;

$R^4$ is selected from:

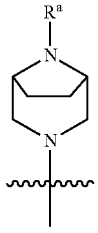 ; 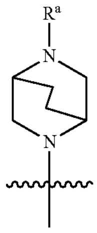 ; 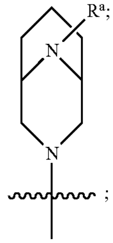 ; 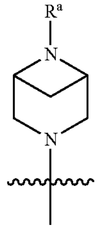 ;

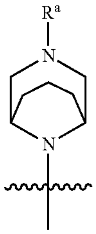 ; 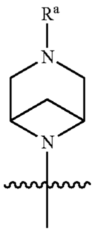 ; 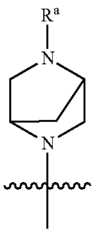 ; and 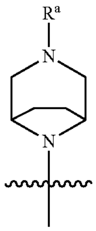 ;

wherein $R^a$ is hydrogen or $C_1$-$C_3$alkyl; and

⌇ denotes the point of attachment to the parent molecular moiety;

$R^5$ is —($C_1$-$C_3$alkyl)-$R^6$ or —($C_1$-$C_6$alkyl)$NR^cR^d$, wherein $R^6$ is selected from a $C_3$-$C_6$cycloalkyl optionally substituted with $NR^cR^d$($C_1$-$C_3$alkyl)-; and a five- to ten-membered monocyclic, bicyclic, or tricyclic fully saturated or fully unsaturated ring containing one nitrogen atom and optionally a second heteroatom selected from oxygen or nitrogen, wherein the ring contains zero to three double bonds and wherein the ring is optionally substituted with one, two, or three groups independently selected from $C_1$-$C_3$alkoxy, $C_1$-$C_3$alkoxy$C_1$-$C_3$alkyl, $C_1$-$C_3$alkyl, benzyl, halo, halo$C_1$-$C_3$alkyl, hydroxy, hydroxy$C_1$-$C_3$alkyl, and oxo; wherein $R^c$ and $R^d$, together with the nitrogen atom to which they are attached, form a five- to ten-membered ring monocyclic or bicyclic ring optionally containing one additional heteroatom selected from nitrogen, oxygen, and sulfur, wherein the ring is optionally substituted with one, two, or three groups independently selected from $C_1$-$C_3$alkoxy, $C_1$-$C_3$alkoxy$C_1$-$C_3$alkyl, $C_1$-$C_3$alkyl, benzyl, halo, halo$C_1$-$C_3$alkyl, hydroxy, hydroxy$C_1$-$C_3$alkyl, and oxo; or one of $R^c$ and $R^d$ is selected from hydrogen and $C_1$-$C_3$alkyl and the other is selected from hydrogen, $C_1$-$C_3$alkyl, $C_1$-$C_3$alkoxycarbonyl, and $C_1$-$C_3$alkylcarbonyl.

In some aspects, $R^2$ and $R^3$ are each halo. In some aspects, $R^2$ is chloro and $R^3$ is fluoro. In another aspect, $R^2$ is hydrogen and $R^3$ is fluoro.

In some aspects, $R^4$ is

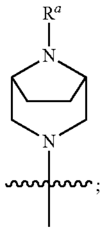

wherein $R^a$ is hydrogen or $C_1$-$C_3$alkyl.

In some aspects, $R^4$ is

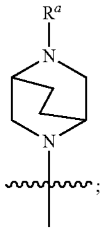

wherein $R^a$ is hydrogen or $C_1$-$C_3$alkyl.

In some aspects, $R^4$ is

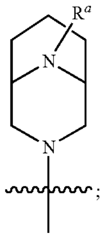

wherein $R^a$ is hydrogen or $C_1$-$C_3$alkyl.

In some aspects, $R^4$ is

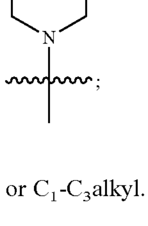

wherein $R^a$ is hydrogen or $C_1$-$C_3$alkyl.

In some aspects, $R^4$ is

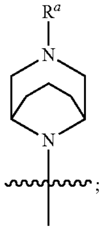

wherein $R^a$ is hydrogen or $C_1$-$C_3$alkyl.

In some aspects, $R^4$ is

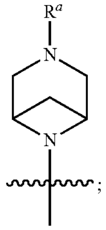

wherein $R^a$ is hydrogen or $C_1$-$C_3$alkyl.

In some aspects, $R^4$ is

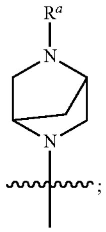

wherein $R^a$ is hydrogen or $C_1$-$C_3$alkyl.

In some aspects, $R^4$ is

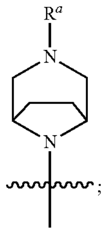

wherein $R^a$ is hydrogen or $C_1$-$C_3$alkyl.

In some aspects, $R^5$ is —($C_1$-$C_3$alkyl)-$R^6$.

In some aspects, $R^1$ is substituted, wherein one of the substituents on $R^1$ is halo$C_1$-$C_3$alkyl.

In some aspects, $R^6$ is a five- to eight-membered monocyclic or bicyclic fully saturated or fully unsaturated ring containing one nitrogen atom and optionally a second heteroatom selected from oxygen or nitrogen, wherein the ring contains zero to three double bonds and wherein the ring is optionally substituted with one, two, or three groups independently selected from $C_1$-$C_3$alkoxy, $C_1$-$C_3$alkyl, halo, halo$C_1$-$C_3$alkyl, and hydroxy.

In some aspects, In some aspects, $R^5$ is selected from:

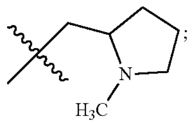 [SMILES: *CC1CCCN1C]

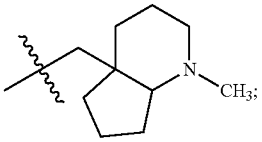

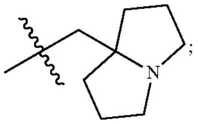

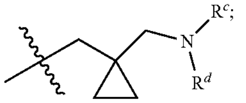

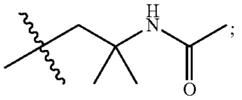

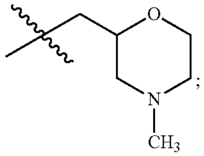

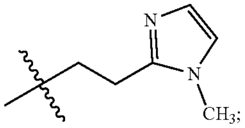

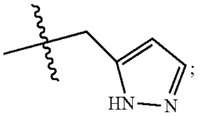

and

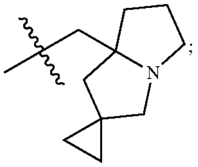

wherein each ring is optionally substituted with 1, 2, or 3 groups independently selected from $C_1$-$C_3$alkoxy, $C_1$-$C_3$alkoxy$C_1$-$C_3$alkyl, $C_1$-$C_3$alkyl, benzyl, halo, halo$C_1$-$C_3$alkyl, hydroxy, hydroxy$C_1$-$C_3$alkyl, and oxo; and wherein denotes the point of attachment to the parent molecular moiety.

In some aspects, $R^5$ is

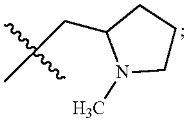

wherein denotes the point of attachment to the parent molecular moiety.

In some aspects, $R^5$ is

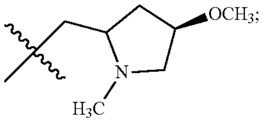

wherein denotes the point of attachment to the parent molecular moiety.

In some aspects, $R^5$ is

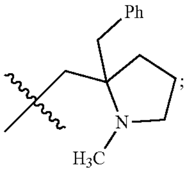

wherein denotes the point of attachment to the parent molecular moiety.

In some aspects, $R^5$ is

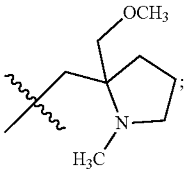

wherein denotes the point of attachment to the parent molecular moiety.

In some aspects, $R^5$ is

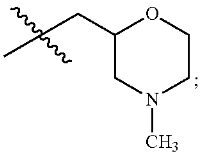

wherein denotes the point of attachment to the parent molecular moiety.

In some aspects, $R^5$ is

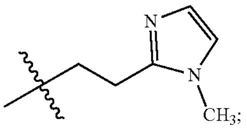

wherein denotes the point of attachment to the parent molecular moiety.

In some aspects, $R^5$ is

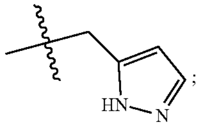

wherein denotes the point of attachment to the parent molecular moiety.

In some aspects, $R^5$ is

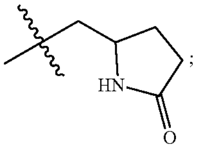

wherein denotes the point of attachment to the parent molecular moiety.

In some aspects, $R^5$ is

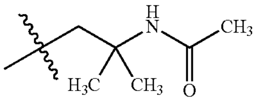

wherein denotes the point of attachment to the parent molecular moiety.

In some aspects, $R^6$ is an eight-membered bicyclic fully saturated or fully unsaturated ring containing one nitrogen atom, optionally substituted with one, two, or three groups independently selected from $C_1$-$C_3$alkoxy, $C_1$-$C_3$alkoxy$C_1$-$C_3$alkyl, $C_1$-$C_3$alkyl, benzyl, halo, halo$C_1$-$C_3$alkyl, hydroxy, hydroxy$C_1$-$C_3$alkyl, and oxo.

In some aspects, $R^5$ is

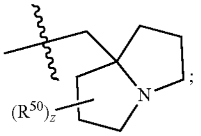

wherein:

z is 1, 2, or 3;

each $R^{50}$ is independently selected from $C_1$-$C_3$alkoxy, $C_1$-$C_3$alkoxy$C_1$-$C_3$alkyl, $C_1$-$C_3$alkyl, benzyl, halo, halo$C_1$-$C_3$alkyl, hydroxy, hydroxy$C_1$-$C_3$alkyl, and oxo; and denotes the point of attachment to the parent molecular moiety.

In some aspects, $R^5$ is

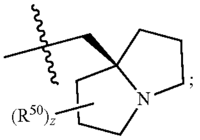

wherein:

z is 1, 2, or 3;

each $R^{50}$ is independently selected from $C_1$-$C_3$alkoxy, $C_1$-$C_3$alkoxy$C_1$-$C_3$alkyl, $C_1$-$C_3$alkyl, benzyl, halo, halo$C_1$-$C_3$alkyl, hydroxy, hydroxy$C_1$-$C_3$alkyl, and oxo; and denotes the point of attachment to the parent molecular moiety.

In some aspects, z is 1 and $R^{50}$ is halo. In some aspects, $R^{50}$ is fluoro. In some aspects, $R^1$ is naphthyl, wherein the naphthyl is optionally substituted with one group selected from $C_1$-$C_3$alkyl and hydroxy.

In some aspects, $R^5$ is

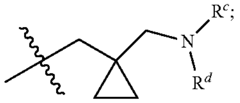

wherein denotes the point of attachment to the parent molecular moiety.

In some aspects, $R^5$ is

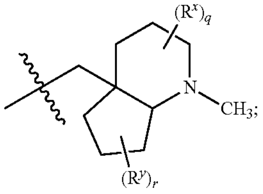

wherein q and r are each independently 0 or 1;

$R^x$ and $R^y$ are independently selected from $C_1$-$C_3$alkoxy, $C_1$-$C_3$alkyl, halo, halo$C_1$-$C_3$alkyl, and hydroxy; and denotes the point of attachment to the parent molecular moiety.

In some aspects, $R^5$ is

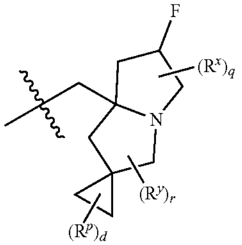

wherein q, r, and d are each independently 0 or 1; wherein $R^x$, $R^y$, and $R^p$ are independently selected from $C_1$-$C_3$alkoxy, $C_1$-$C_3$alkyl, halo, halo$C_1$-$C_3$alkyl, and hydroxy; and denotes the point of attachment to the parent molecular moiety.

In some aspects, $R^5$ is

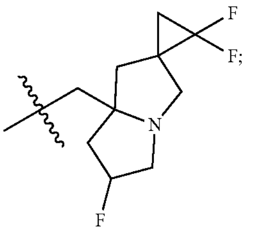

wherein denotes the point of attachment to the parent molecular moiety.

In some aspects, $R^1$ is phenyl, wherein the phenyl is optionally substituted with one or two groups selected from $C_1$-$C_3$alkyl, $C_3$-$C_6$cycloalkyl, halo, and halo$C_1$-$C_3$alkyl.

In some aspects, $R^1$ is naphthyl, wherein the naphthyl is optionally substituted with one, two, or three groups independently selected from $C_1$-$C_3$alkyl, $C_2$-$C_4$alkynyl, $C_3$cycloalkyl, halo, and hydroxy.

In some aspects, $R^1$ is

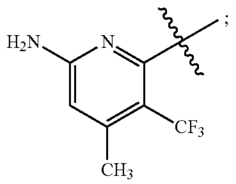

wherein denotes the point of attachment to the parent molecular moiety.

In some aspects, $R^1$ is

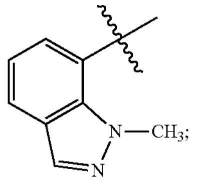

wherein denotes the point of attachment to the parent molecular moiety.

In some aspects, $R^1$ is

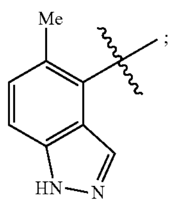

wherein denotes the point of attachment to the parent molecular moiety.

In some aspects, $R^1$ is

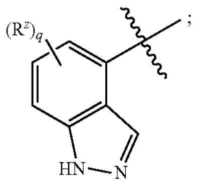

wherein q is 1, 2, or 3; each $R^z$ is independently selected from $C_1$-$C_3$alkyl, and halo; and denotes the point of attachment to the parent molecular moiety.

In some aspects, $R^1$ is

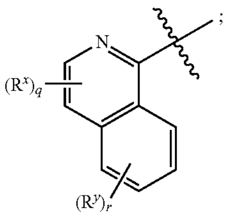

wherein q and r are each independently 0 or 1;

$R^x$ and $R^y$ are independently selected from $C_1$-$C_3$alkoxy, $C_1$-$C_3$alkyl, halo, halo$C_1$-$C_3$alkyl, and hydroxy; and denotes the point of attachment to the parent molecular moiety.

In some aspects, the present disclosure provides a compound of formula (I), or a pharmaceutically acceptable salt thereof, wherein $R^2$ is hydrogen;

$R^3$ is fluoro;

$R^1$ is selected from

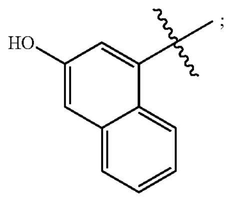

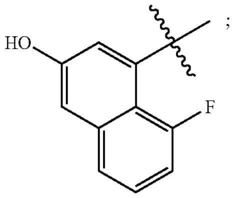

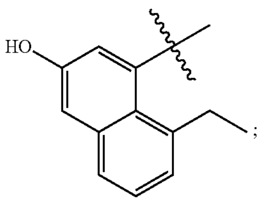

-continued

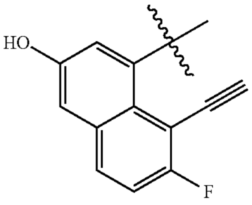 ; and 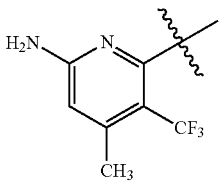 ;

$R^5$ is selected from

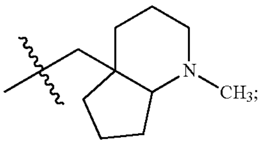 and

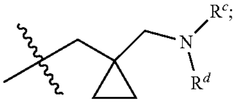

wherein  denotes the point of attachment to the parent molecular moiety.

In some aspects, the present disclosure provides a compound of formula (I), or a pharmaceutically acceptable salt thereof, wherein $R^2$ is chloro;

$R^3$ is fluoro; $R^1$ is selected from

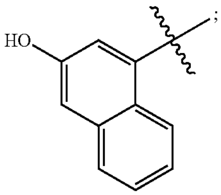 ; 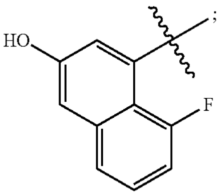 ;

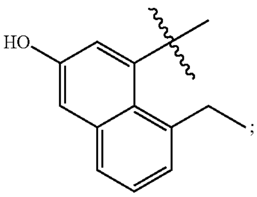 ;

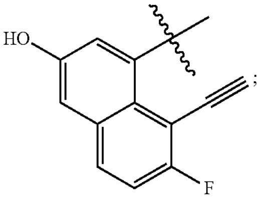 ; and 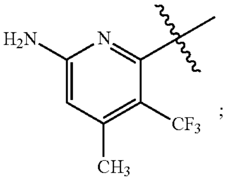 ;

and $R^5$ is selected from

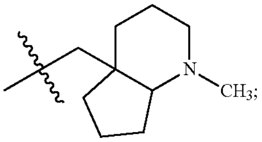 and

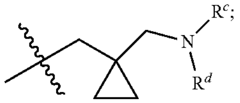

wherein  denotes the point of attachment to the parent molecular moiety.

In certain aspects, the present disclosure provides a compound of formula (II):

(II)

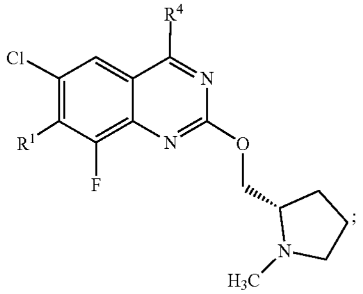 ;

or a pharmaceutically acceptable salt thereof, wherein:

$R^1$ is selected from

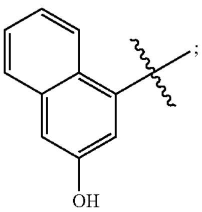 ; 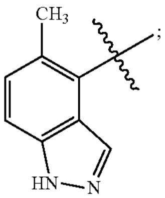 ; and

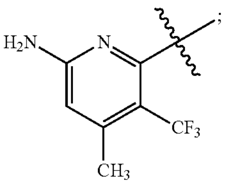 ;

wherein  denotes the point of attachment to the parent molecular moiety; and $R^4$ is selected from:

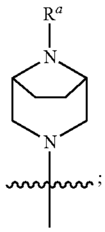; 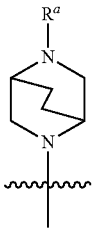; 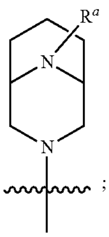; 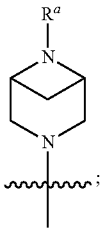;

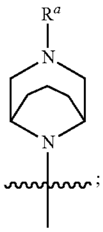; 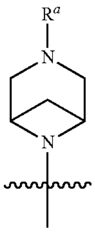; 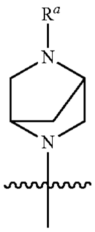; 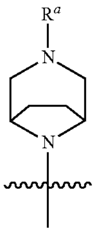;

wherein $R^a$ is hydrogen or $C_1$-$C_3$alkyl; and

 denotes the point of attachment to the parent molecular moiety.

In some aspects, $R^4$ is

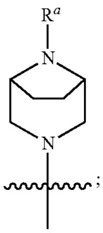;

wherein $R^a$ is hydrogen or $C_1$-$C_3$alkyl.

In some aspects, $R^4$ is

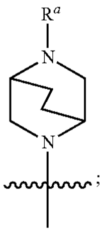;

wherein $R^a$ is hydrogen or $C_1$-$C_3$alkyl.

In some aspects, $R^4$ is

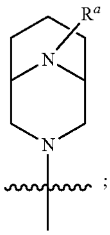;

wherein $R^a$ is hydrogen or $C_1$-$C_3$alkyl.

In some aspects, $R^4$ is

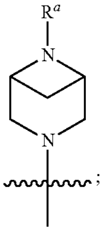;

wherein $R^a$ is hydrogen or $C_1$-$C_3$alkyl.

In some aspects, $R^4$ is

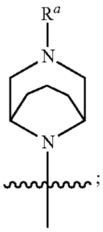;

wherein $R^a$ is hydrogen or $C_1$-$C_3$alkyl.

In some aspects, $R^4$ is

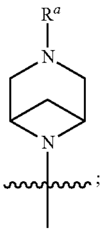;

wherein $R^a$ is hydrogen or $C_1$-$C_3$alkyl.

In some aspects, $R^4$ is

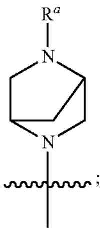;

wherein $R^a$ is hydrogen or $C_1$-$C_3$alkyl.

In some aspects, $R^4$ is

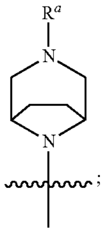

wherein $R^a$ is hydrogen or $C_1$-$C_3$alkyl.

In certain aspects, the present disclosure provides a compound of formula (III):

(III)

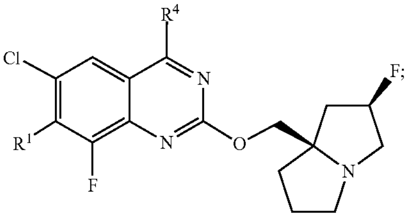

or a pharmaceutically acceptable salt thereof, wherein:

$R^1$ is selected from

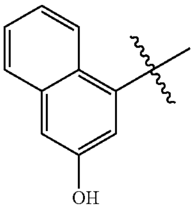

;

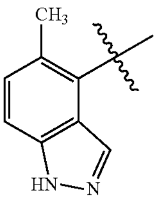

; and

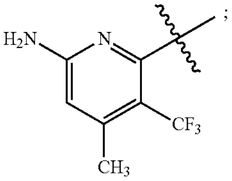

;

wherein  denotes the point of attachment to the parent molecular moiety; and $R^4$ is selected from:

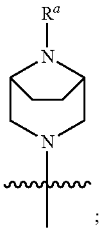

;

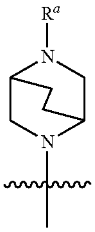

;

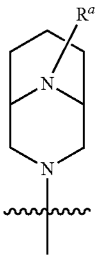

;

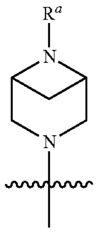

;

-continued

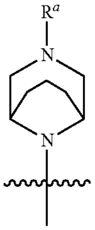

;

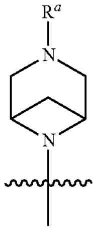

;

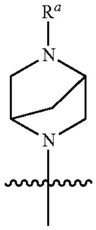

; and

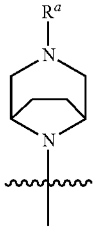

;

wherein $R^a$ is hydrogen or $C_1$-$C_3$alkyl; and

 denotes the point of attachment to the parent molecular moiety.

In some aspects, $R^4$ is

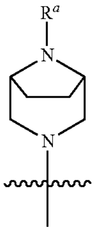

wherein $R^a$ is hydrogen or $C_1$-$C_3$alkyl.

In some aspects, $R^4$ is

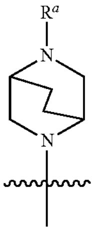

wherein $R^a$ is hydrogen or $C_1$-$C_3$alkyl.

In some aspects, $R^4$ is

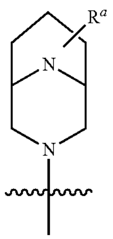

wherein $R^a$ is hydrogen or $C_1$-$C_3$alkyl.

In some aspects, $R^4$ is

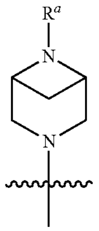

;

wherein $R^a$ is hydrogen or $C_1$-$C_3$alkyl.

In some aspects, $R^4$ is

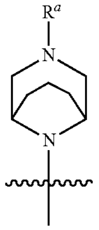

;

wherein $R^a$ is hydrogen or $C_1$-$C_3$alkyl.

In some aspects, $R^4$ is

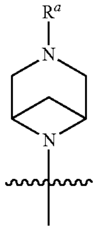

;

wherein $R^a$ is hydrogen or $C_1$-$C_3$alkyl.

In some aspects, $R^4$ is

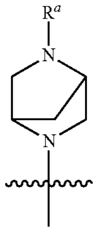

;

wherein $R^a$ is hydrogen or $C_1$-$C_3$alkyl.

In some aspects, $R^4$ is

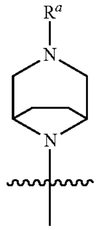

;

wherein $R^a$ is hydrogen or $C_1$-$C_3$alkyl.

In some aspects, the present disclosure provides an atropisomer of a compound of any of the prior aspects. In certain embodiments, the compound is a stable atropisomer as described herein.

In some aspects, the present disclosure provides a pharmaceutical composition comprising a compound of formula (I) (II), or (III), or a pharmaceutically acceptable salt thereof, and one or more pharmaceutically acceptable excipients.

In some aspects, the present disclosure provides an oral dosage form comprising a compound of formula (I), (II), or (III), or a pharmaceutically acceptable salt thereof, and one or more pharmaceutically acceptable excipients.

In certain aspects, the present disclosure provides method of treating cancer expressing KRAS G12D mutation in a subject in need thereof, the method comprising administering to the subject a compound of formula (I):

(I)

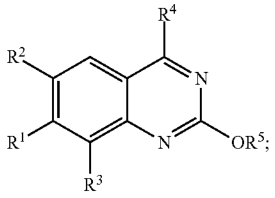

or a pharmaceutically acceptable salt thereof; wherein:

$R^1$ is aryl or heteroaryl, wherein the aryl and the heteroaryl are optionally substituted with one, two, three, four, or five substituents independently selected from $C_1$-$C_3$alkyl, $C_2$-$C_4$alkenyl, $C_2$-$C_4$alkynyl, amino, amino$C_1$-$C_3$alkyl, $C_3$-$C_4$cycloalkyl, halo, halo$C_1$-$C_3$alkyl, hydroxy, and hydroxy$C_1$-$C_3$alkyl;

$R^2$ and $R^3$ are independently selected from hydrogen, $C_1$-$C_3$alkoxy, $C_1$-$C_3$alkyl, cyano, halo, halo$C_1$-$C_3$alkyl, and hydroxy;

$R^4$ is selected from:

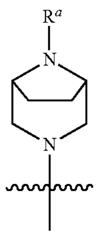 ; 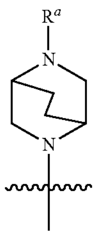 ; 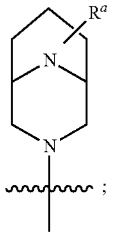 ; 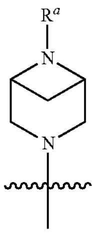 ;

-continued

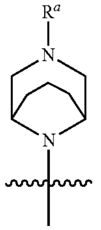 ; 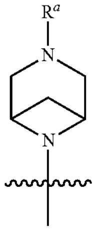 ; 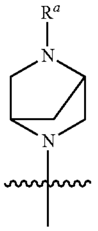 ; and 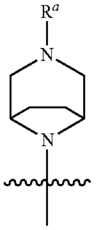 ;

wherein $R^a$ is hydrogen or $C_1$-$C_3$alkyl; and;

 denotes the point of attachment to the parent molecular moiety.

$R^5$ is —($C_1$-$C_3$alkyl)-$R^6$ or —($C_1$-$C_6$alkyl)$NR^cR^d$, wherein $R^6$ is selected from:

a $C_3$-$C_6$cycloalkyl optionally substituted with $NR^cR^d$($C_1$-$C_3$alkyl)-; and a five- to ten-membered monocyclic, bicyclic, or tricyclic fully saturated or fully unsaturated ring containing one nitrogen atom and optionally a second heteroatom selected from oxygen or nitrogen, wherein the ring contains zero to three double bonds and wherein the ring is optionally substituted with one, two, or three groups independently selected from $C_1$-$C_3$alkoxy, $C_1$-$C_3$alkoxy$C_1$-$C_3$alkyl, $C_1$-$C_3$alkyl, benzyl, halo, halo$C_1$-$C_3$alkyl, hydroxy, hydroxy$C_1$-$C_3$alkyl, and oxo; wherein $R^c$ and $R^d$, together with the nitrogen atom to which they are attached, form a five- to ten-membered ring monocyclic or bicyclic ring optionally containing one additional heteroatom selected from nitrogen, oxygen, and sulfur, wherein the ring is optionally substituted with one, two, or three groups independently selected from $C_1$-$C_3$alkoxy, $C_1$-$C_3$alkoxy$C_1$-$C_3$alkyl, $C_1$-$C_3$alkyl, benzyl, halo, halo$C_1$-$C_3$alkyl, hydroxy, hydroxy$C_1$-$C_3$alkyl, and oxo; or one of $R^c$ and $R^d$ is selected from hydrogen and $C_1$-$C_3$alkyl and the other is selected from hydrogen, $C_1$-$C_3$alkyl, $C_1$-$C_3$alkoxycarbonyl, and $C_1$-$C_3$alkylcarbonyl.

In some aspects of the method, $R^2$ and $R^3$ are each halo. In some aspects, $R^2$ is chloro and $R^3$ is fluoro. In other aspects, $R^2$ is hydrogen and $R^3$ is fluoro.

In some aspects of the method, $R^4$ is

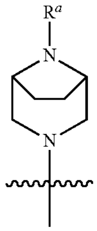 ;

wherein R is hydrogen or $C_1$-$C_3$alkyl.

In some aspects of the method, $R^4$ is

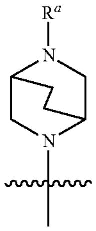 ;

wherein $R^a$ is hydrogen or $C_1$-$C_3$alkyl.

In some aspects of the method, $R^4$ is

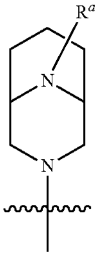 ;

wherein $R^a$ is hydrogen or $C_1$-$C_3$alkyl.

In some aspects of the method, $R^4$ is

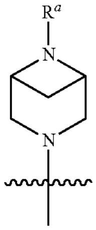 ;

wherein $R^a$ is hydrogen or $C_1$-$C_3$alkyl.

In some aspects of the method, $R^4$ is

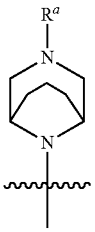 ;

wherein $R^a$ is hydrogen or $C_1$-$C_3$alkyl.

In some aspects of the method, $R^4$ is

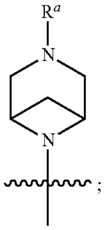

wherein $R^a$ is hydrogen or $C_1$-$C_3$alkyl.

In some aspects of the method, $R^4$ is

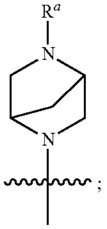

wherein $R^a$ is hydrogen or $C_1$-$C_3$alkyl.

In some aspects of the method, $R^4$ is

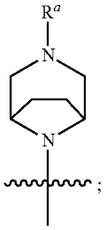

wherein $R^a$ is hydrogen or $C_1$-$C_3$alkyl.

In some aspects of the method, $R^5$ is —($C_1$-$C_3$alkyl)-$R^6$.

In some aspects of the method, $R^1$ is substituted, and wherein one of the substituents on $R^1$ is halo$C_1$-$C_3$alkyl.

In some aspects of the method, $R^5$ is

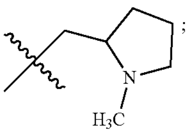

wherein denotes the point of attachment to the parent molecular moiety.

In some aspects, $R^5$ is

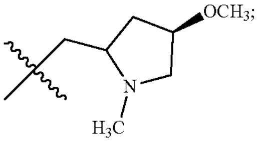

wherein denotes the point of attachment to the parent molecular moiety.

In some aspects, $R^5$ is

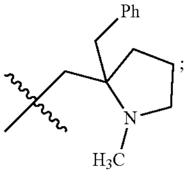

wherein denotes the point of attachment to the parent molecular moiety.

In some aspects, $R^5$ is

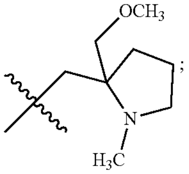

wherein denotes the point of attachment to the parent molecular moiety.

In some aspects, $R^5$ is

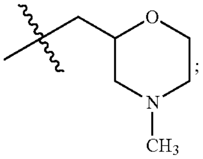

wherein denotes the point of attachment to the parent molecular moiety.

In some aspects, $R^5$ is

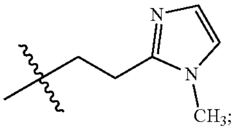

wherein denotes the point of attachment to the parent molecular moiety.

In some aspects, $R^5$ is

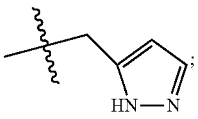

wherein denotes the point of attachment to the parent molecular moiety.

In some aspects, $R^5$ is

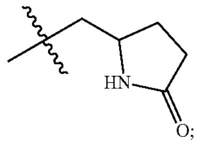

wherein denotes the point of attachment to the parent molecular moiety.

In some aspects, $R^5$ is

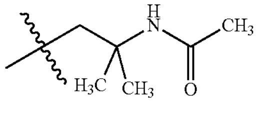

wherein denotes the point of attachment to the parent molecular moiety.

In some aspects of the method, $R^6$ is an eight-membered bicyclic fully saturated or fully unsaturated ring containing one nitrogen atom, optionally substituted with one, two, or three groups independently selected from $C_1$-$C_3$alkoxy, $C_1$-$C_3$alkoxy$C_1$-$C_3$alkyl, $C_1$-$C_3$alkyl, benzyl, halo, halo$C_1$-$C_3$alkyl, hydroxy, hydroxy$C_1$-$C_3$alkyl, and oxo.

In some aspects of the method, $R^5$ is

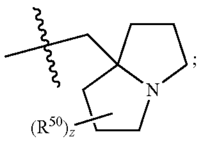

wherein:

z is 1, 2, or 3;

each $R^{50}$ is independently selected from $C_1$-$C_3$alkoxy, $C_1$-$C_3$alkoxy$C_1$-$C_3$alkyl, $C_1$-$C_3$alkyl, benzyl, halo, halo$C_1$-$C_3$alkyl, hydroxy, hydroxy$C_1$-$C_3$alkyl, and oxo; and denotes the point of attachment to the parent molecular moiety.

In some aspects of the method, $R^5$ is

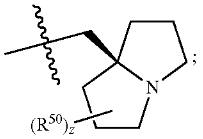

wherein:

z is 1, 2, or 3;

each $R^{50}$ is independently selected from $C_1$-$C_3$alkoxy, $C_1$-$C_3$alkoxy$C_1$-$C_3$alkyl, $C_1$-$C_3$alkyl, benzyl, halo, halo$C_1$-$C_3$alkyl, hydroxy, hydroxy$C_1$-$C_3$alkyl, and oxo; and denotes the point of attachment to the parent molecular moiety In some aspects of the method, z is 1 and $R^{50}$ is halo. In some aspects, $R^{50}$ is fluoro.

In some aspects of the method, $R^5$ is

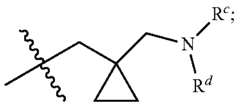

wherein denotes the point of attachment to the parent molecular moiety.

In some aspects of the method, $R^5$ is

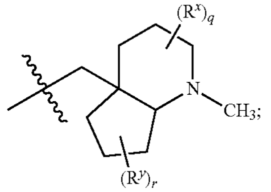

wherein q and r are each independently 0 or 1;

$R^x$ and $R^y$ are independently selected from $C_1$-$C_3$alkoxy, $C_1$-$C_3$alkyl, halo, halo$C_1$-$C_3$alkyl, and hydroxy; and denotes the point of attachment to the parent molecular moiety.

In some aspects of the method, $R^5$ is

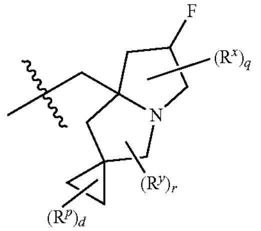

wherein q, r, and d are each independently 0 or 1; wherein $R^x$, $R^y$, and $R^p$ are independently selected from $C_1$-$C_3$alkoxy, $C_1$-$C_3$alkyl, halo, halo$C_1$-$C_3$alkyl, and hydroxy; and denotes the point of attachment to the parent molecular moiety.

In some aspects of the method, $R^5$ is

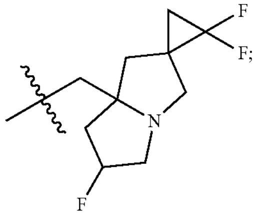

wherein denotes the point of attachment to the parent molecular moiety.

In some aspects of the method, $R^1$ is naphthyl, wherein the naphthyl is optionally substituted with one, two, or three groups independently selected from $C_1$-$C_3$alkyl, $C_2$-$C_4$alkynyl, $C_3$cycloalkyl, halo, and hydroxy. In some aspects of the method, $R^1$ is naphthyl, wherein the naphthyl is optionally substituted with one group selected from $C_1$-$C_3$alkyl and hydroxy.

In some aspects of the method, $R^1$ is phenyl, wherein the phenyl is optionally substituted with one or two groups selected from $C_1$-$C_3$alkyl, $C_3$-$C_6$cycloalkyl, halo, and halo$C_1$-$C_3$alkyl.

In some aspects of the method, $R^1$ is

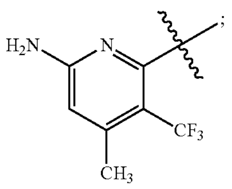 [SMILES: *c1nc(N)cc(C)c1C(F)(F)F]

wherein  denotes the point of attachment to the parent molecular moiety.

In some aspects of the method, $R^1$ is

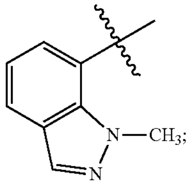 [SMILES: *c1cccc2cnn(C)c12]

wherein  denotes the point of attachment to the parent molecular moiety.

In some aspects of the method, $R^1$ is

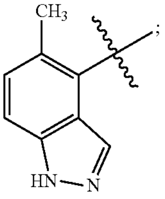 [SMILES: *c1c(C)ccc2[nH]ncc12]

wherein  denotes the point of attachment to the parent molecular moiety.

In some aspects of the method, $R^1$ is

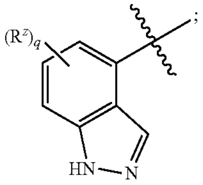

wherein:

q is 1, 2, or 3;

each $R^z$ is independently selected from $C_1$-$C_3$alkyl, and halo; and

 denotes the point of attachment to the parent molecular moiety.

In some aspects of the method, $R^1$ is

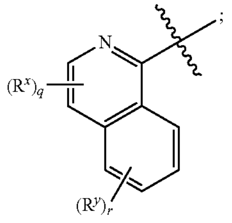

wherein q and r are each independently 0 or 1;

$R^x$ and $R^y$ are independently selected from $C_1$-$C_3$alkoxy, $C_1$-$C_3$alkyl, halo, halo$C_1$-$C_3$alkyl, and hydroxy; and

 denotes the point of attachment to the parent molecular moiety.

In some aspects of the method $R^2$ is hydrogen; $R^3$ is fluoro; $R^1$ is selected from

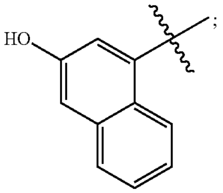

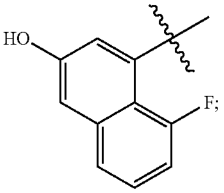

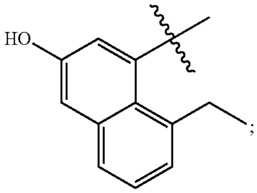

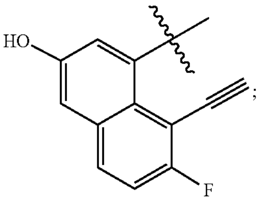

and

-continued

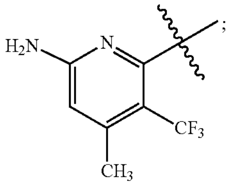

and $R^5$ is selected from

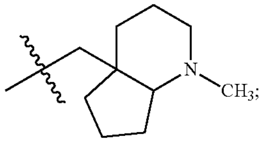

and

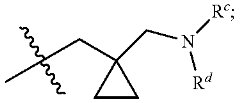

wherein

 denotes the point of attachment to the parent molecular moiety.

In some aspects of the method, $R^2$ is chloro; $R^3$ is fluoro; $R^1$ is selected from

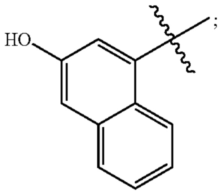

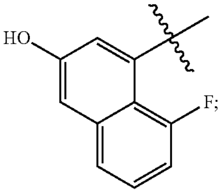

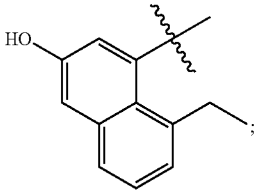

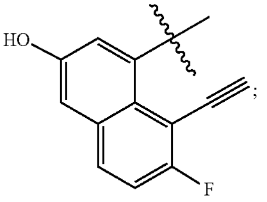

and

-continued

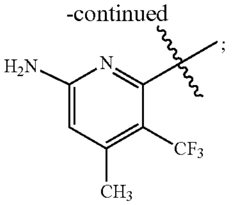

and $R^5$ is selected from

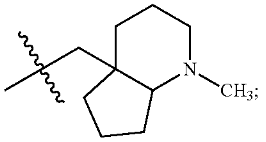

and

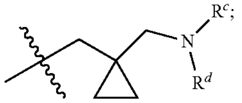

wherein

 denotes the point of attachment to the parent molecular moiety.

In certain aspects of the method, the compound is a compound of formula (II):

(II)

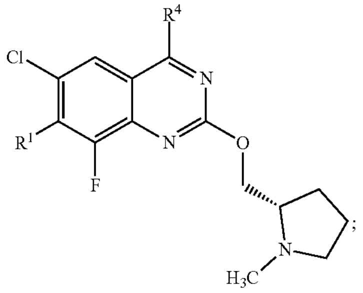

or a pharmaceutically acceptable salt thereof, wherein:

$R^1$ is selected from

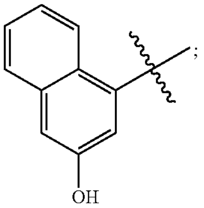

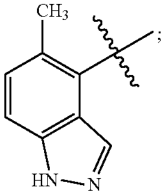

and

-continued

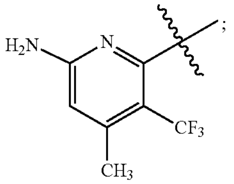

wherein denotes the point of attachment to the parent molecular moiety; and $R^4$ is selected from:

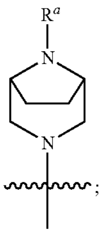
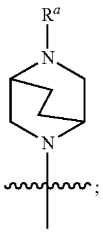
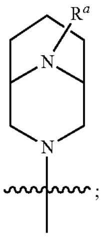
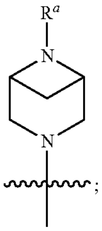
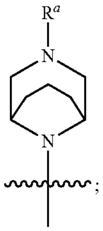
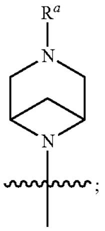
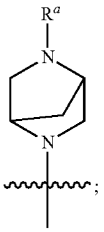

and

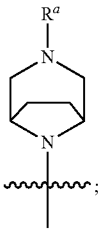

wherein $R^a$ is hydrogen or $C_1$-$C_3$alkyl; and denotes the point of attachment to the parent molecular moiety.

In some aspects of the method, the compound is a compound of formula (II) wherein

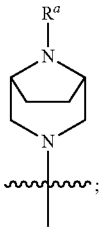

wherein $R^a$ is hydrogen or $C_1$-$C_3$alkyl.

In some aspects of the method, the compound is a compound of formula (II) wherein $R^4$ is

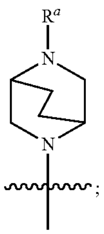

wherein $R^a$ is hydrogen or $C_1$-$C_3$alkyl.

In some aspects of the method, the compound is a compound of formula (II) wherein $R^4$ is

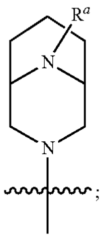

wherein $R^a$ is hydrogen or $C_1$-$C_3$alkyl.

In some aspects of the method, the compound is a compound of formula (II) wherein $R^4$ is

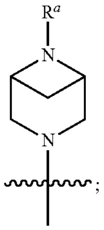

wherein $R^a$ is hydrogen or $C_1$-$C_3$alkyl.

In some aspects of the method, the compound is a compound of formula (II) wherein $R^4$ is

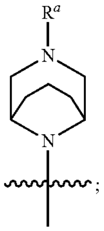

wherein $R^a$ is hydrogen or $C_1$-$C_3$alkyl.

In some aspects of the method, the compound is a compound of formula (II) wherein $R^4$ is

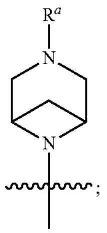

wherein $R^a$ is hydrogen or $C_1$-$C_3$alkyl.

In some aspects of the method, the compound is a compound of formula (II) wherein

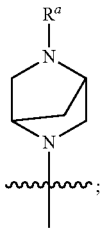

wherein $R^a$ is hydrogen or $C_1$-$C_3$alkyl.

In some aspects of the method, the compound is a compound of formula (II) wherein $R^4$ is

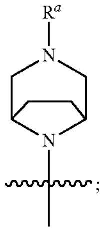

wherein $R^a$ is hydrogen or $C_1$-$C_3$alkyl.

In certain aspects of the method, the compound is a compound of formula (III):

(III)

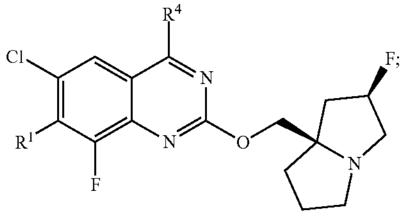

or a pharmaceutically acceptable salt thereof, wherein:

$R^1$ is selected from

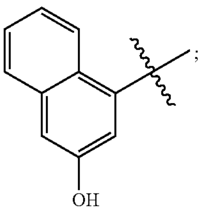

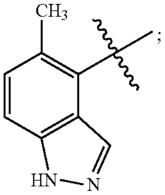

and

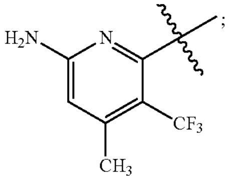

wherein  denotes the point of attachment to the parent molecular moiety; and $R^4$ is selected from:

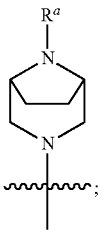

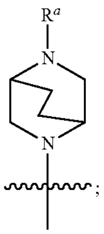

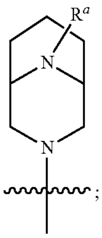

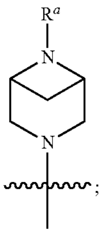

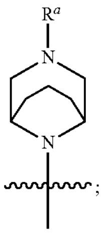

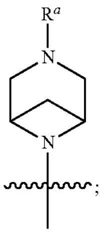

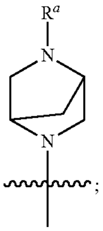

and

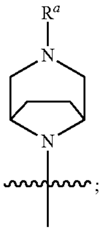

wherein $R^a$ is hydrogen or $C_1$-$C_3$alkyl; and

 denotes the point of attachment to the parent molecular moiety.

In some aspects of the method, the compound is a compound of formula (III) wherein $R^4$ is

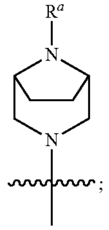

wherein $R^a$ is hydrogen or $C_1$-$C_3$alkyl.

In some aspects of the method, the compound is a compound of formula (III) wherein $R^4$ is

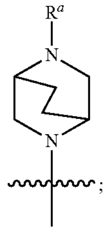

wherein $R^a$ is hydrogen or $C_1$-$C_3$alkyl.

In some aspects of the method, the compound is a compound of formula (III) wherein $R^4$ is

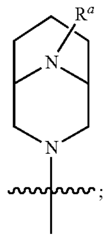

wherein $R^a$ is hydrogen or $C_1$-$C_3$alkyl.

In some aspects of the method, the compound is a compound of formula (III) wherein $R^4$ is

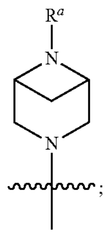

wherein $R^a$ is hydrogen or $C_1$-$C_3$alkyl.

In some aspects of the method, the compound is a compound of formula (III) wherein $R^4$ is

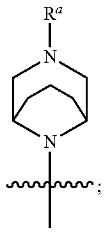

wherein $R^a$ is hydrogen or $C_1$-$C_3$alkyl.

In some aspects of the method, the compound is a compound of formula (III) wherein $R^4$ is

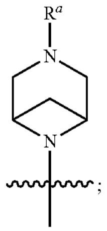

wherein $R^a$ is hydrogen or $C_1$-$C_3$alkyl.

In some aspects of the method, the compound is a compound of formula (III) wherein $R^4$ is

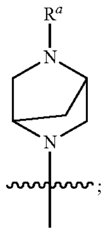

wherein $R^a$ is hydrogen or $C_1$-$C_3$alkyl.

In some aspects of the method, the compound is a compound of formula (III) wherein $R^4$ is

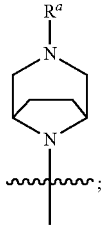

wherein $R^a$ is hydrogen or $C_1$-$C_3$alkyl.

In some aspects of the method, the compound is an atropisomer of a compound of any of the prior aspects. In certain aspects, the compound is a stable atropisomer as described herein.

In another aspect, the present disclosure provides a method for inhibiting KRAS G12D activity in a in a cell, comprising contacting the cell with a compound of formula (I), formula (II), or formula (III), or a pharmaceutically acceptable salt thereof, or a pharmaceutical composition thereof as defined herein. In one aspect, the contacting is in vitro. In one aspect, the contacting is in vivo.

In another aspect, the present disclosure provides a method of inhibiting cell proliferation, in vitro or in vivo, the method comprising contacting a cell with an effective amount of a compound of formula (I), formula (II), or formula (III), or a pharmaceutically acceptable salt thereof, or a pharmaceutical composition thereof as defined herein.

In another aspect, the present disclosure provides a method of treating a KRAS G12D-associated disease or disorder in a subject in need of such treatment, the method comprising administering to the subject a therapeutically effective amount of a compound of formula (I), formula (II), or formula (III), or a pharmaceutically acceptable salt thereof, or a pharmaceutical composition thereof as defined herein.

In another aspect, the present disclosure provides a method for treating a cancer susceptible to KRAS G12D inhibition in a subject in need thereof, the method comprising administering to the subject a compound of formula (I), (II), or formula (III), or a pharmaceutically acceptable salt thereof.

In another aspect, the present disclosure provides a method for treating a cancer in a subject in need thereof, the method comprising administering to the subject a compound of formula (I), formula (II), or formula (III), or a pharmaceutically acceptable salt thereof, wherein the cancer is selected from pancreatic cancer, colorectal cancer, lung cancer, gastric cancer, and combinations thereof.

In another aspect, the present disclosure provides a compound of formula (I), formula (II), or formula (III), or a pharmaceutically acceptable salt thereof, for use in the inhibition of KRAS G12D.

In another aspect, the present disclosure provides a compound of formula (I), formula (II), or formula (III), or a pharmaceutically acceptable salt thereof, or a pharmaceutical composition thereof as defined herein, for use in the treatment of a KRAS G12D-associated disease or disorder.

In another aspect, the present disclosure provides a use of a compound of formula (I), formula (II), or formula (III), or a pharmaceutically acceptable salt thereof, as defined herein in the manufacture of a medicament for the treatment of cancer.

In another aspect, the present disclosure provides the use of a compound of formula (I), formula (II), or formula (III), or a pharmaceutically acceptable salt thereof, as defined herein in the manufacture of a medicament for the inhibition of activity of KRAS G12D.

In another aspect, the present disclosure provides the use of a compound of formula (I), formula (II), or formula (III), or a pharmaceutically acceptable salt thereof, as defined herein, in the manufacture of a medicament for the treatment of a KRAS G12D-associated disease or disorder.

In another aspect, the present disclosure provides a compound selected from

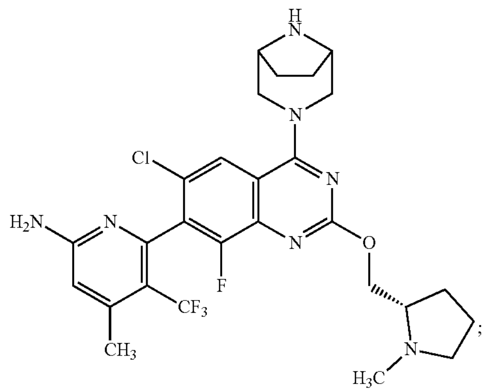
;

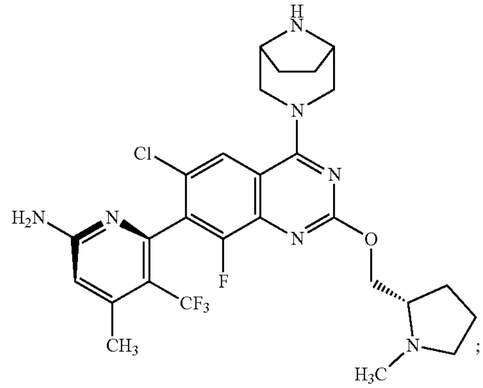
;

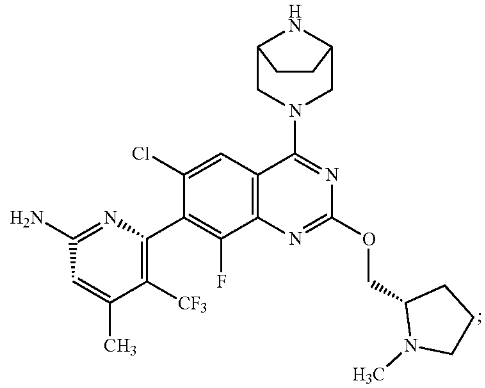
;

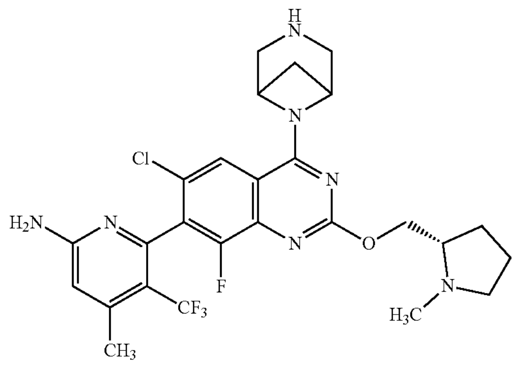
;

-continued
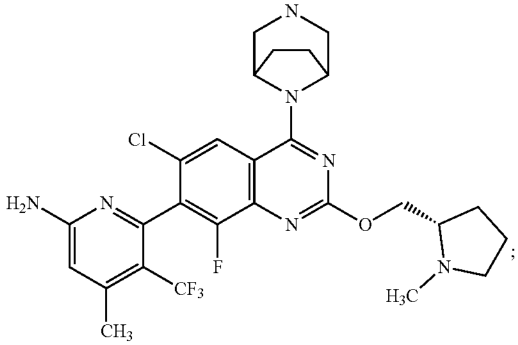
;
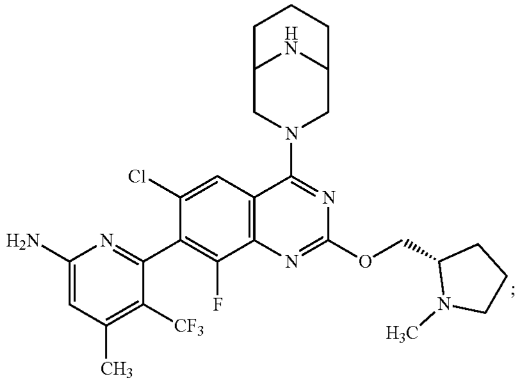
;
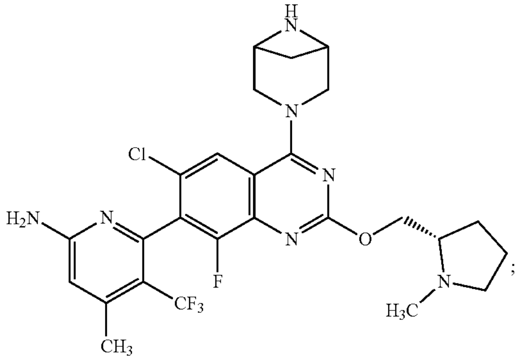
;
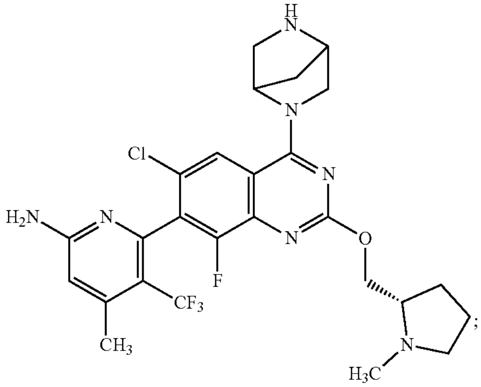
;
-continued
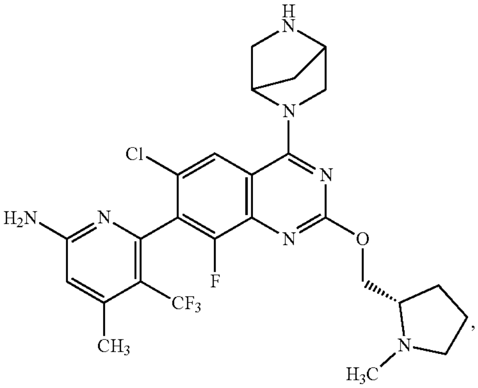
, isomer 1;
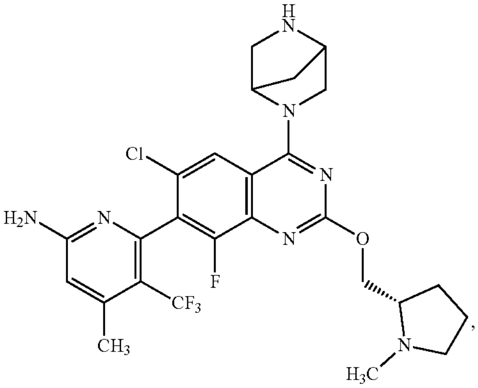
, isomer 2;
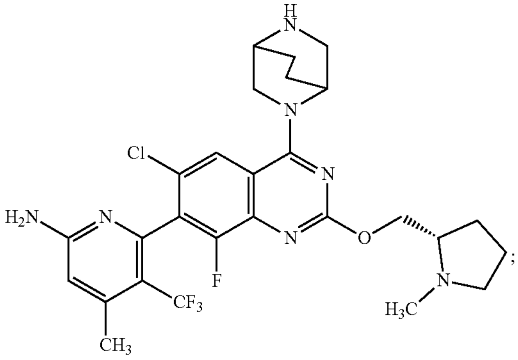
;
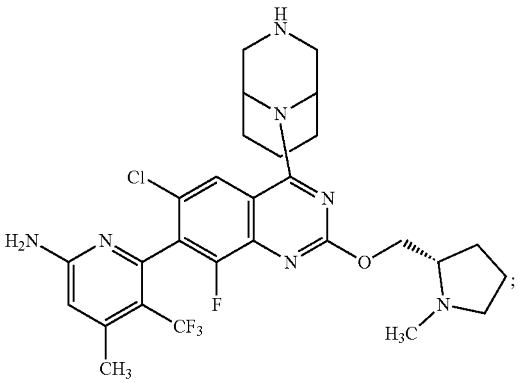
;

-continued
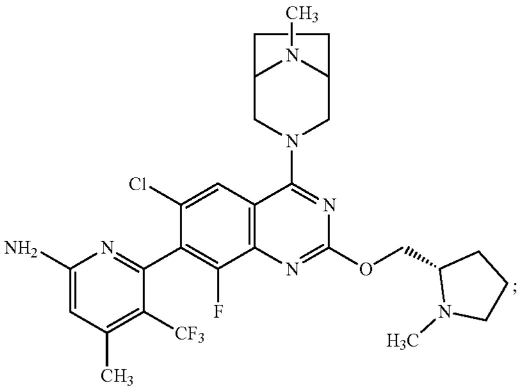
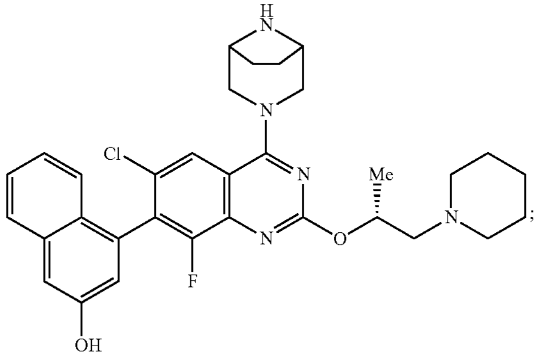
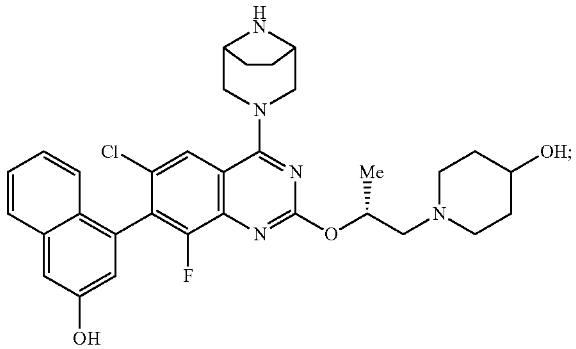
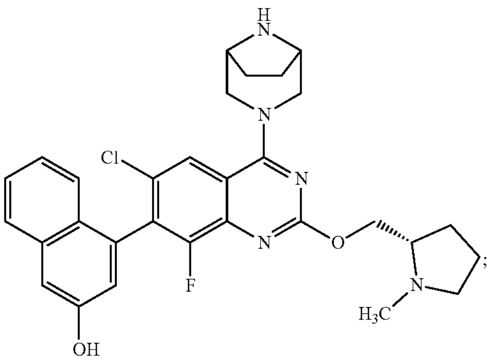
-continued
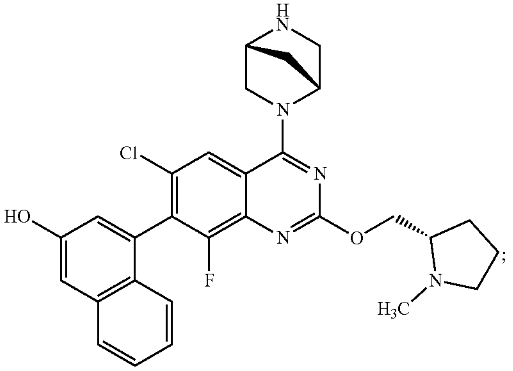
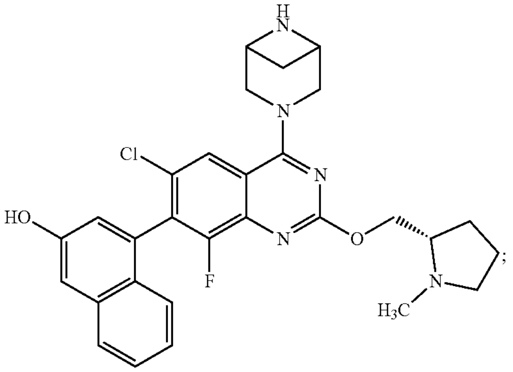
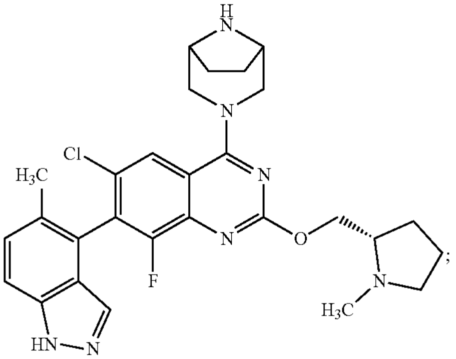
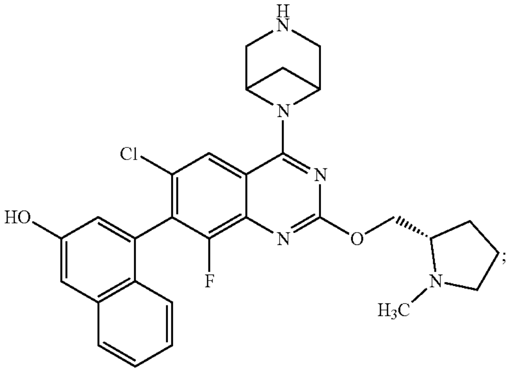

-continued
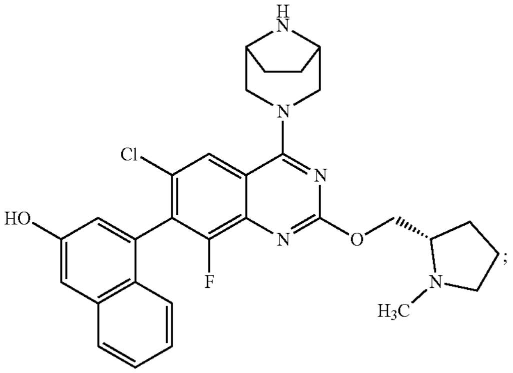
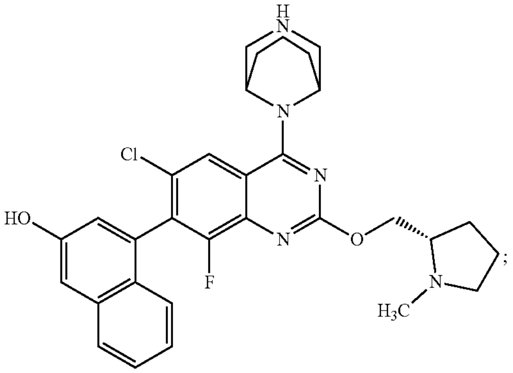
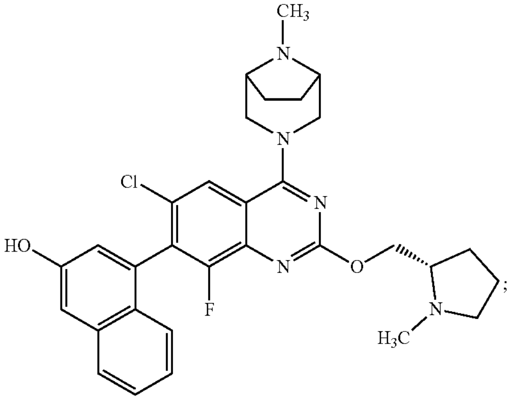
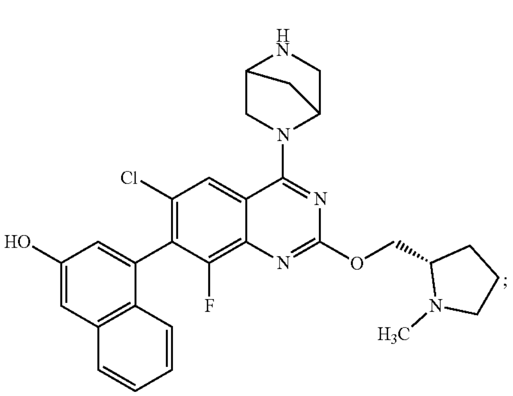
-continued
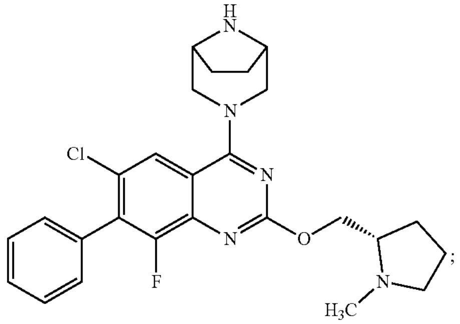
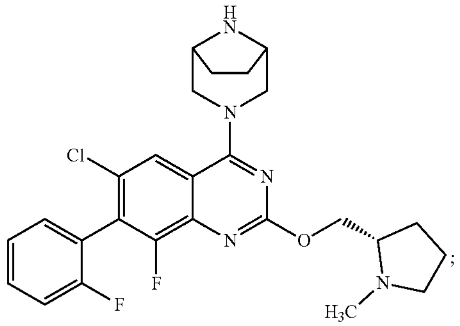
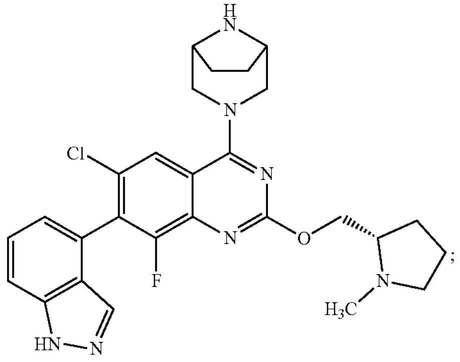
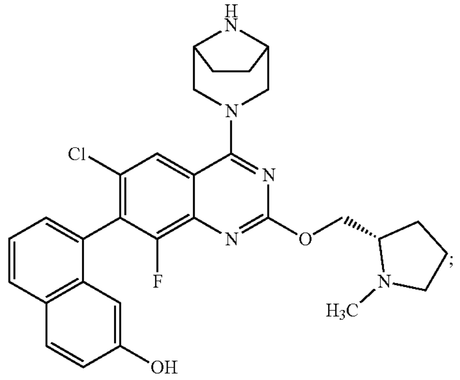

-continued
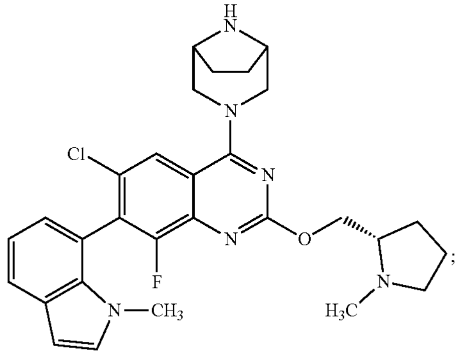
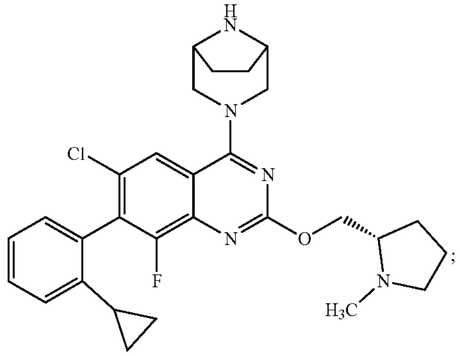
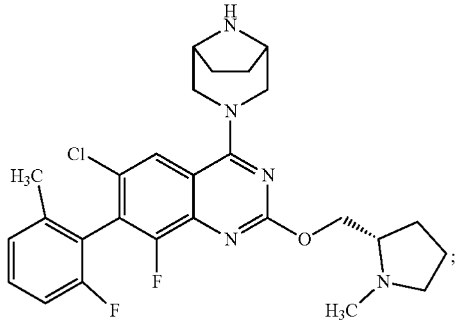
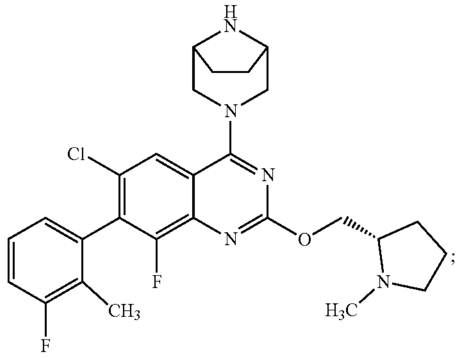
-continued
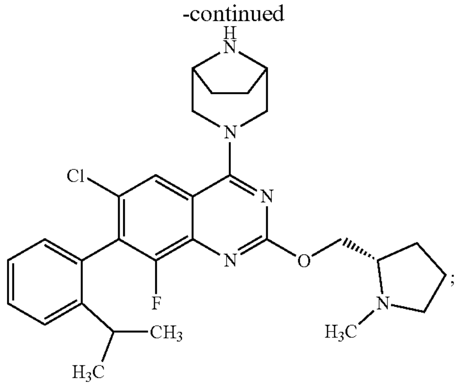
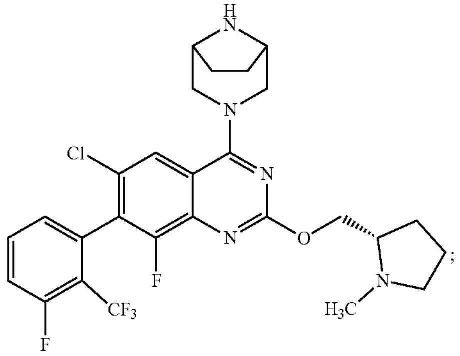
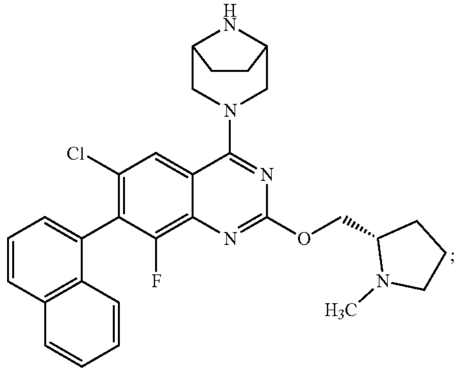
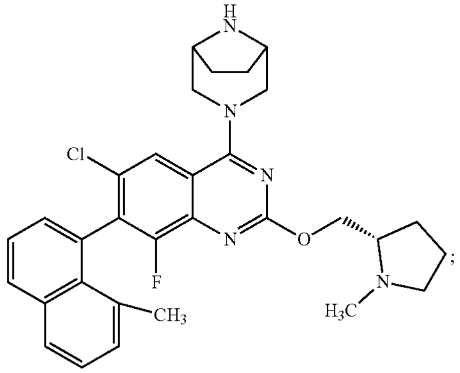

-continued
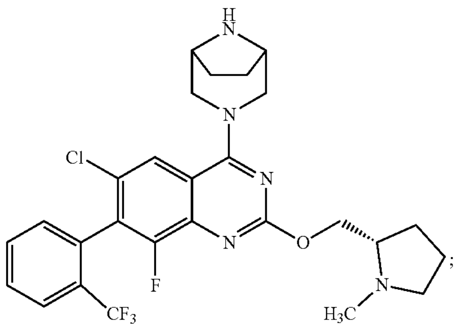
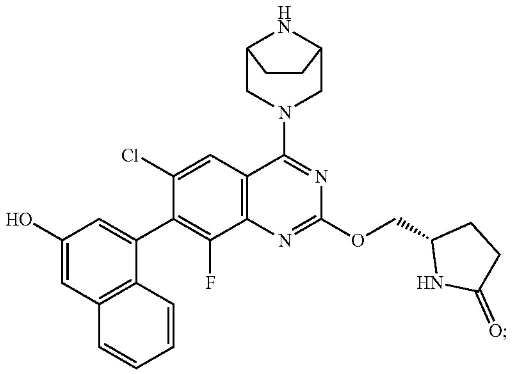
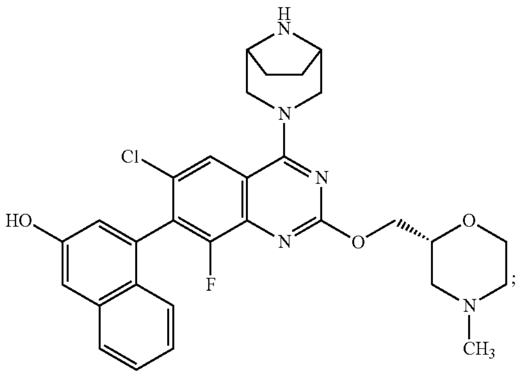
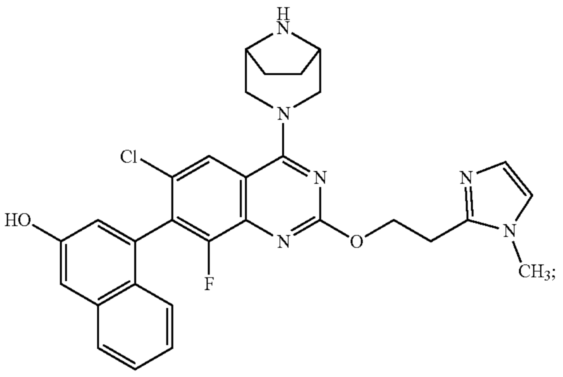
-continued
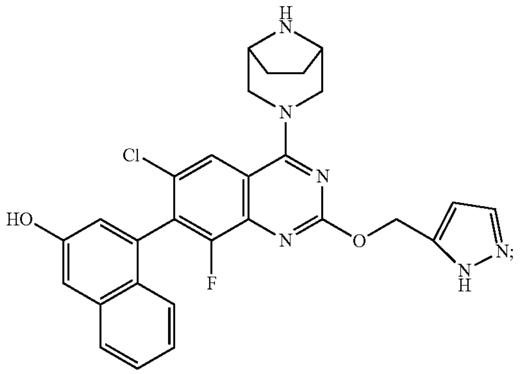
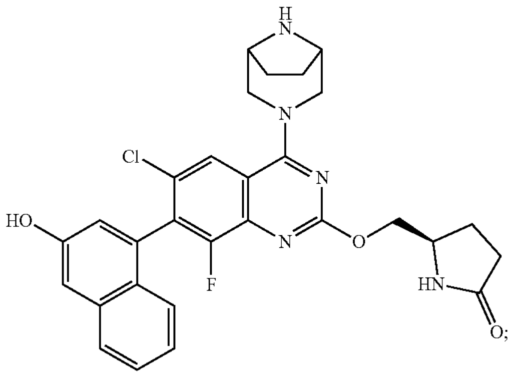
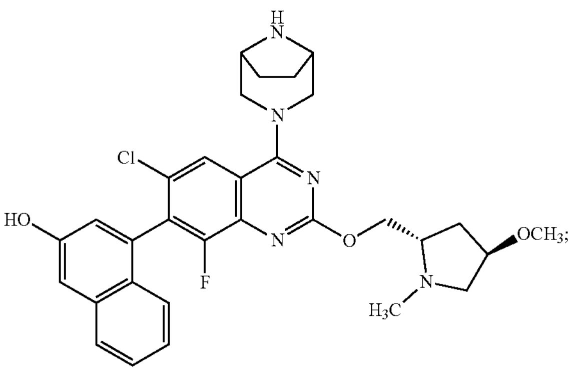
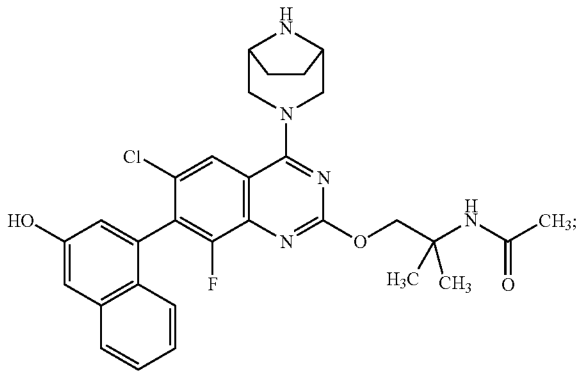

-continued
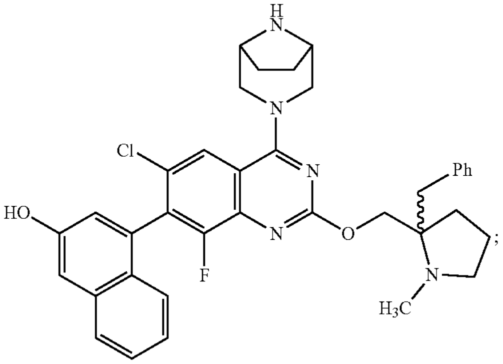
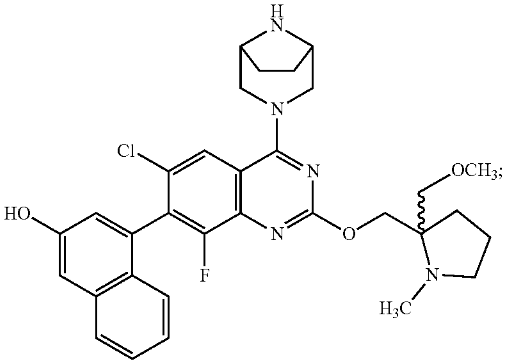
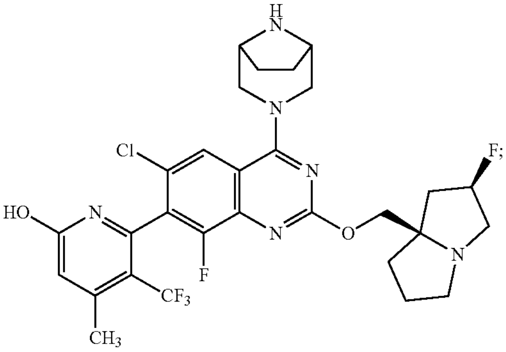
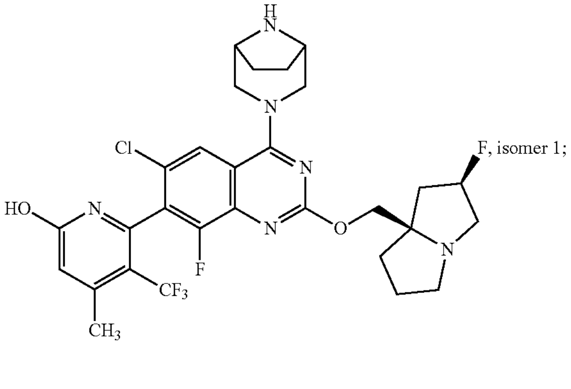
-continued
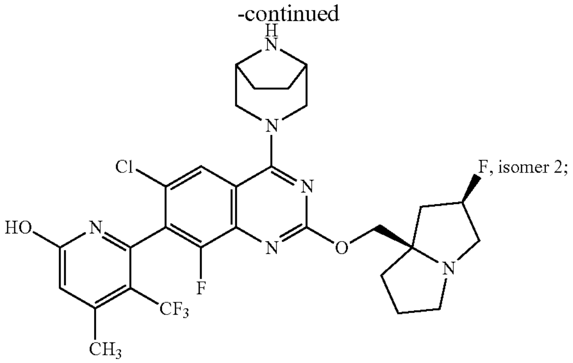
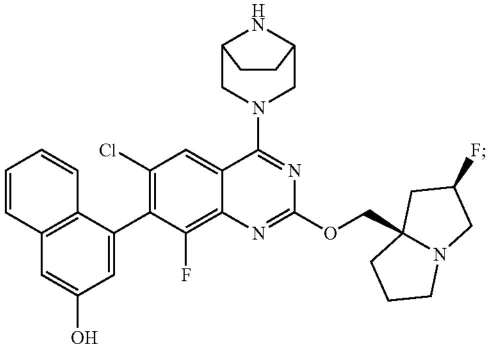
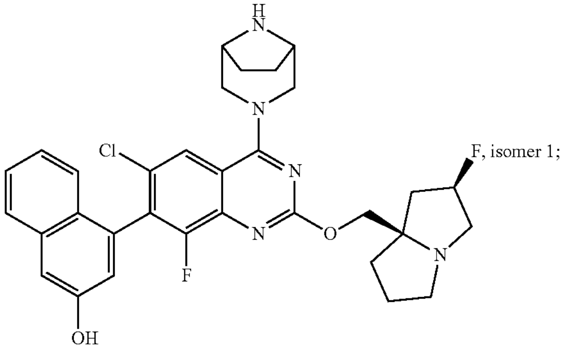
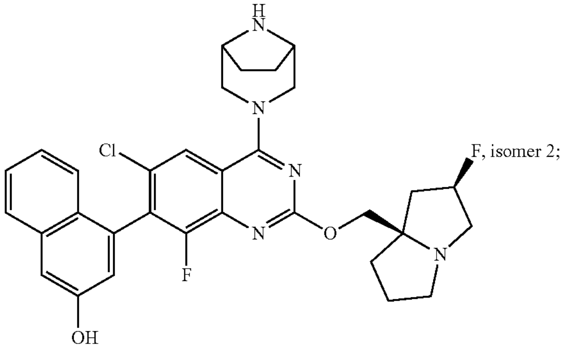
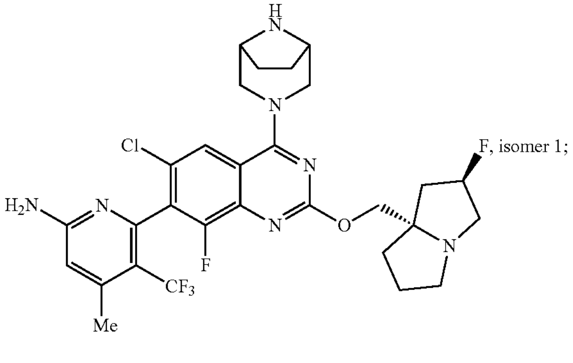

-continued
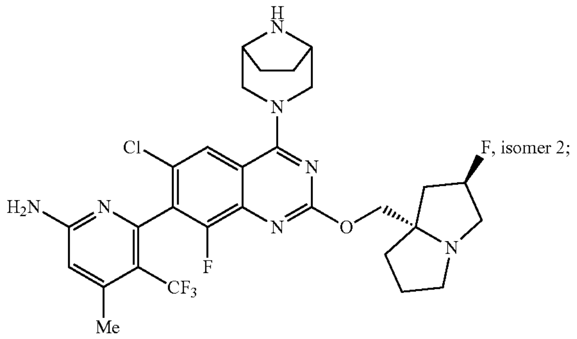
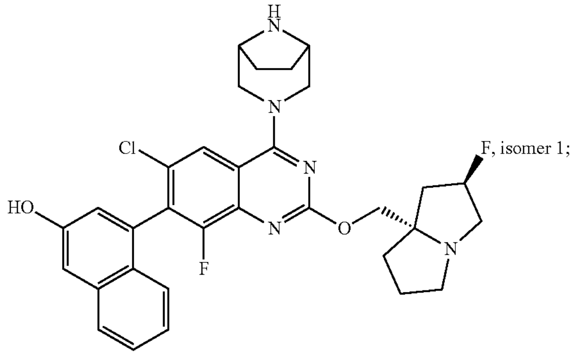
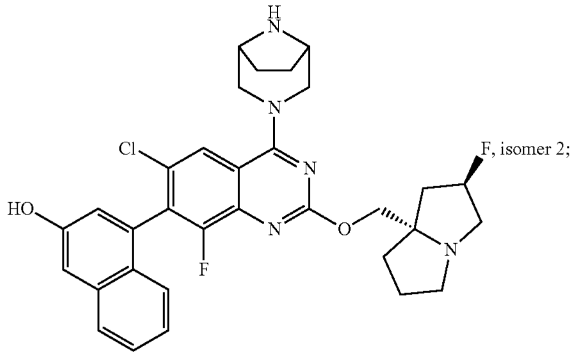
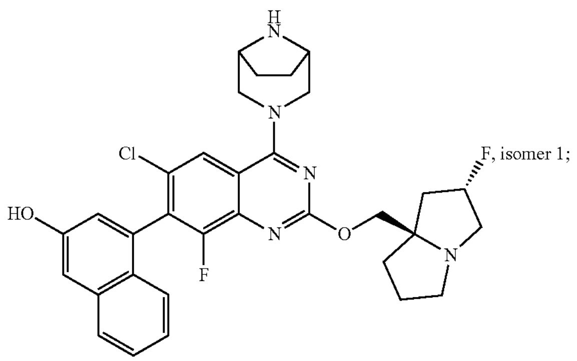
-continued
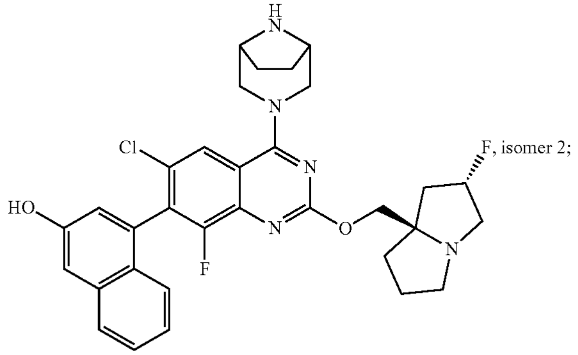
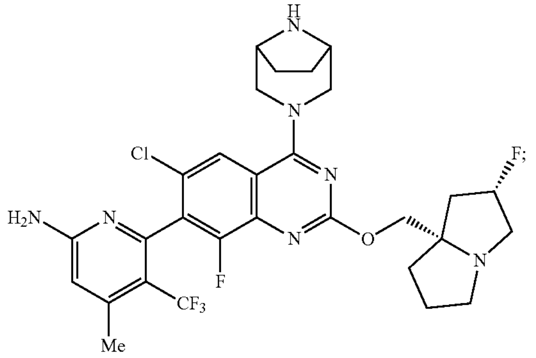
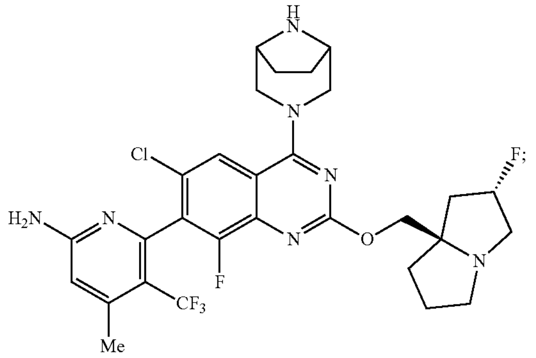
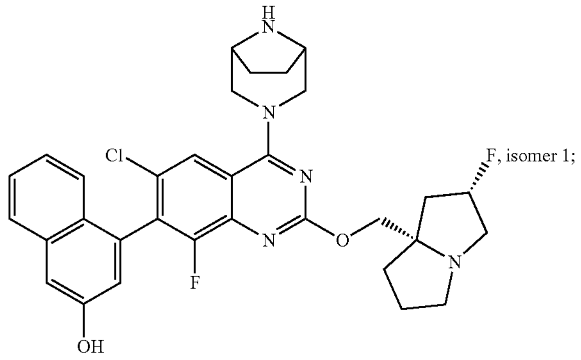

-continued
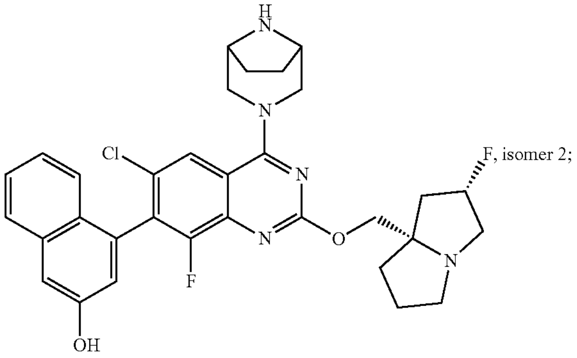
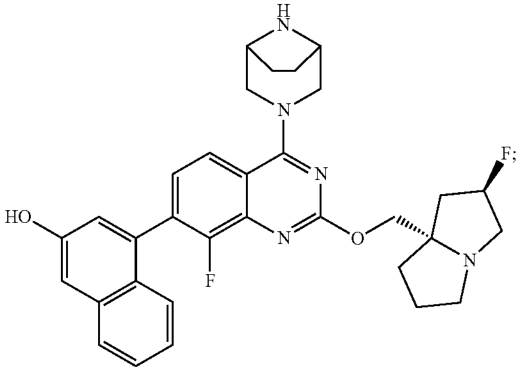
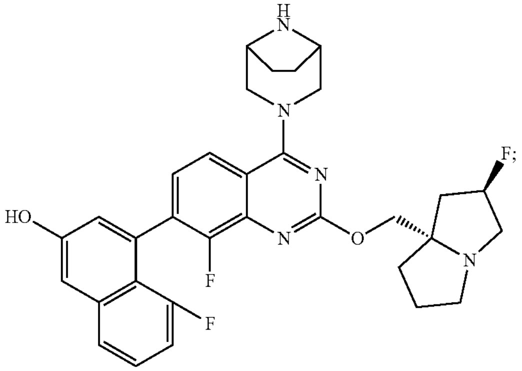
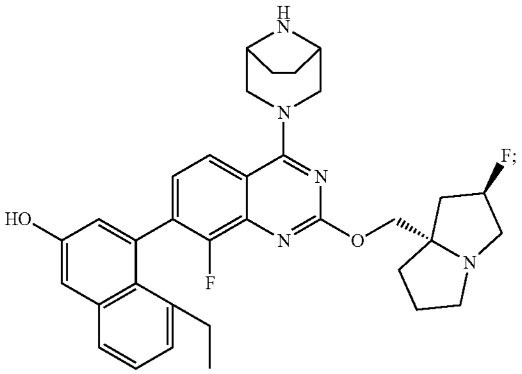
-continued
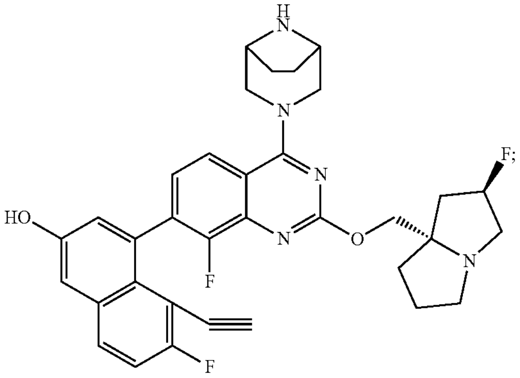
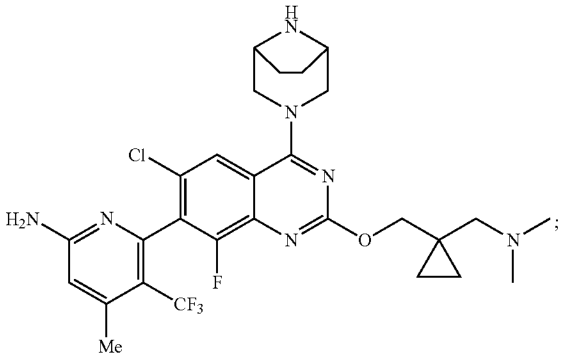
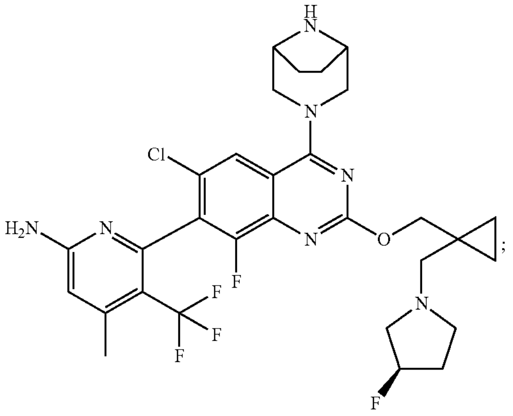
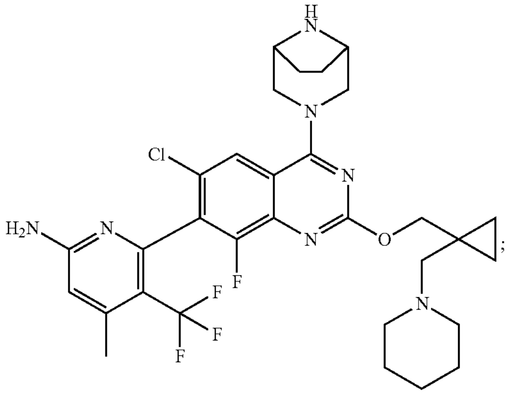

-continued
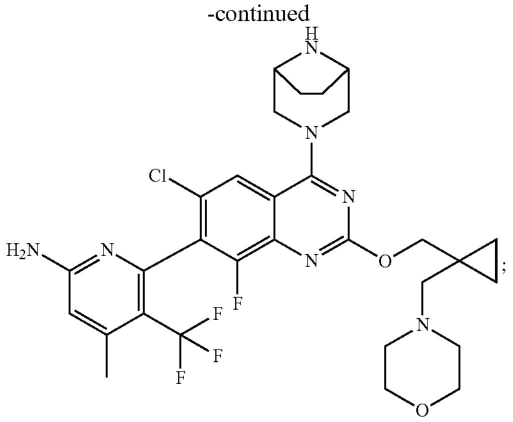
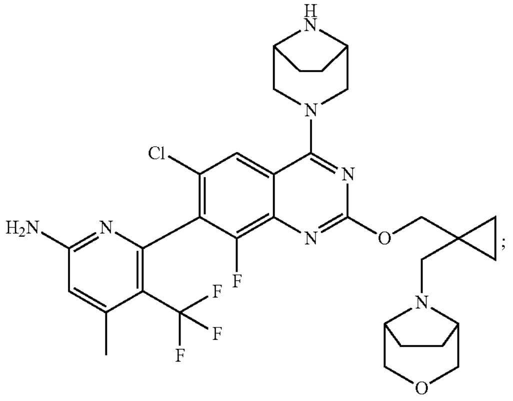
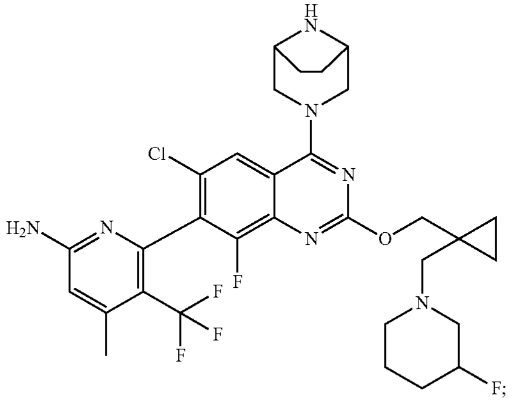
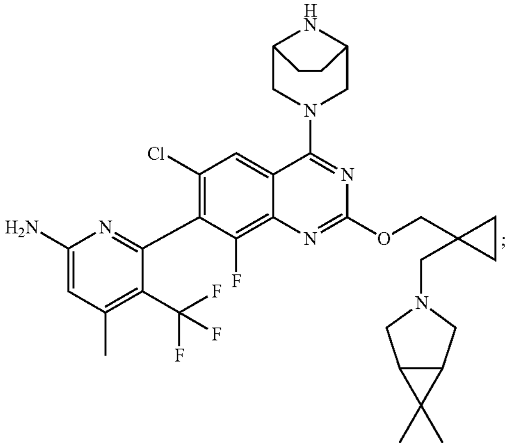
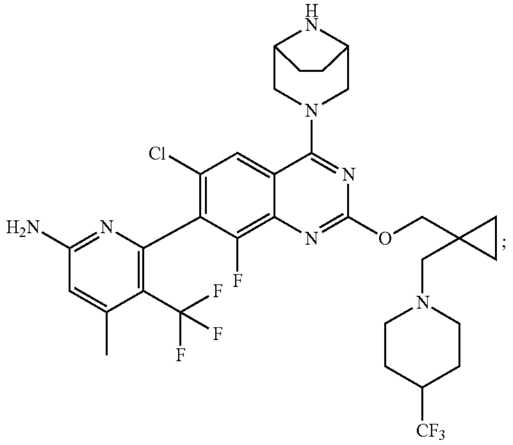
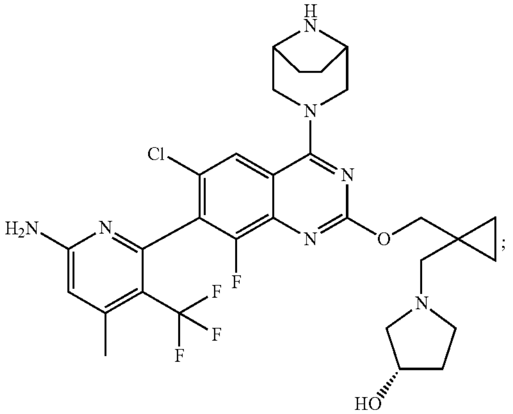
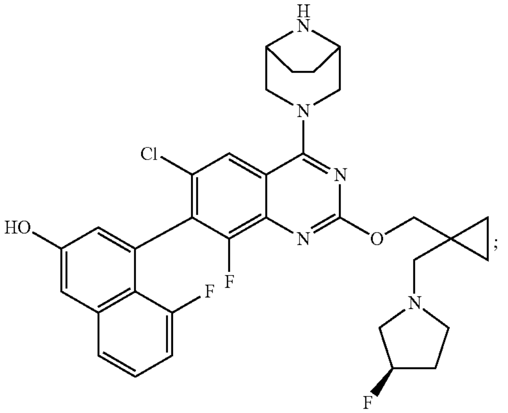
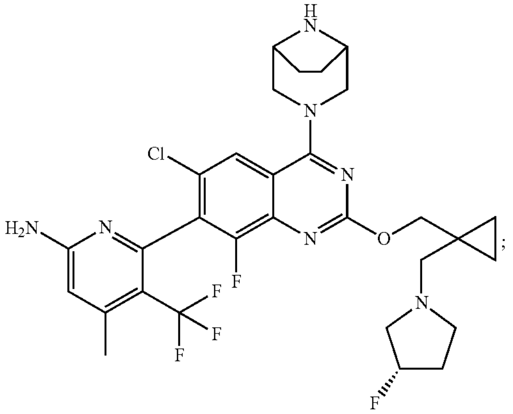

-continued
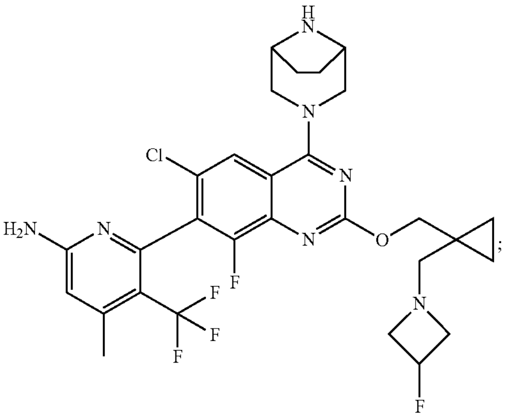
;
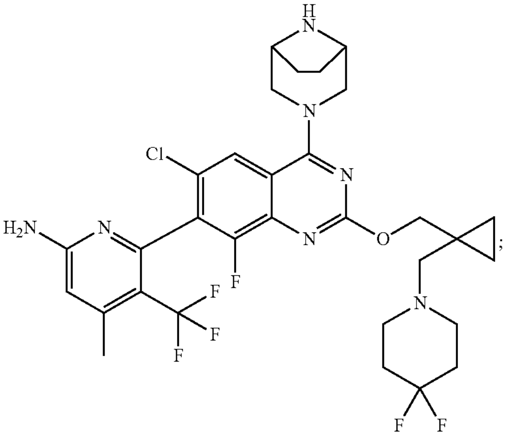
;
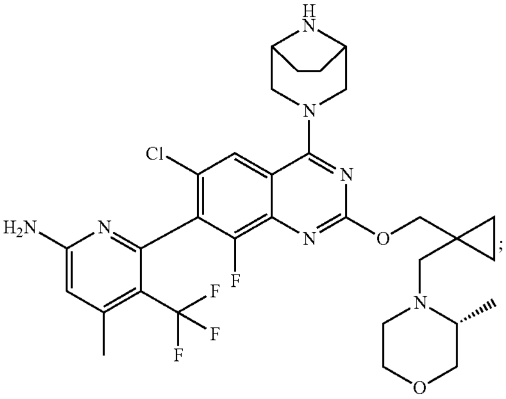
;
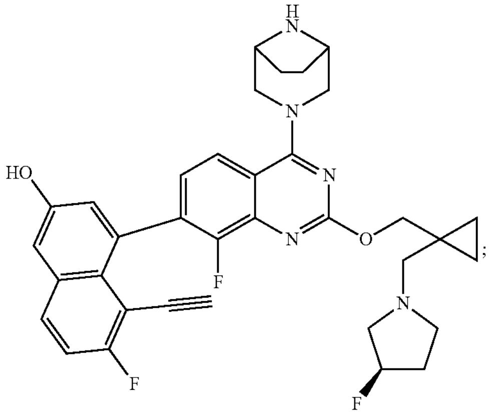
;
-continued
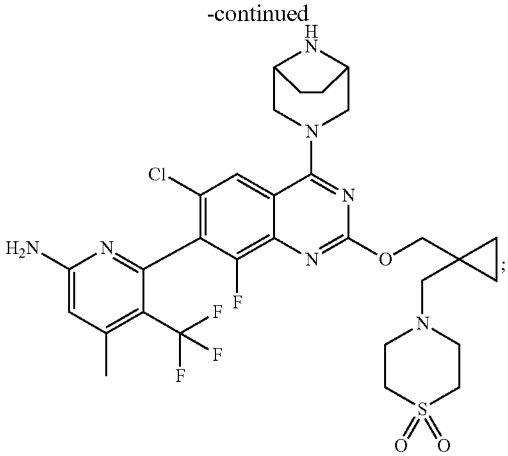
;
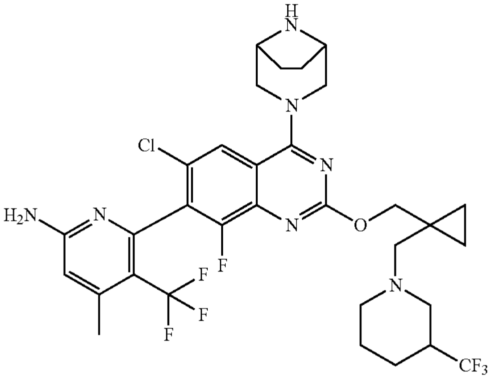
isomer 1;
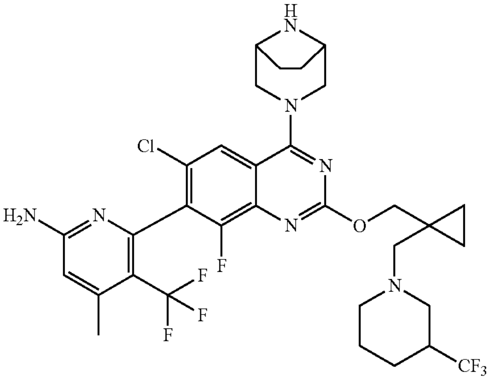
isomer 2;
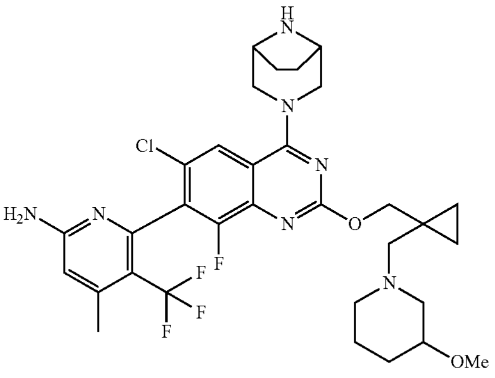
isomer 1;

-continued
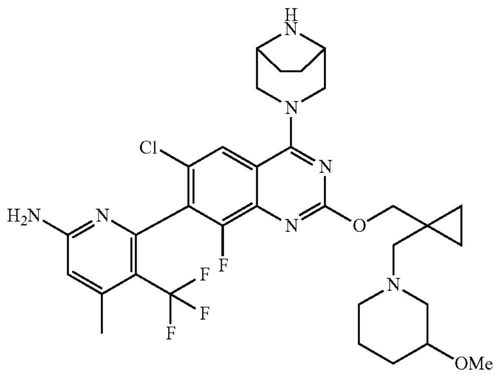
isomer 2;
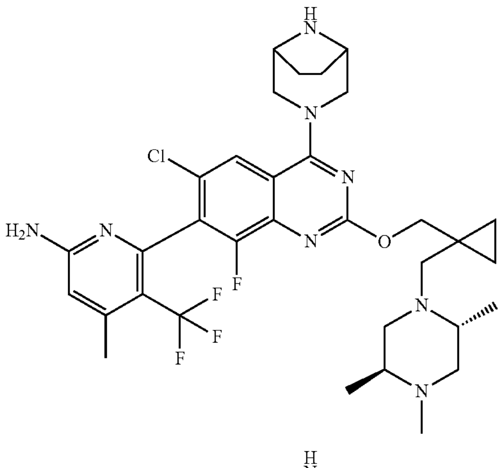
;
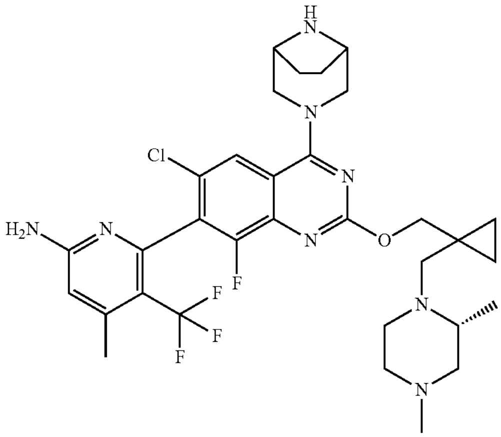
;
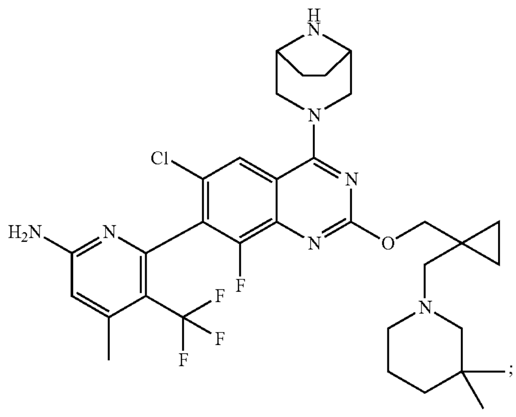
;
-continued
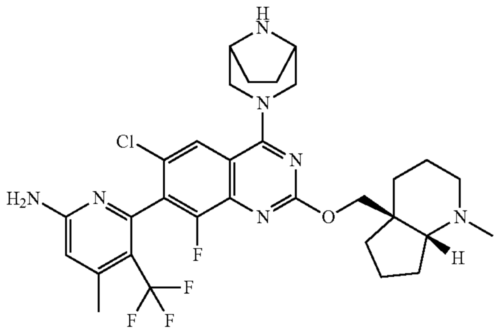
isomer 1;
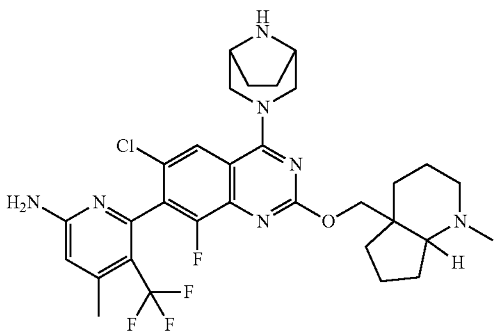
isomer 2;
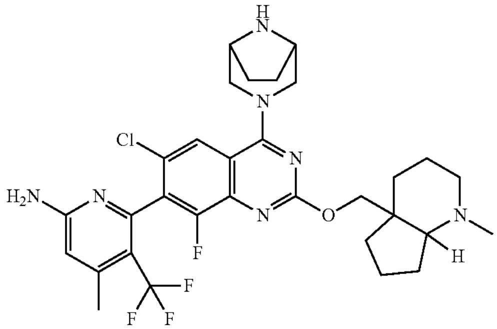
isomer 3;
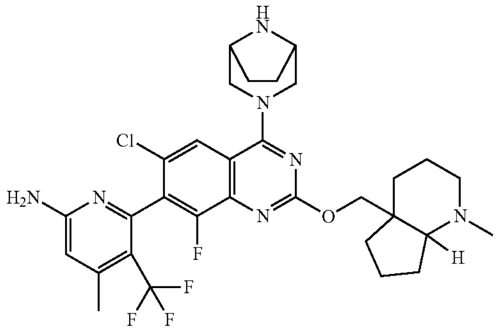
isomer 4;
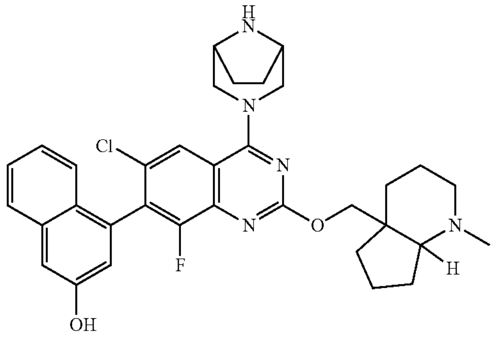
isomer 1;

-continued
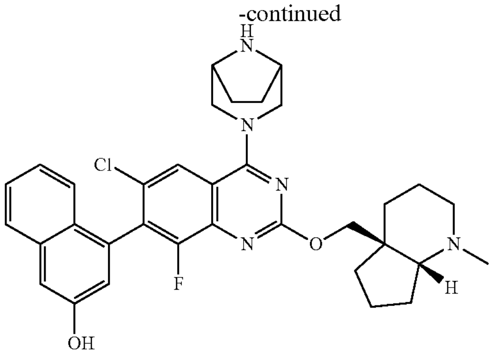
isomer 2;
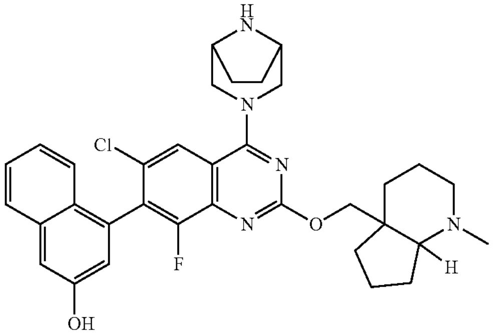
isomer 3;
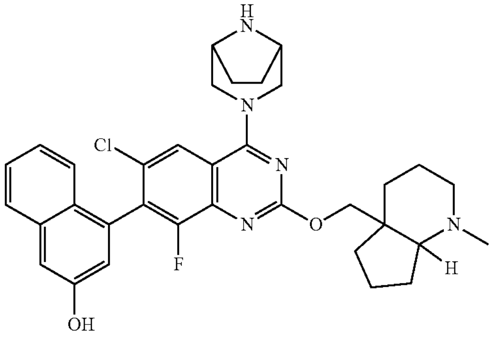
isomer 4;
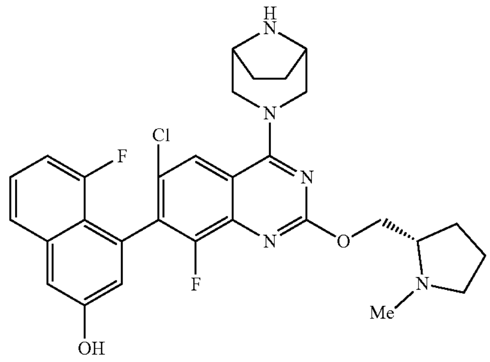
isomer 1;
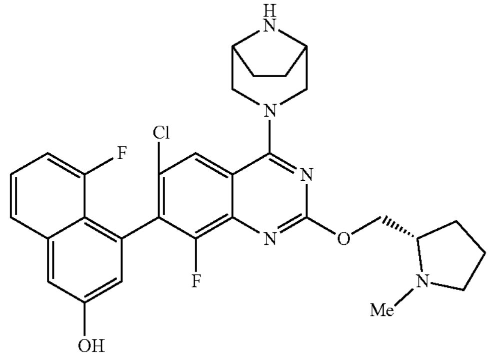
isomer 2;
-continued
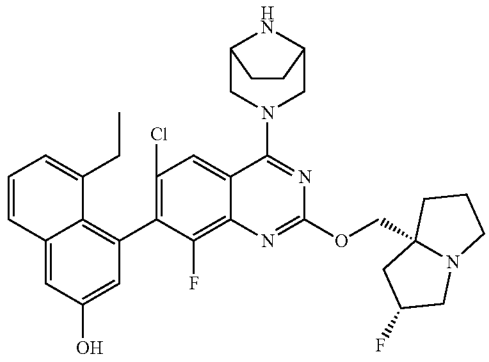
isomer 1;
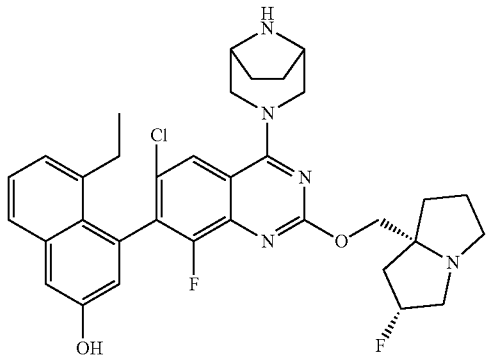
isomer 2;
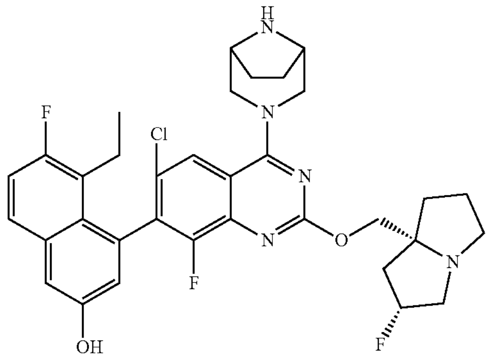
isomer 1;
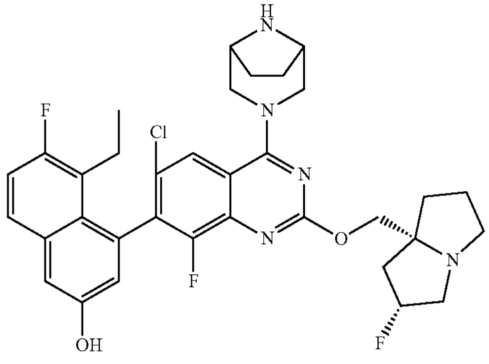
isomer 2;

-continued
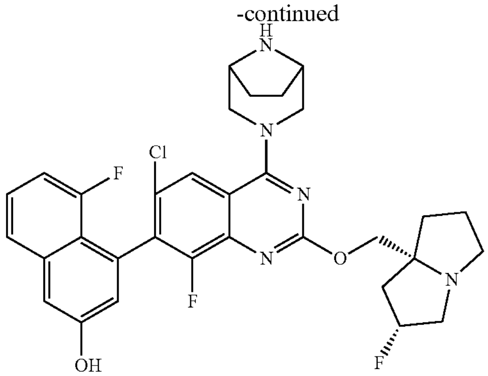
isomer 1;
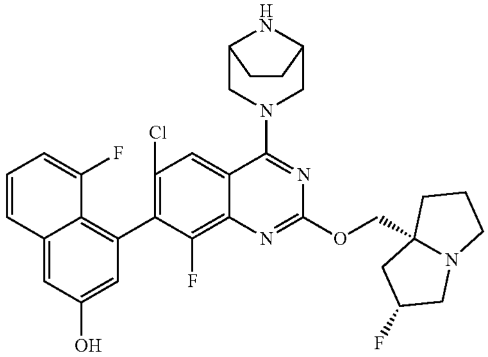
isomer 2;
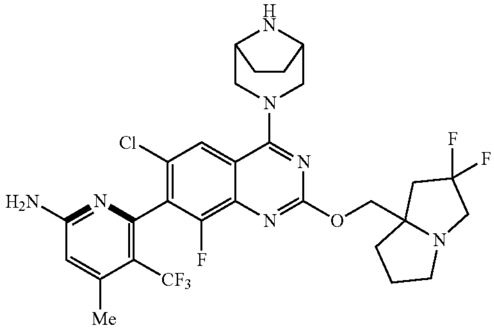
isomer 1;
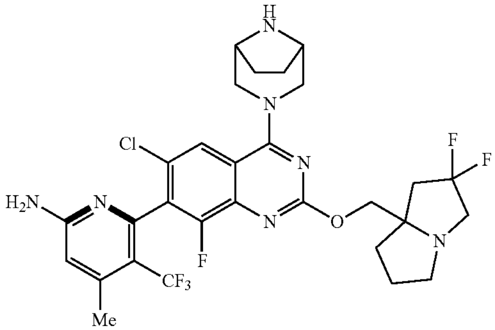
isomer 2;
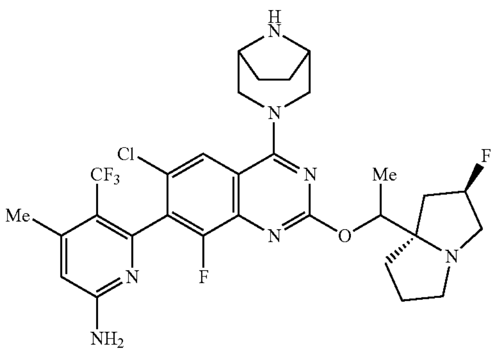
isomer 1;
-continued
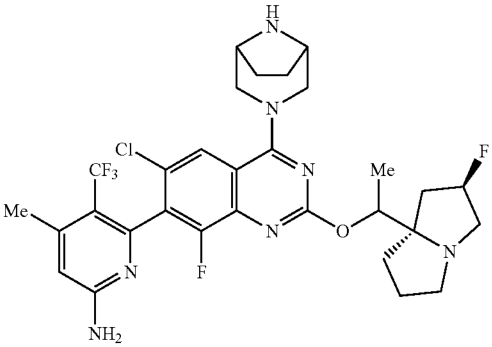
isomer 2;
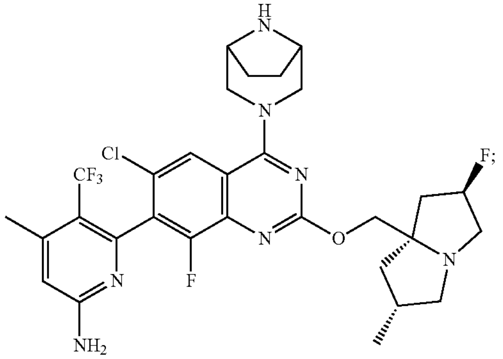
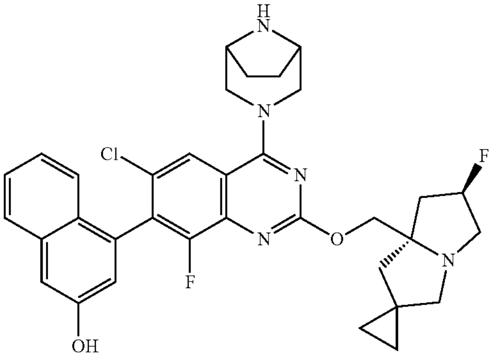
isomer 1;
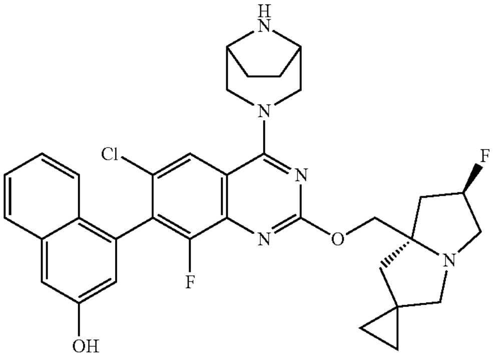
isomer 2;

-continued
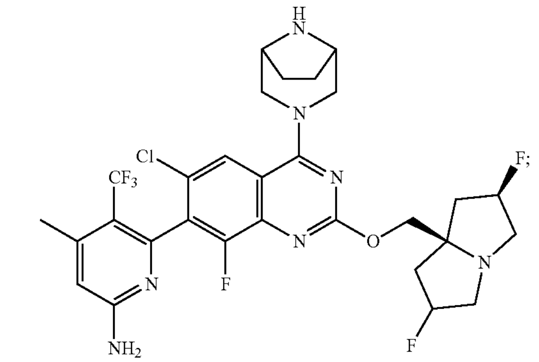
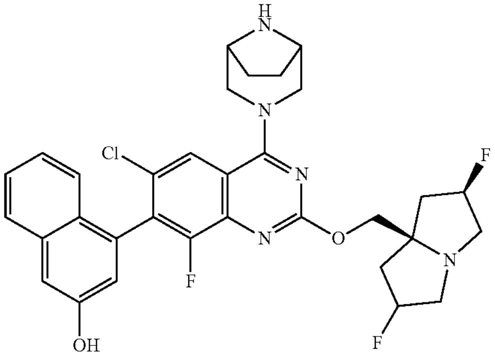
isomer 1;
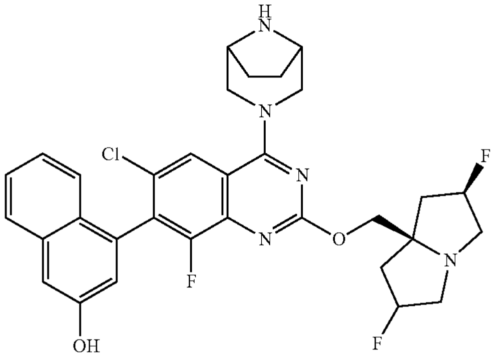
isomer 2;
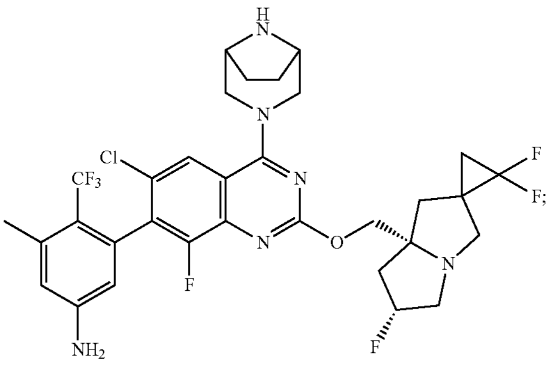
-continued
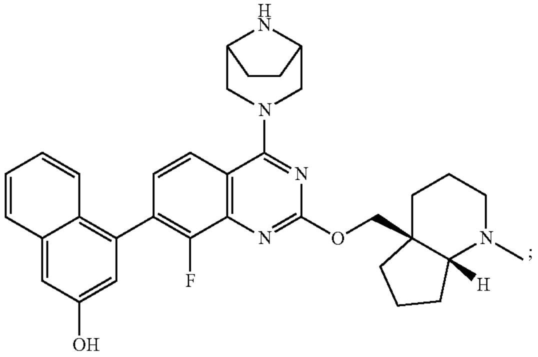
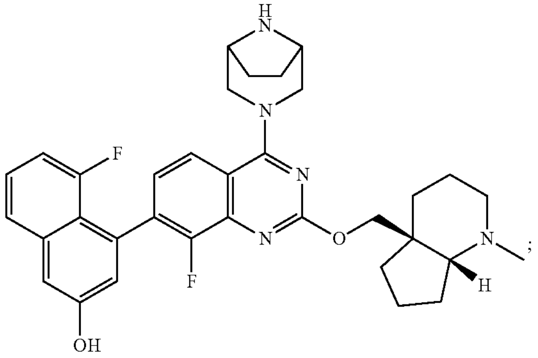
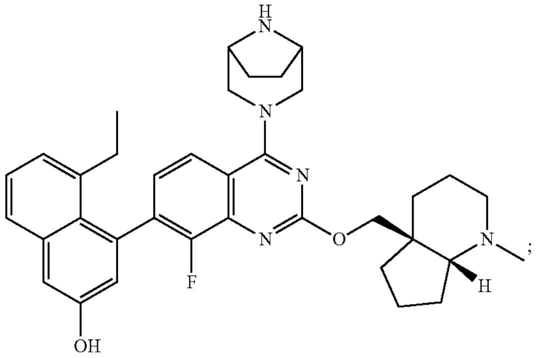
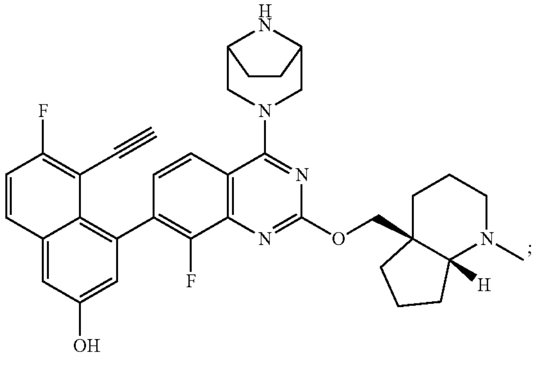

-continued
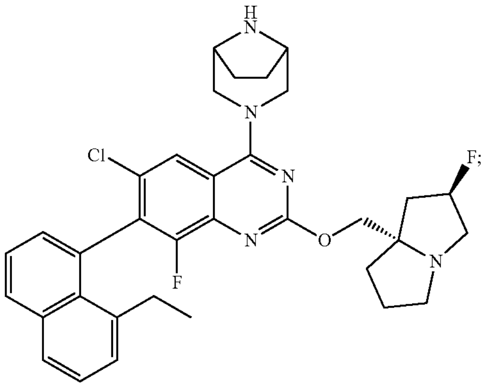
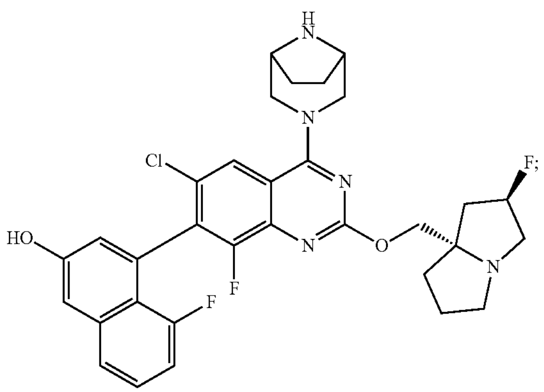
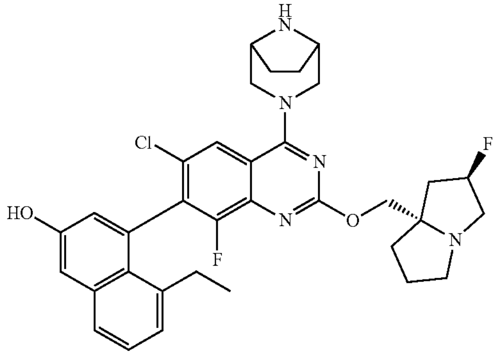
isomer 1;
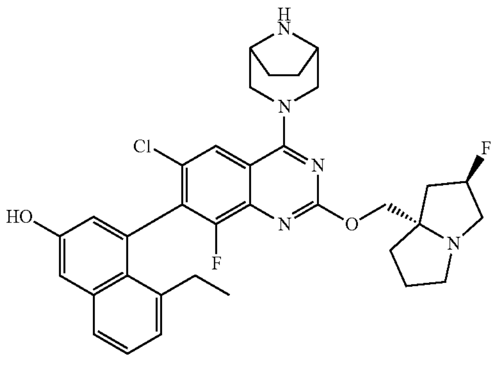
isomer 2;
-continued
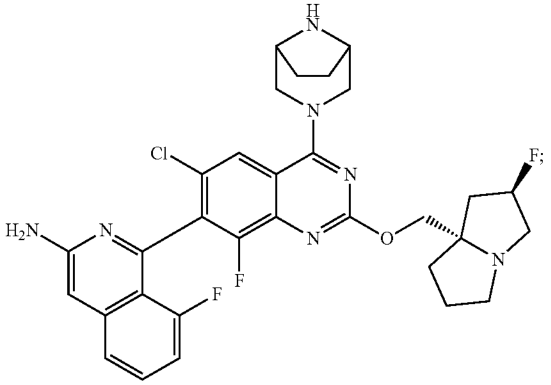
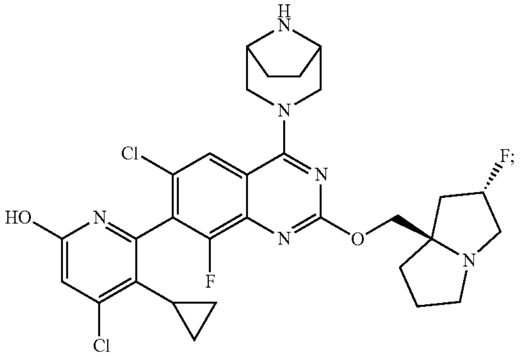
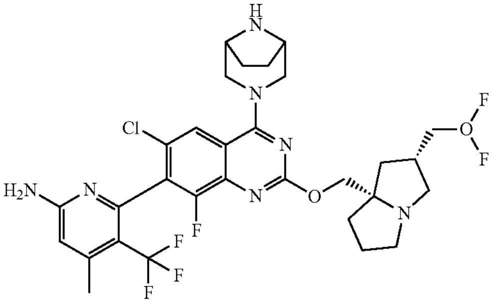
isomer 1;
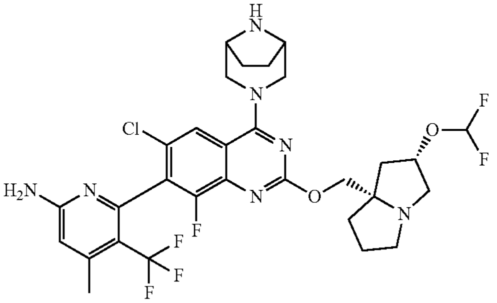
isomer 2;
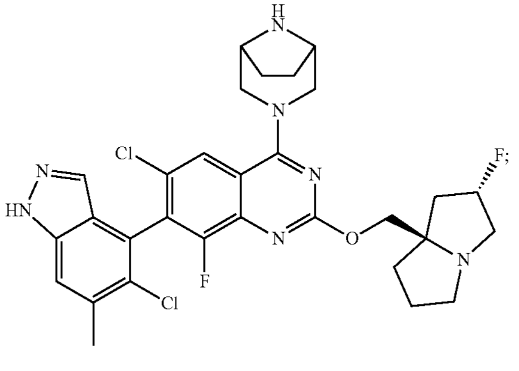

-continued

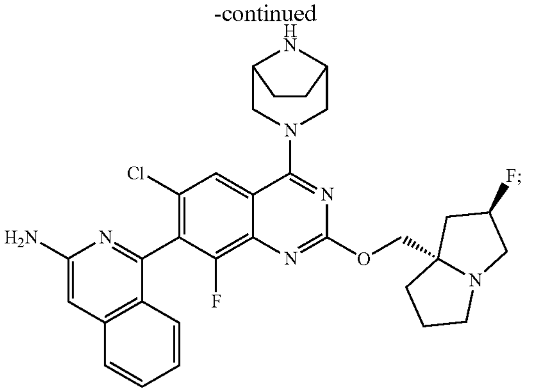

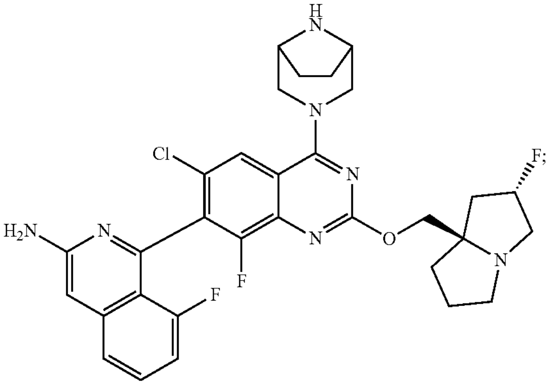

and

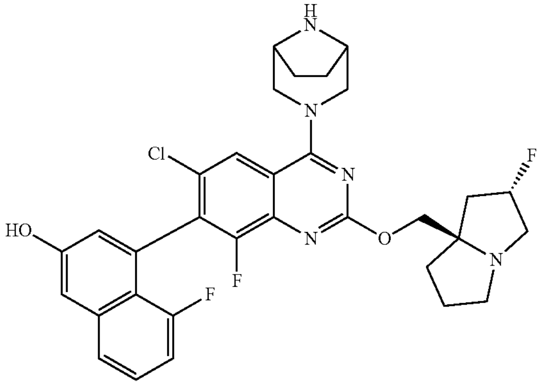

or a pharmaceutically acceptable salt thereof.

In some aspects, the present disclosure provides a compound selected from:

6-(6-chloro-4-{3,8-diazabicyclo[3.2.1]octan-3-yl}-8-fluoro-2-{[(2S)-1-methylpyrrolidin-2-yl]methoxy}quinazolin-7-yl)-4-methyl-5-(trifluoromethyl)pyridin-2-amine;

6-(6-chloro-4-{3,8-diazabicyclo[3.2.1]octan-3-yl}-8-fluoro-2-{[(2S)-1-methylpyrrolidin-2-yl]methoxy}quinazolin-7-yl)-4-methyl-5-(trifluoromethyl)pyridin-2-amine, Isomer 1;

6-(6-chloro-4-{3,8-diazabicyclo[3.2.1]octan-3-yl}-8-fluoro-2-{[(2S)-1-methylpyrrolidin-2-yl]methoxy}quinazolin-7-yl)-4-methyl-5-(trifluoromethyl)pyridin-2-amine, Isomer 2;

6-(6-chloro-4-{3,6-diazabicyclo[3.1.1]heptan-6-yl}-8-fluoro-2-{[(2S)-1-methylpyrrolidin-2-yl]methoxy}quinazolin-7-yl)-4-methyl-5-(trifluoromethyl)pyridin-2-amine;

6-(6-chloro-4-{3,8-diazabicyclo[3.2.1]octan-8-yl}-8-fluoro-2-{[(2S)-1-methylpyrrolidin-2-yl]methoxy}quinazolin-7-yl)-4-methyl-5-(trifluoromethyl)pyridin-2-amine;

6-(6-chloro-4-{3,9-diazabicyclo[3.3.1]nonan-3-yl}-8-fluoro-2-{[(2S)-1-methylpyrrolidin-2-yl]methoxy}quinazolin-7-yl)-4-methyl-5-(trifluoromethyl)pyridin-2-amine;

6-(6-chloro-4-{3,6-diazabicyclo[3.1.1]heptan-3-yl}-8-fluoro-2-{[(2S)-1-methylpyrrolidin-2-yl]methoxy}quinazolin-7-yl)-4-methyl-5-(trifluoromethyl)pyridin-2-amine;

6-(6-chloro-4-{2,5-diazabicyclo[2.2.1]heptan-2-yl}-8-fluoro-2-{[(2S)-1-methylpyrrolidin-2-yl]methoxy}quinazolin-7-yl)-4-methyl-5-(trifluoromethyl)pyridin-2-amine;

6-(6-chloro-4-{2,5-diazabicyclo[2.2.1]heptan-2-yl}-8-fluoro-2-{[(2S)-1-methylpyrrolidin-2-yl]methoxy}quinazolin-7-yl)-4-methyl-5-(trifluoromethyl)pyridin-2-amine (Isomer 1);

6-(6-chloro-4-{2,5-diazabicyclo[2.2.1]heptan-2-yl}-8-fluoro-2-{[(2S)-1-methylpyrrolidin-2-yl]methoxy}quinazolin-7-yl)-4-methyl-5-(trifluoromethyl)pyridin-2-amine (Isomer 2);

6-(6-chloro-4-{2,5-diazabicyclo[2.2.2]octan-2-yl}-8-fluoro-2-{[(2S)-1-methylpyrrolidin-2-yl]methoxy}quinazolin-7-yl)-4-methyl-5-(trifluoromethyl)pyridin-2-amine;

6-(6-chloro-4-{3,9-diazabicyclo[3.3.1]nonan-9-yl}-8-fluoro-2-{[(2S)-1-methylpyrrolidin-2-yl]methoxy}quinazolin-7-yl)-4-methyl-5-(trifluoromethyl)pyridin-2-amine;

6-(6-chloro-4-{2,5-diazabicyclo[2.2.1]heptan-2-yl}-8-fluoro-2-{[(2S)-1-methylpyrrolidin-2-yl]methoxy}quinazolin-7-yl)-4-methyl-5-(trifluoromethyl)pyridin-2-amine;

6-(6-chloro-8-fluoro-4-{8-methyl-3,8-diazabicyclo[3.2.1]octan-3-yl}-2-{[(2S)-1-methylpyrrolidin-2-yl]methoxy}quinazolin-7-yl)-4-methyl-5-(trifluoromethyl)pyridin-2-amine;

4-(6-chloro-4-{3,8-diazabicyclo[3.2.1]octan-3-yl}-8-fluoro-2-{[(2R)-1-(piperidin-1-yl)propan-2-yl]oxy}quinazolin-7-yl)naphthalen-2-ol;

1-[(2R)-2-[(6-chloro-4-{3,8-diazabicyclo[3.2.1]octan-3-yl}-8-fluoro-7-(3-hydroxynaphthalen-1-yl)quinazolin-2-yl)oxy]propyl]piperidin-4-ol;

4-(6-chloro-4-{3,8-diazabicyclo[3.2.1]octan-3-yl}-8-fluoro-2-{[(2S)-1-methylpyrrolidin-2-yl]methoxy}quinazolin-7-yl)naphthalen-2-ol;

4-{6-chloro-4-[(1R,4R)-2,5-diazabicyclo[2.2.1]heptan-2-yl]-8-fluoro-2-{[(2S)-1-methylpyrrolidin-2-yl]methoxy}quinazolin-7-yl}naphthalen-2-ol;

4-(6-chloro-4-{3,6-diazabicyclo[3.1.1]heptan-3-yl}-8-fluoro-2-{[(2S)-1-methylpyrrolidin-2-yl]methoxy}quinazolin-7-yl)naphthalen-2-ol;

6-chloro-4-{3,8-diazabicyclo[3.2.1]octan-3-yl}-8-fluoro-7-(5-methyl-1H-indazol-4-yl)-2-{[(2S)-1-methylpyrrolidin-2-yl]methoxy}quinazoline;

6-chloro-4-{3,8-diazabicyclo[3.2.1]octan-3-yl}-8-fluoro-2-{[(2S)-1-methylpyrrolidin-2-yl]methoxy}-7-phenylquinazoline;

6-chloro-4-{3,8-diazabicyclo[3.2.1]octan-3-yl}-8-fluoro-7-(2-fluorophenyl)-2-{[(2S)-1-methylpyrrolidin-2-yl]methoxy}quinazoline;

6-chloro-4-{3,8-diazabicyclo[3.2.1]octan-3-yl}-8-fluoro-7-(1H-indazol-4-yl)-2-{[(2S)-1-methylpyrrolidin-2-yl]methoxy}quinazoline;

8-(6-chloro-4-{3,8-diazabicyclo[3.2.1]octan-3-yl}-8-fluoro-2-{[(2S)-1-methylpyrrolidin-2-yl]methoxy}quinazolin-7-yl)naphthalen-2-ol;

-chloro-4-{3,8-diazabicyclo[3.2.1]octan-3-yl}-8-fluoro-7-(1-methyl-1H-indazol-7-yl)-2-{[(2S)-1-methylpyrrolidin-2-yl]methoxy}quinazoline;

6-chloro-7-(2-cyclopropylphenyl)-4-{3,8-diazabicyclo[3.2.1]octan-3-yl}-8-fluoro-2-{[(2S)-1-methylpyrrolidin-2-yl]methoxy}quinazoline;

6-chloro-4-{3,8-diazabicyclo[3.2.1]octan-3-yl}-8-fluoro-7-(2-fluoro-6-methylphenyl)-2-{[(2S)-1-methylpyrrolidin-2-yl]methoxy}quinazoline;

6-chloro-4-{3,8-diazabicyclo[3.2.1]octan-3-yl}-8-fluoro-7-(3-fluoro-2-methylphenyl)-2-{[(2S)-1-methylpyrrolidin-2-yl]methoxy}quinazoline;

4-((1R,5S)-6-chloro-4-{3,8-diazabicyclo[3.2.1]octan-3-yl}-8-fluoro-2-{[(2S)-1-methylpyrrolidin-2-yl]methoxy}-7-[2-(propan-2-yl)phenyl]quinazoline;

6-chloro-4-{3,8-diazabicyclo[3.2.1]octan-3-yl}-8-fluoro-7-[3-fluoro-2-(trifluoromethyl)phenyl]-2-{[(2S)-1-methylpyrrolidin-2-yl]methoxy}quinazoline;

6-chloro-4-{3,8-diazabicyclo[3.2.1]octan-3-yl}-8-fluoro-2-{[(2S)-1-methylpyrrolidin-2-yl]methoxy}-7-(naphthalen-1-yl)quinazoline;

6-chloro-4-{3,8-diazabicyclo[3.2.1]octan-3-yl}-8-fluoro-7-(2-methylnaphthalen-1-yl)-2-{[(2S)-1-methylpyrrolidin-2-yl]methoxy}quinazoline;

6-chloro-4-{3,8-diazabicyclo[3.2.1]octan-3-yl}-8-fluoro-2-{[(2S)-1-methylpyrrolidin-2-yl]methoxy}-7-[2-(trifluoromethyl)phenyl]quinazoline;

4-(6-chloro-4-{3,6-diazabicyclo[3.1.1]heptan-6-yl}-8-fluoro-2-{[(2S)-1-methylpyrrolidin-2-yl]methoxy}quinazolin-7-yl)naphthalen-2-ol;

4-(6-chloro-4-{3,8-diazabicyclo[3.2.1]octan-8-yl}-8-fluoro-2-{[(2S)-1-methylpyrrolidin-2-yl]methoxy}quinazolin-7-yl)naphthalen-2-ol;

4-(6-chloro-4-{3,9-diazabicyclo[3.3.1]nonan-9-yl}-8-fluoro-2-{[(2S)-1-methylpyrrolidin-2-yl]methoxy}quinazolin-7-yl)naphthalen-2-ol;

4-(6-chloro-8-fluoro-4-{8-methyl-3,8-diazabicyclo[3.2.1]octan-3-yl}-2-{[(2S)-1-methylpyrrolidin-2-yl]methoxy}quinazolin-7-yl)naphthalen-2-ol;

4-(6-chloro-4-{2,5-diazabicyclo[2.2.1]heptan-2-yl}-8-fluoro-2-{[(2S)-1-methylpyrrolidin-2-yl]methoxy}quinazolin-7-yl)naphthalen-2-ol;

(5S)-5-{[(6-chloro-4-{3,8-diazabicyclo[3.2.1]octan-3-yl}-8-fluoro-7-(3-hydroxynaphthalen-1-yl)quinazolin-2-yl)oxy]methyl}pyrrolidin-2-one;

4-(6-chloro-4-{3,8-diazabicyclo[3.2.1]octan-3-yl}-8-fluoro-2-{[(2R)-4-methylmorpholin-2-yl]methoxy}quinazolin-7-yl)naphthalen-2-ol;

4-(6-chloro-4-{3,8-diazabicyclo[3.2.1]octan-3-yl}-8-fluoro-2-[2-(1-methyl-1H-imidazol-2-yl)ethoxy]quinazolin-7-yl)naphthalen-2-ol;

4-(6-chloro-4-{3,8-diazabicyclo[3.2.1]octan-3-yl}-8-fluoro-2-[(1H-pyrazol-5-yl)methoxy]quinazolin-7-yl)naphthalen-2-ol;

(5R)-5-{[(6-chloro-4-{3,8-diazabicyclo[3.2.1]octan-3-yl}-8-fluoro-7-(3-hydroxynaphthalen-1-yl)quinazolin-2-yl)oxy]methyl}pyrrolidin-2-one;

4-(6-chloro-4-{3,8-diazabicyclo[3.2.1]octan-3-yl}-8-fluoro-2-{[(2S,4R)-4-methoxy-1-methylpyrrolidin-2-yl]methoxy}quinazolin-7-yl)naphthalen-2-ol;

N-{1-[(6-chloro-4-{3,8-diazabicyclo[3.2.1]octan-3-yl}-8-fluoro-7-(3-hydroxynaphthalen-1-yl)quinazolin-2-yl)oxy]-2-methylpropan-2-yl}acetamide;

4-{2-[(2-benzyl-1-methylpyrrolidin-2-yl)methoxy]-6-chloro-4-{3,8-diazabicyclo[3.2.1]octan-3-yl}-8-fluoroquinazolin-7-yl}naphthalen-2-ol;

4-(6-chloro-4-{3,8-diazabicyclo[3.2.1]octan-3-yl}-8-fluoro-2-{[2-(methoxymethyl)-1-methylpyrrolidin-2-yl]methoxy}quinazolin-7-yl)naphthalen-2-ol;

6-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine;

6-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine, Isomer 1;

6-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine, Isomer 2;

4-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol;

4-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol, Isomer 1;

4-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol, Isomer 2;

6-(2-{[(2R,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine;

6-(2-{[(2R,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine, Isomer 1;

6-(2-{[(2R,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine, Isomer 2;

4-(2-{[(2R,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol;

4-(2-{[(2R,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol, Isomer 1;

4-(2-{[(2R,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol, Isomer 2;

4-(2-{[(2S,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol;

4-(2-{[(2S,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol, Isomer 1;

4-(2-{[(2S,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol, Isomer 2;

6-(2-{[(2S,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine;

6-(2-{[(2S,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine;

4-(2-{[(2S,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol;

4-(2-{[(2S,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol, Isomer 1;

4-(2-{[(2S,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol, Isomer 2;

4-(2-{[(2R,7aS)-2-fluoro-hexahydro-1H-pyrrolizin-7a-yl]methoxy}-6-chloro-4-{3,8-; diazabicyclo[3.2.1]octan-3-yl}-8-fluoroquinazolin-7-yl)naphthalen-2-ol;

4-(2-{[(2R,7aS)-2-fluoro-hexahydro-1H-pyrrolizin-7a-yl]methoxy}-4-{3,8-diazabicyclo[3.2.1]octan-3-yl}-8-fluoroquinazolin-7-yl)-5-fluoronaphthalen-2-ol;

4-(2-{[(2R,7aS)-2-fluoro-hexahydro-1H-pyrrolizin-7a-yl]methoxy}-4-{3,8-diazabicyclo[3.2.1]octan-3-yl}-8-fluoroquinazolin-7-yl)-5-ethylnaphthalen-2-ol;

4-(2-{[(2R,7aS)-2-fluoro-hexahydro-1H-pyrrolizin-7a-yl]methoxy}-4-{3,8-diazabicyclo[3.2.1]octan-3-yl}-8-fluoroquinazolin-7-yl)-5-ethynyl-6-fluoronaphthalen-2-ol;

6-(6-chloro-4-{3,8-diazabicyclo[3.2.1]octan-3-yl}-2-({1-[(dimethylamino)methyl]cyclopropyl}methoxy)-8-fluoroquinazolin-7-yl)-4-methyl-5-(trifluoromethyl)pyridin-2-amine;

6-(6-chloro-4-{3,8-diazabicyclo[3.2.1]octan-3-yl}-8-fluoro-2-[(1-{[(3R)-3-fluoropyrrolidin-1-yl]methyl}cyclopropyl)methoxy]quinazolin-7-yl)-4-methyl-5-(trifluoromethyl)pyridin-2-amine;

6-(6-chloro-4-{3,8-diazabicyclo[3.2.1]octan-3-yl}-8-fluoro-2-({1-[(piperidin-1-yl)methyl]cyclopropyl}methoxy)quinazolin-7-yl)-4-methyl-5-(trifluoromethyl)pyridin-2-amine;

6-(6-chloro-4-{3,8-diazabicyclo[3.2.1]octan-3-yl}-8-fluoro-2-({1-[(morpholin-4-yl)methyl]cyclopropyl}methoxy)quinazolin-7-yl)-4-methyl-5-(trifluoromethyl)pyridin-2-amine;

6-(6-chloro-4-{3,8-diazabicyclo[3.2.1]octan-3-yl}-8-fluoro-2-({1-[(3-fluoropiperidin-1-yl)methyl]cyclopropyl}methoxy)quinazolin-7-yl)-4-methyl-5-(trifluoromethyl)pyridin-2-amine;

6-(6-chloro-4-{3,8-diazabicyclo[3.2.1]octan-3-yl}-8-fluoro-2-[(1-{[4-(trifluoromethyl)piperidin-1-yl]methyl}cyclopropyl)methoxy]quinazolin-7-yl)-4-methyl-5-(trifluoromethyl)pyridin-2-amine;

4-(6-chloro-4-{3,8-diazabicyclo[3.2.1]octan-3-yl}-8-fluoro-2-[(1-{[(3R)-3-fluoropyrrolidin-1-yl]methyl}cyclopropyl)methoxy]quinazolin-7-yl)-5-fluoronaphthalen-2-ol;

6-(6-chloro-4-{3,8-diazabicyclo[3.2.1]octan-3-yl}-8-fluoro-2-{[1-({3-oxa-8-azabicyclo[3.2.1]octan-8-yl}methyl)cyclopropyl]methoxy}quinazolin-7-yl)-4-methyl-5-(trifluoromethyl)pyridin-2-amine;

6-(6-chloro-4-{3,8-diazabicyclo[3.2.1]octan-3-yl}-2-{[1-({6,6-dimethyl-3-azabicyclo[3.1.0]hexan-3-yl}methyl)cyclopropyl]methoxy}-8-fluoroquinazolin-7-yl)-4-methyl-5-(trifluoromethyl)pyridin-2-amine;

(3S)-1-({1-[({7-[6-amino-4-methyl-3-(trifluoromethyl)pyridin-2-yl]-6-chloro-4-{3,8-diazabicyclo[3.2.1]octan-3-yl}-8-fluoroquinazolin-2-yl}oxy)methyl]cyclopropyl}methyl)pyrrolidin-3-ol;

6-(6-chloro-4-{3,8-diazabicyclo[3.2.1]octan-3-yl}-8-fluoro-2-[(1-{[(3S)-3-fluoropyrrolidin-1-yl]methyl}cyclopropyl)methoxy]quinazolin-7-yl)-4-methyl-5-(trifluoromethyl)pyridin-2-amine;

6-(6-chloro-4-{3,8-diazabicyclo[3.2.1]octan-3-yl}-8-fluoro-2-({1-[(3-fluoroazetidin-1-yl)methyl]cyclopropyl}methoxy)quinazolin-7-yl)-4-methyl-5-(trifluoromethyl)pyridin-2-amine;

6-(6-chloro-4-{3,8-diazabicyclo[3.2.1]octan-3-yl}-2-({1-[(4,4-difluoropiperidin-1-yl)methyl]cyclopropyl}methoxy)-8-fluoroquinazolin-7-yl)-4-methyl-5-(trifluoromethyl)pyridin-2-amine;

6-(6-chloro-4-{3,8-diazabicyclo[3.2.1]octan-3-yl}-8-fluoro-2-[(1-{[(3R)-3-methylmorpholin-4-yl]methyl}cyclopropyl)methoxy]quinazolin-7-yl)-4-methyl-5-(trifluoromethyl)pyridin-2-amine;

4-(4-{3,8-diazabicyclo[3.2.1]octan-3-yl}-8-fluoro-2-[(1-{[(3R)-3-fluoropyrrolidin-1-yl]methyl}cyclopropyl)methoxy]quinazolin-7-yl)-5-ethynyl-6-fluoronaphthalen-2-ol;

4-({1-[({7-[6-amino-4-methyl-3-(trifluoromethyl)pyridin-2-yl]-6-chloro-4-{3,8-diazabicyclo[3.2.1]octan-3-yl}-8-fluoroquinazolin-2-yl}oxy)methyl]cyclopropyl}methyl)-1lambda6-thiomorpholine-1,1-dione;

6-(6-chloro-4-{3,8-diazabicyclo[3.2.1]octan-3-yl}-8-fluoro-2-[(1-{[3-(trifluoromethyl)piperidin-1-yl]methyl}cyclopropyl)methoxy]quinazolin-7-yl)-4-methyl-5-(trifluoromethyl)pyridin-2-amine;

6-(6-chloro-4-{3,8-diazabicyclo[3.2.1]octan-3-yl}-8-fluoro-2-[(1-{[3-(trifluoromethyl)piperidin-1-yl]methyl}cyclopropyl)methoxy]quinazolin-7-yl)-4-methyl-5-(trifluoromethyl)pyridin-2-amine;

6-(6-chloro-4-{3,8-diazabicyclo[3.2.1]octan-3-yl}-8-fluoro-2-({1-[(3-methoxypiperidin-1-yl)methyl]cyclopropyl}methoxy)quinazolin-7-yl)-4-methyl-5-(trifluoromethyl)pyridin-2-amine;

6-(6-chloro-4-{3,8-diazabicyclo[3.2.1]octan-3-yl}-8-fluoro-2-({1-[(3-methoxypiperidin-1-yl)methyl]cyclopropyl}methoxy)quinazolin-7-yl)-4-methyl-5-(trifluoromethyl)pyridin-2-amine;

6-(6-chloro-4-{3,8-diazabicyclo[3.2.1]octan-3-yl}-8-fluoro-2-[(1-{[(2R,5S)-2,4,5-trimethylpiperazin-1-yl]methyl}cyclopropyl)methoxy]quinazolin-7-yl)-4-methyl-5-(trifluoromethyl)pyridin-2-amine;

6-(6-chloro-4-{3,8-diazabicyclo[3.2.1]octan-3-yl}-2-[(1-{[(2R)-2,4-dimethylpiperazin-1-yl]methyl}cyclopropyl)methoxy]-8-fluoroquinazolin-7-yl)-4-methyl-5-(trifluoromethyl)pyridin-2-amine;

6-(6-chloro-4-{3,8-diazabicyclo[3.2.1]octan-3-yl}-2-({1-[(3,3-dimethylpiperidin-1-yl)methyl]cyclopropyl}methoxy)-8-fluoroquinazolin-7-yl)-4-methyl-5-(trifluoromethyl)pyridin-2-amine;

6-(2-{[(4aS,7aR)-1-methyl-octahydro-1H-cyclopenta[b]pyridin-4a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine;

6-(6-chloro-4-{3,8-diazabicyclo[3.2.1]octan-3-yl}-8-fluoro-2-({1-methyl-octahydro-1H-cyclopenta[b]pyridin-4a-yl}methoxy)quinazolin-7-yl)-4-methyl-5-(trifluoromethyl)pyridin-2-amine;

6-(6-chloro-4-{3,8-diazabicyclo[3.2.1]octan-3-yl}-8-fluoro-2-({1-methyl-octahydro-1H-cyclopenta[b]pyridin-4a-yl}methoxy)quinazolin-7-yl)-4-methyl-5-(trifluoromethyl)pyridin-2-amine, Isomer 1;

6-(6-chloro-4-{3,8-diazabicyclo[3.2.1]octan-3-yl}-8-fluoro-2-({1-methyl-octahydro-1H-cyclopenta[b]pyridin-4a-yl}methoxy)quinazolin-7-yl)-4-methyl-5-(trifluoromethyl)pyridin-2-amine, Isomer 2;

6-(6-chloro-4-{3,8-diazabicyclo[3.2.1]octan-3-yl}-8-fluoro-2-({1-methyl-octahydro-1H-cyclopenta[b]pyridin-4a-yl}methoxy)quinazolin-7-yl)-4-methyl-5-(trifluoromethyl)pyridin-2-amine, Isomer 3;

4-(6-chloro-4-{3,8-diazabicyclo[3.2.1]octan-3-yl}-8-fluoro-2-({1-methyl-octahydro-1H-cyclopenta[b]pyridin-4a-yl}methoxy)quinazolin-7-yl)naphthalen-2-ol;

4-(6-chloro-4-{3,8-diazabicyclo[3.2.1]octan-3-yl}-8-fluoro-2-({1-methyl-octahydro-1H-cyclopenta[b]pyridin-4a-yl}methoxy)quinazolin-7-yl)naphthalen-2-ol, Isomer 1;

4-(6-chloro-4-{3,8-diazabicyclo[3.2.1]octan-3-yl}-8-fluoro-2-({1-methyl-octahydro-1H-cyclopenta[b]pyridin-4a-yl}methoxy)quinazolin-7-yl)naphthalen-2-ol, Isomer 2;

4-(6-chloro-4-{3,8-diazabicyclo[3.2.1]octan-3-yl}-8-fluoro-2-({1-methyl-octahydro-1H-cyclopenta[b]pyridin-4a-yl}methoxy)quinazolin-7-yl)naphthalen-2-ol, Isomer 3;

4-(2-{[(4aS,7aR)-1-methyl-octahydro-1H-cyclopenta[b]pyridin-4a-yl]methoxy}-6-chloro-4-{3,8-diazabicyclo[3.2.1]octan-3-yl}-8-fluoroquinazolin-7-yl)naphthalen-2-ol;

4-(6-chloro-4-{3,8-diazabicyclo[3.2.1]octan-3-yl}-8-fluoro-2-{[(2S)-1-methylpyrrolidin-2-yl]methoxy}quinazolin-7-yl)-5-fluoronaphthalen-2-ol;

4-(6-chloro-4-{3,8-diazabicyclo[3.2.1]octan-3-yl}-8-fluoro-2-{[(2S)-1-methylpyrrolidin-2-yl]methoxy}quinazolin-7-yl)-5-fluoronaphthalen-2-ol, Isomer 2;

4-(6-chloro-4-{3,8-diazabicyclo[3.2.1]octan-3-yl}-8-fluoro-2-{[(2S)-1-methylpyrrolidin-2-yl]methoxy}quinazolin-7-yl)-5-fluoronaphthalen-2-ol, Isomer 2;

4-(6-chloro-4-{3,8-diazabicyclo[3.2.1]octan-3-yl}-8-fluoro-2-{[(2S)-1-methylpyrrolidin-2-yl]methoxy}quinazolin-7-yl)-5-fluoronaphthalen-2-ol;

4-(6-chloro-4-{3,8-diazabicyclo[3.2.1]octan-3-yl}-8-fluoro-2-{[(2S)-1-methylpyrrolidin-2-yl]methoxy}quinazolin-7-yl)-5-fluoronaphthalen-2-ol, Isomer 1;

4-(6-chloro-4-{3,8-diazabicyclo[3.2.1]octan-3-yl}-8-fluoro-2-{[(2S)-1-methylpyrrolidin-2-yl]methoxy}quinazolin-7-yl)-5-fluoronaphthalen-2-ol, Isomer 2;

4-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-ethylnaphthalen-2-ol;

4-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-ethylnaphthalen-2-ol, Isomer 1;

4-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-ethylnaphthalen-2-ol, Isomer 2;

4-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-ethyl-6-fluoronaphthalen-2-ol;

4-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-ethyl-6-fluoronaphthalen-2-ol, Isomer 1;

4-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-ethyl-6-fluoronaphthalen-2-ol, Isomer 2;

4-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-fluoronaphthalen-2-ol;

4-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-fluoronaphthalen-2-ol, Isomer 1;

4-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-fluoronaphthalen-2-ol, Isomer 2;

6-(2-{[(7aR)-2,2-difluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine;

6-(2-{[(7aR)-2,2-difluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine, Isomer 1;

6-(2-{[(7aR)-2,2-difluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine, Isomer 2;

6-{2-[(1S)-1-[(2R,7aR)-2-fluoro-hexahydro-1H-pyrrolizin-7a-yl]ethoxy]-6-chloro-4-{3,8-diazabicyclo[3.2.1]octan-3-yl}-8-fluoroquinazolin-7-yl}-4-methyl-5-(trifluoromethyl)pyridin-2-amine;

6-{2-[(1S)-1-[(2R,7aR)-2-fluoro-hexahydro-1H-pyrrolizin-7a-yl]ethoxy]-6-chloro-4-{3,8-diazabicyclo[3.2.1]octan-3-yl}-8-fluoroquinazolin-7-yl}-4-methyl-5-(trifluoromethyl)pyridin-2-amine, Isomer 1;

6-{2-[(1S)-1-[(2R,7aR)-2-fluoro-hexahydro-1H-pyrrolizin-7a-yl]ethoxy]-6-chloro-4-{3,8-diazabicyclo[3.2.1]octan-3-yl}-8-fluoroquinazolin-7-yl}-4-methyl-5-(trifluoromethyl)pyridin-2-amine, Isomer 2;

6-(2-{[(2R,6R,7aR)-2-fluoro-6-methyl-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine;

4-(2-{[(6'R,7'aR)-6'-fluoro-hexahydrospiro[cyclopropane-1,2'-pyrrolizine]-7'a-yl]methoxy}-6-chloro-4-{3,8-diazabicyclo[3.2.1]octan-3-yl}-8-fluoroquinazolin-7-yl)naphthalen-2-ol;

4-(2-{[(6'R,7'aR)-6'-fluoro-hexahydrospiro[cyclopropane-1,2'-pyrrolizine]-7'a-yl]methoxy}-6-chloro-4-{3,8-diazabicyclo[3.2.1]octan-3-yl}-8-fluoroquinazolin-7-yl)naphthalen-2-ol, Isomer 1;

4-(2-{[(6'R,7'aR)-6'-fluoro-hexahydrospiro[cyclopropane-1,2'-pyrrolizine]-7'a-yl]methoxy}-6-chloro-4-{3,8-diazabicyclo[3.2.1]octan-3-yl}-8-fluoroquinazolin-7-yl)naphthalen-2-ol, Isomer 2;

6-(2-{[(2R,6S,7ar)-2,6-difluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine;

4-(2-{[(2R,6S,7ar)-2,6-difluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol;

4-(2-{[(2R,6S,7ar)-2,6-difluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol, Isomer 1;

4-(2-{[(2R,6S,7ar)-2,6-difluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol, Isomer 2;

6-(2-{[(6'R,7'aR)-3,3,6'-trifluoro-hexahydrospiro[cyclopropane-1,2'-pyrrolizine]-7'a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine;

4-(2-{[(4aS,7aR)-1-methyl-octahydro-1H-cyclopenta[b]pyridin-4a-yl]methoxy}-4-{3,8-diazabicyclo[3.2.1]octan-3-yl}-8-fluoroquinazolin-7-yl)naphthalen-2-ol;

4-(2-{[(4aS,7aR)-1-methyl-octahydro-1H-cyclopenta[b]pyridin-4a-yl]methoxy}-4-{3,8-diazabicyclo[3.2.1]octan-3-yl}-8-fluoroquinazolin-7-yl)-5-fluoronaphthalen-2-ol;

4-(2-{[(4aS,7aR)-1-methyl-octahydro-1H-cyclopenta[b]pyridin-4a-yl]methoxy}-4-{3,8-diazabicyclo[3.2.1]octan-3-yl}-8-fluoroquinazolin-7-yl)-5-ethylnaphthalen-2-ol;

4-(2-{[(4aS,7aR)-1-methyl-octahydro-1H-cyclopenta[b]pyridin-4a-yl]methoxy}-4-{3,8-diazabicyclo[3.2.1]octan-3-yl}-8-fluoroquinazolin-7-yl)-5-ethynyl-6-fluoronaphthalen-2-ol;

2-{[(2R,7aS)-2-fluoro-hexahydro-1H-pyrrolizin-7a-yl]methoxy}-6-chloro-4-{3,8-diazabicyclo[3.2.1]octan-3-yl}-7-(8-ethylnaphthalen-1-yl)-8-fluoroquinazoline;

4-(2-{[(2R,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-fluoronaphthalen-2-ol;

4-(2-{[(2R,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-ethylnaphthalen-2-ol, Isomer 1;

4-(2-{[(2R,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-ethylnaphthalen-2-ol, Isomer 2;

1-(2-{[(2R,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-8-fluoroisoquinoline-3-amine;

3-(2-{[(2S,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-chloro-4-cyclopropylphenol;

6-(2-{[(2S,7aS)-2-(difluoromethoxy)-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine, Isomer 1;

6-(2-{[(2S,7aS)-2-(difluoromethoxy)-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine, Isomer 2;

6-(2-{[(2S,7aR)-2-fluoro-hexahydro-1H-pyrrolizin-7a-yl]methoxy}-6-chloro-7-(5-chloro-6-methyl-1H-indazol-4-yl)-4-{3,8-diazabicyclo[3.2.1]octan-3-yl}-8-fluoroquinazoline;

1-(2-{[(2R,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)isoquinolin-3-amine;

1-(2-{[(2S,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-8-fluoroisoquinolin-3-amine; and 4-(2-{[(2S,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-fluoronaphthalen-2-ol;

or a pharmaceutically acceptable salt thereof.

In some aspects, the present disclosure provides a pharmaceutical composition comprising a compound as described in any of the above aspects, or a pharmaceutically acceptable salt thereof, and one or more pharmaceutically acceptable excipients.

In another aspect, the present disclosure provides a method for treating cancer in a subject, the method comprising administering a therapeutically effective amount of a compound or pharmaceutical composition of any of the above aspects, or a pharmaceutically acceptable salt thereof to a subject in need thereof.

In another aspect, the present disclosure provides a method for treating a cancer susceptible to KRAS G12D inhibition in a subject, the method comprising administering a therapeutically effective amount of a compound or pharmaceutical composition of any of the above aspects, or a pharmaceutically acceptable salt thereof to a subject in need thereof.

In another aspect, the present disclosure provides a method for treating a cancer expressing KRAS G12D inhibition in a subject, the method comprising administering a therapeutically effective amount of a compound or pharmaceutical composition of any of the above aspects, or a pharmaceutically acceptable salt thereof to a subject in need thereof.

DETAILED DESCRIPTION

Unless otherwise indicated, any atom with unsatisfied valences is assumed to have hydrogen atoms sufficient to satisfy the valences.

The singular forms "a," "an," and "the" include plural referents unless the context dictates otherwise.

As used herein, the term "or" is a logical disjunction (i.e., and/or) and does not indicate an exclusive disjunction unless expressly indicated such as with the terms "either," "unless," "alternatively," and words of similar effect.

As used herein, the phrase "or a pharmaceutically acceptable salt thereof" refers to at least one compound, or at least one salt of the compound, or a combination thereof. For example, "a compound of Formula (I) or a pharmaceutically acceptable salt thereof" includes, but is not limited to, a compound of Formula (I), two compounds of Formula (I), a pharmaceutically acceptable salt of a compound of Formula (I), a compound of Formula (I) and one or more pharmaceutically acceptable salts of the compound of Formula (I), and two or more pharmaceutically acceptable salts of a compound of Formula (I).

The term "$C_2$-$C_4$alkenyl," as used herein, refers to a group derived from a straight or branched chain hydrocarbon containing from two to four carbon atoms and one double bond.

The term "$C_1$-$C_3$alkoxy," as used herein, refers to a $C_1$-$C_3$alkyl group attached to the parent molecular moiety through an oxygen atom.

The term "$C_1$-$C_3$alkoxy$C_1$-$C_3$alkyl," as used herein, refers to a $C_1$-$C_3$alkoxy group attached to the parent molecular moiety through a $C_1$-$C_3$alkyl group.

The term "$C_1$-$C_3$alkoxycarbonyl," as used herein, refers to a $C_1$-$C_3$alkoxy group attached to the parent molecular moiety through a carbonyl group.

The term "$C_1$-$C_3$alkyl," as used herein, refers to a group derived from a straight or branched chain saturated hydrocarbon containing from one to three carbon atoms.

The term "$C_1$-$C_6$alkyl," as used herein, refers to a group derived from a straight or branched chain saturated hydrocarbon containing from one to three carbon atoms.

The term "$C_1$-$C_3$alkylcarbonyl," as used herein, refers to a $C_1$-$C_3$alkyl group attached to the parent molecular moiety through a carbonyl group.

The term "$C_2$-$C_4$alkynyl," as used herein, refers to a group derived from a straight or branched chain hydrocarbon containing from two to four carbon atoms and one triple bond.

The term "amino," as used herein, refers to —$NH_2$.

The term "amino$C_1$-$C_3$alkyl," as used herein, refers to an amino group attached to the parent molecular moiety through a $C_1$-$C_3$alkyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl.

The term "cyano," as used herein, refers to —CN.

The term "$C_3$-$C_4$cycloalkyl," as used herein, refers to a saturated monocyclic hydrocarbon ring system having three or four carbon atoms and zero heteroatoms.

The terms "halo" and "halogen," as used herein, refer to F, Cl, Br, or I.

The term "halo$C_1$-$C_3$alkyl," as used herein, refers to a $C_1$-$C_3$alkyl group substituted with one, two, or three halogen atoms.

The term "heteroaryl," as used herein, refers to an aromatic five- or six-membered ring where at least one atom is selected from N, O, and S, and the remaining atoms are carbon. The term "heteroaryl" also includes bicyclic systems where a heteroaryl ring is fused to a four- to six-membered aromatic or non-aromatic ring containing zero, one, or two additional heteroatoms selected from N, O, and S; and tricyclic systems where a bicyclic system is fused to a four- to six-membered aromatic or non-aromatic ring containing zero, one, or two additional heteroatoms selected from N, O, and S. The heteroaryl groups are attached to the parent molecular moiety through any substitutable carbon or nitrogen atom in the group. Representative examples of heteroaryl groups include, but are not limited to, alloxazine, benzo[1,2-d:4,5-d']bisthiazole, benzoxadiazolyl, benzoxazolyl, benzofuranyl, benzothienyl, furanyl, imidazolyl, indazolyl, indolyl, isoxazolyl, isoquinolinyl, isothiazolyl, naphthyridinyl, oxadiazolyl, oxazolyl, purine, pyridinyl, pyridazinyl, pyrimidinyl, pyrazinyl, pyrazolyl, pyrrolyl, quinolinyl, thiazolyl, thienopyridinyl, thienyl, triazolyl, thiadiazolyl, and triazinyl.

The term "hydroxy," as used herein, refers to —OH.

The term "hydroxy$C_1$-$C_3$alkyl," as used herein, refers to a hydroxy group attached to the parent molecular moiety through a $C_1$-$C_3$alkyl group.

The term "oxo," as used herein, refers to =O.

An additional aspect of the subject matter described herein is the use of the disclosed compounds as radiolabeled ligands for development of ligand binding assays or for monitoring of in vivo adsorption, metabolism, distribution, receptor binding or occupancy, or compound disposition. For example, a compound described herein can be prepared using a radioactive isotope and the resulting radiolabeled compound can be used to develop a binding assay or for metabolism studies. Alternatively, and for the same purpose, a compound described herein can be converted to a radiolabeled form by catalytic tritiation using methods known to those skilled in the art.

Certain compounds of the present disclosure exist as stereoisomers. It should be understood that when stereochemistry is not specified, the present disclosure encompasses all stereochemical isomeric forms, or mixtures thereof, which possess the ability inhibit KRAS G12D. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure can exist as tautomers, which are compounds produced by the phenomenon where a proton of a molecule shifts to a different atom within that molecule. The term "tautomer" also refers to one of two or more structural isomers that exist in equilibrium and are readily converted from one isomer to another. All tautomers of the compounds described herein are included within the present disclosure.

Certain compounds of the present disclosure exist as atropisomers. The term "atropisomers" refers to conformational stereoisomers which occur when rotation about a single bond in the molecule is prevented, or greatly slowed, as a result of steric interactions with other parts of the molecule and the substituents at both ends of the single bond are asymmetrical (i.e., optical activity arises without requiring an asymmetric carbon center or stereocenter). Where the rotational barrier about the single bond is high enough, and interconversion between conformations is slow enough, separation and isolation of the isomeric species may be permitted. Atropisomers are enantiomers (or epimers) without a single asymmetric atom.

The atropisomers can be considered stable if the barrier to interconversion is high enough to permit the atropisomers to undergo little or no interconversion at room temperature for at least a week. In some aspects the atropisomers undergo little or no interconversion at room temperature for at least a year. In some aspects, an atropisomeric compound of the disclosure does not undergo more than about 5% interconversion to its opposite atropisomer at room temperature during one week when the atropisomeric compound is in substantially pure form, which is generally a solid state. In some aspects, an atropisomeric compound of the disclosure does not undergo more than about 5% interconversion to its opposite atropisomer at room temperature (approximately 25° C.) during one year. In some aspects, the atropisomeric compounds of the disclosure are stable enough to undergo no more than about 5% interconversion in an aqueous pharmaceutical formulation held at 0° C. for at least one week. The present chemical entities, pharmaceutical compositions and methods are meant to include all such possible atropisomers, including racemic mixtures, diastereomeric mixtures, epimeric mixtures, optically pure forms of single atropisomers, and intermediate mixtures.

The energy barrier to thermal racemization of atropisomers may be determined by the steric hindrance to free rotation of one or more bonds forming a chiral axis. Certain biaryl compounds exhibit atropisomerism where rotation around an interannular bond lacking $C_2$ symmetry is restricted. The free energy barrier for isomerization (enantiomerization) is a measure of the stability of the interannular bond with respect to rotation. Optical and thermal excitation can promote racemization of such isomers, dependent on electronic and steric factors.

Ortho-substituted biaryl compounds may exhibit this type of conformational, rotational isomerism. Such biaryls are enantiomeric, chiral atropisomers where the $sp^2$-$sp^2$ carbon-carbon, interannular bond between the aryl rings has a sufficiently high energy barrier to prevent free rotation, and where substituents $W^1 \neq W^2$ and $W^3$¿$W^4$ render the molecule asymmetric.

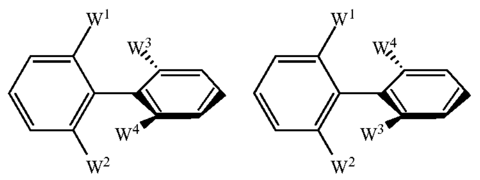

The steric interaction between $W^1$:$W^3$, $W^1$:$W^4$, and/or $W^2$:$W^4$, $W^2$:$W^3$ is large enough to make the planar conformation an energy maximum. Two non-planar, axially chiral enantiomers then exist as atropisomers when their interconversion is slow enough such that they can be isolated free of each other. Bold lines and dashed lines in the figures shown above indicate those moieties, or portions of the molecule, which are sterically restricted due to a rotational energy barrier. Balded moieties exist orthogonally above the plane of the page, and dashed moieties exist orthogonally below the plane of the page. The 'flat' part of the molecule (the left ring in each of the two depicted biaryls) is in the plane of the page.

The pharmaceutical compositions of the disclosure can include one or more pharmaceutically acceptable salts. A "pharmaceutically acceptable salt" refers to a salt that retains the desired biological activity of the parent compound and does not impart any undesired toxicological effects (see e.g., Berge, S. M. et al., *J. Pharm. Sci.,* 66:1-19 (1977)). The salts can be obtained during the final isolation and purification of the compounds described herein, or separately be reacting a free base function of the compound with a suitable acid or by reacting an acidic group of the compound with a suitable base. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Pharmaceutical Compositions

In another aspect, the present disclosure provides a composition, e.g., a pharmaceutical composition, containing one or a combination of the compounds described within the present disclosure, formulated together with a pharmaceutically acceptable carrier. Pharmaceutical compositions of the disclosure also can be administered in combination therapy, i.e., combined with other agents, as described herein.

As used herein, "pharmaceutically acceptable carrier" includes any and all solvents, dispersion media, coatings, antibacterial and antifungal agents, isotonic and absorption delaying agents, and the like that are physiologically compatible. In some aspects, the carrier is suitable for intravenous, intramuscular, subcutaneous, parenteral, spinal or epidermal administration (e.g., by injection or infusion). Depending on the route of administration, the active compound can be coated in a material to protect the compound from the action of acids and other natural conditions that can inactivate the compound.

The pharmaceutical compositions of the present disclosure can be administered via one or more routes of administration using one or more of a variety of methods known in the art. As will be appreciated by the skilled artisan, the route and/or mode of administration will vary depending upon the desired results. In some aspects, the routes of administration for compounds of the disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, some methods of preparation are vacuum drying and freeze-drying (lyophilization) that yield a powder of the active ingredient plus any additional desired ingredient from a previously sterile-filtered solution thereof.

Examples of suitable aqueous and non-aqueous carriers that can be employed in the pharmaceutical compositions of the disclosure include water, ethanol, polyols (such as glycerol, propylene glycol, polyethylene glycol, and the like), and suitable mixtures thereof, vegetable oils, and injectable organic esters. Proper fluidity can be maintained, for example, by the use of coating materials, such as lecithin, by the maintenance of the required particle size in the case of dispersions, and by the use of surfactants.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically must be sterile and stable under the conditions of manufacture and storage. The composition can be formulated as a solution or as a liquid with ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be desirable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Alternatively, the compounds of the disclosure can be administered via a non-parenteral route, such as a topical, epidermal or mucosal route of administration, for example, intranasally, orally, vaginally, rectally, sublingually or topically.

Any pharmaceutical composition contemplated herein can, for example, be delivered orally via any acceptable and suitable oral preparation. Exemplary oral preparations include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the disclosure can contain at least one agent selected from sweetening agents, flavoring agents, coloring agents, demulcents, antioxidants, and preserving agents.

A tablet can, for example, be prepared by admixing at least one compound of Formula (I) and/or at least one pharmaceutically acceptable salt thereof with at least one non-toxic pharmaceutically acceptable excipient suitable for the manufacture of tablets.

An aqueous suspension can be prepared, for example, by admixing at least one compound of Formula (I) and/or at least one pharmaceutically acceptable salt thereof with at least one excipient suitable for the manufacture of an aqueous suspension, including, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example, heptadecathylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) and/or at least one pharmaceutically acceptable salt thereof in either a vegetable oil, such as, for example, arachis oil, sesame oil, and coconut oil; or in mineral oil, such as, for example, liquid paraffin. An oily suspension can also contain at least one thickening agent, such as, for example, beeswax, hard paraffin, and cetyl alcohol. In order to provide a palatable oily suspension, at least one of the sweetening agents already described herein above, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) and/or at least one pharmaceutically acceptable salt thereof with at least one dispersing and/or wetting agent, at least one suspending agent, and/or at least one preservative. Suitable dispersing agents, wetting agents, and suspending agents are already described above. Exemplary preservatives include, but are not limited to, for example, anti-oxidants, e.g., ascorbic acid. In addition, dispersible powders and granules can also contain at least one excipient, including, but not limited to, for example, sweetening agents, flavoring agents, and coloring agents.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Robinson, J. R., ed., *Sustained and Controlled Release Drug Delivery Systems*, Marcel Dekker, Inc., New York (1978).

Therapeutic compositions can be administered with medical devices known in the art. For example, in one aspect, a therapeutic composition of the disclosure can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medication through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain aspects, the compounds of the present disclosure can be administered parenterally, i.e., by injection, including, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and/or infusion.

In some aspects, the compounds of the present disclosure can be administered orally, i.e, via a gelatin capsule, tablet, hard or soft capsule, or a liquid capsule.

Use of KRAS Inhibitors/Methods of Treating

Administration of a therapeutic agent described herein includes, without limitation, administration of a therapeutically effective amount of therapeutic agent. The term "therapeutically effective amount" as used herein refers, without limitation, to an amount of a therapeutic agent to treat a condition treatable by administration of a composition comprising the KRAS inhibitors described herein. That amount is the amount sufficient to exhibit a detectable therapeutic or ameliorative effect. The effect can include, for example and without limitation, treatment of the conditions listed herein. The precise effective amount for a subject will depend upon the subject's size and health, the nature and extent of the condition being treated, recommendations of the treating physician, and therapeutics or combination of therapeutics selected for administration.

For administration of the compounds described herein, the dosage ranges from about 0.0001 to 100 mg/kg, and more usually 0.01 to 40 mg/kg, of the host body weight. An exemplary treatment regime entails administration once per day, bi-weekly, tri-weekly, weekly, once every two weeks, once every three weeks, once every four weeks, once a month, once every 3 months or once every three to 6 months.

The disclosed compounds strongly inhibit anchorage-independent cell growth and therefore have the potential to inhibit tumor metastasis. Accordingly, in another aspect the disclosure provides a method for inhibiting tumor metastasis, the method comprising administering an effective amount a pharmaceutical composition of comprising any of the compounds disclosed herein and a pharmaceutically acceptable carrier to a subject in need thereof.

Ras mutations including but not limited to KRAS mutations have also been identified in hematological malignancies (e.g., cancers that affect blood, bone marrow and/or lymph nodes). Accordingly, certain aspects are directed to administration of a disclosed compounds (e.g., in the form of a pharmaceutical composition) to a patient in need of treatment of a hematological malignancy. Such malignancies include, but are not limited to leukemias and lymphomas. For example, the presently disclosed compounds can be used for treatment of diseases such as Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AMoL) and/or other leukemias. In other aspects, the compounds are useful for treatment of lymphomas such as all subtypes of Hodgkins lymphoma or non-Hodgkins lymphoma.

Determining whether a tumor or cancer comprises a KRAS mutation can be undertaken by assessing the nucleotide sequence encoding the KRAS protein, by assessing the amino acid sequence of KRAS protein, or by assessing the characteristics of a putative KRAS mutant protein. The sequence of wild-type human KRAS proteins is known in the art.

Methods for detecting a KRAS mutation are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some aspects, samples are evaluated for KRAS mutations including by real-time PCR. In real-time PCR, fluorescent probes specific for the KRAS mutation are used. When a mutation is present, the probe binds and fluorescence is detected. In some aspects, the KRAS mutation is identified using a direct sequencing method of specific regions (e.g., exon 2 and/or exon 3) in the KRAS gene, for example. This technique will identify all possible mutations in the region sequenced.

Methods for detecting a mutation in a KRAS protein are known by those of skill in the art. These methods include, but are not limited to, detection of a KRAS mutant using a binding agent (e.g., an antibody) specific for the mutant protein, protein electrophoresis and Western blotting, and direct peptide sequencing.

Methods for determining whether a tumor or cancer comprises a KRAS mutation can use a variety of samples. In some aspects, the sample is taken from a subject having a tumor or cancer. In some aspects, the sample is taken from a subject having a cancer or tumor. In some aspects, the sample is a fresh tumor/cancer sample. In some aspects, the sample is a frozen tumor/cancer sample. In some aspects, the sample is a formalin-fixed paraffin-embedded sample. In some aspects, the sample is processed to a cell lysate. In some aspects, the sample is processed to DNA or RNA. he disclosure also relates to a method of treating a hyperproliferative disorder in a mammal that comprises administering to said mammal a therapeutically effective amount of a compound of the present disclosure, or a pharmaceutically acceptable salt, ester, prodrug, solvate, hydrate or derivative thereof. In some aspects, said method relates to the treatmentof cancer such as acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, isletcell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some aspects, said method relates to the treatment of a non-cancerous hyperproliferative disorder such as benign hyperplasia of the skin (e.g., psoriasis), restenosis, or prostate (e. g., benign prostatic hypertrophy (BPH)).

In certain aspects, the disclosure relates to methods for treatment of lung cancers, the methods comprise administering an effective amount of any of the above described compound (or a pharmaceutical composition comprising the same) to a subject in need thereof. In certain aspects the lung cancer is a non-small cell lung carcinoma (NSCLC), for example adenocarcinoma, squamous-cell lung carcinoma or large-cell lung carcinoma. In other aspects, the lung cancer is a small cell lung carcinoma. Other lung cancers treatable with the disclosed compounds include, but are not limited to, glandular tumors, carcinoid tumors and undifferentiated carcinomas. Subjects that can be treated with compounds of the disclosure, or pharmaceutically acceptable salt, ester, prodrug, solvate, tautomer, hydrate or derivative of said compounds, according to the methods of this disclosure include, for example, subjects that have been diagnosed as having acute myeloid leukemia, acute myeloid leukemia, cancer in adolescents, adrenocortical carcinoma childhood, AIDS-related cancers (e.g. Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germcell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, hodgkin lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-hodgkin lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasalcavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some aspects subjects that are treated with the compounds of the disclosure include subjects that have been diagnosed as having a non-cancerous hyperproliferative disorder such as benign hyperplasia of the skin (e. g., psoriasis), restenosis, or prostate (e. g., benign prostatic hypertrophy (BPH)). The disclosure further provides methods of modulating a mutant KRAS protein activity by contacting the protein with an effective amount of a compound of the disclosure. Modulation can be inhibiting or activating protein activity. In some aspects, the disclosure provides methods of inhibiting protein activity by contacting the mutant KRAS protein with an effective amount of a compound of the disclosure in solution. In some aspects, the disclosure provides methods of inhibiting the mutant KRAS protein activity by contacting a cell, tissue, organ that express the protein of interest. In some aspects, the disclosure provides methods of inhibiting protein activity in a subject including but not limited to rodents and mammal (e.g., human) by administering into the subject an effective amount of a compound of the disclosure. In some aspects, the percentage modulation exceeds 25%, 30%, 40%, 50%, 60%, 70%, 80%, or 90%. In some aspects, the percentage of inhibiting exceeds 25%, 30%, 40%, 50%, 60%, 70%, 80%, or 90%.In some aspects, the disclosure provides methods of inhibiting KRAS activity in a cell by contacting said cell with an amount of a compound of the disclosure sufficient to inhibit the activity of a KRAS mutant in said cell. In some aspects, the disclosure provides methods of inhibiting mutant KRAS in a tissue by contacting said tissue with an amount of a compound of the disclosure sufficient to inhibit the activity of mutant KRAS in said tissue. In some aspects, the disclosure provides methods of inhibiting KRAS in an organism by contacting said organism with an amount of a compound of the disclosure sufficient to inhibit the activity of KRAS in said organism. In some aspects, the disclosure provides methods of inhibiting KRAS activity in an animal by contacting said animal with an amount of a compound of the disclosure sufficient to inhibit the activity of KRAS in said animal. In some aspects, the disclosure provides methods of inhibiting KRAS including in a mammal by contacting said mammal with an amount of a compound of the disclosure sufficient to inhibit the activity of KRAS in said mammal. In some aspects, the disclosure provides methods of inhibiting KRAS activity in a human by contacting said human with an amount of a compound of the disclosure sufficient to inhibit the activity of KRAS in said human. The present disclosure provides methods of treating a disease mediated by KRAS activity in a subject in need of such treatment. he present disclosure also provides methods for combination therapies in which an agent known to modulate other pathways, or other components of the same pathway, or even overlapping sets of target enzymes are used in combination with a compound of the present disclosure, or a pharmaceutically acceptable salt, ester, prodrug, solvate, tautomer, hydrate or derivative thereof. In one aspect, such therapy includes but is not limited to the combination of one or more compounds of the disclosure with chemotherapeutic agents, therapeutic antibodies, and radiation treatment.

Many chemotherapeutics are presently known in the art and can be used in combination with the compounds of the disclosure. In some aspects, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. In some aspects, the chemotherapeutic agent is an immunooncology (IO) agent that can enhance, stimulate, or upregulate the immune system.

The compounds described herein can be used in combination with the agents disclosed herein or other suitable agents, depending on the condition being treated. Hence, in some aspects the one or more compounds of the disclosure will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the disclosure and any of the agents described above can be simultaneously administered, wherein both the agents are present in separate formulations. In another alternative, a compound of the present disclosure can be administered just followed by and any of the agents described above, or vice versa. In some aspects of the separate administration protocol, a compound of the disclosure and any of the agents described above are administered a few minutes apart, or a few hours apart, or a few days apart.

The compounds can be made by methods known in the art including those described below and including variations within the skill of the art. Some reagents and intermediates are known in the art. Other reagents and intermediates can be made by methods known in the art using readily available materials. Any variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the disclosure.

Synthesis

General Schemes

The compounds described herein can be prepared as shown below and as described in Methods 1-4.

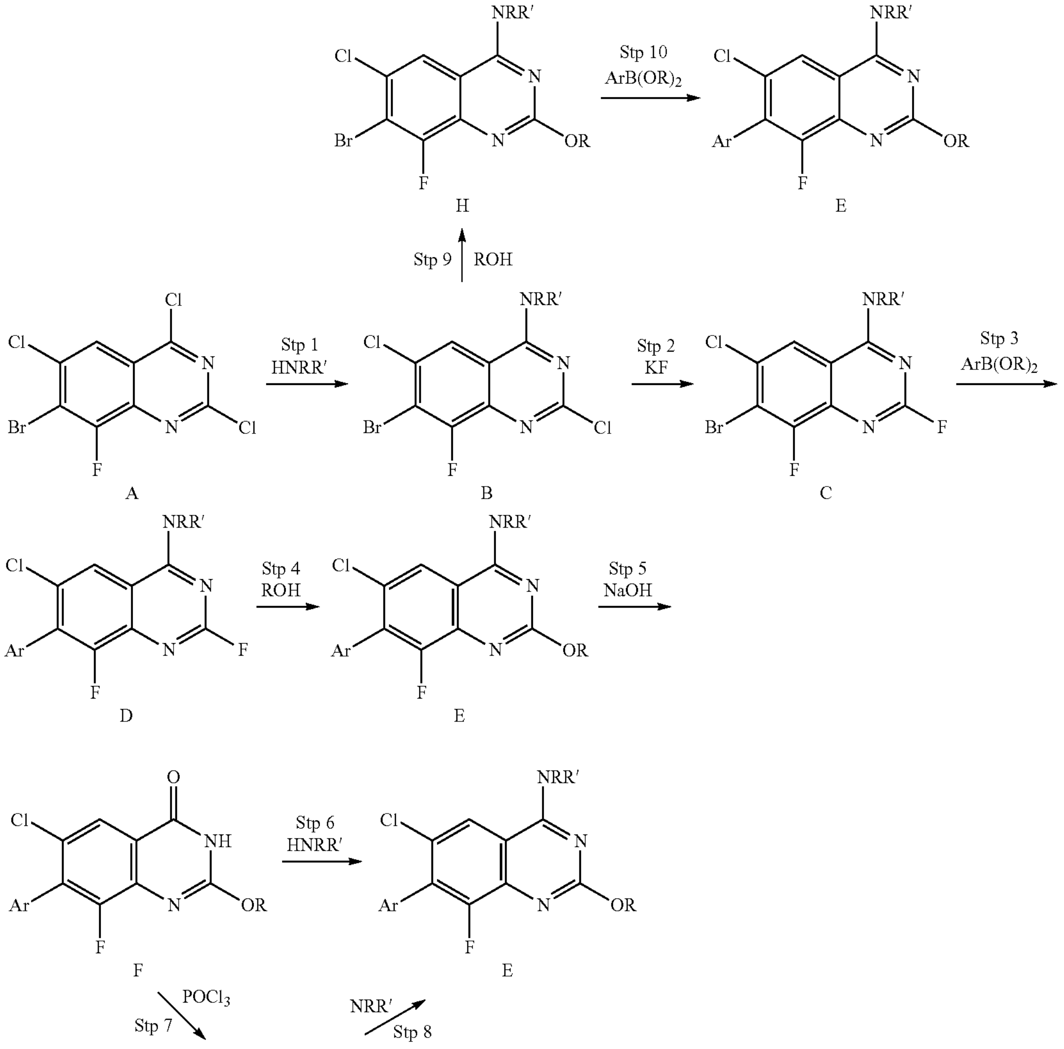

H E A B C D E F E

-continued

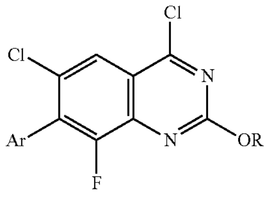

G

Method 1: In Step 1, known compound A (CAS 1698028-11-3) is reacted with an amine in a suitable solvent such as THE with a base such as diisopropylethylamine to provide compound B. In Step 2, treatment of compound B with potassium fluoride in a solvent such as dimethylacetamide provides compound C. In Step 3, compound C is coupled with an arylboronic acid or ester under Suzuki conditions to provide compound D. In Step 4, compound D is treated with ROH in the presence of a base in a solvent such as THE to provide compound E.

Method 2: The amino group of compound E may be switched to a different amino group by the following sequence. In Step 5, base hydrolysis provides compound F. In step 6, introduction of an amine substituent is accomplished with using a coupling agent such as BOP in the presence of base in solvent such as dichloromethane to provide compound E.

Method 3: In Step 7, treatment of compound H with $POCl_3$ in the presence of a base provides compound G. Treatment of compound G with an appropriate amine in the presence of a base in a solvent such as dimethylacetamide provides compound E.

Method 4: In Step 9, treatment of compound B with an alcohol of formula R—OH in the presence of base provides compound H. In Step 10, compound H is coupled with an arylboronic acid or ester under Suzuki conditions to provide compound E. Protecting groups such as Boc, PMB, MOM, etc. may be introduced and removed as required by one skilled in the art and are described in the Examples. Functionalization and elaboration of the Aryl, NRR', and OR groups to prepare compounds of general structure E are described in the Examples.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather is defined by the claims appended hereto.

Abbreviations

The following abbreviations are used in the example section below and elsewhere herein:

| Abbreviation | Full Name |
|---|---|
| Ac | acetyl |
| ACN | acetonitrile |

-continued

| Abbreviation | Full Name |
|---|---|
| aq. | aqueous |
| DCM | dichloromethane |
| DMSO | dimethylsulfoxide |
| DMOCP | 2-chloro-5,5-dimethyl-1,3,2-dioxaphosphorinane 2-oxide |
| EtOAc | ethyl acetate |
| $Et_3N$ or TEA | triethylamine |
| EtOH | ethanol |
| HPLC | high-performance liquid chromatography |
| iPr | isopropyl |
| MeOH | methanol |
| RT, R.T. | room temperature |
| sat., satd. or sat'd | saturated |
| TBAF | Tetrabutylammonia fluoride |
| TBS | t-Butyldimethylsilyl |
| TFA | Trifluoroacetic acid |
| $t_R$ | retention time |

Examples 1-1 and 1-2

6-(6-chloro-4-{3,8-diazabicyclo[3.2.1]octan-3-yl}-8-fluoro-2-{[(2S)-1-methylpyrrolidin-2-yl]methoxy}quinazolin-7-yl)-4-methyl-5-(trifluoromethyl)pyridin-2-amine

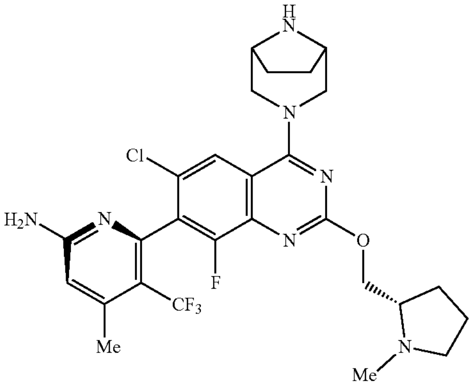

1-1 (Isomer 1)

-continued

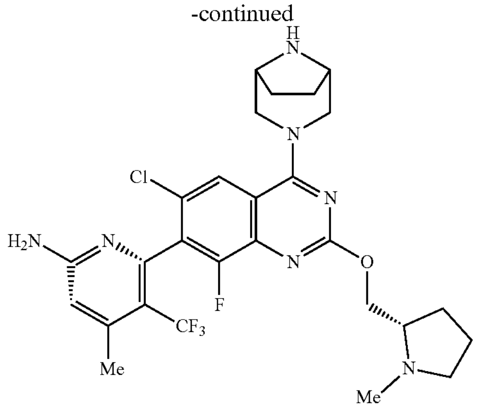

1-2 (Isomer 2)

Preparation of Intermediate 1A: 6-bromo-N,N-bis(4-methoxybenzyl)-4-methylpyridin-2-amine

1A

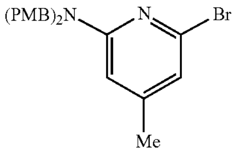

To a solution of 6-bromo-4-methylpyridin-2-amine (1 g, 5.35 mmol) in DMF (20 mL) was added NaH (0.64 g, 16 mmol, 60%) at 0° C. The mixture was stirred at 0° C. for 0.5 h. Then 1-(chloromethyl)-4-methoxybenzene (2.1 g, 13.4 mmol) was added. The mixture was stirred at 0° C. for 1.5 h. TLC (on silica gel, petroleum ether:ethyl acetate=5:1) showed the reaction was completed. The reaction was quenched with saturated $NH_4Cl$ (20 mL) and extracted with ethyl acetate (20 mL×3), washed with brine (50 mL) and dried over anhydrous $Na_2SO_4$. The mixture was filtered. The filtrate was concentrated in vacuo. The residue was purified by column chromatography (silica gel, petroleum ether:ethyl acetate=5:1) to afford 6-bromo-N,N-bis(4-methoxybenzyl)-4-methylpyridin-2-amine (2 g, 4.68 mmol, 87.5% yield) as a colorless oil. $^1$H NMR (400 MHz, $CDCl_3$) δ 7.16 (d, J=8.8 Hz, 4H), 6.88-6.84 (m, 4H), 6.60 (s, 1H), 6.16 (s, 1H), 4.64 (s, 4H), 3.80 (s, 6H), 2.13 (s, 3H).

Preparation of Intermediate 1B: (6-(bis(4-methoxybenzyl)amino)-4-methylpyridin-2-yl)boronic acid

1B

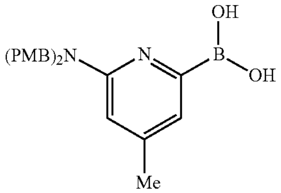

To a solution of 6-bromo-N,N-bis(4-methoxybenzyl)-4-methylpyridin-2-amine (1000 mg, 2.34 mmol), bis(pinacolato)diboron (832.5 mg, 3.28 mmol), (1,1'-bis(diphenylphosphino)ferrocene)palladium(II) dichloride (171 mg, 0.23 mmol) in 1,4-dioxane (20 mL) was added KOAc (459.32 mg, 4.68 mmol). The mixture was stirred at 90° C. for 5 h under N2. The reaction mixture was filtered. The filtrate containing the crude product (6-(bis(4-methoxybenzyl)amino)-4-methylpyridin-2-yl)boronic acid (918 mg, 2.34 mmol, crude) in 1,4-dioxane (20 mL)) was used in the next step without purification. MS (ESI) m/z 393.3 $[M+1]^+$.

Preparation of Intermediate 1C: tert-butyl 4-(7-bromo-2,6-dichloro-8-fluoroquinazolin-4-yl)piperazine-1-carboxylate

1C

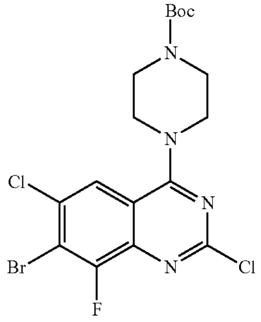

To a solution of 7-bromo-2,4,6-trichloro-8-fluoroquinazoline (1 g, 3.03 mmol) and DIPEA (1.32 mL, 7.57 mmol) in THE (15 mL) was added tert-butyl piperazine-1-carboxylate (0.56 g, 3.03 mmol) under N2. The reaction mixture was stirred at 25° C. for 2 h. The mixture was concentrated. The residue was diluted with ethyl acetate (60 mL),washed with water (30 mL×2) and brine (50 mL). The organic phase was dried over anhydrous sodium sulphate, filtered and concentrated under reduced pressure. The residue was purified by silica gel column chromatography (silica gel, petroleum ether:ethyl acetate=10:1 to 4:1) to afford tert-butyl 4-(7-bromo-2,6-dichloro-8-fluoroquinazolin-4-yl)piperazine-1-carboxylate (1.33 g, 2.77 mmol, 91.5% yield) as a yellow solid. MS (ESI) m/z 481.0 $[M+3]^+$. $^1$H NMR (400 MHz, $CDCl_3$) δ 7.77 (d, J=1.6 Hz, 1H), 3.93-3.84 (m, 4H), 3.72-3.61 (m, 4H), 1.50 (s, 9H).

Preparation of Intermediate 1D: tert-butyl 4-(7-bromo-6-chloro-2,8-difluoroquinazolin-4-yl)piperazine-1-carboxylate

1D

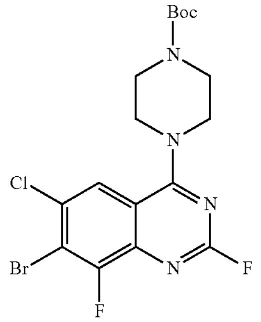

A solution of tert-butyl 4-(7-bromo-2,6-dichloro-8-fluoroquinazolin-4-yl)piperazine-1-carboxylate (1000 mg, 2.08 mmol) and potassium fluoride (2420 mg, 41.65 mmol) in DMA (10 mL) was stirred at 110° C. for 12 h under N2. The reaction mixture was quenched with water (30 mL) and extracted with EtOAc (30 mL×3). The combined organic layers were washed with brine (30 mL×3) and dried over anhydrous $Na_2SO_4$. The mixture was filtered, and the filtrate was concentrated under reduced pressure. The residue was purified by silica gel column chromatography (silica gel, petroleum ether:ethyl acetate=20:1 to 3:1) to provide tert-butyl 4-(7-bromo-6-chloro-2,8-difluoroquinazolin-4-yl)piperazine-1-carboxylate (730 mg, 1.57 mmol, 75.6% yield) as a yellow solid. MS (ESI) m/z 463.1 $[M+1]^+$.

Preparation of Intermediate 1E: tert-butyl 4-(7-(6-(bis(4-methoxybenzyl)amino)-4-methylpyridin-2-yl)-6-chloro-2,8-difluoroquinazolin-4-yl)piperazine-1-carboxylate

1E

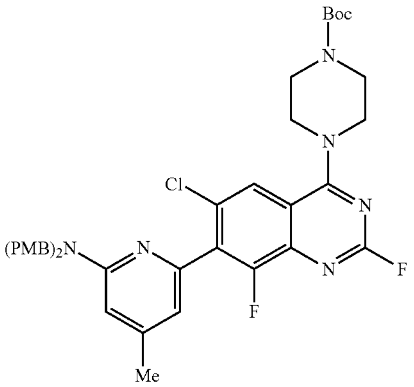

A solution of tert-butyl 4-(7-bromo-6-chloro-2,8-difluoroquinazolin-4-yl)piperazine-1-carboxylate (600 mg, 1.29 mmol), (6-(bis(4-methoxybenzyl)amino)-4-methylpyridin-2-yl)boronic acid (756 mg, 1.93 mmol), (1,1'-bis(diphenylphosphino)ferrocene)palladium(II) dichloride (104 mg, 0.14 mmol) and potassium phosphate (548 mg, 2.59 mmol) in 1,4-dioxane (20 mL) and water (2 mL) was stirred at 60° C. for 12 under N2. The mixture was filtered. The filtrate was concentrated in vacuo. The residue was purified by silica gel column chromatography (silica gel, petroleum ether:ethyl acetate=10:1 to 3:1) to provide tert-butyl 4-(7-(4-(bis(4-methoxybenzyl)amino)-6-methylpyridin-2-yl)-6-chloro-2,8-difluoroquinazolin-4-yl)piperazine-1-carboxylate (600 mg, 0.82 mmol, 63.4% yield) as a yellow oil. MS (ESI) m/z 731.4 [M+1]+; $^1H$ NMR (400 MHz, $CDCl_3$) δ 7.76 (d, J=1.2 Hz, 1H), 7.18 (d, J=8.8 Hz, 4H), 6.85 (d, J=8.8 Hz, 4H), 6.59 (s, 1H), 6.37 (s, 1H), 4.69 (s, 4H), 3.98-3.87 (m, 4H), 3.80 (s, 6H), 3.69-3.65 (m, 4H), 2.27 (s, 3H), 1.51 (s, 9H).

Preparation of Intermediate 1F: tert-butyl 4-(7-(6-(bis(4-methoxybenzyl)amino)-3-iodo-4-methylpyridin-2-yl)-6-chloro-2,8-difluoroquinazolin-4-yl)piperazine-1-carboxylate

1F

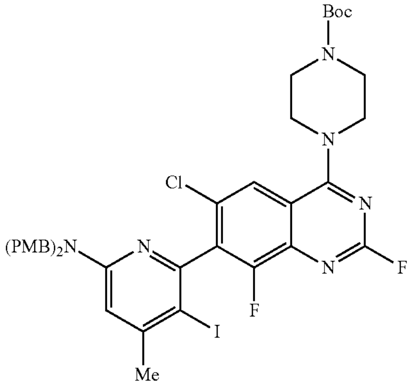

A solution of tert-butyl 4-(7-(4-(bis(4-methoxybenzyl)amino)-6-methylpyridin-2-yl)-6-chloro-2,8-difluoroquinazolin-4-yl)piperazine-1-carboxylate (800 mg, 1.09 mmol), TosOH (5 mg, 0.05 mmol) and NIS (1200 mg, 5.33 mmol) in DMF (10 mL) was stirred at 25° C. for 12 h. The reaction mixture was diluted with water (15 mL) and EtOAc (15 mL). The mixture was extracted with EtOAc (30 mL×3). The combined organic layers were washed with brine (30 mL×3), dried over anhydrous sodium sulfate, filtered and concentrated under reduced pressure. The residue was purified by column chromatography (silica gel, petroleum ether: ethyl acetate=10:1 to 3:1) to afford tert-butyl-4-(7-(6-(bis(4-methoxybenzyl)amino)-3-iodo-4-methylpyridin-2-yl)-6-chloro-2,8-difluoroquinazolin-4-yl)piperazine-1-carboxylate (400 mg, 0.467 mmol, 42.7% yield) as a yellow solid. MS (ESI) m/z 857.2 [M+1]+; $^1H$ NMR (400 MHz, $CDCl_3$) δ 7.82 (d, J=1.2 Hz, 1H), 7.17 (d, J=8.4 Hz, 4H), 6.86 (d, J=8.4 Hz, 4H), 6.48 (s, 1H), 4.76-4.65 (m, 2H), 4.62-4.50 (m, 2H), 4.01-3.92 (m, 4H), 3.82 (s, 6H), 3.72-3.63 (m, 4H), 2.38 (s, 3H), 1.52 (s, 9H).

Preparation of Intermediate 1G: tert-butyl 4-(7-(6-(bis(4-methoxybenzyl)amino)-4-methyl-3-(trifluoromethyl)pyridin-2-yl)-6-chloro-2,8-difluoroquinazolin-4-yl)piperazine-1-carboxylate

1G

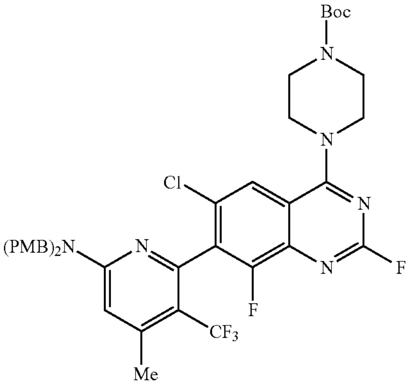

A mixture of tert-butyl 4-(7-(6-(bis(4-methoxybenzyl)amino)-3-iodo-4-methylpyridin-2-yl)-6-chloro-2,8-difluoroquinazolin-4-yl)piperazine-1-carboxylate (400 mg, 0.4700 mmol), methyl 2,2-difluoro-2-fluorosulfonyl-acetate (1345 mg, 7 mmol) and CuI (267 mg, 1.4 mmol) in DMA (10 mL) was stirred at 80° C. for 5 h under $N_2$. The reaction mixture was then cooled to room temperature and additional CuI (267 mg, 1.4 mmol) and methyl 2,2-difluoro-2-fluorosulfonyl-acetate (1345 mg, 7 mmol) were added to the mixture. The reaction mixture was stirred at 80° C. for another 12 h under $N_2$. The mixture was diluted with EtOAc (50 mL) and filtered. The filtrate was washed with brine (30 mL×3) and dried over anhydrous $Na_2SO_4$ and filtered. The filtrate was concentrated in vacuo. The residue was purified by column chromatography (silica gel, petroleum ether:ethyl acetate=10:1 to 3:1) to afford tert-butyl 4-(7-(6-(bis(4-methoxybenzyl)amino)-4-methyl-3-(trifluoromethyl)pyridin-2-yl)-6-chloro-2,8-difluoroquinazolin-4-yl)piperazine-1-carboxylate (270 mg, 0.34 mmol, 72.4% yield) as a yellow solid. MS (ESI) m/z 799.0 $[M+1]^+$.

Preparation of Intermediate 1H: tert-butyl 4-(7-(6-(bis(4-methoxybenzyl)amino)-4-methyl-3-(trifluoromethyl)pyridin-2-yl)-6-chloro-2,8-difluoroquinazolin-4-yl)piperazine-1-carboxylate

1H

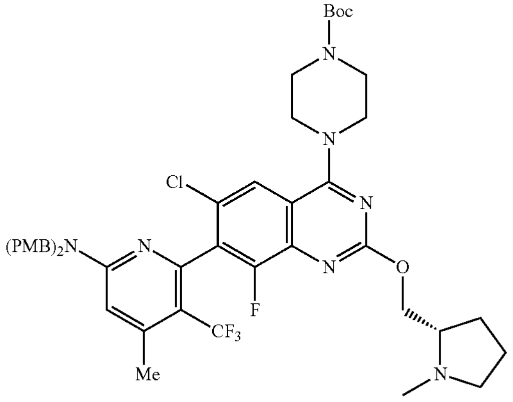

To a solution of (2S)-1-methylpyrrolidin-2-yl methanol (97.6 mg, 0.85 mmol) in THE (10 mL) was added NaH (81 mg, 2.03 mmol, 60%) at 0° C. The mixture was stirred at 0° C. for 0.5 h. tert-butyl 4-(7-(6-(bis(4-methoxybenzyl)amino)-4-methyl-3-(trifluoromethyl)pyridin-2-yl)-6-chloro-2,8-difluoroquinazolin-4-yl)piperazine-1-carboxylate (270 mg, 0.34 mmol) in THE (5 mL) was added. The mixture was stirred at 0° C. for 1 h. The reaction mixture was quenched with saturated $NH_4Cl$ (20 mL) and extracted with EtOAc (20 mL×3). The combined organic layers were washed with brine (30 mL) and dried over anhydrous $Na_2SO_4$. The mixture was filtered, the filtrate was concentrated under reduced pressure. The residue was purified by column chromatography (silica gel, DCM: MeOH=10:1) to provide tert-butyl 4-(7-(6-(bis(4-methoxybenzyl)amino)-4-methyl-3-(trifluoromethyl)pyridin-2-yl)-6-chloro-2,8-difluoroquinazolin-4-yl)piperazine-1-carboxylate (250 mg, 0.28 mmol, 82.7% yield) as a white solid. MS (ESI) m/z 894.5 $[M+1]^+$.

Preparation of Intermediate 1I: 7-(6-(bis(4-methoxybenzyl)amino)-4-methyl-3-(trifluoromethyl)pyridin-2-yl)-6-chloro-8-fluoro-2-(((S)-1-methylpyrrolidin-2-yl)methoxy)quinazolin-4(3H)-one

1I

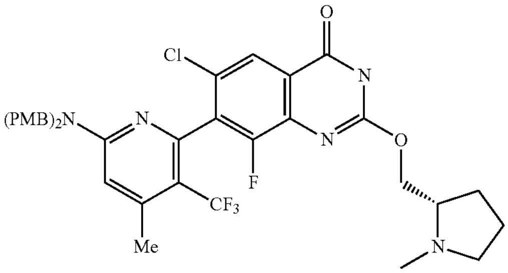

A mixture of tert-butyl 4-(7-(6-(bis(4-methoxybenzyl)amino)-4-methyl-3-(trifluoromethyl)pyridin-2-yl)-6-chloro-2,8-difluoroquinazolin-4-yl)piperazine-1-carboxylate (250 mg, 0.28 mmol) and NaOH (224 mg, 5.59 mmol) in ethanol (30 mL) and water (10 mL) was stirred at 45° C. for 3 d. The mixture was quenched with 2N HCl to pH=6-7. The mixture was concentrated in vacuo to remove EtOH. The residue was extracted with DCM (20 mL×3). The combined organic layers were washed with brine (30 mL) and dried over anhydrous $Na_2SO_4$. The mixture was filtered and the filtrate was concentrated under reduced pressure to afford 7-(6-(bis(4-methoxybenzyl)amino)-4-methyl-3-(trifluoromethyl)pyridin-2-yl)-6-chloro-8-fluoro-2-(((S)-1-methylpyrrolidin-2-yl)methoxy)quinazolin-4(3H)-one (200 mg, 0.28 mmol, 98.5% yield) as a light yellow solid. MS (ESI) m/z 726.3 $[M+1]^+$; $^1H$ NMR (400 MHz, $CDCl_3$) δ 8.07 (s, 1H), 7.14 (d, J=8.4 Hz, 4H), 6.85 (d, J=8.4 Hz, 4H), 6.41 (s, 1H), 4.98-4.65 (m, 4H), 4.59-4.49 (m, 2H), 3.80 (s, 6H), 3.55-3.38 (m, 1H), 2.90 (d, J=8.0 Hz, 3H), 2.41 (s, 3H), 2.31-2.21 (m, 2H), 2.14-2.03 (m, 2H), 1.37-1.19 (m, 2H).

Preparation of Intermediate 1J: 7-(6-amino-4-methyl-3-(trifluoromethyl)pyridin-2-yl)-6-chloro-8-fluoro-2-(((S)-1-methylpyrrolidin-2-yl)methoxy)quinazolin-4(3H)-one

1J

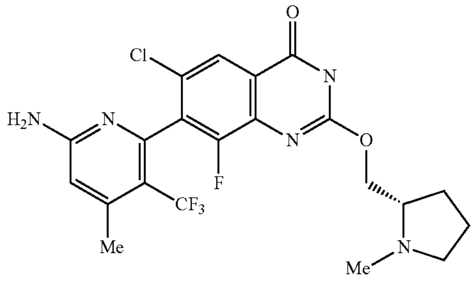

A solution of 7-(6-(bis(4-methoxybenzyl)amino)-4-methyl-3-(trifluoromethyl)pyridin-2-yl)-6-chloro-8-fluoro-2-(((S)-1-methylpyrrolidin-2-yl)methoxy)quinazolin-4(3H)-one (300. mg, 0.4100 mmol) in TFA (10 mL, 130 mmol) was stirred at 50° C. for 4 hours. The reaction mixture was concentrated under reduced pressure to afford the crude product 7-(6-amino-4-methyl-3-(trifluoromethyl)

pyridin-2-yl)-6-chloro-8-fluoro-2-(((S)-1-methylpyrrolidin-2-yl)methoxy)quinazolin-4(3H)-one (247 mg, 0.41 mmol, 99.7% yield) as a brown oil. MS (ESI) m/z: 486.1 $[M+H]^+$.

Preparation of Intermediate 1K: tert-butyl 3-(7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3,8-diazabicyclo[3.2.1]octane-8-carboxylate

1K

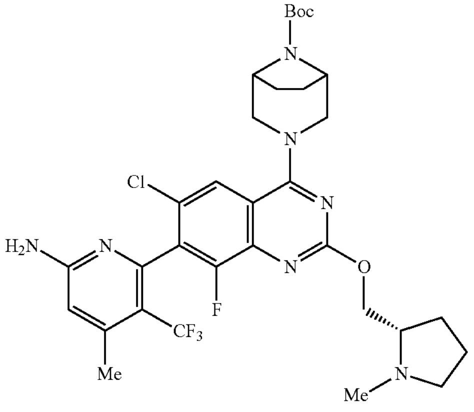

To a solution of 7-(6-amino-4-methyl-3-(trifluoromethyl)pyridin-2-yl)-6-chloro-8-fluoro-2-(((S)-1-methylpyrrolidin-2-yl)methoxy)quinazolin-4(3H)-one (80 mg, 0.13 mmol) in DCM (3 mL) were added tert-butyl 3,8-diazabicyclo[3.2.1]octane-8-carboxylate (85 mg, 0.40 mmol), DIPEA (51 mg, 0.39 mmol) and BOP (192 mg, 0.43 mmol) at 25° C. The reaction mixture was stirred at 25° C. for 12 hours. The reaction mixture was diluted with water (15 mL), then extracted with DCM (15 mL×3). The combined organic layers were washed with brine (20 mL), dried over anhydrous sodium sulfate, filtered and concentrated under reduced pressure. The residue was purified by preparative HPLC (Instrument: ACSWH-GX-N; Column: Phenomenex Synergi C18 150×25 mm 10 um; Mobile phase: A for $H_2O$ (0.1% TFA) and B for Acetonitrile; Gradient: B 38%-68% in 10 min linearly; Flow rate: 25 mL/min; Column temperature: R.T.; Wavelength: 220 nm and 254 nm) to afford the desired tert-butyl 3-(7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3,8-diazabicyclo[3.2.1]octane-8-carboxylate (25 mg, 0.037 mmol, 27.6% yield) as a yellow solid, which was used in the next step directly. MS (ESI) m/z: 680.2 $[M+H]^+$.

Examples 1-1 and 1-2

6-(6-chloro-4-{3,8-diazabicyclo[3.2.1]octan-3-yl}-8-fluoro-2-{[(2S)-1-methylpyrrolidin-2-yl]methoxy}quinazolin-7-yl)-4-methyl-5-(trifluoromethyl)pyridin-2-amine

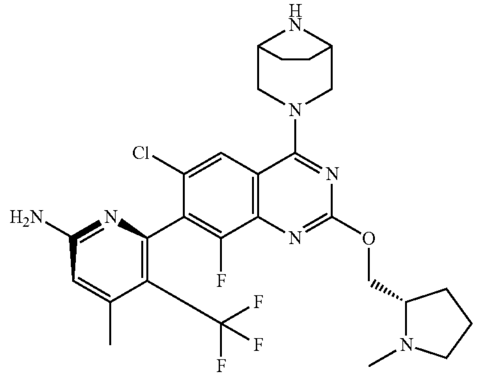

1-1 (Isomer 1)

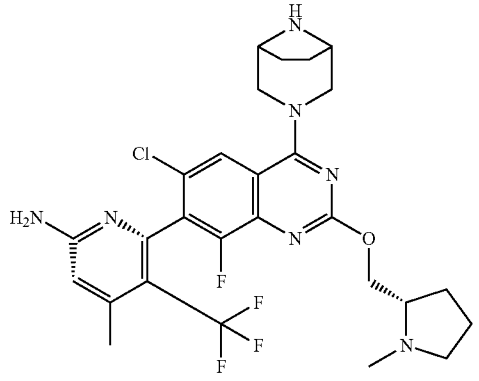

1-2 (Isomer 2)

To a solution of tert-butyl 3-(7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3,8-diazabicyclo[3.2.1]octane-8-carboxylate (20. mg, 0.03 mmol) in DCM (1.5 mL) was added TFA (0.5 mL, 6.53 mmol) at 25° C. The reaction mixture was stirred at 25° C. for 3 hours. The reaction mixture was filtered and the filtrate was collected. The filtrate was concentrated under reduced pressure. The residue was purified by preparation HPLC (FA as additive, Instrument: GX-p; Column: Phenomenex Synergi C18 150×25 mm, 10 um; Mobile phase: A for $H_2O$ (0.225% FA) and B for Acetonitrile; Gradient: B 3%-33% in 10 min linearly; Flow rate: 15 mL/min; Column temperature: R.T.; Wavelength: 220 nm, 254 nm) to afford the desired product. The mixture of atropisomers was separated by chiral SFC (Column: Cellucoat 50×4.6 mm I.D., 3 um Mobile phase: Phase A for $CO_2$, and Phase B for IPA (0.05% DEA); Gradient elution: 40% IPA (0.05% DEA) in $CO_2$ Flow rate: 3 mL/min; Detector: PDA; Column Temp: 35° C.; Back Pressure: 100 Bar) to obtain two products peaks. The peak 1 product: 1-1 (4.88 mg, 0.0082 mmol, 27.9% yield). MS (ESI) m/z 580.0 $[M+1]^+$; $^1$H NMR (400 MHz, METHANOL-$d_4$) δ 7.89 (s, 1H), 6.62 (s, 1H), 4.77 (br dd, J=13.6, 2.8 Hz, 1H), 4.63-4.52 (m, 3H), 3.95-3.87 (m, 2H), 3.76-3.69 (m, 2H), 3.64-3.48

(m, 2H), 3.16-3.02 (m, 1H), 2.96 (s, 3H), 2.45 (d, J=1.2 Hz, 3H), 2.39-2.28 (m, 1H), 2.13-1.93 (m, 7H). The peak 2 product 1-2 (3.79 mg, 0.0064 mmol, 21.7% yield) as a brown solid, MS (ESI) m/z 580.0 $[M+1]^+$; $^1H$ NMR (400 MHz, METHANOL-$d_4$) δ 7.85 (d, J=1.2 Hz, 1H), 6.61 (s, 1H), 4.62-4.36 (m, 4H), 3.73-3.59 (m, 4H), 3.28-3.21 (m, 1H), 3.15-3.03 (m, 1H), 2.67 (s, 3H), 2.60 (br d, J=9.2 Hz, 1H), 2.45 (d, J=1.2 Hz, 3H), 2.21 (s, 1H), 1.97-1.78 (m, 7H).

Examples in Table 1 were prepared according to procedures described for Example 1 from Intermediate 1J and the appropriate amine.

TABLE 1

| Example Number | Structure | Name | MS m/z: [M + H]+ | $^1H$ NMR |
|---|---|---|---|---|
| 1-3 | 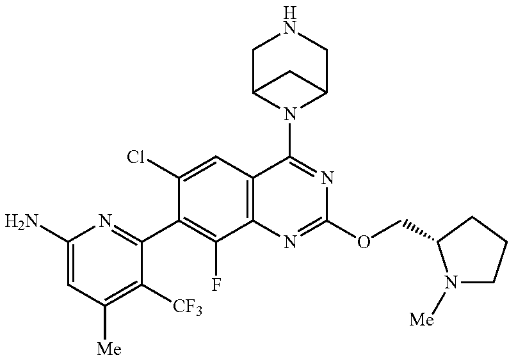 [SMILES: Cc1cc(N)nc(-c2c(Cl)cc3c(N4C5CNCC4C5)nc(OC[C@@H]4CCCN4C)nc3c2F)c1C(F)(F)F] | 6-(6-chloro-4-{3,6-diazabicyclo[3.1.1]heptan-6-yl}-8-fluoro-2-{[(2S)-1-methylpyrrolidin-2-yl]methoxy}quinazolin-7-yl)-4-methyl-5-(trifluoromethyl)pyridin-2-amine | 566.0 | (400 MHz, METHANOL-$d_4$) δ 7.84 (s, 1H), 6.66 (s, 1H), 5.20 (br s, 2H), 4.87-4.81 (m, 1H), 4.66 (br dd, J = 12.4, 6.4 Hz, 1H), 4.05-3.80 (m, 3H), 3.79-3.62 (m, 3H), 3.28-3.18 (m, 2H), 3.10 (s, 3H), 2.46 (br d, J = 1.2 Hz, 4H), 2.20 (br d, J = 2.4 Hz, 1H), 2.13-2.02 (m, 3H) |
| 1-4 | 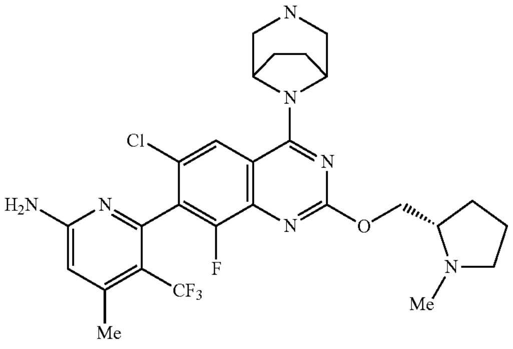 [SMILES: Cc1cc(N)nc(-c2c(Cl)cc3c(N4C5CCC4CNC5)nc(OC[C@@H]4CCCN4C)nc3c2F)c1C(F)(F)F] | 6-(6-chloro-4-{3,8-diazabicyclo[3.2.1]octan-8-yl}-8-fluoro-2-{[(2S)-1-methylpyrrolidin-2-yl]methoxy}quinazolin-7-yl)-4-methyl-5-(trifluoromethyl)pyridin-2-amine | 580.0 | (400 MHz, METHANOL-$d_4$) δ 7.95 (s, 1H), 6.62 (s, 1H), 5.08 (br s, 2H), 4.86-4.80 (m, 1H), 4.66 (br dd, J = 12.0, 6.0 Hz, 1H), 3.87-3.46 (m, 4H), 3.30-3.15 (m, 3H), 3.05 (s, 3H), 2.45 (br d, J = 1.2 Hz, 3H), 2.42-2.32 (m, 1H), 2.30-2.02 (m, 7H) |
| 1-5 | 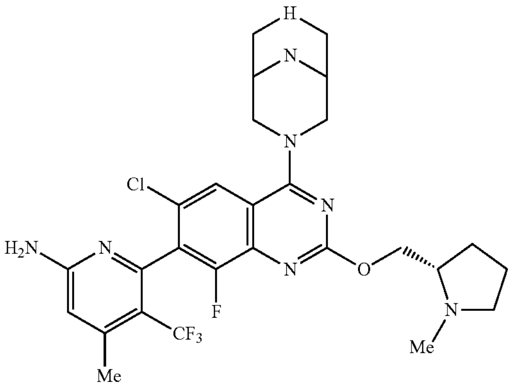 | 6-(6-chloro-4-{3,9-diazabicyclo[3.3.1]nonan-3-yl}-8-fluoro-2-{[(2S)-1-methylpyrrolidin-2-yl]methoxy}quinazolin-7-yl)-4-methyl-5-(trifluoromethyl)pyridin-2-amine | 594.3 | (400 MHz, $CD_3OD$) δ 8.50 (s, 1.8H), 7.94 (d, J = 1.2 Hz, 1H), 6.62 (s, 1H), 4.84-4.59 (m, 5H), 3.99-3.85 (m, 2H), 3.78-3.56 (m, 4H), 3.16-3.07 (m, 1H), 2.98 (s, 3H), 2.45 (d, J = 1.6 Hz, 3H), 2.40-2.29 (m, 1H), 2.20-2.01 (m, 8H) |

TABLE 1-continued

| Example Number | Structure | Name | MS m/z: [M + H]+ | $^1$H NMR |
|---|---|---|---|---|
| 1-6 | 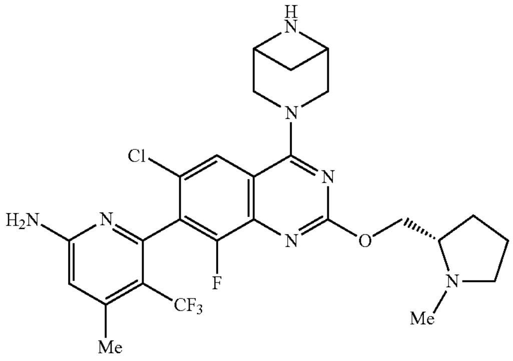 [SMILES: Cc1cc(N)nc(-c2c(Cl)cc3c(N4CC5CC(C4)N5)nc(OC[C@@H]4CCCN4C)nc3c2F)c1C(F)(F)F] | 6-(6-chloro-4-{3,6-diazabicyclo[3.1.1]heptan-3-yl}-8-fluoro-2-{[(2S)-1-methylpyrrolidin-2-yl]methoxy}quinazolin-7-yl)-4-methyl-5-(trifluoromethyl)pyridin-2-amine | 566.3 | (400 MHz, $CD_3OD$) δ 8.49 (s, 1H), 8.36 (s, 1H), 6.62 (s, 1H), 4.83-4.76 (m, 1H), 4.68-4.57 (m, 3H), 4.51-4.43 (m, 2H), 4.35-4.28 (m, 2H), 3.74-3.57 (m, 2H), 3.16-3.06 (m, 1H), 3.03-2.92 (m, 4H), 2.45 (s, 3H), 2.40-2.29 (m, 1H), 2.18-1.97 (m, 3H), 1.88 (d, J = 10..0 Hz, 1H) |
| 1-7 Isomer 1 | 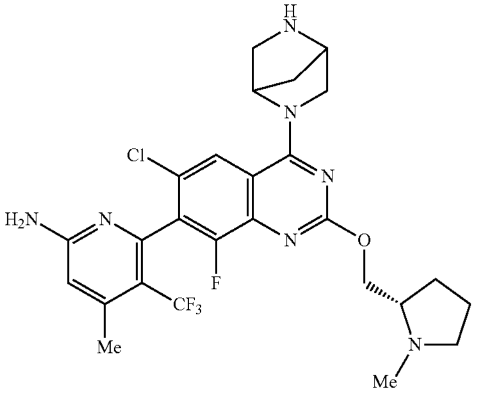 [SMILES: Cc1cc(N)nc(-c2c(Cl)cc3c(N4CC5CC4CN5)nc(OC[C@@H]4CCCN4C)nc3c2F)c1C(F)(F)F] | 6-(6-chloro-4-{2,5-diazabicyclo[2.2.1]heptan-2-yl}-8-fluoro-2-{[(2S)-1-methylpyrrolidin-2-yl]methoxy}quinazolin-7-yl)-4-methyl-5-(trifluoromethyl)pyridin-2-amine (Isomer 1) | 566.0 | (400 MHz, METHANOL-d4) δ 8.01 (s, 1H), 6.61 (s, 1H), 5.36 (s, 1H), 4.76 (br dd, J = 12.4, 3.2 Hz, 1H), 4.59 (dd, J = 12.4, 6.4 Hz, 1H), 4.45-4.27 (m, 2H), 4.02 (br d, J = 10.63 Hz, 1H), 3.67-3.42 (m, 3H), 3.35 (br s, 1H), 3.04 (br d, J = 10.8 Hz, 1H), 2.95 (s, 3H), 2.45 (d, J = 1.6 Hz, 3H), 2.37-223 (m, 2H), 2.15-1.92 (m, 4H) |
| 1-8 Isomer 2 | 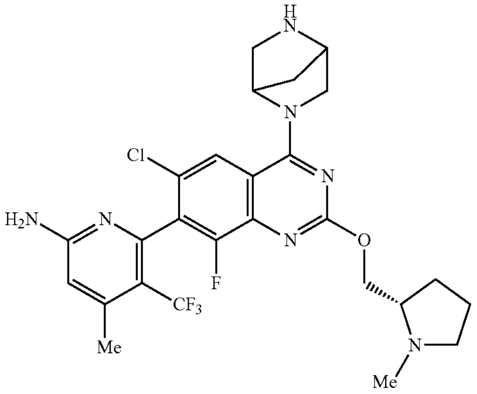 [SMILES: Cc1cc(N)nc(-c2c(Cl)cc3c(N4CC5CC4CN5)nc(OC[C@@H]4CCCN4C)nc3c2F)c1C(F)(F)F] | 6-(6-chloro-4-{2,5-diazabicyclo[2.2.1]heptan-2-yl}-8-fluoro-2-{[(2S)-1-methylpyrrolidin-2-yl]methoxy}quinazolin-7-yl)-4-methyl-5-(trifluoromethyl)pyridin-2-amine (Isomer 2) | 566.0 | (400 MHz, METHANOL-d4) δ 8.00 (s, 1H), 6.62 (s, 1H), 5.40 (s, 1H), 4.79 (br dd, J = 12.4, 2.8 Hz, 1H), 4.63 (dd, J = 12.4, 6.4 Hz, 1H), 4.48-4.40 (m, 2H), 4.06 (br d, J = 10.8 Hz, 1H), 3.78-3.67 (m, 1H), 3.65-3.54 (m, 2H),, 3.43 (br s, 1H), 3.18-3.07 (m, 1H), 3.00 (s, 3H), 2.45 (d, J = 1.2 Hz, 3H), 2.39-2.29 (m, 2H), 2.17-2.01 (m, 4H). |

Example 2-1

6-(6-chloro-4-{2,5-diazabicyclo[2.2.2]octan-2-yl}-8-fluoro-2-{[(2S)-1-methylpyrrolidin-2-yl]methoxy}quinazolin-7-yl)-4-methyl-5-(trifluoromethyl)pyridin-2-amine

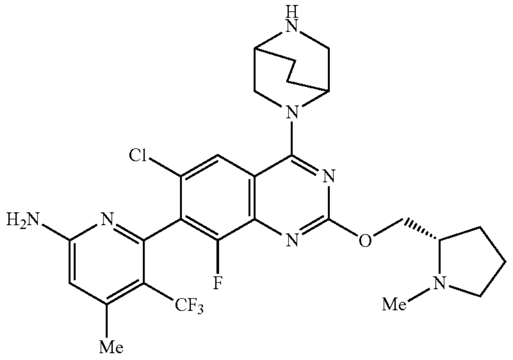 [SMILES: Cc1cc(N)nc(-c2c(Cl)cc3c(N4CC5CCC4CN5)nc(OC[C@@H]4CCCN4C)nc3c2F)c1C(F)(F)F]

Preparation of Intermediate 2A: 6-(4,6-dichloro-8-fluoro-2-(((S)-1-methylpyrrolidin-2-yl)methoxy)quinazolin-7-yl)-N,N-bis(4-methoxybenzyl)-4-methyl-5-(trifluoromethyl)pyridin-2-amine

2A

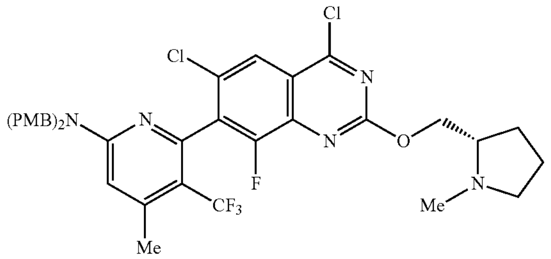

To a solution of 7-(6-(bis(4-methoxybenzyl)amino)-4-methyl-3-(trifluoromethyl)-pyridin-2-yl)-6-chloro-8-fluoro-2-(((S)-1-methylpyrrolidin-2-yl)methoxy)-quinazolin-4(3H)-one (50 mg, 0.07 mmol) in $POCl_3$ (1.5 mL, 16.09 mmol) was added DIEA (0.01 mL, 0.07 mmol). The reaction mixture was stirred at 50° C. for 3 hours. The reaction mixture was concentrated under reduced pressure and treated with ethyl acetate (10 mL). The mixture was poured into water (20 mL) and extracted with ethyl acetate (10 mL×2). The combined organic layers were washed with saturated $NaHCO_3$solution (20 mL) and brine (20 mL), dried over anhydrous sodium sulfate, filtered and concentrated under reduced pressure to provide the crude product 6-(4,6-dichloro-8-fluoro-2-(((S)-1-methylpyrrolidin-2-yl)methoxy)quinazolin-7-yl)-N,N-bis(4-methoxybenzyl)-4-methyl-5-(trifluoromethyl)pyridin-2-amine (50 mg, 0.067 mmol, 97.5% yield) as a yellow solid. MS (ESI) m/z: 744.0 $[M+H]^+$.

Preparation of Intermediate 2B: tert-butyl 5-(7-(6-(bis(4-methoxybenzyl)amino)-4-methyl-3-(trifluoromethyl)pyridin-2-yl)-6-chloro-8-fluoro-2-(((S)-1-methylpyrrolidin-2-yl)methoxy)quinazolin-4-yl)-2,5-diazabicyclo[2.2.2]octane-2-carboxylate

2B

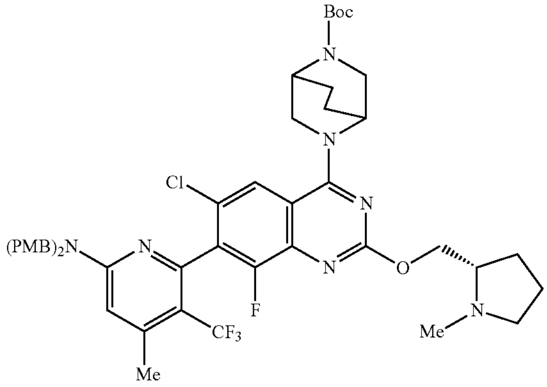

To a solution of 6-(4,6-dichloro-8-fluoro-2-(((S)-1-methylpyrrolidin-2-yl)methoxy)-quinazolin-7-yl)-N,N-bis(4-methoxybenzyl)-4-methyl-5-(trifluoromethyl)pyridin-2-amine (40 mg, 0.05 mmol) in DMA (2 mL) were added DIEA (0.02 mL, 0.2700 mmol) and tert-butyl 2,5-diazabicyclo[2.2.2]octane-2-carboxylate (31.7 mg, 0.15 mmol). The mixture was stirred at 50° C. for 12 hours. The reaction mixture was diluted with water (10 mL), and extracted with ethyl acetate (10 mL×3). The combined organic layers were washed with brine (20 mL×3), dried over anhydrous sodium sulfate, filtered and concentrated under reduced pressure. The residue was purified by preparation TLC (silica gel plate, dichloromethane: methanol=10:1) to provide the product (40 mg, 0.044 mmol, 80.9% yield) as a colorless oil. MS (ESI) m/z: 920.3 $[M+H]^+$.

Examples 2-1

6-(4,6-dichloro-8-fluoro-2-(((S)-1-methylpyrrolidin-2-yl)methoxy)quinazolin-7-yl)-N,N-bis(4-methoxybenzyl)-4-methyl-5-(trifluoromethyl)pyridin-2-amine

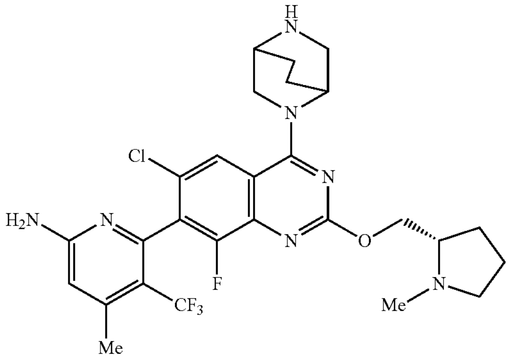 [SMILES: Cc1cc(N)nc(-c2c(Cl)cc3c(N4CC5CCC4CN5)nc(OC[C@@H]4CCCN4C)nc3c2F)c1C(F)(F)F]

A solution of tert-butyl 5-(7-(6-(bis(4-methoxybenzyl)amino)-4-methyl-3-(trifluoromethyl)pyridin-2-yl)-6-chloro-8-fluoro-2-(((S)-1-methylpyrrolidin-2-yl)methoxy)-quinazolin-4-yl)-2,5-diazabicyclo[2.2.2]octane-2-carboxylate (40 mg, 0.040 mmol) in TFA (4 mL, 52.24 mmol) was stirred at 50° C. for 4 hours. The mixture was then concentrated to dryness. The residue was purified by preparative HPLC (formic acid as additive, Instrument: ACSWH-GX-Q; Column: Shim-pack C18 150×25, 10 um; Mobile phase: A for $H_2O$ (0.225% FA) and B for Acetonitrile; Gradient: B 2%-35% in 11 min linearly; Flow rate: 25 mL/m; Column temperature: R.T.; Wavelength: 220 nm.254 nm) to afford the desired product (11.1 mg, 0.019 mmol, 44.2% yield) as a white solid. MS (ESI) m/z: 580.2 $[M+H]^+$; $^1H$ NMR (400 MHz, $CD_3OD$) δ 8.53 (s, 0.4H), 8.05 (s, 1H), 6.61 (s, 1H), 4.95 (br s, 1H), 4.68-4.49 (m, 2H), 4.35 (d, J=11.6 Hz, 1H), 4.27-4.19 (m, 1H), 3.62-3.33 (m, 4H), 2.86-2.70 (m, 4H), 2.45 (d, J=1.2 Hz, 3H), 2.40-2.18 (m, 2H), 2.16-1.79 (m, 7H).

Examples in Table 2 were prepared according to procedures described for Example 2 from Intermediate 2A and the appropriate amine.

TABLE 2

| Example Number | Structure | Name | m/z: [M + H]+ | $^1H$ NMR |
|---|---|---|---|---|
| 2-2 | 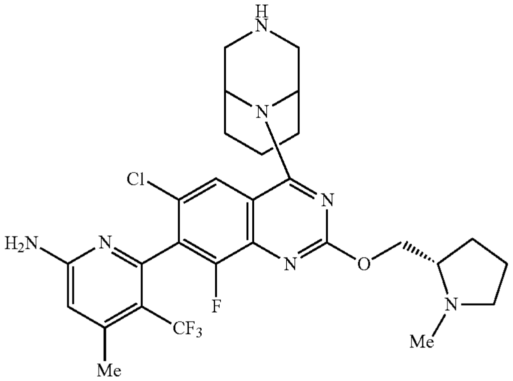 [SMILES: Cc1cc(N)nc(-c2c(Cl)cc3c(N4C5CCCC4CNC5)nc(OC[C@@H]4CCCN4C)nc3c2F)c1C(F)(F)F] | 6-(6-chloro-4-{3,9-diazabicyclo[3.3.1]nonan-9-yl}-8-fluoro-2-{[(2S)-1-methylpyrrolidin-2-yl]methoxy}quinazolin-7-yl)-4-methyl-5-(trifluoromethyl)pyridin-2-amine | 594.0 | (400 MHz, METHANOL-$d_4$) δ7.78 (s, 1H), 6.65 (br d, J = 7.2 Hz, 1H), 4.89-4.84 (m, 3H), 4.67 (br dd, J = 13.2, 7.2 Hz, 1H), 3.90 (br d, J = 6.00 Hz, 1H), 3.79-3.63 (m, 3H), 3.60-3.52 (m, 2H), 3.28-3.21 (m, 1H), 3.10 (s, 3H), 2.46 (br s, 3H), 2.43-2.29 (m, 3H), 2.28-2.16 (m, 2H), 2.14-2.01 (m, 4H), 2.00-1.90 (m, 1H) |

Example 3-1

6-(6-chloro-4-{2,5-diazabicyclo[2.2.1]heptan-2-yl}-8-fluoro-2-{[(2S)-1-methylpyrrolidin-2-yl]methoxy}quinazolin-7-yl)-4-methyl-5-(trifluoromethyl)pyridin-2-amine 3-1

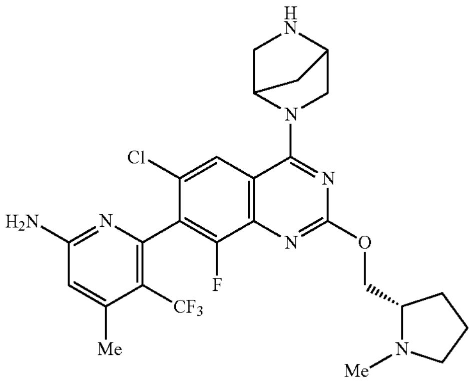

Preparation of Intermediate 3A: tert-butyl 5-(7-bromo-2,6-dichloro-8-fluoroquinazolin-4-yl)-2,5-diazabicyclo[2.2.1]heptane-2-carboxylate

3A

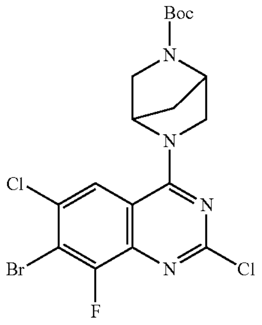

To a mixture of 7-bromo-2,4,6-trichloro-8-fluoro-quinazoline (2. g, 6.05 mmol) and tert-butyl 2,5-diazabicyclo [2.2.1]heptane-2-carboxylate (1.2 g, 6.05 mmol) in THE (100 mL) was added triethylamine (1.84 g, 18.16 mmol) and the mixture was stirred at 25° C. for 12h. The mixture was poured into water (200 mL). The mixture was separated and the aqueous phase was extracted with ethyl acetate (50 mL×2). The combine organic phase was washed with brine (30 mL), dried over anhydrous $Na_2SO_4$, filtered and the filtrate was concentrated. The residue was triturated in petroleum ether/ethyl acetate (50 mL/5 mL), then filtered and the filtrate was dried under reduced pressure to provide a yellow solid. $^1$H NMR (400 MHz, $CDCl_3$) δ=7.89-7.85 (m, 1H), 5.41-5.34 (m, 1H), 4.80-4.67 (m, 1H), 4.16-4.10 (m, 1H), 3.98-3.80 (m, 1H), 3.68-3.54 (m, 2H), 2.05-2.03 (m, 2H), 1.47-1.44 (m, 9H).

Preparation of Intermediate 3B: tert-butyl 5-(7-bromo-6-chloro-2,8-difluoroquinazolin-4-yl)-2,5-diazabicyclo[2.2.1]heptane-2-carboxylate

3B

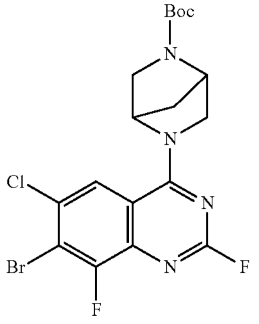

A mixture of tert-butyl 5-(7-bromo-2,6-dichloro-8-fluoro-quinazolin-4-yl)-2,5-diazabicyclo[2.2.1]heptane-2-carboxylate (1.8 g, 3.66 mmol) and THF (4.25 g, 73.15 mmol) in DMA (20 mL) was stirred at 140° C. for 12h. The mixture was added to water (100 mL), and extracted with ethyl acetate (30 mL×3). The combined organic phase was washed with brine (30 mL), dried over anhydrous $Na_2SO_4$, filtered and the filtrate was concentrated. The residue was purified by column chromatography ($SiO_2$, petroleum ether/ethyl acetate=7/1 to 4/1). tert-Butyl 5-(7-bromo-6-chloro-2,8-difluoro-quinazolin-4-yl)-2,5-diazabicyclo[2.2.1]heptane-2-carboxylate (1.4 g, 2.943 mmol, 80.5% yield) was obtained as a yellow solid. MS (ESI) m/z 476.9 $[M+1]^+$.

Preparation if Intermediate 3C: tert-butyl 5-(7-(6-(bis(4-methoxybenzyl)amino)-4-methylpyridin-2-yl)-6-chloro-2,8-difluoroquinazolin-4-yl)-2,5-diazabicyclo[2.2.1]heptane-2-carboxylate

3C

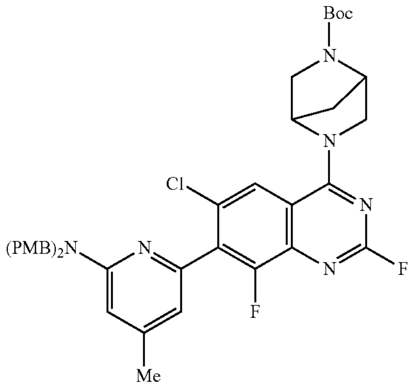

To a mixture of N,N-bis[(4-methoxyphenyl)methyl]-4-methyl-6-(4,4,5,5-tetramethyl-1,3,2-dioxaborolan-2-yl) pyridin-2-amine (2.09 g, 4.41 mmol), tert-butyl 5-(7-bromo-6-chloro-2,8-difluoro-quinazolin-4-yl)-2,5-diazabicyclo [2.2.1]heptane-2-carboxylate (1.4 g, 2.94 mmol), $K_3PO_4$ (1.25 g, 5.89 mmol) in 1,4-dioxane (20 mL) and water (5 mL) was added Pd(dppf)$Cl_2$·DCM (240 mg, 0.29 mmol) and the mixture was stirred at 60° C. for 4h under $N_2$ atmosphere. The mixture was diluted with water (100 mL), and extracted with ethyl acetate (30 mL×3). The combined organic phase was washed with brine (30 mL), dried over anhydrous $Na_2SO_4$, filtered and the filtrate was concentrated. The residue was purified by column chromatography ($SiO_2$, petroleum ether/ethyl acetate=5/1 to 3/1,). tert-Butyl 5-[7-[6-[bis[(4-methoxyphenyl)methyl]amino]-4-methyl-2-pyridyl]-6-chloro-2,8-difluoro-quinazolin-4-yl]-2,5-diazabicyclo[2.2.1]heptane-2-carboxylate (500 mg, 0.6727 mmol, 22. 9% yield) was obtained as a yellow solid. MS (ESI) m/z 743.5 $[M+1]^+$.

Preparation of Intermediate 3D: tert-butyl 5-(7-(6-(bis(4-methoxybenzyl)amino)-3-iodo-4-methylpyridin-2-yl)-6-chloro-2,8-difluoroquinazolin-4-yl)-2,5-diazabicyclo[2.2.1]heptane-2-carboxylate

3D

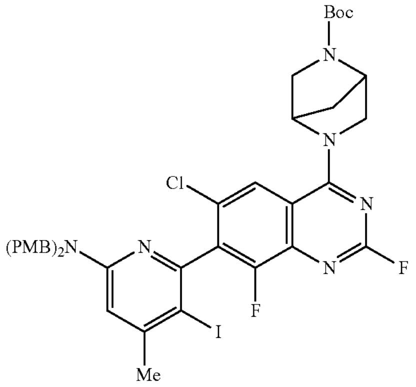

To a solution of tert-butyl 5-[7-[6-[bis[(4-methoxyphenyl)methyl]amino]-4-methyl-2-pyridyl]-6-chloro-2,8-difluoro-quinazolin-4-yl]-2,5-diazabicyclo[2.2.1]heptane-2-carboxylate (500. mg, 0.6700 mmol) in DMA (6 mL) was added N-iodosuccinimide (151.35 mg, 0.6700 mmol). Then TsOH (10 mg, 0.01 eq.) was added and the mixture was stirred at 25° C. for 12h. The mixture was diluted with water (100 mL), extracted with ethyl acetate (20 mL×3). The combined organic phase was washed with brine (20 mL), dried over anhydrous $Na_2SO_4$, filtered and the filtrate was concentrated. The residue was purified by column chromatography ($SiO_2$, petroleum ether/ethyl acetate=5/1 to 3/1). tert-Butyl 5-[7-[6-[bis[(4-methoxyphenyl)methyl]amino]-3-iodo-4-methyl-2-pyridyl]-6-chloro-2,8-difluoro-quinazolin-4-yl]-2,5-diazabicyclo[2.2.1]heptane-2-carboxylate (410 mg, 0.4717 mmol, 70.1% yield) was obtained as a yellow solid. MS (ESI) m/z 869.4 $[M+1]^+$.

Preparation of Intermediate 3E: tert-butyl 5-(7-(6-(bis(4-methoxybenzyl)amino)-4-methyl-3-(trifluoromethyl)pyridin-2-yl)-6-chloro-2,8-difluoroquinazolin-4-yl)-2,5-diazabicyclo[2.2.1]heptane-2-carboxylate

3E

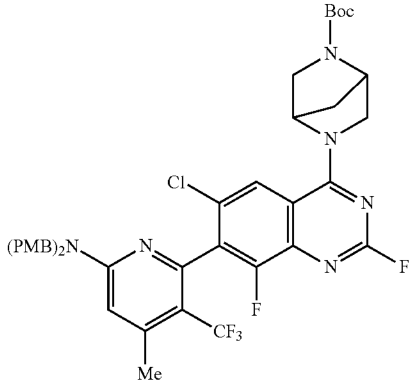

To a mixture of tert-butyl 5-[7-[6-[bis[(4-methoxyphenyl)methyl]amino]-3-iodo-4-methyl-2-pyridyl]-6-chloro-2,8-difluoro-quinazolin-4-yl]-2,5-diazabicyclo[2.2.1]heptane-2-carboxylate (400. mg, 0.4600 mmol) and CuI (262 mg, 1.38 mmol) in DMA (6 mL) was added methyl 2,2-difluoro-2-fluorosulfonyl-acetate (1326.21 mg, 6.9 mmol) and the mixture was stirred at 75° C. for 12h. The mixture was diluted with water (100 mL), extracted with ethyl acetate (30 mL×2). The combined organic phase was washed with brine (20 mL), dried over anhydrous $Na_2SO_4$, filtered and the filtrate was concentrated. The residue was purified by column chromatography ($SiO_2$, petroleum ether/ethyl acetate=4/1 to 3/1). tert-Butyl 5-[7-[6-[bis[(4-methoxyphenyl)methyl]amino]-4-methyl-3-(trifluoromethyl)-2-pyridyl]-6-chloro-2,8-difluoro-quinazolin-4-yl]-2,5-diazabicyclo[2.2.1]heptane-2-carboxylate (240 mg, 0.2958 mmol, 64.3% yield) was obtained as a yellow solid. MS (ESI) m/z 811.5 $[M+1]^+$.

Preparation of Intermediate 3F: tert-butyl 5-(7-(6-(bis(4-methoxybenzyl)amino)-4-methyl-3-(trifluoromethyl)pyridin-2-yl)-6-chloro-8-fluoro-2-(((S)-1-methylpyrrolidin-2-yl)methoxy)quinazolin-4-yl)-2,5-diazabicyclo[2.2.1]heptane-2-carboxylate

3F

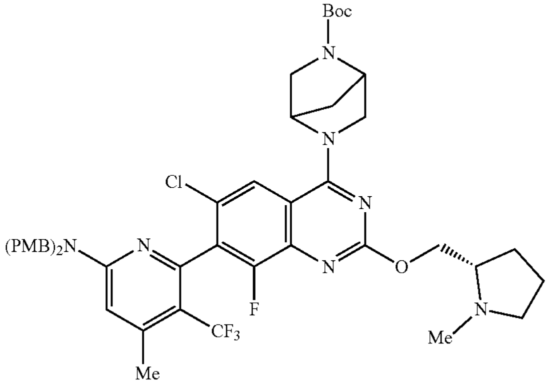

To a solution of (2S)-1-methylpyrrolidin-2-yl]methanol (102.22 mg, 0.8900 mmol) in THF (10 mL) was added NaH (59.17 mg, 1.48 mmol) at 0° C. and the mixture was stirred at 0° C. for 20 min. Then tert-butyl 5-[7-[6-[bis[(4-methoxyphenyl)methyl]amino]-4-methyl-3-(trifluoromethyl)-2-pyridyl]-6-chloro-2,8-difluoro-quinazolin-4-yl]-2,5-diazabicyclo[2.2.1]heptane-2-carboxylate (240. mg, 0.30 mmol) was added and the mixture was stirred at 0° C. for 1h. The mixture was added to cold sat·$NH_4Cl$ (30 mL), and extracted with ethyl acetate (30 mL×3). The combined organic phase was washed with brine (20 mL), dried over anhydrous $Na_2SO_4$, filtered and the filtrate was concentrated. The residue was purified by prep-TLC (DCM/MeOH=10/1). tert-Butyl 5-[7-[6-[bis[(4-methoxyphenyl)methyl]amino]-4-methyl-3-(trifluoromethyl)-2-pyridyl]-6-chloro-8-fluoro-2-[[rac-(2S)-1-methylpyrrolidin-2-yl]methoxy]quinazolin-4-yl]-2,5-diazabicyclo[2.2.1]heptane-2-carboxylate (160 mg, 0.1765 mmol, 59.7% yield) was obtained as a yellow solid. MS (ESI) m/z 906.9 $[M+1]^+$.

Example 3-1

6-(6-chloro-4-{2,5-diazabicyclo[2.2.1]heptan-2-yl}-8-fluoro-2-{[(2S)-1-methylpyrrolidin-2-yl]methoxy}quinazolin-7-yl)-4-methyl-5-(trifluoromethyl)pyridin-2-amine 3-1

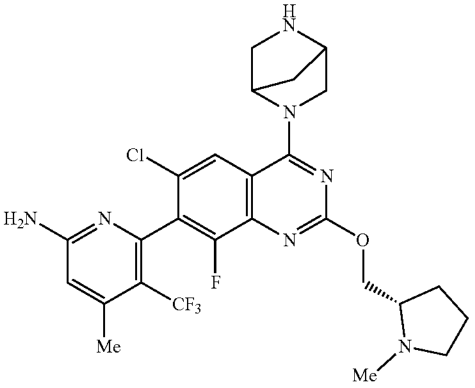

A solution of tert-butyl 5-[7-[6-[bis[(4-methoxyphenyl)methyl]amino]-4-methyl-3-(trifluoromethyl)-2-pyridyl]-6-chloro-8-fluoro-2-[[rac-(2S)-1-methylpyrrolidin-2-yl]methoxy]-quinazolin-4-yl]-2,5-diazabicyclo[2.2.1]heptane-2-carboxylate (140. mg, 0.1500 mmol) in TFA (5. mL, 65.3 mmol) was stirred at 50° C. for 4h. The mixture was concentrated under reduced pressure and the crude material was purified by prep-HPLC (formic acid as additive, Instrument: ACS-WH-GX-F; Column: Phenomenex luna C18 150×25 mm, 10 um; Mobile phase: A for $H_2O$ (0.225% FA) and B for Acetonitrile; Gradient: B 10%-35% in 10 min linearly; Flow rate: 25 mL/min; Column temperature: R.T.; Wavelength: 220 nm.254 nm) to afford the desired product. 6-[6-chloro-4-(2,5-diazabicyclo[2.2.1]heptan-2-yl)-8-fluoro-2-[[rac-(2S)-1-methylpyrrolidin-2-yl]methoxy]quinazolin-7-yl]-4-methyl-5-(trifluoromethyl)pyridin-2-amine (2.26 mg, 0.0039 mmol, 2.5% yield) was obtained as an off-white solid (14.86 mg, 0.0256 mmol,)$^1$H NMR (400 MHz, $CDCl_3$) δ=8.00 (d, J=1.6 Hz, 1H), 6.61 (s, 1H), 5.41 (s, 1H), 4.83-4.76 (m, 2H), 468-4.60 (m, 1H), 4.53-4.41 (m, 2H), 4.12-4.05 (m, 1H), 3.83-3.72 (m, 1H), 3.69-3.58 (m, 2H), 3.49-3.41 (m, 1H), 3.21-3.12 (m, 1H), 3.02 (s, 3H), 2.44 (s, 3H), 2.41-2.30 (m, 2H), 2.21-1.98 (m, 4H). MS (ESI) m/z 566.3 $[M+1]^+$.

Example 4-1

6-(6-chloro-8-fluoro-4-{8-methyl-3,8-diazabicyclo[3.2.1]octan-3-yl}-2-{[(2S)-1-methylpyrrolidin-2-yl]methoxy}quinazolin-7-yl)-4-methyl-5-(trifluoromethyl)pyridin-2-amine 4-1

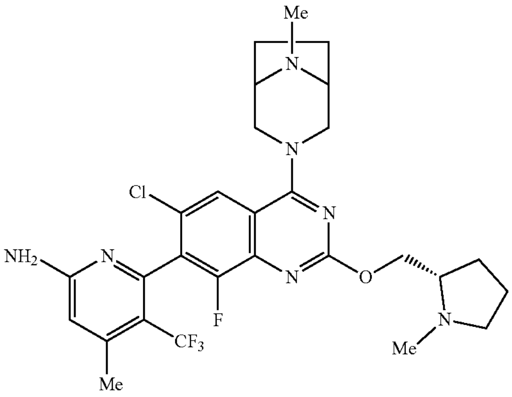

Preparation of Intermediate 4A: tert-butyl 3-(7-(6-(bis(4-methoxybenzyl)amino)-4-methyl-3-(trifluoromethyl)pyridin-2-yl)-6-chloro-8-fluoro-2-(((S)-1-methylpyrrolidin-2-yl)methoxy)quinazolin-4-yl)-3,8-diazabicyclo[3.2.1]octane-8-carboxylate

4A

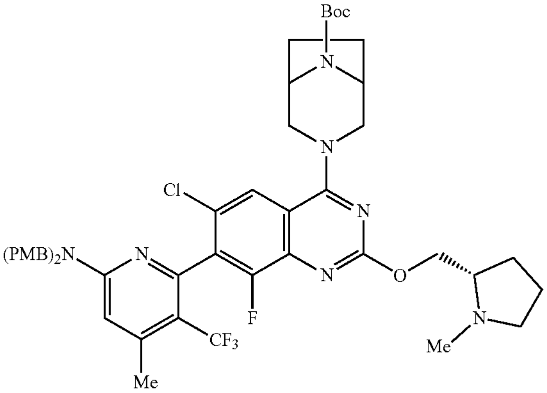

A solution of 7-(6-(bis(4-methoxybenzyl)amino)-4-methyl-3-(trifluoromethyl)pyridin-2-yl)-6-chloro-8-fluoro-2-(((S)-1-methylpyrrolidin-2-yl)methoxy)quinazolin-4(3H)-one (60. mg, 0.080 mmol), tert-butyl 3,8-diazabicyclo[3.2.1]octane-8-carboxylate (51.4 mg, 0.2400 mmol), BOP (108. mg, 0.2400 mmol) and DIEA (0.04 mL, 0.5000 mmol) in DCM (2 mL) was stirred at 25° C. for 12 hours. The reaction mixture was diluted with water (10 mL), then extracted with dichloromethane (15 mL×3). The combined organic layers were washed with brine (20 mL), dried over anhydrous sodium sulfate, filtered and concentrated under reduced pressure. The residue was purified by preparative HPLC (TFA as additive, Instrument: ACSWH-GX-N; Column: Phenomenex Synergi C18 150×25 mm, 10 um; Mobile phase: A for $H_2O$ (0.1% TFA) and B for Acetonitrile; Gradient: B 55%-85% in 10 min linearly; Flow rate: 25 mL/min; Column temperature: R.T.; Wavelength: 220 nm, 254 nm) to afford the product tert-butyl 3-(7-(6-(bis(4-methoxybenzyl)amino)-4-methyl-3-(trifluoromethyl)pyridin-2-yl)-6-chloro-8-fluoro-2-(((S)-1-methylpyrrolidin-2-yl)methoxy)quinazolin-4-yl)-3,8-diazabicyclo[3.2.1]octane-8-carboxylate (50 mg, 0.054 mmol, 65.7% yield) as a white solid. MS (ESI) m/z: 920.2 $[M+H]^+$.

Preparation of Intermediate 4B: 6-(4-(3,8-diazabicyclo[3.2.1]octan-3-yl)-6-chloro-8-fluoro-2-(((S)-1-methylpyrrolidin-2-yl)methoxy)quinazolin-7-yl)-N,N-bis(4-methoxybenzyl)-4-methyl-5-(trifluoromethyl)pyridin-2-amine

4B

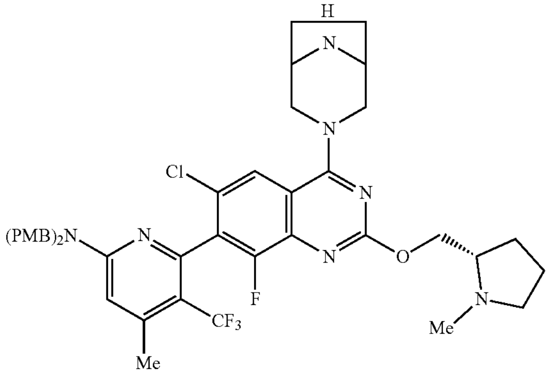

To a solution of tert-butyl 3-(7-(6-(bis(4-methoxybenzyl)amino)-4-methyl-3-(trifluoromethyl)pyridin-2-yl)-6-chloro-8-fluoro-2-(((S)-1-methylpyrrolidin-2-yl)methoxy)quinazolin-4-yl)-3,8-diazabicyclo[3.2.1]octane-8-carboxylate (45. mg, 0.05 mmol) in DCM (6 mL) was added HCl/EtOAc (2 mL, 0.05 mmol). The mixture was stirred at 20° C. for 2 hours. The reaction mixture was concentrated to afford the crude product 6-(4-(3,8-diazabicyclo[3.2.1]octan-3-yl)-6-chloro-8-fluoro-2-(((S)-1-methylpyrrolidin-2-yl)methoxy)quinazolin-7-yl)-N,N-bis(4-methoxybenzyl)-4-methyl-5-(trifluoromethyl)pyridin-2-amine (41 mg, 0.048 mmol, 97.9% yield, HCl salt) as a yellow solid. MS (ESI) m/z: 820.0 $[M+H]^+$.

Preparation of Intermediate 4C: 6-(6-chloro-8-fluoro-4-(8-methyl-3,8-diazabicyclo[3.2.1]octan-3-yl)-2-(((S)-1-methylpyrrolidin-2-yl)methoxy)quinazolin-7-yl)-N,N-bis(4-methoxybenzyl)-4-methyl-5-(trifluoromethyl)pyridin-2-amine

4C

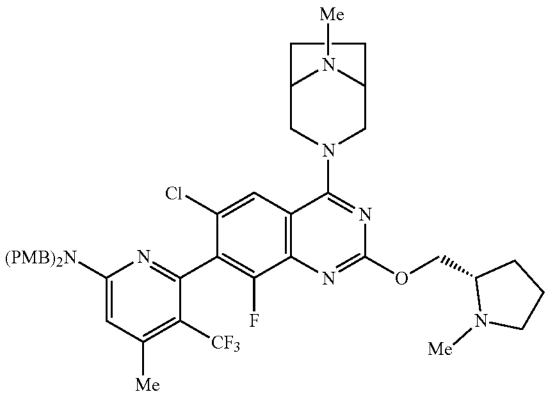

To a solution of 6-(4-(3,8-diazabicyclo[3.2.1]octan-3-yl)-6-chloro-8-fluoro-2-(((S)-1-methylpyrrolidin-2-yl)methoxy)quinazolin-7-yl)-N,N-bis(4-methoxybenzyl)-4-methyl-5-(trifluoromethyl)pyridin-2-amine (41 mg, 0.05 mmol) in methanol (5 mL) was added $Et_3N$ (0.01 mL, 0.10 mmol). Then AcOH (0.01 mL, 0.1000 mmol), HCHO (0.03 mL, 0.1500 mmol) and $NaBH_3CN$ (9. mg, 0.1400 mmol) were added. The mixture was stirred at 20° C. for 12 hours. The reaction mixture was diluted with EtOAc (10 mL) and water (10 mL). The mixture was extracted with EtOAc (10 mL×3). The combined organic layers were washed with brine (20 mL), dried over anhydrous $Na_2SO_4$, filtered and concentrated in vacuum to afford the crude product 6-(6-chloro-8-fluoro-4-(8-methyl-3,8-diazabicyclo[3.2.1]octan-3-yl)-2-(((S)-1-methylpyrrolidin-2-yl)methoxy)quinazolin-7-yl)-N,N-bis(4-methoxybenzyl)-4-methyl-5-(trifluoromethyl)pyridin-2-amine (40 mg, 0.048 mmol, 100% yield) as a colorless solid. MS (ESI) m/z: 834.3 $[M+H]^+$.

Example 4-1

6-(6-chloro-8-fluoro-4-{8-methyl-3,8-diazabicyclo[3.2.1]octan-3-yl}-2-{[(2S)-1-methylpyrrolidin-2-yl]methoxy}quinazolin-7-yl)-4-methyl-5-(trifluoromethyl)pyridin-2-amine 4-1

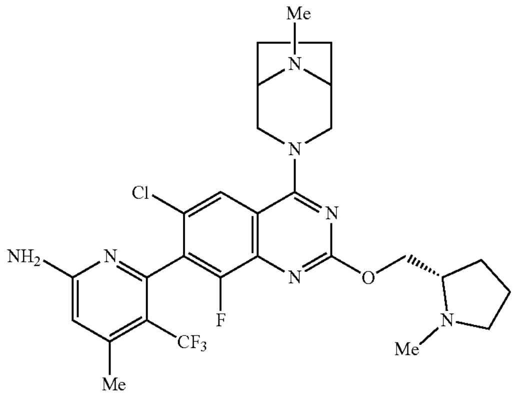

A solution of 6-(6-chloro-8-fluoro-4-(8-methyl-3,8-diazabicyclo[3.2.1]octan-3-yl)-2-(((S)-1-methylpyrrolidin-2-yl)methoxy)quinazolin-7-yl)-N,N-bis(4-methoxybenzyl)-4-methyl-5-(trifluoromethyl)pyridin-2-amine (40 mg, 0.05 mmol) in TFA (4 mL, 52.24 mmol) was stirred at 50° C. for 4 hours. The mixture was concentrated reduced pressure. The residue was purified by preparative HPLC (formic acid as additive, Instrument: GX-p; Column: Phenomenex luna C18 150*25 mm*10 um; Mobile phase: A for $H_2O$ (0.225% FA) and B for Acetonitrile; Gradient: B 3%-33% in 10 min linearly; Flow rate: 25 mL/min.; Column temperature: R.T.; Wavelength: 220 nm.254 nm) to afford 6-(6-chloro-8-fluoro-4-(8-methyl-3,8-diazabicyclo[3.2.1]octan-3-yl)-2-(((S)-1-methylpyrrolidin-2-yl)methoxy)quinazolin-7-yl)-4-methyl-5-(trifluoromethyl)pyridin-2-amine (12.28 mg, 0.021 mmol, 43% yield) as a yellow solid. MS (ESI) m/z: 594.2 $[M+H]^+$, $^1H$ NMR (400 MHz, $CD_3OD$) δ 8.46 (s, 1.9H), 7.91 (s, 1H), 6.62 (s, 1H), 4.86-4.79 (m, 1H), 4.70-4.51 (m, 3H), 3.91-3.79 (m, 3H), 3.76 (br s, 2H), 3.72-3.63 (m, 1H), 3.25-3.16 (m, 1H), 3.05 (s, 3H), 2.67 (s, 3H), 2.45 (d, J=1.2 Hz, 3H), 2.41-2.33 (m, 1H), 2.26-2.15 (m, 3H), 2.12-2.02 (m, 2H), 1.98-1.87 (m, 2H).

Example 5-1

4-(6-chloro-4-{3,8-diazabicyclo[3.2.1]octan-3-yl}-8-fluoro-2-{[(2R)-1-(piperidin-1-yl)propan-2-yl]oxy}quinazolin-7-yl)naphthalen-2-ol 5-1

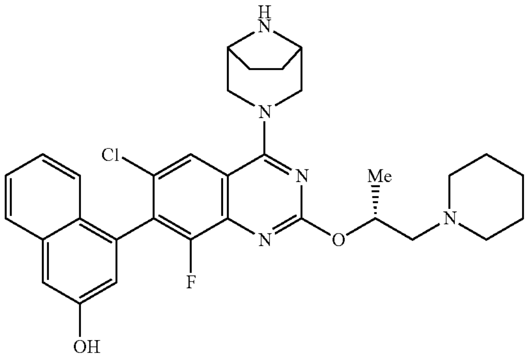

Preparation of Intermediate 5A: tert-butyl 3-(7-bromo-2,6-dichloro-8-fluoroquinazolin-4-yl)-3,8-diazabicyclo[3.2.1]octane-8-carboxylate

5A

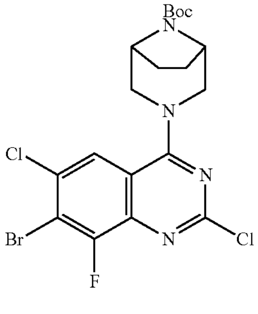

To a solution of 7-bromo-2,4,6-trichloro-8-fluoroquinazoline (3.5 g, 10.6 mmol) and tert-butyl 3,8-diazabicyclo[3.2.1]octane-8-carboxylate (2240 mg, 10.55 mmol) in THE (50 mL) was added DIEA (2.48 mL, 26.5 mmol). The mixture was stirred at 20° C. for 12 h. LCMS showed the reaction was completed and desired product was detected. The reaction mixture was diluted with EtOAc (40 mL) and water (40 mL). The mixture was extracted with EtOAc (40 mL×3). The combined organic layers were washed with brine (100 mL), dried over anhydrous $Na_2SO_4$, filtered and concentrated in vacuum. The crude product tert-butyl 3-(7-bromo-2,6-dichloro-8-fluoroquinazolin-4-yl)-3,8-diazabicyclo[3.2.1]octane-8-carboxylate (5.3 g, 10.5 mmol, 98.8% yield 0 was used in the next step without purification. MS (ESI) m/z: 506.9 $[M+3]^+$. $^1H$ NMR (400 MHz, $CDCl_3$) δ 7.75 (d, J=2.0 Hz, 1H), 4.40 (s, 4H), 3.78-3.51 (m, 2H), 2.02-1.90 (m, 2H), 1.77-1.67 (m, 2H), 1.53 (s, 9H).

Preparation of Intermediate 5B: tert-butyl 3-(7-bromo-6-chloro-2-(((R)-1,1-dimethoxypropan-2-yl)oxy)-8-fluoroquinazolin-4-yl)-3,8-diazabicyclo[3.2.1]octane-8-carboxylate

5B

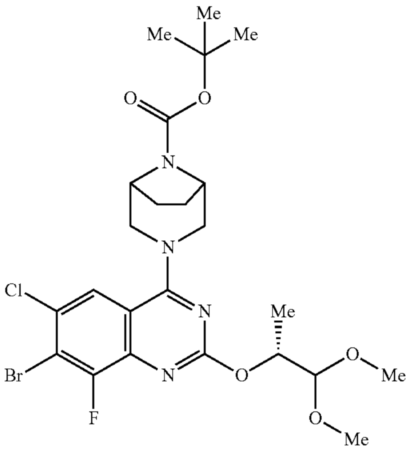

To a solution of tert-butyl 3-(7-bromo-2,6-dichloro-8-fluoroquinazolin-4-yl)-3,8-diazabicyclo[3.2.1]octane-8-carboxylate (1000 mg, 1.98 mmol) in MeCN (80 mL) was added cesium carbonate (1280 mg, 3.93 mmol), 1,4-diazabicyclo[2.2.2]octane (40 mg, 0.36 mmol) and (R)-1,1-dimethoxypropan-2-ol (400 mg, 3.33 mmol) at 20° C. The mixture was stirred at 45° C. for 2 h. TLC (petroleum ether:ethyl acetate=4:1) indicated one major new spot with larger polarity was observed. The reaction was diluted with EtOAc (30 mL), and filtered. The filtrate was concentrated in vacuum. The residue was purified by column chromatography (silica gel, petroleum ether: EtOAc=20:1 to 4:1, Rf=0.3) to afford tert-butyl 3-(7-bromo-6-chloro-2-(((R)-1,1-dimethoxypropan-2-yl)oxy)-8-fluoroquinazolin-4-yl)-3,8-diazabicyclo[3.2.1]octane-8-carboxylate (1000 mg, 1.70 mmol, 85.8% yield) as a yellow oil. MS (ESI) m/z: 591.0 $[M+3]^+$. $^1H$ NMR (400 MHz, $CDCl_3$) δ 7.70 (d, J=2.0 Hz, 1H), 5.48-5.37 (m, 1H), 4.51 (d, J=5.6 Hz, 1H), 4.31 (d, J=12.0 Hz, 4H), 3.64-3.52 (m, 2H), 3.49-3.45 (m, 6H), 2.00-1.91 (m, 2H), 1.83-1.73 (m, 2H), 1.52 (s, 9H), 1.40 (d, J=6.4 Hz, 3H).

Preparation of Intermediate 5C: (2R)-2-((4-(3,8-diazabicyclo[3.2.1]octan-3-yl)-6-chloro-8-fluoro-7-(3-hydroxynaphthalen-1-yl)quinazolin-2-yl)oxy)propanal

5C

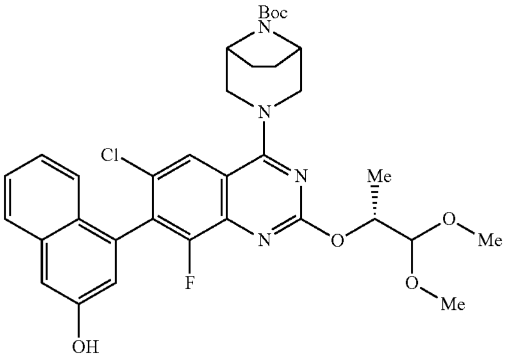

To a solution of tert-butyl 3-(7-bromo-6-chloro-2-(((R)-1,1-dimethoxypropan-2-yl)oxy)-8-fluoroquinazolin-4-yl)-3,8-diazabicyclo[3.2.1]octane-8-carboxylate (950 mg, 1.61 mmol) and (3-hydroxynaphthalen-1-yl)boronic acid (285 mg, 1.52 mmol) in THE (20 mL) and water (2 mL) was added potassium phosphate (703 mg, 3.31 mmol) and Xphos-Pd-G3 (133 mg, 0.16 mmol). The reaction was stirred at 60° C. for 12 h under $N_2$. LCMS showed the reaction was completed. The mixture was filtered, and the filtrate was concentrated. The residue was purified by flash silica gel chromatography (petroleum ether:ethyl acetate=10:1 to 2:1) to afford (2R)-2-((4-(3,8-diazabicyclo[3.2.1]octan-3-yl)-6-chloro-8-fluoro-7-(3-hydroxynaphthalen-1-yl)quinazolin-2-yl)oxy)propanal (0.8 g, 1.22 mmol, 76.0% yield) as a yellow solid. MS (ESI) m/z: 653.1 $[M+H]^+$. $^1H$ NMR (400 MHz, $CDCl_3$) δ 7.71-7.63 (m, 2H), 7.37-7.30 (m, 1H), 7.26-7.20 (m, 2H), 7.17-7.10 (m, 1H), 7.04 (dd, J=8.8, 2.4 Hz, 1H), 5.36-5.23 (m, 1H), 4.48-4.23 (m, 5H), 3.68-3.46 (m, 2H), 3.40-3.34 (m, 6H), 1.94-1.86 (m, 2H), 1.82-1.73 (m, 2H), 1.46 (s, 9H), 1.36-1.30 (m, 3H).

Preparation of Intermediate 5D: tert-butyl 3-(6-chloro-2-(((R)-1,1-dimethoxypropan-2-yl)oxy)-8-fluoro-7-(3-hydroxynaphthalen-1-yl)quinazolin-4-yl)-3,8-diazabicyclo[3.2.1]octane-8-carboxylate

5D

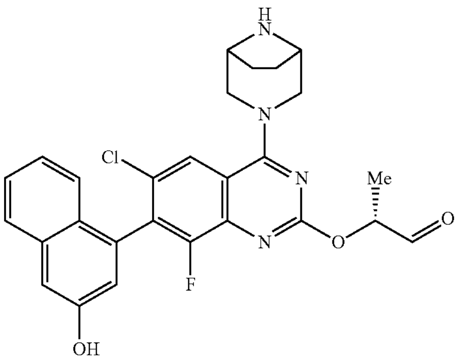

To a solution of tert-butyl 3-(6-chloro-2-(((R)-1,1-dimethoxypropan-2-yl)oxy)-8-fluoro-7-(3-hydroxynaphthalen-1-yl)quinazolin-4-yl)-3,8-diazabicyclo[3.2.1]octane-8-carboxylate (750 mg, 1.15 mmol) in 1,4-dioxane (20 mL) was added HCl (1.05 mL, 12.63 mmol). The mixture was stirred at 20° C. for 12 h. LCMS showed the desired product. The residue was concentrated in vacuum. The crude product (2R)-2-((4-(3,8-diazabicyclo[3.2.1]octan-3-yl)-6-chloro-8-fluoro-7-(3-hydroxynaphthalen-1-yl)quinazolin-2-yl)oxy)propanal (624 mg, 1.15 mmol, 100% yield) as a yellow solid, which was used into next step without purification. MS (ESI) m/z: 507.2 $[M+H]^+$.

Preparation of Intermediate 5E: tert-butyl 3-(6-chloro-8-fluoro-7-(3-hydroxynaphthalen-1-yl)-2-(((R)-1-(piperidin-1-yl)propan-2-yl)oxy)quinazolin-4-yl)-3,8-diazabicyclo[3.2.1]octane-8-carboxylate

5E

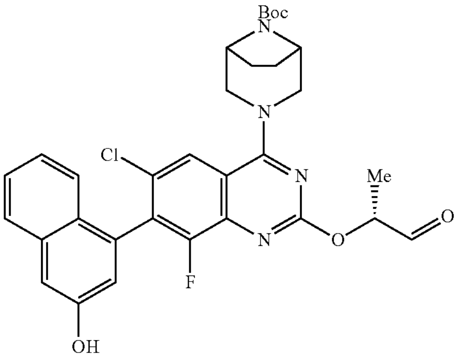

To a solution of (2R)-2-((4-(3,8-diazabicyclo[3.2.1]octan-3-yl)-6-chloro-8-fluoro-7-(3-hydroxynaphthalen-1-yl)quinazolin-2-yl)oxy)propanal (624 mg, 1.15 mmol) in THE (30 mL) and water (10 mL) was added $NaHCO_3$(0.81 mL, 5.94 mmol) and $(Boc)_2O$ (0.42 mL, 1.83 mmol). The mixture was stirred at 20° C. for 2 h. LCMS showed the reaction was completed and the desired MS was detected. The reaction mixture was diluted with EtOAc (20 mL) and water (20 mL). The mixture was extracted with EtOAc (20 mL×3). The combined organic layers were washed with brine (40 mL), dried over anhydrous $Na_2SO_4$, filtered and concentrated in vacuum. The residue was purified by column chromatography (silica gel, Petroleum ether: Ethyl acetate=5:1 to 1:1) to afford tert-butyl 3-(6-chloro-8-fluoro-7-(3-hydroxynaphthalen-1-yl)-2-(((R)-1-(piperidin-1-yl)propan-2-yl)oxy)quinazolin-4-yl)-3,8-diazabicyclo[3.2.1]octane-8-carboxylate (470 mg, 0.7742 mmol, 67.3% yield) as a yellow solid. MS (ESI) m/z: 607.2 $[M+H]^+$.

Preparation of Intermediate 5F: tert-butyl 3-(6-chloro-8-fluoro-7-(3-hydroxynaphthalen-1-yl)-2-(((R)-1-oxopropan-2-yl)oxy)quinazolin-4-yl)-3,8-diazabicyclo[3.2.1]octane-8-carboxylate

5F

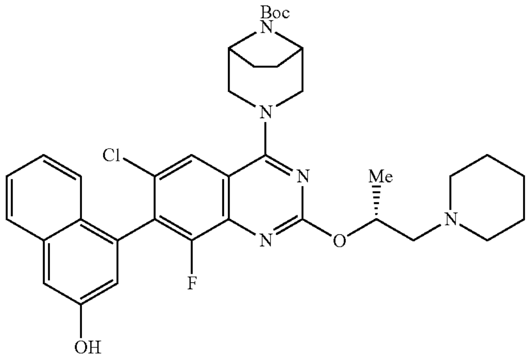

A mixture of tert-butyl 3-(6-chloro-8-fluoro-7-(3-hydroxynaphthalen-1-yl)-2-(((R)-1-oxopropan-2-yl)oxy)quinazolin-4-yl)-3,8-diazabicyclo[3.2.1]octane-8-carboxylate (80 mg, 0.13 mmol), piperidine (32 mg, 0.38 mmol) and AcOH (0.01 mL, 0.09 mmol) in methanol (2 mL) was added $NaBH_3CN$ (32 mg, 0.51 mmol). The mixture was stirred at 20° C. for 12 hours. LCMS showed the reaction was completed and the desired product was detected. The reaction mixture was diluted with EtOAc (10 mL) and water (10 mL). The mixture was extracted with EtOAc (10 mL×3). The combined organic layers were washed with brine (20 mL), dried over anhydrous $Na_2SO_4$, filtered and concentrated in vacuum. The residue was purified by column chromatography (silica gel, Petroleum ether/Ethyl acetate=10/1 to 1/2) to afford tert-butyl 3-(6-chloro-8-fluoro-7-(3-hydroxynaphthalen-1-yl)-2-(((R)-1-(piperidin-1-yl)propan-2-yl)oxy)quinazolin-4-yl)-3,8-diazabicyclo[3.2.1]octane-8-carboxylate (80 mg, 0.118 mmol, 89.8% yield) as a yellow solid. MS (ESI) m/z: 676.2 $[M+H]^+$.

Example 5-1

4-(6-chloro-4-{3,8-diazabicyclo[3.2.1]octan-3-yl}-8-fluoro-2-{[(2R)-1-(piperidin-1-yl)propan-2-yl]oxy}quinazolin-7-yl)naphthalen-2-ol 5-1

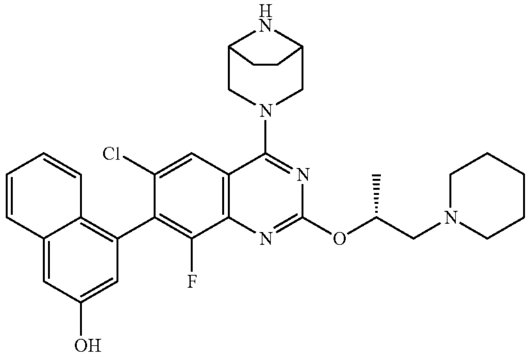

To a solution of tert-butyl 3-(6-chloro-8-fluoro-7-(3-hydroxynaphthalen-1-yl)-2-(((R)-1-(piperidin-1-yl)propan-2-yl)oxy)quinazolin-4-yl)-3,8-diazabicyclo[3.2.1]octane-8-carboxylate (60 mg, 0.09 mmol) in DCM (3 mL) was added TFA (0.5 mL, 6.53 mmol). The mixture was stirred at 20° C. for 12 h. LCMS showed that the desired product was detected. The reaction mixture was concentrated in vacuum. The residue was purified by preparation HPLC (formic acid as additive, Instrument: GX-c; Column: Phenomenex luna C18 150×25 mm×10 um; Mobile phase: A for $H_2O$ (0.225% FA) and B for Acetonitrile; Gradient: B 3%-33% in 10 min linearly; Flow rate: 25 mL/m; Column temperature: R.T.; Wavelength: 220 nm.254 nm) to afford the desired product 4-(4-(3,8-diazabicyclo[3.2.1]octan-3-yl)-6-chloro-8-fluoro-2-(((R)-1-(piperidin-1-yl)propan-2-yl)oxy)quinazolin-7-yl)naphthalen-2-ol (32.9 mg, 0.0571 mmol, 64.4% yield) as yellow solid. MS (ESI) m/z: 576.3 $[M+H]^+$. $^1H$ NMR (400 MHz, $CD_3OD$) δ 8.50 (s, 1H), 8.00 (d, J=1.2 Hz, 1H), 7.76 (d, J=8.0 Hz, 1H), 7.48-7.36 (m, 1H), 7.27 (d, J=2.4 Hz, 1H), 7.25-7.16 (m, 2H), 7.07-7.00 (m, 1H), 5.74-5.62 (m, 1H), 4.67-4.53 (m, 2H), 3.94 (s, 2H), 3.77 (dd, J=13.2, 10.0 Hz, 2H), 3.46-3.33 (m, 2H), 3.27-3.08 (m, 4H), 2.00 (s, 4H), 1.85-1.70 (m, 4H), 1.66-1.55 (m, 2H), 1.47 (d, J=5.6 Hz, 3H).

Example 5-2

1-[(2R)-2-[(6-chloro-4-{3,8-diazabicyclo[3.2.1]octan-3-yl}-8-fluoro-7-(3-hydroxynaphthalen-1-yl)quinazolin-2-yl)oxy]propyl]piperidin-4-ol 5-2

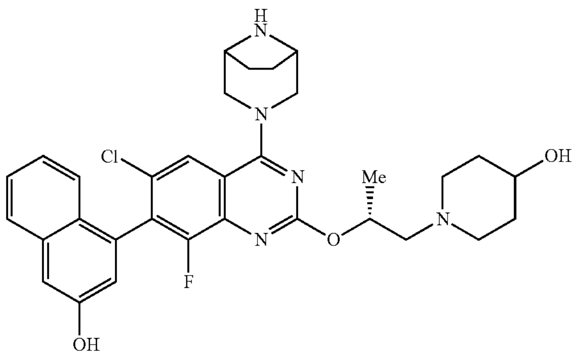

Preparation of Intermediate 5G: tert-butyl 3-(6-chloro-8-fluoro-7-(3-hydroxynaphthalen-1-yl)-2-(((R)-1-(4-hydroxypiperidin-1-yl)propan-2-yl)oxy)quinazolin-4-yl)-3,8-diazabicyclo[3.2.1]octane-8-carboxylate

5G

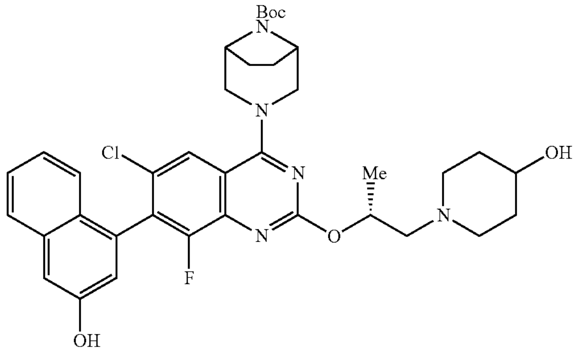

To a mixture of tert-butyl 3-(6-chloro-8-fluoro-7-(3-hydroxynaphthalen-1-yl)-2-(((R)-1-oxopropan-2-yl)oxy)quinazolin-4-yl)-3,8-diazabicyclo[3.2.1]octane-8-carboxylate (100. mg, 0.1600 mmol), piperidin-4-ol (47. mg, 0.4600 mmol) and AcOH (0. mL, 0.0800 mmol) in methanol (5 mL) was added $NaBH_3CN$ (40. mg, 0.6400 mmol). The mixture was stirred at 25° C. for 12 hours. LCMS showed the reaction was complete and one peak with the desired mass was detected. The reaction mixture was diluted with water (20 mL), then extracted with ethyl acetate (15 mL*3). The combined organic layers were washed with brine (30 mL), dried over anhydrous sodium sulfate, filtered and concentrated under reduced pressure to provide a residue. The residue was purified by preparation TLC (silica gel plate, dichloromethane: methanol=10:1) to provide desired product tert-butyl 3-(6-chloro-8-fluoro-7-(3-hydroxynaphthalen-1-yl)-2-(((R)-1-(4-hydroxypiperidin-1-yl)propan-2-yl)oxy)quinazolin-4-yl)-3,8-diazabicyclo[3.2.1]octane-8-carboxylate (70 mg, 0.10 mmol, 61.4% yield) as an off-white solid. MS (ESI) m/z: 692.4 $[M+H]^+$.

Example 5-2

1-[(2R)-2-[(6-chloro-4-{3,8-diazabicyclo[3.2.1]octan-3-yl}-8-fluoro-7-(3-hydroxynaphthalen-1-yl)quinazolin-2-yl)oxy]propyl]piperidin-4-ol 5-2

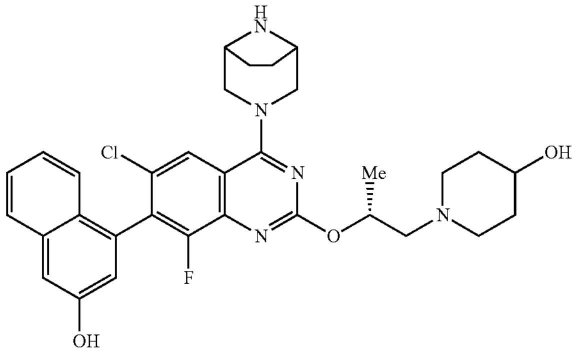

To a solution of tert-butyl 3-(6-chloro-8-fluoro-7-(3-hydroxynaphthalen-1-yl)-2-(((R)-1-(4-hydroxypiperidin-1-yl)propan-2-yl)oxy)quinazolin-4-yl)-3,8-diazabicyclo[3.2.1]octane-8-carboxylate (70. mg, 0.10 mmol) in DCM (3 mL) was added TFA (1. mL, 13.06 mmol). The mixture was stirred at 25° C. for 2 hours. LCMS showed the reactant 1 was consumed completely and one main peak with the desired MS was detected. The reaction mixture was concentrated under reduced pressure. The residue was purified by preparation HPLC (formic acid as additive, Instrument: GX-c; Column: Phenomenex luna C18 150×25 mmx 10 um; Mobile phase: A for H2O (0.225% FA) and B for Acetonitrile; Gradient: B 3%-33% in 10 min linearly; Flow rate: 25 mL/m; Column temperature: R.T.; Wavelength: 220 nm.254 nm) to afford the desired product 1-((2R)-2-((4-(3,8-diazabicyclo[3.2.1]octan-3-yl)-6-chloro-8-fluoro-7-(3-hydroxynaphthalen-1-yl)quinazolin-2-yl)oxy)propyl)piperidin-4-ol (24.99 mg, 0.041 mmol, 41.0% yield, 1.1 FA salt) as a yellow solid. MS (ESI) m/z: 592.2 $[M+H]^+$. $^1H$ NMR (400 MHz, $CD_3OD$) δ 8.46 (s, 1.1H), 8.00 (s, 1H), 7.76 (d, J=8.4 Hz, 1H), 7.47-7.39 (m, 1H), 7.28 (d, J=2.4 Hz, 1H), 7.25-7.16 (m, 2H), 7.05-6.99 (m, 1H), 5.78-5.62 (m, 1H), 4.64 (t, J=11.2 Hz, 2H), 4.11 (br s, 2H), 3.84 (dd, J=13.2, 6.0 Hz, 3H), 3.53-3.42 (m, 1H), 3.41-3.32 (m, 2H), 3.21 (d, J=12.8 Hz, 2H), 3.09-2.97 (m, 1H), 2.09 (br s, 4H), 2.03-1.88 (m, 2H), 1.79-1.64 (m, 2H), 1.47 (d, J=6.0 Hz, 3H).

Examples 6-1

4-(6-chloro-4-{3,8-diazabicyclo[3.2.1]octan-3-yl}-8-fluoro-2-{[(2S)-1-methylpyrrolidin-2-yl]methoxy}quinazolin-7-yl)naphthalen-2-ol 6-1

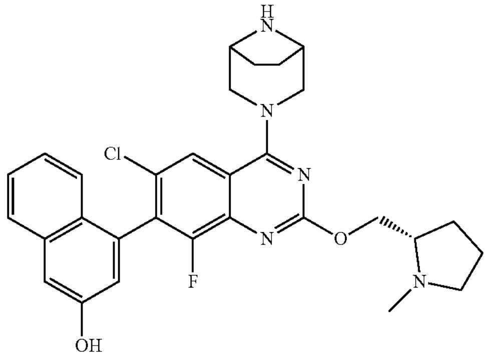

Preparation of Intermediate 6A: tert-butyl 3-(7-bromo-2,6-dichloro-8-fluoroquinazolin-4-yl)-3,8-diazabicyclo[3.2.1]octane-8-carboxylate

6A

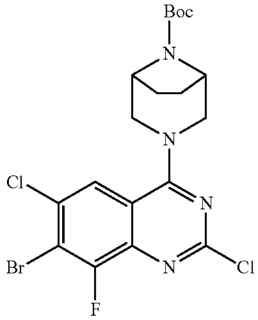

To a solution of 7-bromo-2,4,6-trichloro-8-fluoroquinazoline (300 mg, 3.03 mmol) in dioxane (8 mL) was added DIPEA (0.476 mL, 2.72 mmol) and tert-butyl 3,8-diazabicyclo[3.2.1]octane-8-carboxylate (193 mg, 0.908 mmol). The resulting mixture was stirred at 25° C. for 2 hours. LCMS showed the reaction was completed. The mixture was concentrated. The residue was diluted with ethyl acetate (50 mL) and washed with water (30 mL×2) and brine (50 mL). The organic phase was dried over anhydrous sodium sulphate, filtered and concentrated under reduced pressure. The residue was purified by silica gel column chromatography (12 g ISCO column, MeOH/DCM, 0-5%, 20 min.) to afford tert-butyl 4-(7-bromo-2,6-dichloro-8-fluoroquinazolin-4-yl)piperazine-1-carboxylate (415 mg, 0.82 mmol, 90% yield) as a white solid. MS (ESI) m/z 507.0 $[M+1]^+$. $^1H$ NMR (499 MHz, DMSO-$d_6$) δ 8.10 (d, J=1.9 Hz, 1H), 4.38 (br d, J=10.6 Hz, 2H), 4.25 (br s, 2H), 3.66 (m, 2H) 1.79 (m, 2H), 1.62 (m, 2H), 1.47 s, 9H).

Preparation of Intermediate 6B: tert-butyl-3-(7-bromo-6-chloro-8-fluoro-2-(((S)-1-methylpyrrolidin-2-yl)methoxy)quinazolin-4-yl)-3,8-diazabicyclo[3.2.1]octane-8-carboxylate

6B

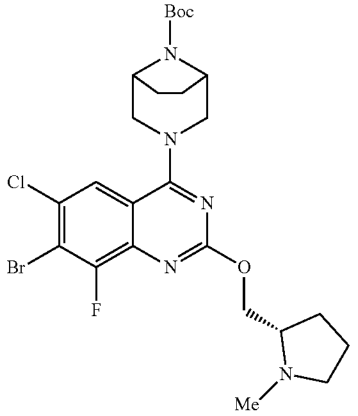

To a solution of tert-butyl 3-(7-bromo-2,6-dichloro-8-fluoroquinazolin-4-yl)-3,8-diazabicyclo[3.2.1]octane-8-carboxylate (415 mg, 0.820 mmol) in DMSO (6 mL) was added cesium fluoride (187 mg, 1.230 mmol), and (S)-(1-methylpyrrolidin-2-yl)methanol (236 mg, 2.050 mmol). The mixture was heated to 100° C. for 2 hours. The residue was diluted with DCM (50 mL) and washed with water (30 mL×2) and brine (50 mL). The organic phase was dried over anhydrous sodium sulphate, filtered and concentrated under reduced pressure. The residue was purified by silica gel column chromatography (12 g ISCO column, MeOH/DCM, 0-15%, 30 min.) to provide tert-butyl 3-(7-bromo-6-chloro-8-fluoro-2-{[(2S)-1-methylpyrrolidin-2-yl]methoxy}quinazolin-4-yl)-3,8-diazabicyclo[3.2.1]octane-8-carboxylate (108 mg, 0.185 mmol, 22.5% yield) as a yellow oil. MS (ESI) m/z 586.1 $[M+1]^+$.

Preparation of Intermediate 6C: tert-butyl 3-[6-chloro-8-fluoro-7-(3-hydroxynaphthalen-1-yl)-2-{[(2S)-1-methylpyrrolidin-2-yl]methoxy}quinazolin-4-yl]-3,8-diazabicyclo[3.2.1]octane-8-carboxylate

6C

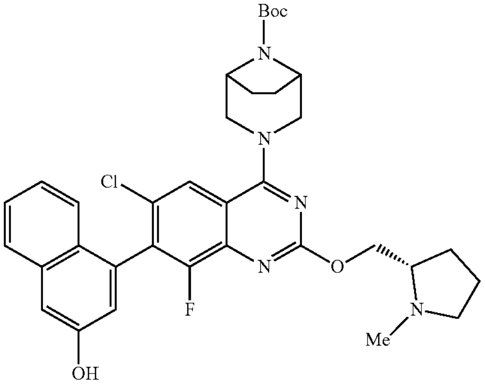

A suspension of tert-butyl 3-(7-bromo-6-chloro-8-fluoro-2-{[(2S)-1-methylpyrrolidin-2-yl]methoxy}quinazolin-4-yl)-3,8-diazabicyclo[3.2.1]octane-8-carboxylate (108 mg, 0.185 mmol) and $Na_2CO_3$ in 1,4-dioxane (2954 μl) and water (739 μl) was degassed and $Pd(Ph_3)_4$ (42.7 mg, 0.037 mmol) was added in one portion. The mixture was degassed again and heated in a pressure vial at 95° C. for 1 hour. The reaction mixture was diluted with water (10 mL) and DCM (10 mL). The mixture was extracted with DCM (10 mL×2). The combined organic layers were washed with brine (20 mL), dried over anhydrous sodium sulfate, filtered and concentrated under reduced pressure to provide a crude tert-butyl 3-[6-chloro-8-fluoro-7-(3-hydroxynaphthalen-1-yl)-2-{[(2S)-1-methylpyrrolidin-2-yl]methoxy}quinazolin-4-yl]-3,8-diazabicyclo[3.2.1]octane-8-carboxylate, MS (ESI) m/z 857.2 [M+1]+, which was used directly in the next step.

Examples 6-1

4-(6-chloro-4-{3,8-diazabicyclo[3.2.1]octan-3-yl}-8-fluoro-2-{[(2S)-1-methylpyrrolidin-2-yl]methoxy}quinazolin-7-yl)naphthalen-2-ol 6-1

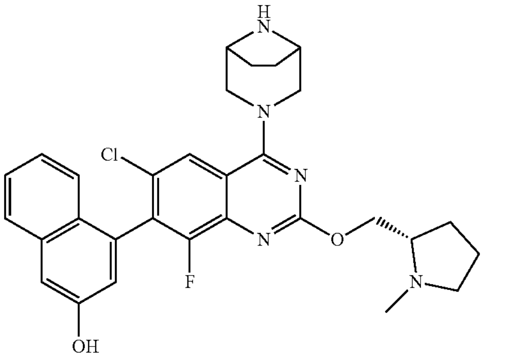

To a solution of crude tert-butyl 3-[6-chloro-8-fluoro-7-(3-hydroxynaphthalen-1-yl)-2-{[(2S)-1-methylpyrrolidin-2-yl]methoxy}quinazolin-4-yl]-3,8-diazabicyclo[3.2.1]octane-8-carboxylate in DCM (4 mL) was added TFA (0.8 mL) at 25° C. The reaction mixture was stirred at 25° C. for 1 hour. The reaction mixture was concentrated under reduced pressure to provide a residue, which was purified via preparative HPLC with the following conditions: Column: XBridge C18, 200 mm×19 mm, 5-μm particles; Mobile Phase A: 5:95 acetonitrile: water with 0.05% trifluoroacetic acid; Mobile Phase B: 95:5 acetonitrile: water with 0.05% trifluoroacetic acid; Gradient: a 0-minute hold at 5% B, 5-45% B over 20 minutes, then a 0-minute hold at 100% B; Flow Rate: 20 mL/min; Column Temperature: 25 C. Fractions containing the desired product were combined and dried via centrifugal evaporation. The material was further purified via preparative HPLC with the following conditions: Column: XBridge C18, 200 mm×19 mm, 5-μm particles; Mobile Phase A: 5:95 acetonitrile: water with 0.05% trifluoroacetic acid; Mobile Phase B: 95:5 acetonitrile: water with 0.05% trifluoroacetic acid; Gradient: a 0-minute hold at 4% B, 4-44% B over 20 minutes, then a 0-minute hold at 100% B; Flow Rate: 20 mL/min; Column Temperature: 25 C. Fractions containing the desired product were combined and dried via centrifugal evaporation to afford the desired product (22.3 mg, 0.039 mmol) as a white solid. MS (ESI) m/z 547.93 [M+1]+; $^1$H NMR (500 MHz, DMSO-$d_6$) δ 8.02 (s, 1H), 7.82 (br d, J=8.2 Hz, 1H), 7.46 (br t, J=7.5 Hz, 1H), 7.36-7.15 (m, 3H), 7.24 (m, 1H), 4.63 (br d, 1H), 4.60 (m, 3H), 4.21 (br s, 2H), 3.83 (m, 2H), 2.97 (m, 2H), 2.55 (m, 4H), 2.28 (s, 1H), 2.08 (m, 2H), 1.97 (m, 5H).

Examples in Table 3 were prepared according to procedures described for Example 6-1 with the appropriate amine and/or the appropriate boronic ester/acid.

TABLE 3

| Example Number | Structure | Name | MS m/z: [M + H]+ | $^1$H NMR |
|---|---|---|---|---|
| 6-2 | 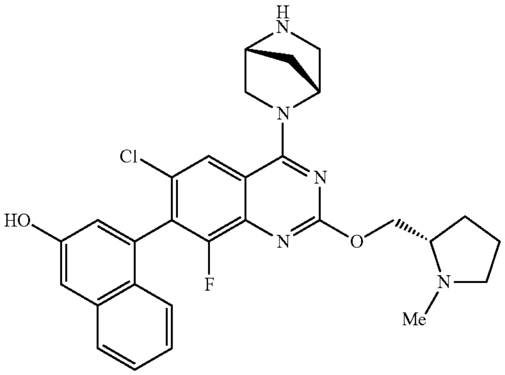 [SMILES: CN1CCC[C@H]1COc1nc(N2C[C@H]3C[C@@H]2CN3)c2cc(Cl)c(-c3cc(O)cc4ccccc34)c(F)c2n1] | 4-{6-chloro-4-[(1R,4R)-2,5-diazabicyclo[2.2.1]heptan-2-yl]-8-fluoro-2-{[(2S)-1-methylpyrrolidin-2-yl]methoxy}quinazolin-7-yl}naphthalen-2-ol | 534.4 | $^1$H NMR (500 MHz, DMSO-$d_6$) δ 8.05 (s, 1H), 7.79 (br d, J = 8.4 Hz, 1H), 7.50-7.40 (m, 1H), 7.28 (br d, J = 1.8 Hz, 1H), 7.26-7.19 (m, 1H), 7.17-7.12 (m, 1H), 7.03 (d, J = 2.2 Hz, 1H), 5.19-5.10 (m, 1H), 4.43-4.33 (m, 1H), 4.31-4.22 (m, 1H), 4.21-4.12 (m, 1H), 3.93-3.85 (m, 1H), 3.65-3.58 (m, 2H), 3.16-2.99 (m, 2H), 2.97-2.90 (m, 1H), 2.67-2.58 (m, 1H), 2.42-2.31 (m, 3H), 2.24-2.12 (m, 1H), 2.01-1.91 (m, 2H), |

TABLE 3-continued

| Example Number | Structure | Name | MS m/z: [M + H]+ | $^{1}$H NMR |
|---|---|---|---|---|
| | | | | 1.83-1.76 (m, 1H), 1.71-1.53 (m, 3H) |
| 6-3 | 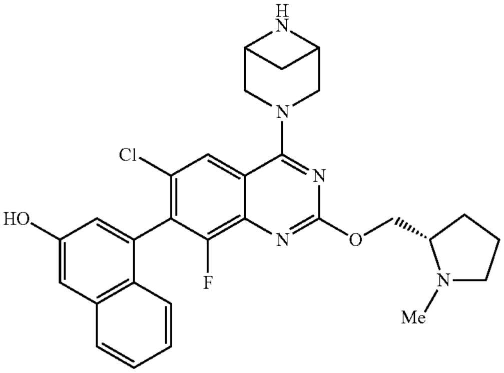 [SMILES: CN1CCC[C@H]1COc1nc(N2CC3CC(C2)N3)c2cc(Cl)c(-c3cc(O)cc4ccccc34)c(F)c2n1] | 4-(6-chloro-4-{3,6-diazabicyclo[3.1.1]heptan-3-yl}-8-fluoro-2-{[(2S)-1-methylpyrrolidin-2-yl]methoxy}quinazolin-7-yl)naphthalen-2-ol | 534.3 | $^{1}$H NMR (500 MHz, DMSO-$d_6$) δ 8.42 (s, 1H), 7.80 (br d, J = 8.2 Hz, 1H), 7.44 (br t, J = 6.9 Hz, 1H), 7.29 (d, J = 1.9 Hz, 1H), 7.26-7.21 (m, 1H), 7.20-7.14 (m, 1H), 7.06 (d, J = 2.2 Hz, 1H), 4.39 (dt, J = 10.8, 5.4 Hz, 1H), 4.31-4.14 (m, 4H), 3.86-3.75 (m, 1H), 3.72-3.5 (m, 1H), 3.03-2.87 (m, 1H), 2.65-2.55 (m, 2H), 2.42-2.30 (m, 3H), 2.19 (q, J = 8.8 Hz, 1H), 2.00-1.91 (m, 1H), 1.73-1.51 (m, 5H) |
| 6-4 | 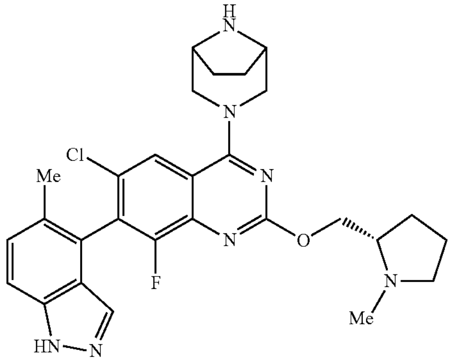 [SMILES: Cc1ccc2[nH]ncc2c1-c1c(Cl)cc2c(N3CC4CCC(C3)N4)nc(OC[C@@H]3CCCN3C)nc2c1F] | 6-chloro-4-{3,8-diazabicyclo[3.2.1]octan-3-yl}-8-fluoro-7-(5-methyl-1H-indazol-4-yl)-2-{[(2S)-1-methylpyrrolidin-2-yl]methoxy}quinazoline | 536.2 | $^{1}$H NMR (500 MHz, DMSO-$d_6$) δ 7.95 (s, 1H), 7.64-7.52 (m, 2H), 7.39 (br d, J = 8.5 Hz, 1H), 4.47-4.22 (m, 2H), 4.21-4.06 (m, 1H), 3.58-3.33 (m, 1H), 3.05-2.80 (m, 1H), 2.62-2.56 (m, 2H), 2.23-2.18 (m, 1H), 2.20-2.09 (s, 3H), 2.04-1.76 (m, 5H), 1.76-1.50 (m, 6H) |
| 6-5 | 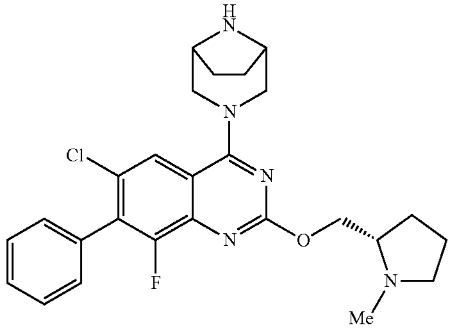 [SMILES: CN1CCC[C@H]1COc1nc(N2CC3CCC(C2)N3)c2cc(Cl)c(-c3ccccc3)c(F)c2n1] | 6-chloro-4-{3,8-diazabicyclo[3.2.1]octan-3-yl}-8-fluoro-2-{[(2S)-1-methylpyrrolidin-2-yl]methoxy}-7-phenylquinazoline | 482.2 | $^{1}$H-NMR (400 MHz, DMSO-$d_6$): δ 9.97 (s, 1H), 9.43 (s, 1H), 9.20 (s, 1H) 7.97 (s, 1H), 7.59-7.50 (m, 3H), 7.41-7.43 (m, 2H), 4.70-4.74 (m, 1H), 4.59-4.64 (m, 1H), 4.5-4.56 (m, 3H), 4.189 (s, 2H), 3.78-3.83 (m, 3H), 3.61-3.63 (m, 1H), 3.13-3.17 (m, 1H), 2.97 (s, 3H), 2.26-2.33 (m, 1H), 2.05-2.09 (m, 1H), 1.82-1.97 (m, 6H). |

TABLE 3-continued

| Example Number | Structure | Name | MS m/z: [M + H]+ | $^1$H NMR |
|---|---|---|---|---|
| 6-6 | 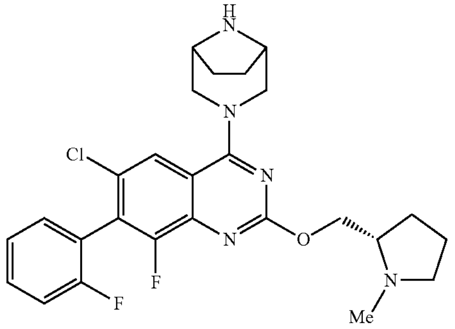 [SMILES: CN1CCC[C@H]1COc1nc(N2CC3CCC(C2)N3)c2cc(Cl)c(-c3ccccc3F)c(F)c2n1] | 6-chloro-4-{3,8-diazabicyclo[3.2.1]octan-3-yl}-8-fluoro-7-(2-fluorophenyl)-2-{[(2S)-1-methylpyrrolidin-2-yl]methoxy}quinazoline | 500.2 | $^1$H-NMR (400 MHz, DMSO-$d_6$): δ 9.93 (s, 1H), 9.40 (s, 1H), 9.18 (s, 1H) 8.0 (s, 1H), 7.59-7.65 (m, 1H), 7.39-7.50 (m, 3H), 4.70-4.73 (m, 1H), 4.60-4.65 (m, 1H), 4.50-4.58 (m, 3H), 4.189 (s, 2H), 3.78-3.84 (m, 4H), 3.15-3.17 (m, 1H), 2.96 (s, 3H), 2.26-2.34 (m, 1H), 2.05-2.09 (m, 1H), 1.86-1.93 (m, 7H). |
| 6-7 | 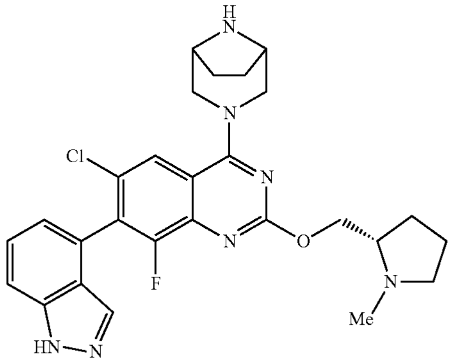 [SMILES: CN1CCC[C@H]1COc1nc(N2CC3CCC(C2)N3)c2cc(Cl)c(-c3cccc4[nH]ncc34)c(F)c2n1] | 6-chloro-4-{3,8-diazabicyclo[3.2.1]octan-3-yl}-8-fluoro-7-(1H-indazol-4-yl)-2-{[(2S)-1-methylpyrrolidin-2-yl]methoxy}quinazoline | 522.2 | $^1$H-NMR (400 MHz, DMSO-$d_6$): δ 13.4 (s, 1H), 9.88 (s, 1H), 9.37 (s, 1H), 9.13 (s, 1H) 8.02 (s, 1H), 7.70-7.73 (m, 2H), 7.51-7.55 (m, 1H), 7.14-7.16 (m, 1H), 4.71-4.72 (m, 1H), 4.62-4.64 (m, 4H), 4.2 (s, 2H), 3.73-3.83 (m, 5H), 3.16-3.18 (m, 1H), 2.97 (s, 3H), 2.33-2.34 (m, 1H), 2.08-2.09 (m, 1H), 1.9-1.95 (m, 7H). |
| 6-8 | 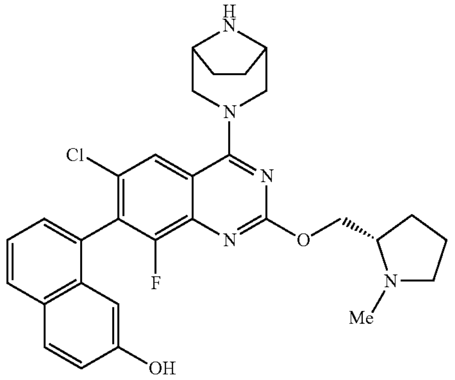 [SMILES: CN1CCC[C@H]1COc1nc(N2CC3CCC(C2)N3)c2cc(Cl)c(-c3cccc4ccc(O)cc34)c(F)c2n1] | 8-(6-chloro-4-{3,8-diazabicyclo[3.2.1]octan-3-yl}-8-fluoro-2-{[(2S)-1-methylpyrrolidin-2-yl]methoxy}quinazolin-7-yl)naphthalen-2-ol | 548.2 | $^1$H-NMR (400 MHz, DMSO-$d_6$): δ 9.74 (s, 2H), 9.22 (s, 1H), 8.99 (s, 1H) 8.06 (s, 1H), 7.90-7.96 (m, 2H), 7.38-7.44 (m, 2H), 7.15-7.17 (m, 1H), 6.55 (s, 1H), 4.71-4.72 (m, 1H), 4.55-4.64 (m, 4H), 4.2 (s, 2H), 3.75-3.85 (m, 3H), 3.16-3.18 (m, 1H), 2.97 (s, 3H), 2.26-2.33 (m, 1H), 2.08-2.09 (m, 1H), 1.9-1.97 (m, 7H). |

TABLE 3-continued

| Example Number | Structure | Name | MS m/z: [M + H]+ | $^1$H NMR |
|---|---|---|---|---|
| 6-9 | 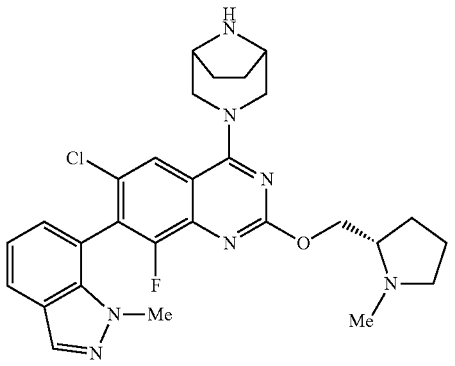 [SMILES: CN1CCC[C@H]1COc1nc(N2CC3CCC(C2)N3)c2cc(Cl)c(-c3cccc4cnn(C)c34)c(F)c2n1] | -chloro-4-{3,8-diazabicyclo[3.2.1] octan-3-yl}-8-fluoro-7-(1-methyl-1H-indazol-7-yl)-2-{[(2S)-1-methylpyrrolidin-2-yl]methoxy} quinazoline | 536.2 | $^1$H-NMR (400 MHz, DMSO-$d_6$): δ 9.86 (s, 1H), 9.35 (s, 1H), 9.11 (s, 1H), 8.2 (s, 1H), 8.05 (s, 1H), 7.93-7.96 (m, 1H), 7.13-7.33(m, 2H), 4.63-4.71 (m, 1H), 4.49-4.59 (m, 4H), 4.2 (s, 2H), 3.76-3.86 (m, 3H), 3.57-3.61 (m, 5H) 3.16-3.18 (m, 1H), 2.97 (s, 3H), 2.26-2.33 (m, 1H), 2.07-2.08 (m, 1H), 1.91-1.96 (m, 7H). |
| 6-10 | 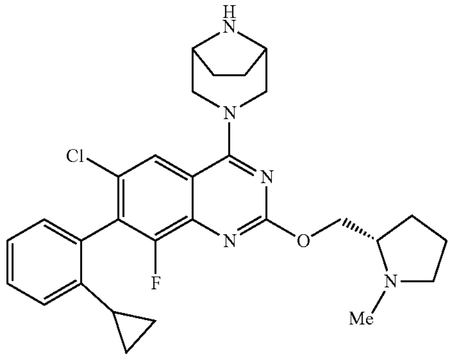 [SMILES: CN1CCC[C@H]1COc1nc(N2CC3CCC(C2)N3)c2cc(Cl)c(-c3ccccc3C3CC3)c(F)c2n1] | 6-chloro-7-(2-cyclopropylphenyl)-4-{3,8-diazabicyclo[3.2.1] octan-3-yl}-8-fluoro-2-{[(2S)-1-methylpyrrolidin-2-yl]methoxy} quinazoline | 522.2 | $^1$H-NMR (400 MHz, DMSO-$d_6$): δ 9.97 (s, 1H), 9.42 (d, J = 9.60 Hz, 1H), 9.21 (s, 1H), 7.99 (s, 1H), 7.41 (dd, J = 1.20, 10.80 Hz, 1H), 7.32 (t, J = 6.80 Hz, 1H), 7.17 (dd, J = 1.20, 7.60 Hz, 1H), 7.09 (d, J = 8.00 Hz, 1H), 4.72 (d, J = 3.20 Hz, 1H), 4.62 (dd, J = 6.80, 12.40 Hz, 1H), 4.51 (dd, J = 11.60, Hz, 2H), 4.20 (s, 2H), 3.78 (d, J = 10.80 Hz, 2H), 3.17 (d, J = 2.80 Hz, 1H), 2.97 (s, 3H), 2.33 (d, J = 2.00 Hz, 1H), 2.17 (dd, J = 10.00, 82.60 Hz, 1H), 1.91 (d, J = 7.60 Hz, 6H), 1.48 (t, J = 2.40 Hz, 1H), 0.63-0.74 (m, 4H). |
| 6-11 | 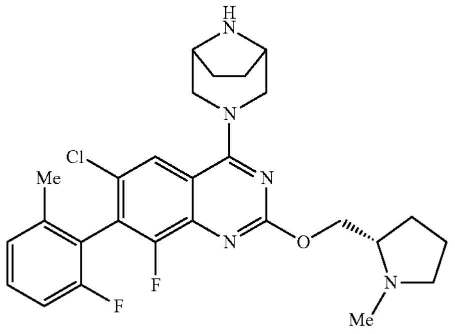 [SMILES: Cc1cccc(F)c1-c1c(Cl)cc2c(N3CC4CCC(C3)N4)nc(OC[C@@H]3CCCN3C)nc2c1F] | 6-chloro-4-{3,8-diazabicyclo[3.2.1] octan-3-yl}-8-fluoro-7-(2-fluoro-6-methylphenyl)-2-{[(2S)-1-methylpyrrolidin-2-yl]methoxy} quinazoline | 514.2 | $^1$H-NMR (400 MHz, DMSO-$d_6$): δ 8.33 (s, 3H), 7.95 (d, J = 1.60 Hz, 1H), 7.45-7.50 (m, 1H), 7.20-7.29 (m, 2H), 4.41-4.31 (m, 3H), 4.15-4.21 (m, 1H), 3.64 (s, 2H), 3.56-3.60 (m, 2H), 2.95-2.98 (m, 1H), 2.53-2.63 (m, 1H), 2.37 (s, 3H), 2.17-2.21 (m, 1H), 2.09 (s, 3H), 1.93-1.98 |

TABLE 3-continued

| Example Number | Structure | Name | MS m/z: [M + H]+ | $^1$H NMR |
|---|---|---|---|---|
| | | | | (m, 1H), 1.62-1.70 (m, 7H). |
| 6-12 | 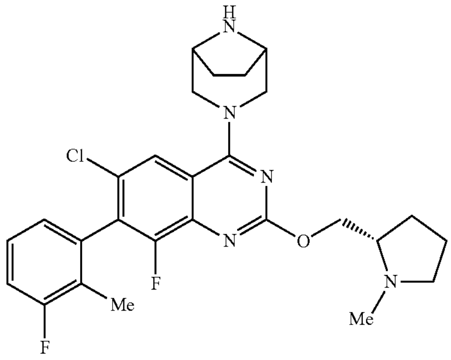 [SMILES: Cc1c(F)cccc1-c1c(Cl)cc2c(N3CC4CCC(C3)N4)nc(OC[C@@H]3CCCN3C)nc2c1F] | 6-chloro-4-{3,8-diazabicyclo[3.2.1]octan-3-yl}-8-fluoro-7-(3-fluoro-2-methylphenyl)-2-{[(2S)-1-methylpyrrolidin-2-yl]methoxy}quinazoline | 514.2 | $^1$H-NMR (400 MHz, DMSO-$d_6$): δ 8.25 (s, 3H), 7.92 (d, J = 1.20 Hz, 1H), 7.37-7.41 (m, 1H), 7.29-7.34 (m, 1H), 7.10 (d, J = 7.20 Hz, 1H), 4.32-4.38 (m, 3H), 4.15-4.20 (m, 1H), 3.67 (s, 2H), 3.56-3.60 (m, 2H), 2.95-3.00 (m, 1H), 2.60-2.68 (m, 1H), 2.37 (s, 3H) 2.20-2.22 (m, 1H), 2.09 (s, 3H), 1.96-2.00 (m, 1H), 1.64-1.70 (m, 7H). |
| 6-13 | 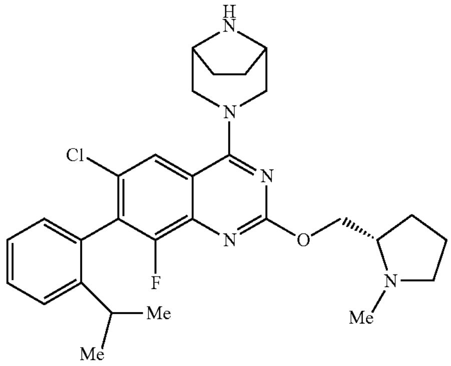 [SMILES: CC(C)c1ccccc1-c1c(Cl)cc2c(N3CC4CCC(C3)N4)nc(OC[C@@H]3CCCN3C)nc2c1F] | 4-((1R,5S)-6-chloro-4-{3,8-diazabicyclo[3.2.1]octan-3-yl}-8-fluoro-2-{[(2S)-1-methylpyrrolidin-2-yl]methoxy}-7-[2-(propan-2-yl)phenyl]quinazoline | 524.3 | $^1$H-NMR (400 MHz, DMSO-$d_6$): δ 8.28 (s, 3H), 7.90 (s, 1H), 7.46-7.53 (m, 2H), 7.31-7.35 (m, 1H), 7.13 (d, J = 7.20 Hz, 1H), 4.31-4.40 (m, 3H), 4.16-4.20 (m, 1H), 3.68 (s, 2H), 3.56-3.60 (m, 2H), 2.96-2.98 (m, 1H), 2.55-2.61 (m, 2H), 2.37 (s, 3H), 2.18-2.22 (m, 1H), 1.93-1.96 (m, 1H), 1.63-1.72 (m, 8H), 1.14 (d, J = 6.80 Hz, 3H), 1.08 (d, J = 6.80 Hz, 3H), |
| 6-14 | 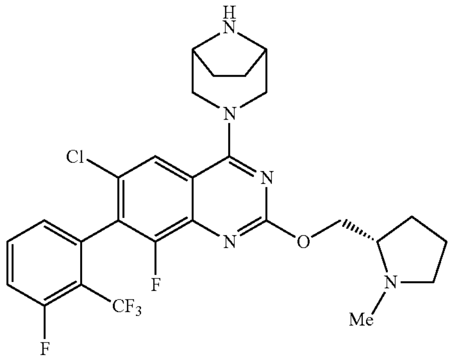 [SMILES: CN1CCC[C@H]1COc1nc(N2CC3CCC(C2)N3)c2cc(Cl)c(-c3cccc(F)c3C(F)(F)F)c(F)c2n1] | 6-chloro-4-{3,8-diazabicyclo[3.2.1]octan-3-yl}-8-fluoro-7-[3-fluoro-2-(trifluoromethyl)phenyl]-2-{[(2S)-1-methylpyrrolidin-2-yl]methoxy}quinazoline | 568.2 | $^1$H-NMR (400 MHz, DMSO-$d_6$): δ 8.22 (s, 1H), 7.94-7.89 (m, 2H), 7.71 (t, J = 8.80 Hz, 1H), 7.35 (d, J = 7.60 Hz, 1H), 4.31-4.38 (m, 2H), 4.26 (d, J = 4.80 Hz, 2H), 4.14-4.22 (m, 2H), 3.51 (dd, J = 4.80, 11.40 Hz, 2H), 2.94-2.97 (m, 1H), 2.51 (dd, J = 1.60, 3.60 Hz, 1H), 2.36 (d, J = 0.40 Hz, 3H), 2.18 (t, J = 8.80 Hz, 1H), 1.93 (dd, J = 9.20, 12.60 Hz, 1H), 1.66-1.72 (m, 7H). |

TABLE 3-continued

| Example Number | Structure | Name | MS m/z: [M + H]+ | $^1$H NMR |
|---|---|---|---|---|
| 6-15 | 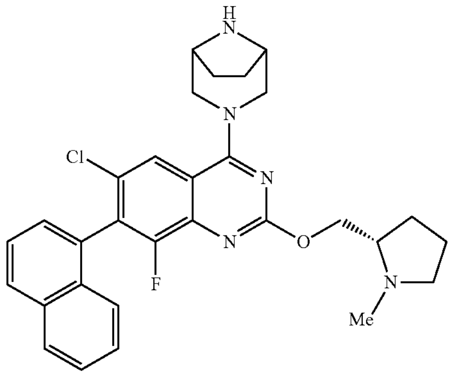 [SMILES: CN1CCC[C@H]1COc1nc(N2CC3CCC(C2)N3)c2cc(Cl)c(-c3cccc4ccccc34)c(F)c2n1] | 6-chloro-4-{3,8-diazabicyclo[3.2.1]octan-3-yl}-8-fluoro-2-{[(2S)-1-methylpyrrolidin-2-yl]methoxy}-7-(naphthalen-1-yl)quinazoline | 532.2 | $^1$H-NMR (400 MHz, DMSO-$d_6$): δ 8.08 (dd, J = 8.00, 13.00 Hz, 2H), 7.96 (s, 1H), 7.68 (t, J = 8.40 Hz, 1H), 7.59 (t, J = 8.00 Hz, 1H), 7.51 (dd, J = 7.20, 14.40 Hz, 2H), 7.40 (d, J = 8.40 Hz, 1H), 4.35-4.39 (m, 3H), 4.13-4.17 (m, 1H), 3.49-3.58 (m, 4H), 2.93-2.96 (m, 1H), 2.51 (d, J = 1.60 Hz, 2H), 2.40 (s, 3H), 2.33-2.34 (m, 1H), 1.94 (d, J = 5.20 Hz, 1H), 1.69 (d, J = 8.80 Hz, 7H). |
| 6-16 | 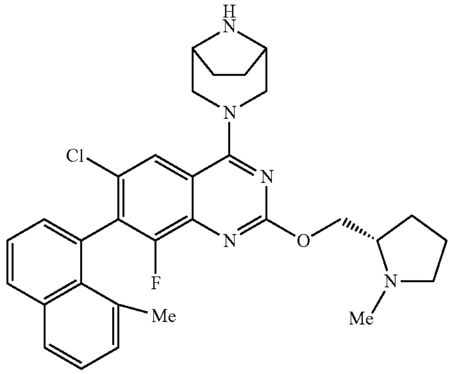 [SMILES: Cc1cccc2cccc(-c3c(Cl)cc4c(N5CC6CCC(C5)N6)nc(OC[C@@H]5CCCN5C)nc4c3F)c12] | 6-chloro-4-{3,8-diazabicyclo[3.2.1]octan-3-yl}-8-fluoro-7-(2-methylnaphthalen-1-yl)-2-{[(2S)-1-methylpyrrolidin-2-yl]methoxy}quinazoline | 546.2 | $^1$H-NMR (400 MHz, DMSO-$d_6$): δ 8.26 (s, 1H), 8.03 (d, J = 8.40 Hz, 1H), 7.95 (d, J = 6.00 Hz, 2H), 7.59 (t, J = 8.00 Hz, 1H), 7.44 (t, J = 11.60 Hz, 2H), 7.16 (s, 1H), 4.36 (s, 3H), 4.17 (s, 1H), 3.33 (s, 4H), 2.19 (s, 6H), 2.09 (d, J = 10.40 Hz, 1H), 1.68 (d, J = 16.80 Hz, 1H), 1.36 (s, 9H). |
| 6-17 | 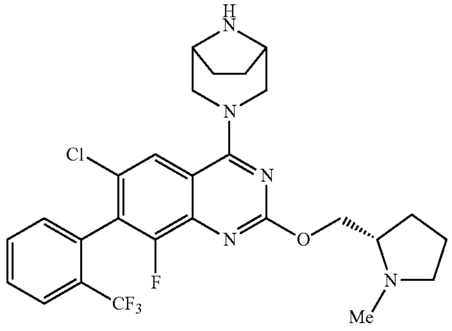 [SMILES: CN1CCC[C@H]1COc1nc(N2CC3CCC(C2)N3)c2cc(Cl)c(-c3ccccc3C(F)(F)F)c(F)c2n1] | 6-chloro-4-{3,8-diazabicyclo[3.2.1]octan-3-yl}-8-fluoro-2-{[(2S)-1-methylpyrrolidin-2-yl]methoxy}-7-[2-(trifluoromethyl)phenyl]quinazoline | 550.2 | $^1$H-NMR (400 MHz, DMSO-$d_6$): δ 8.25 (s, 2H), 7.96 (d, J = 7.60 Hz, 1H), 7.90 (d, J = 1.20 Hz, 1H), 7.86 (t, J = 7.60 Hz, 1H), 7.76 (t, J = 7.60 Hz, 1H), 7.51 (d, J = 7.60 Hz, 1H), 4.35 (dd, J = 4.80, Hz, 1H), 4.26-4.30 (m, 1H), 4.14-4.19 (m, 3H), 3.53 (dd, J = 4.80, 11.40 Hz, 2H), 2.95 (dd, J = 4.00, Hz, 1H), 2.68 (t, J = 1.60 Hz, 2H), 2.36 (t, J = 6.00 Hz, 3H), 2.34 (dd, J = 1.60, Hz, 1H), 2.34 (dd, J = 1.60, Hz, 1H), |

TABLE 3-continued

| Example Number | Structure | Name | MS m/z: [M + H]+ | $^1$H NMR |
|---|---|---|---|---|
| | | | | 1.95-2.20 (m, 1H), 1.66 (d, J = 16.00 Hz, 6H), (t, J = Hz, 1H). |

Examples 7-1

4-(6-chloro-4-{3,6-diazabicyclo[3.1.1]heptan-6-yl}-8-fluoro-2-{[(2S)-1-methylpyrrolidin-2-yl]methoxy}quinazolin-7-yl)naphthalen-2-ol 7-1

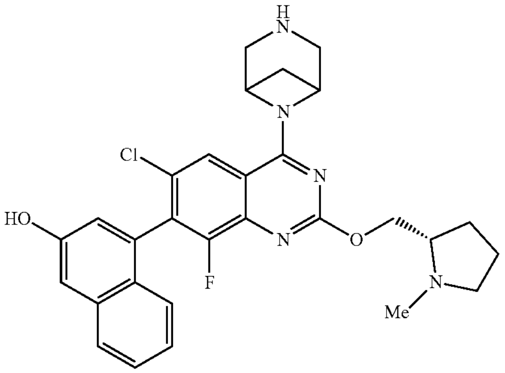

Preparation of Intermediate 7A: tert-butyl 4-(7-bromo-2,6-dichloro-8-fluoroquinazolin-4-yl)piperazine-1-carboxylate

7A

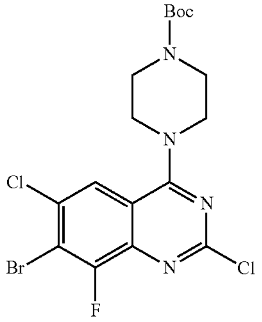

To a solution of 7-bromo-2,4,6-trichloro-8-fluoroquinazoline (1 g, 3.03 mmol) and DIPEA (1.32 mL, 7.57 mmol) in THE (15 mL) was added tert-butyl piperazine-1-carboxylate (0.56 g, 3.03 mmol) under $N_2$. The reaction was stirred at 25° C. for 2 h. LCMS showed the reaction was complete. The mixture was concentrated. The residue was diluted with ethyl acetate (60 mL) and washed with water (30 mL×2) and brine (50 mL). The organic phase was dried over anhydrous sodium sulphate, filtered and concentrated under reduced pressure. The residue was purified by silica gel column chromatography (silica gel, petroleum ether:ethyl acetate=10:1 to 4:1) to afford tert-butyl 4-(7-bromo-2,6-dichloro-8-fluoroquinazolin-4-yl)piperazine-1-carboxylate (1.33 g, 2.77 mmol, 91.5% yield) as a yellow solid. MS (ESI) m/z 481.0 [M+1]$^+$. $^1$H NMR (400 MHz, $CDCl_3$) δ 7.77 (d, J=1.6 Hz, 1H), 3.93-3.84 (m, 4H), 3.72-3.61 (m, 4H), 1.50 (s, 9H).

Preparation of Intermediate 7B: tert-butyl (S)-4-(7-bromo-6-chloro-8-fluoro-2-((1-methylpyrrolidin-2-yl)methoxy)quinazolin-4-yl)piperazine-1-carboxylate

7B

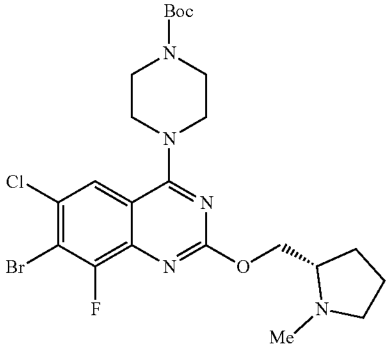

To a solution of tert-butyl 4-(7-bromo-2,6-dichloro-8-fluoroquinazolin-4-yl)piperazine-1-carboxylate (540 mg, 1.125 mmol) in DMSO (6 mL) was added cesium fluoride (342 mg, 2.249 mmol) and (S)-(1-methylpyrrolidin-2-yl)methanol (324 mg, 2.81 mmol). The mixture was heated to 100° C. for 2 h. After the mixture was cooled to room temperature, sat. $NaHCO_3$ (50 mL) was added. Aqueous phase was extracted with DCM (50 mL×2). The combined DCM phase was washed with brine and dried ($Na_2SO_4$), then concentrated. The residue was purified on 40 g silica column, eluted with 0-10% MeOH/DCM (w/0.5% TEA) to provide tert-butyl (S)-4-(7-bromo-6-chloro-8-fluoro-2-((1-methylpyrrolidin-2-yl)methoxy)quinazolin-4-yl)piperazine-1-carboxylate (0.43 g, 0.769 mmol, 68.4% yield) as a yellow solid. MS (ESI) m/z 558.2/560.2 [M+1]$^+$.

Preparation of Intermediate 7C: tert-butyl 4-(6-chloro-8-fluoro-7-(3-hydroxynaphthalen-1-yl)-2-(((S)-1-methylpyrrolidin-2-yl)methoxy)quinazolin-4-yl)piperazine-1-carboxylate

7C

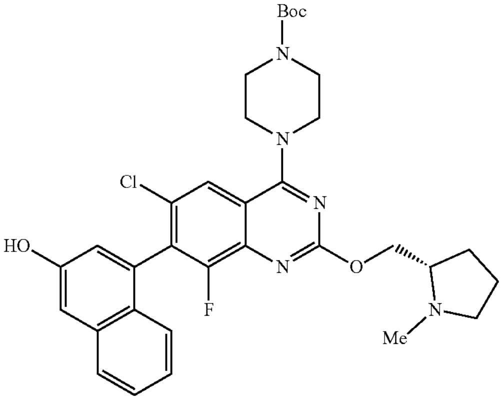

A suspension of tert-butyl (S)-4-(7-bromo-6-chloro-8-fluoro-2-((1-methylpyrrolidin-2-yl)methoxy)quinazolin-4-yl)piperazine-1-carboxylate (430 mg, 0.769 mmol), 4-(4,4,5,5-tetramethyl-1,3,2-dioxaborolan-2-yl)naphthalen-2-ol (249 mg, 0.923 mmol), $Na_2CO_3$ (245 mg, 2.308 mmol) in 1,4-dioxane (10 mL) and water (2 mL) was degassed with $N_2$ for 5 min, then tetrakis(triphenylphosphine)palladium(0) (178 mg, 0.154 mmol) was added in one portion. The resulting mixture was degassed with $N_2$, then heated in microwave at 95° C. for 1 h. The reaction was cooled to room temperature, filtered and the filter cake was washed with dioxane 2 mL×3. The filtrate and washes were combined and concentrated. The residue was purified on 24 g of silica, eluting with 0-10% MeOH/DCM (w 0.5% TEA) to provide tert-butyl 4-(6-chloro-8-fluoro-7-(3-hydroxynaphthalen-1-yl)-2-(((S)-1-methylpyrrolidin-2-yl)methoxy)quinazolin-4-yl)piperazine-1-carboxylate (174 mg, 0.280 mmol, 36.4% yield) as a yellow solid. MS (ESI) m/z 622.4 $[M+1]^+$.

Preparation of Intermediate 7D: 6-chloro-8-fluoro-7-(3-hydroxynaphthalen-1-yl)-2-(((S)-1-methylpyrrolidin-2-yl)methoxy)quinazolin-4(3H)-one

7D

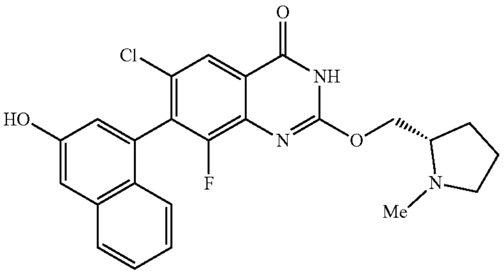

A solution of tert-Butyl 4-(6-chloro-8-fluoro-7-(3-hydroxynaphthalen-1-yl)-2-(((S)-1-methylpyrrolidin-2-yl)methoxy)quinazolin-4-yl)piperazine-1-carboxylate (400 mg, 0.643 mmol) in EtOH (5 mL) and water (0.5 mL) was treated with sodium hydroxide (1.286 mL, 1.286 mmol). The reaction was stirred at 50° C. for 16 h. The mixture was concentrated reduced pressure. The residue was purified by flash chromatography on silica gel eluting with 0-10% MeOH/DCM (w 0.5% TEA) to afford the desired compound (174 mg, 0.383 mmol, 59.6% yield) as a white solid. MS (ESI) m/z: 454.1 $[M+H]^+$.

Preparation of Intermediate 7E: tert-butyl 6-(6-chloro-8-fluoro-7-(3-hydroxynaphthalen-1-yl)-2-(((S)-1-methylpyrrolidin-2-yl)methoxy)quinazolin-4-yl)-3,6-diazabicyclo[3.1.1]heptane-3-carboxylate

7E

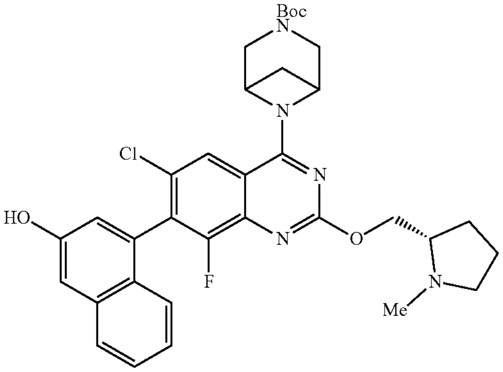

To a mixture of 6-chloro-8-fluoro-7-(3-hydroxynaphthalen-1-yl)-2-(((S)-1-methylpyrrolidin-2-yl)methoxy)quinazolin-4-ol (10 mg, 0.022 mmol), tert-butyl 3,6-diazabicyclo[3.1.1]heptane-3-carboxylate (5.24 mg, 0.026 mmol) and DIEA (11.54 µL, 0.066 mmol) in dichloromethane (2 mL) was added BOP (12.18 mg, 0.028 mmol) and the reaction was stirred for 16 h at room temperature till completion. The reaction was quenched with 4 mL of $NaHCO_3$aq, extracted with DCM (5 mL×3). The combined organic was washed with brine, dried over $Na_2SO_4$ and concentrated reduced pressure. The residue was dissolved in 2 mL of THE and TBAF (88 µL, 0.088 mmol) was added. The mixture was stirred at room temperature for 15 min. The reaction was concentrated and the residue was purified on 4 g of silica eluting with 0-10% MeOH/DCM (w 0.5% TEA) to provide the desired compound (10 mg, 0.016 mmol, 71.6% yield). MS (ESI) m/z: 634.1$[M+H]^+$.

Preparation of Example 7-1:4-(6-chloro-4-{3,6-diazabicyclo[3.1.1]heptan-6-yl}-8-fluoro-2-{[(2S)-1-methylpyrrolidin-2-yl]methoxy}quinazolin-7-yl) naphthalen-2-ol 7-1

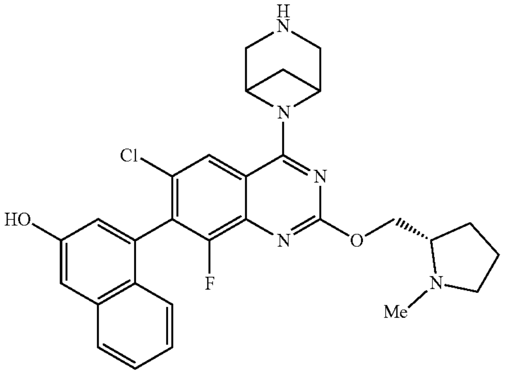

tert-Butyl 6-(6-chloro-8-fluoro-7-(3-hydroxynaphthalen-1-yl)-2-(((S)-1-methylpyrrolidin-2-yl)methoxy)quinazolin-4-yl)-3,6-diazabicyclo[3.1.1]heptane-3-carboxylate (10 mg, 0.016 mmol) was treated with 1 mL of 30% TFA/DCM for 30 min at room temperature. Then the reaction mixture was concentrated. The residue was purified via preparative LC/MS with the following conditions: Column: XBridge C18, 200 mm×19 mm, 5-A particles; Mobile Phase A: 5:95 acetonitrile: water with 0.05% trifluoroacetic acid; Mobile Phase B: 95:5 acetonitrile: water with 0.05% trifluoroacetic acid; Gradient: a 0-minute hold at 7% B, 7-47% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to provide final compound Example 7-1 (4.6 mg, 6 mmol, 37.7% yield). MS (ESI) m/z 534.4 [M+1]+; $^1$H NMR (500 MHz, DMSO-$d_6$) δ 7.93 (s, 1H), 7.82 (br d, J=8.5 Hz, 1H), 7.45 (br t, J=7.3 Hz, 1H), 7.31 (d, J=1.9 Hz, 1H), 7.24 (br t, J=7.3 Hz, 1H), 7.19-7.13 (m, 1H), 7.10-7.03 (m, 1H), 5.28-5.06 (m, 1H), 4.78-4.67 (m, 1H), 4.66-4.51 (m, 1H), 3.89-3.76 (m, 1H), 3.75-3.31 (m, 5H), 3.15-2.75 (m, 5H), 2.32-2.20 (m, 1H), 2.11-1.99 (m, 2H), 2.00-1.77 (m, 3H)

Examples in Table 4 were prepared according to procedures described for Example 7-1 from intermediate 7D and the appropriate amine.

TABLE 4

| Example Number | Structure | Name | MS m/z: [M + H]+ | $^1$H NMR |
|---|---|---|---|---|
| 7-2 | 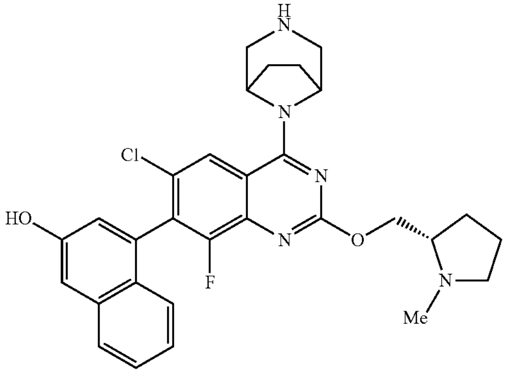 [SMILES: CN1CCC[C@H]1COc1nc(N2C3CCC2CNC3)c2cc(Cl)c(-c3cc(O)cc4ccccc34)c(F)c2n1] | 4-(6-chloro-4-{3,8-diazabicyclo[3.2.1]octan-8-yl}-8-fluoro-2-{[(2S)-1-methylpyrrolidin-2-yl]methoxy}quinazolin-7-yl)naphthalen-2-ol | 548.2 | $^1$H NMR (500 MHz, DMSO-$d_6$) δ 8.09 (s, 1H), 7.83 (br d, J = 7.9 Hz, 1H), 7.58-7.42 (m, 1H), 7.39-7.29 (m, 1H), 7.24 (br t, J = 7.6 Hz, 1H), 7.21-7.15 (m, 1H), 7.07 (d, J = 2.1 Hz, 1H), 5.12-5.01 (m, 1H), 4.78-4.65 (m, 1H), 4.64-4.53 (m, 1H), 3.61-3.42 (m, 7H), 3.39-3.26 (m, 1H, 2.98-2.85 (m, 2H), 2.31-2.20 (m, 1H), 2.20-2.11 (m, 1H), 2.11-1.99 (m, 2H), 1.98-1.83 (m, 3H), 1.27-1.21 (m, 1H), 1.20-1.10 (m, 1H) |
| 7-3 | 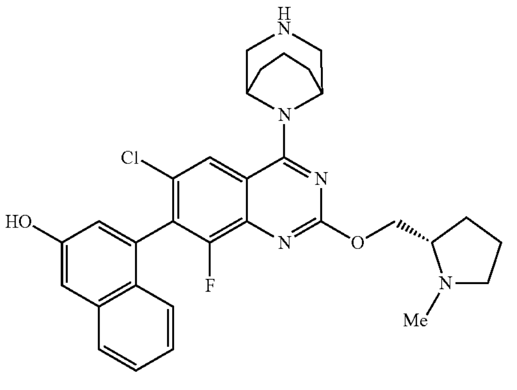 [SMILES: CN1CCC[C@H]1COc1nc(N2C3CCCC2CNC3)c2cc(Cl)c(-c3cc(O)cc4ccccc34)c(F)c2n1] | 4-(6-chloro-4-{3,9-diazabicyclo[3.3.1]nonan-9-yl}-8-fluoro-2-{[(2S)-1-methylpyrrolidin-2-yl]methoxy}quinazolin-7-yl)naphthalen-2-ol | 562.2 | $^1$H NMR (500 MHz, DMSO-$d_6$) δ 7.91-7.73 (m, 1H), 7.90-7.70 (m, 1H), 7.55-7.41 (m, 1H), 7.31 (d, J = 1.8 Hz, 1H), 7.27-7.21 (m, 1H), 7.21-7.16 (m, 1H), 7.07 (d, J = 1.8 Hz, 1H), 4.81 (m, 2H), 4.77-4.69 (m, 1H), 4.68-4.57 (m, 1H), 3.95-3.73 (m, 1H), 3.55-3.39 (m, 2H), 3.24-3.06 (m, 1H), |

TABLE 4-continued

| Example Number | Structure | Name | MS m/z: [M + H]+ | $^1$H NMR |
|---|---|---|---|---|
| | | | | 3.01-2.91 (s, 3H), 2.86-2.73 (m, 1H), 2.33-2.12 (m, 5H), 2.12-2.00 (m, 1H), 2.01-1.70 (m, 4H), 1.30-0.98 (m, 2H) |
| 7-4 | 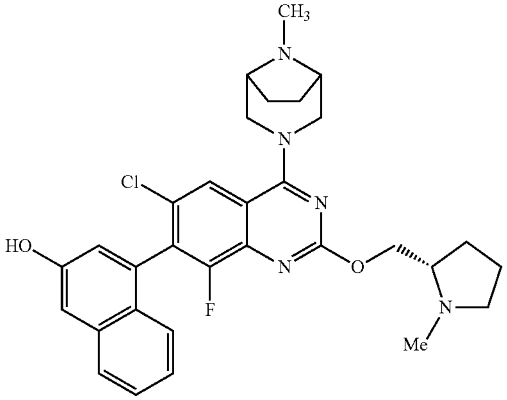 [SMILES: CN1C2CCC1CN(c1nc(OC[C@@H]3CCCN3C)nc3c(F)c(-c4cc(O)cc5ccccc45)c(Cl)cc13)C2] | 4-(6-chloro-8-fluoro-4-{8-methyl-3,8-diazabicyclo[3.2.1]octan-3-yl}-2-{[(2S)-1-methylpyrrolidin-2-yl]methoxy}quinazolin-7-yl)naphthalen-2-ol | 562.2 | (500 MHz, DMSO-$d_6$) δ 7.97 (s, 1H), 7.81 (br d, J = 8.2 Hz, 1H), 7.45 (br s, 1H), 7.29 (s, 1H), 7.22 (br s, 2H), 7.08 (s, 1H), 4.93 (br s, 2H), 4.47-4.29 (m, 1H), 4.24-4.06 (m, 1H), 3.03-2.91 (m, 1H), 2.85 (br d, J = 10.1 Hz, 1H), 2.62-2.57 (m, 1H), 2.44 (br d, J = 10.4 Hz, 1H), 2.35 (s, 3H), 2.26 (s, 3H), 2.21-2.11 (m, 1H), 2.03-1.83 (m, 5H), 1.74-1.57 (m, 3H) |
| 7-5 | 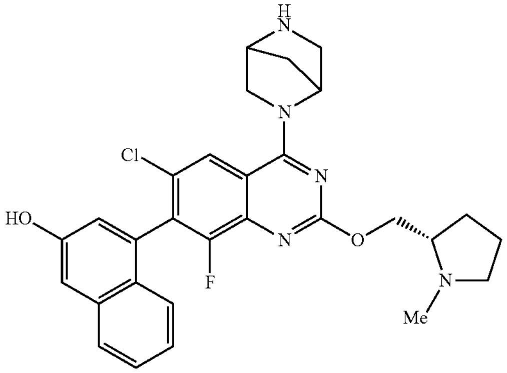 [SMILES: CN1CCC[C@H]1COc1nc(N2CC3CC2CN3)c2cc(Cl)c(-c3cc(O)cc4ccccc34)c(F)c2n1] | 4-(6-chloro-4-{2,5-diazabicyclo[2.2.1]heptan-2-yl}-8-fluoro-2-{[(2S)-1-methylpyrrolidin-2-yl]methoxy}quinazolin-7-yl)naphthalen-2-olol | 534.4 | $^1$H NMR (500 MHz, DMSO-$d_6$) δ 8.09-8.00 (m, 1H), 7.82 (br d, J = 8.1 Hz, 1H), 7.51-7.40 (m, 1H), 7.34-7.28 (m, 1H), 7.27-7.23 (m, 1H), 7.19-7.12 (m, 1H), 7.12-7.04 (m, 1H), 5.21 (br d, J = 3.3 Hz, 1H), 4.45-4.33 (m, 2H), 4.28-4.14 (m, 2H), 4.02-3.92 (m, 1H), 3.71-3.63 (m, 1H), 3.50-3.38 (m, 1H), 3.37-3.26 (m, 1H), 3.22-3.12 (m, 1H), 3.05-2.94 (m, 1H), 2.62-2.56 (m, 1H), 2.43-2.31 (s, 3H), 2.30-2.19 (m, 1H), 2.15-2.03 (m, 1H), 2.03-1.82 (m, 2H), 1.79-1.60 (m, 3H) |

Examples 8-1

(5S)-5-{[(6-chloro-4-{3,8-diazabicyclo[3.2.1]octan-3-yl}-8-fluoro-7-(3-hydroxynaphthalen-1-yl)quinazolin-2-yl)oxy]methyl}pyrrolidin-2-one 8-1

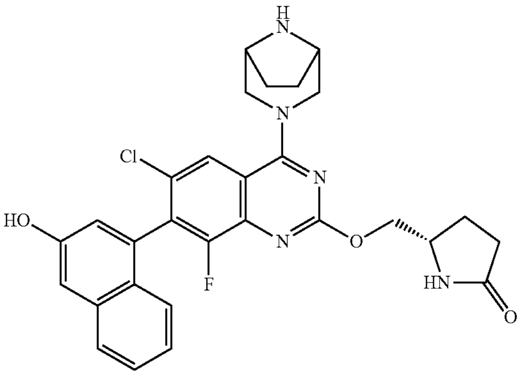

To a degassed solution of tert-butyl 3-(7-bromo-2,6-dichloro-8-fluoroquinazolin-4-yl)-3,8-diazabicyclo[3.2.1]octane-8-carboxylate (1 g, 3.03 mmol) in DMA (80 mL) was added cesium fluoride (5.25 g, 34.6 mmol). This was degassed with nitrogen gas for 10 min and was heated at 88° C. for 5 h in a sealed tube. Water (200 mL) and ethyl acetate (150 mL) were added and this was stirred for 15 min. The separated aqueous layer was extracted with ethyl acetate (2×100 mL) and the combined organic layers were dried over anhydrous $Na_2SO_4$, filtered, and concentrated. The resulting residue was purified by flash column chromatography using 15-25% ethyl acetate in petroleum ether as an eluent to provide tert-butyl 3-(7-bromo-6-chloro-2,8-difluoroquinazolin-4-yl)-3,8-diazabicyclo[3.2.1]octane-8-carboxylate (4.7 g, 8.77 mmol, 63.4% yield) as a pale yellow solid. MS (ESI) m/z 489.0 [M+1].

Preparation of Intermediate 8B: tert-butyl 3-(7-bromo-6-chloro-8-fluoro-2-(((S)-5-oxopyrrolidin-2-yl)methoxy)quinazolin-4-yl)-3,8-diazabicyclo[3.2.1]octane-8-carboxylate

8B

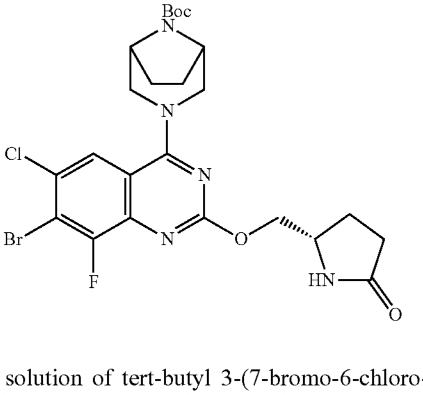

To a solution of tert-butyl 3-(7-bromo-6-chloro-2,8-difluoroquinazolin-4-yl)-3,8-diazabicyclo[3.2.1]octane-8-carboxylate (0.2 g, 0.408 mmol) in acetonitrile (5.0 mL) was added (S)-5-(hydroxymethyl)pyrrolidin-2-one (0.071 g, 0.613 mmol) and DABCO (0.055 g, 0.490 mmol). The reaction mixture was stirred at 80° C. for 16 h. The reaction mixture was quenched with saturated ammonium chloride and extracted with ethyl acetate. Combined organic layers were washed with water and saturated brine solution, dried over anhydrous $Na_2SO_4$, filtered and concentrated. The resulting residue was purified by column chromatography (Grace, 25 g snap, dry pack) over neutral alumina by eluting with 50-100% ethyl acetate in petroleum ether to provide tert-butyl tert-butyl 3-(7-bromo-6-chloro-8-fluoro-2-(((S)-5-oxopyrrolidin-2-yl)methoxy)quinazolin-4-yl)-3,8-diazabicyclo[3.2.1]octane-8-carboxylate (0.150 g, 0.180 mmol, 44.1% yield) as a gum solid. MS (ESI) m/z 584.0/586.0 $[M+1]^+$.

Preparation of Intermediate 8C: tert-butyl 3-(6-chloro-8-fluoro-7-(3-hydroxynaphthalen-1-yl)-2-(((S)-5-oxopyrrolidin-2-yl)methoxy)quinazolin-4-yl)-3,8-diazabicyclo[3.2.1]octane-8-carboxylate

8C

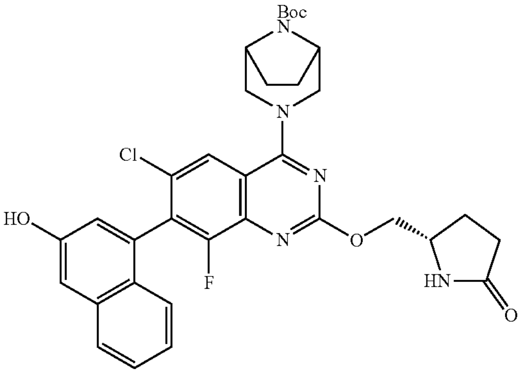

To a degassed solution of tert-butyl 3-(7-bromo-6-chloro-8-fluoro-2-(((S)-5-oxopyrrolidin-2-yl)methoxy)quinazolin-4-yl)-3,8-diazabicyclo[3.2.1]octane-8-carboxylate (0.150 g, 0.256 mmol) in 1,4-dioxane (3.0 mL) and water (0.5 mL) was added 4-(4,4,5,5-tetramethyl-1,3,2-dioxaborolan-2-yl)naphthalen-2-ol (0.173 g, 0.641 mmol), potassium phosphate, dibasic (0.089 g, 0.513 mmol) and $PdCl_2$(dppf) (0.019 g, 0.026 mmol). The reaction mixture was stirred at 80° C. for 16 h. After cooling, the reaction was diluted with ethyl acetate, filtered through a bed of diatomaceous earth (Celite®), and concentrated to afford tert-butyl 3-(6-chloro-8-fluoro-7-(3-hydroxynaphthalen-1-yl)-2-(((S)-5-oxopyrrolidin-2-yl)methoxy)quinazolin-4-yl)-3,8-diazabicyclo[3.2.1]octane-8-carboxylate (0.2 g, 0.173 mmol, 67.4% yield) as a brown solid. MS (ESI) m/z 648.2/649.2 $[M+1]^+$.

Examples 8-1

(5S)-5-{[(6-chloro-4-{3,8-diazabicyclo[3.2.1]octan-3-yl}-8-fluoro-7-(3-hydroxynaphthalen-1-yl)quinazolin-2-yl)oxy]methyl}pyrrolidin-2-one 8-1

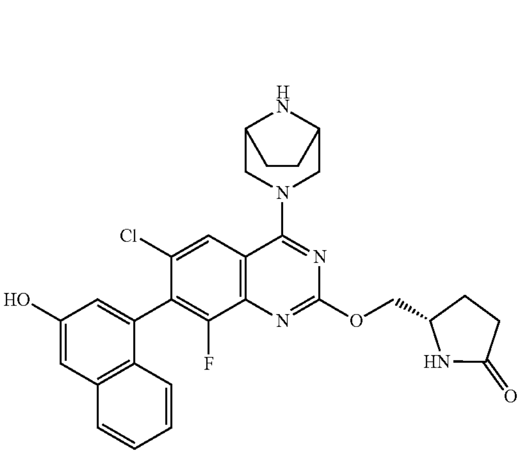

To a stirred solution of tert-butyl 3-(6-chloro-8-fluoro-7-(3-hydroxynaphthalen-1-yl)-2-(((S)-5-oxopyrrolidin-2-yl)methoxy)quinazolin-4-yl)-3,8-diazabicyclo[3.2.1]octane-8-carboxylate (0.2 g, 0.309 mmol) in DCM (5.0 mL) was added hydrogen chloride solution 4.0 M in dioxane (2.0 mL, 8.00 mmol) at 0° C. The reaction mixture was stirred at ambient temperature for 16 h. The reaction mixture was concentrated under reduced pressure to provide a residue, which was purified via preparative HPLC with the following conditions: YMC Triart C18 (250×20)mm, 5-μm particles; Mobile Phase A=10 mM Ammonium acetate in water, Mobile Phase B=Acetonitrile, Flow: 15 mL/min, mobile phase-A=grade-80-40%, mobile phase-B grade-20-60% in 15 min. Fractions containing the desired product were lyophilized to afford (5S)-5-(((4-(3,8-diazabicyclo[3.2.1]octan-3-yl)-6-chloro-8-fluoro-7-(3-hydroxynaphthalen-1-yl)quinazolin-2-yl)oxy)methyl)pyrrolidin-2-one, AcOH (50 mg, 0.079 mmol, 25.5% yield) as an off-white solid. MS (ESI) m/z 548.2 [M+1]+; 1H NMR (500 MHz, DMSO-$d_6$) δ 10.06 (s, 1H), 7.96 (s, 1H), 7.80-7.85 (m, 2H), 7.42-7.48 (m, 1H), 7.29 (d, J=2.40 Hz, 1H), 7.23-7.25 (m, 2H), 7.22-7.20 (m, 1H), 4.24-4.37 (m, 4H), 3.90-3.93 (m, 1H), 3.48-3.58 (m, 4H), 2.11-2.22 (m, 4H), 1.90-1.91 (m, 1H), 1.86-1.88 (m, 1H), 1.66-1.76 (m, 4H).

Examples in Table 5 were prepared according to procedures described for Example 8-1 from intermediate 8A and the appropriate alcohol.

TABLE 5

| Example Number | Structure | Name | MS m/z: [M + H]+ | $^1$H NMR |
|---|---|---|---|---|
| 8-2 | 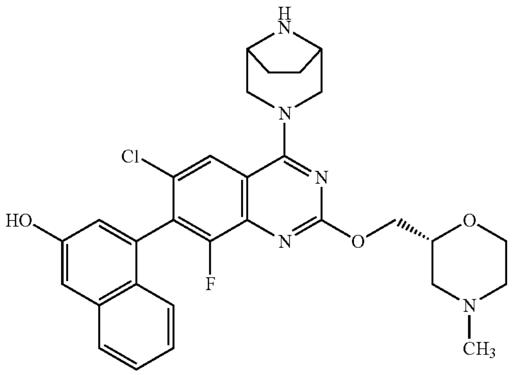 [SMILES: CN1CCO[C@@H](COc2nc(N3CC4CCC(C3)N4)c3cc(Cl)c(-c4cc(O)cc5ccccc45)c(F)c3n2)C1] | 4-(6-chloro-4-{3,8-diazabicyclo[3.2.1]octan-3-yl}-8-fluoro-2-{[(2R)-4-methylmorpholin-2-yl]methoxy}quinazolin-7-yl)naphthalen-2-ol | 563.5 | $^1$H NMR (500 MHz, DMSO-$d_6$) δ 10.25 (s, 1H), 10.08 (s, 1H), 9.37 (s, 1H), 9.16 (s, 1H), 8.01-8.01 (m, 1H), 7.83 (d, J = 8.40 Hz, 1H), 7.44-7.48 (m, 1H), 7.31-7.31 (m, 1H), 7.25-7.26 (m, 2H), 7.19-7.24 (m, 1H), 4.51-4.57 (m, 4H), 4.44-4.45 (m, 2H), 4.08-4.21 (m, 2H), 3.55-3.84 (m, 4H), 3.41-3.47 (m, 2H), 3.47-3.09 (m, 2H), 2.86 (s, 3H), 1.97-2.08 (m, 4H) |
| 8-3 | 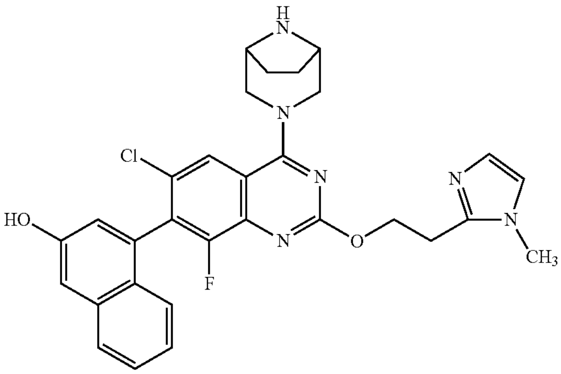 [SMILES: Cn1ccnc1CCOc1nc(N2CC3CCC(C2)N3)c2cc(Cl)c(-c3cc(O)cc4ccccc34)c(F)c2n1] | 4-(6-chloro-4-{3,8-diazabicyclo[3.2.1]octan-3-yl}-8-fluoro-2-[2-(1-methyl-1H-imidazol-2-yl)ethoxy]quinazolin-7-yl)naphthalen-2-ol | 558.5 | $^1$H NMR (500 MHz, DMSO-$d_6$) δ 10.19 (s, 1H), 9.42 (s, 1H), 9.22 (s, 1H), 7.97-9.98 (m,, 1H), 7.83 (d, J = 8.40 Hz, 1H), 7.56- 7.57 (m, 2H), 7.44-7.48 (m, 1H), 7.31-7.32 (m, 1H), 7.23-7.24 (m, 1H), 7.17-7.19 (m, 1H), 7.06-7.07 (m, 1H), 4.72-4.75 (m, 2H), 4.49-4.54 (m, 2H), 4.18-4.19 (m, 3H), 3.78 (s, 3H), 3.77-3.80 (m, 3H), 3.49-3.52 (m, 2H), 1.92-1.98 (m, 1H), 1.95-2.08 (m, 4H) |

TABLE 5-continued

| Example Number | Structure | Name | MS m/z: [M + H]+ | $^1$H NMR |
|---|---|---|---|---|
| 8-4 | 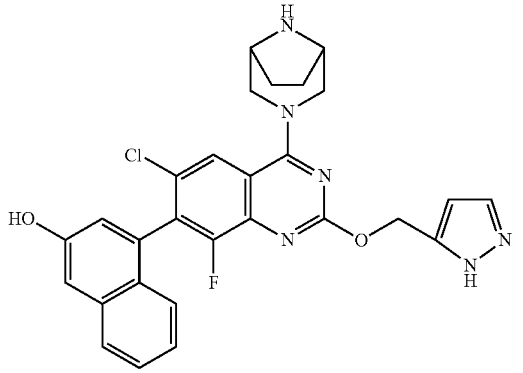 [SMILES: Oc1cc(-c2c(Cl)cc3c(N4CC5CCC(C4)N5)nc(OCc4ccn[nH]4)nc3c2F)c2ccccc2c1] | 4-(6-chloro-4-{3,8-diazabicyclo[3.2.1]octan-3-yl}-8-fluoro-2-[(1H-pyrazol-5-yl)methoxy]quinazolin-7-yl)naphthalen-2-ol | 531.0 | (500 MHz, DMSO-$d_6$) δ 10.04 (s, 1H), 7.99 (s, 1H), 7.83 (d, J = 7.84 Hz, 1H), 7.45 (m, 2H), 7.30 (m, 1H), 7.25 (d, J = 7.24 Hz, 2H), 7.07 (d, J = 7.08 Hz, 1H) 6.38 (s, 1H), 5.40 (s, 2H), 4.43-4.46 (m, 2H), 4.16 (m, 1H), 3.65-3.80 (m, 4H), 1.85-2.00 (m, 4H) |
| 8-5 | 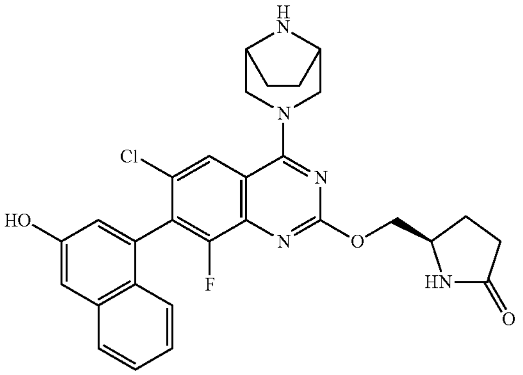 [SMILES: O=C1CC[C@H](COc2nc(N3CC4CCC(C3)N4)c3cc(Cl)c(-c4cc(O)cc5ccccc45)c(F)c3n2)N1] | (5R)-5-{[(6-chloro-4-{3,8-diazabicyclo[3.2.1]octan-3-yl}-8-fluoro-7-(3-hydroxynaphthalen-1-yl)quinazolin-2-yl)oxy]methyl}pyrrolidin-2-one | 548.0 | $^1$H NMR (500 MHz, DMSO-$d_6$) δ 7.96 (s, 1H), 7.80-7.85 (m, 2H), 7.42-7.46 (m, 1H), 7.29 (d, J = 2.00 Hz, 1H), 7.22-7.23 (m, 2H), 7.06 (d, J = 2.40 Hz, 1H), 4.23-4.37 (m, 4H), 3.90-3.93 (m, 1H), 3.52-3.58 (m, 4H), 2.11-2.17 (m, 3H), 1.87-1.91 (m, 2H), 1.85-1.86 (m, 4H) |
| 8-6 | 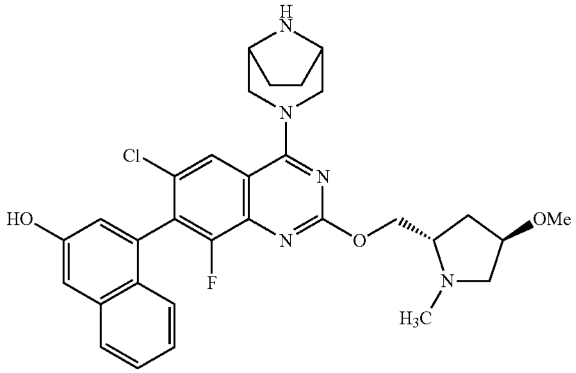 [SMILES: CO[C@@H]1C[C@@H](COc2nc(N3CC4CCC(C3)N4)c3cc(Cl)c(-c4cc(O)cc5ccccc45)c(F)c3n2)N(C)C1] | 4-(6-chloro-4-{3,8-diazabicyclo[3.2.1]octan-3-yl}-8-fluoro-2-{[(2S,4R)-4-methoxy-1-methylpyrrolidin-2-yl]methoxy}quinazolin-7-yl)naphthalen-2-ol | 578.2 | $^1$H NMR (500 MHz, DMSO-$d_6$) δ 10.07 (s, 1H), 9.08 (s, 1H), 8.02 (s, 1H), 7.83 (d, J = 8.40 Hz, 1H), 7.47 (t, J = 5.20 Hz, 1H), 7.44-7.46 (m, 1H), 7.18-7.24 (m, 2H), 7.06-7.06 (m, 1H), 4.51 (m, 4H), 4.01-4.20 (m, 2H), 3.82-3.84 (m, 1H), 3.75 (m, 2H), 3.25 (s, 3H), 2.90-3.01 (m, 2H), 2.49-2.50 (m, 3H), 1.96 (s, 3H) |

TABLE 5-continued

| Example Number | Structure | Name | MS m/z: [M + H]+ | $^1$H NMR |
|---|---|---|---|---|
| 8-7 | 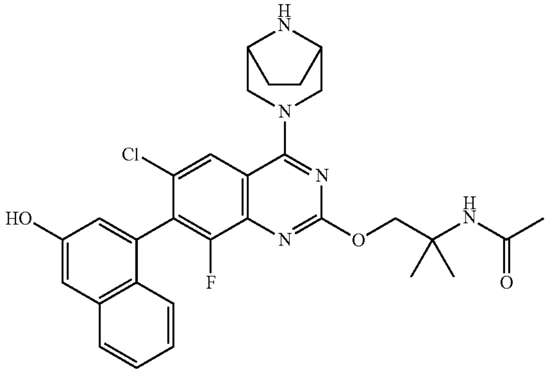 [SMILES: CC(=O)NC(C)(C)COc1nc(N2CC3CCC(C2)N3)c2cc(Cl)c(-c3cc(O)cc4ccccc34)c(F)c2n1] | N-{1-[(6-chloro-4-{3,8-diazabicyclo[3.2.1]octan-3-yl}-8-fluoro-7-(3-hydroxynaphthalen-1-yl)quinazolin-2-yl)oxy]-2-methylpropan-2-yl}acetamide | 564.2 | $^1$H NMR (500 MHz, DMSO-$d_6$) δ 7.94 (d, J = 1.20 Hz, 1H), 7.81 (d, J = 8.40 Hz, 1H), 7.65 (s, 1H), 7.40-7.50 (m, 1H), 7.29 (d, J = 2.40 Hz, 1H), 7.22 (d, J = 4.00 Hz, 2H), 7.07 (d, J = 2.40 Hz, 1H), 8 4.41 (s, 1H), 4.33 (d, J = 10.40 Hz, 2H), 3.51-3.54 (m, 5H), 1.88 (s, 2H), 1.77 (d, J = 8.80 Hz, 3H), 1.66 (s, 4H), 1.33 (s, 6H) |
| 8-8 | 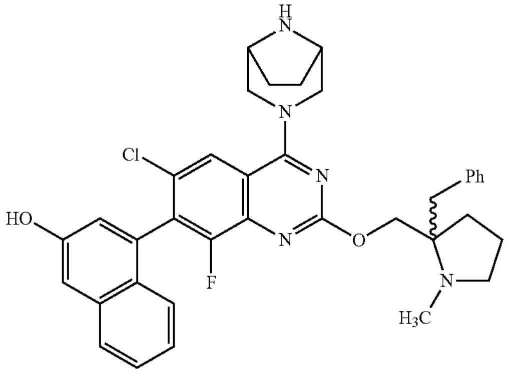 [SMILES: CN1CCCC1(COc1nc(N2CC3CCC(C2)N3)c2cc(Cl)c(-c3cc(O)cc4ccccc34)c(F)c2n1)Cc1ccccc1] | 4-{2-[(2-benzyl-1-methylpyrrolidin-2-yl)methoxy]-6-chloro-4-{3,8-diazabicyclo[3.2.1]octan-3-yl}-8-fluoroquinazolin-7-yl}naphthalen-2-ol | 638.1 | $^1$H NMR (500 MHz, DMSO-$d_6$) δ 8.15 (s, 1H), 7.96 (s, 1H), 7.82 (d, J = 8.40 Hz, 1H), 7.43-7.47 (m, 1H), 7.29 (d, J = 2.40 Hz, 1H), 7.18-7.24 (m, 8H), 7.06 (d, J = 2.00 Hz, 1H), δ 4.38-4.47 (m, 2H), 4.23-4.33 (m, 2H), 3.92 (s, 2H), 3.70 (t, J = 16.00 Hz, 2H), 2.81-2.93 (m, 2H), 2.67 (d, J = 2.00 Hz, 1H), 2.49 (q, J = 13.60 Hz, 2H), 1.80 (q, J = 23.20 Hz, 6H), 1.53-1.67 (m, 3H) |
| 8-9 | 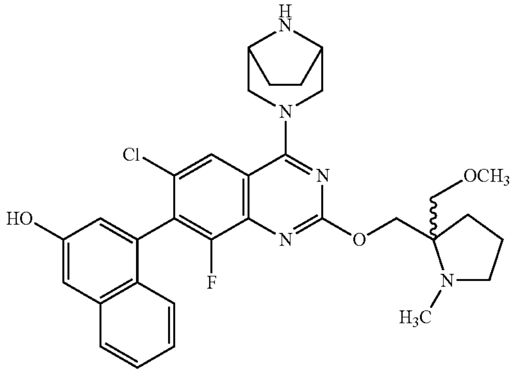 [SMILES: COCC1(COc2nc(N3CC4CCC(C3)N4)c3cc(Cl)c(-c4cc(O)cc5ccccc45)c(F)c3n2)CCCN1C] | 4-(6-chloro-4-{3,8-diazabicyclo[3.2.1]octan-3-yl}-8-fluoro-2-{[2-(methoxymethyl)-1-methylpyrrolidin-2-yl]methoxy}quinazolin-7-yl)naphthalen-2-ol | 592.3 | $^1$H NMR (500 MHz, DMSO-$d_6$) δ 8.20 (s, 2H), 7.95 (s, 1H), 7.81 (d, J = 8.40 Hz, 1H), 7.43-7.47 (m, 1H), 7.29 (d, J = 2.40 Hz, 1H), 7.22 (d, J = 4.00 Hz, 2H), 7.06 (d, J = 2.40 Hz, 1H), 4.39 (t, J = 22.00 Hz, 2H), 4.21-4.30 (m, 2H), 3.78 (s, 2H), 3.63 (t, J = 24.40 Hz, 2H), 3.43 (d, J = 9.60 Hz, 1H), 3.35 (d, J = 9.60 Hz, 1H), 3.27 (d, J = 12.40 Hz, 3H), 2.79 (q, J = 13.60 Hz, 1H), 2.72 (t, J = 14.80 Hz, 1H), 2.41 (s, 3H), 1.68-1.82 (m, 8H) |

Examples 9-1 and 9-2

6-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine

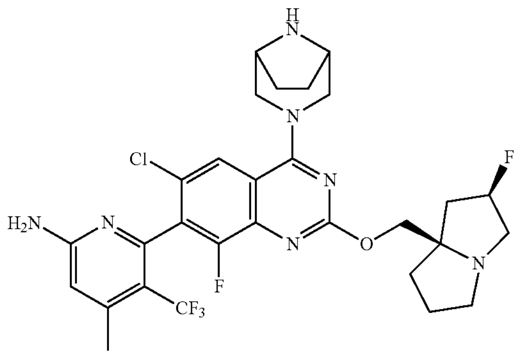

9-1 (isomer 1)
9-2 (isomer 2)

Preparation of Intermediate 9A: (3-bromopropoxy)(tert-butyl)dimethylsilane

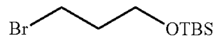

To a stirred solution of 3-bromopropan-1-ol (10.00 g, 71.9 mmol) in anhydrous dichloromethane (50 mL) under nitrogen at 0° C. were added imidazole (4.90 g, 71.9 mmol) followed by tert-butyldimethylsilyl chloride (14.10 g, 94 mmol). Reaction mixture was slowly warmed to room temperature and stirred at the same temperature for 12 h. Reaction mixture was quenched with saturated aq. ammonium chloride solution (20 mL) and diluted with water (50 mL). The suspension was extracted with dichloromethane (3×200 mL). Combined organic layers were dried over anhydrous sodium sulphate, filtered, and concentrated reduced pressure to obtain the crude residue of the product. The residue was purified by silica gel column chromatography with 0-5% of ethyl acetate in petroleum ether to obtain the (3-bromopropoxy)(tert-butyl)dimethylsilane (8.00 g, 31.6 mmol, 43.9% yield) as colorless oil. $^1$H NMR (400 MHz, $CD_3OD$): δ 3.69 (t, J=4.0 Hz, 2H), 3.57 (t, J=6.4 Hz, 2H), 1.99-1.93 (m, 2H), 0.87 (s, 9H), 0.06 (s, 6H) ppm.

Preparation of Intermediate 9B: 1-(tert-butyl) 2-methyl (2R,4R)-2-(3-((tert-butyldimethylsilyl)oxy)propyl)-4-fluoropyrrolidine-1,2-dicarboxylate

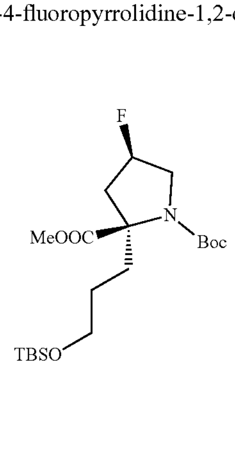

To a stirred solution of 1-(tert-butyl) 2-methyl (2S,4R)-4-fluoropyrrolidine-1,2-dicarboxylate (5.00 g, 20.22 mmol) in anhydrous THE (30 mL) under nitrogen atmosphere at −25° C. was added LiHMDS (1M in THF, 30.3 mL, 30.3 mmol) dropwise. Reaction mixture was stirred at same temperature for 30 min prior dropwise addition of (3-bromopropoxy)(tert-butyl)dimethylsilane (7.68 g, 30.3 mmol). The reaction mixture was stirred at the same temperature for 30 min and then slowly warmed to room temperature. Reaction mixture was quenched with saturated aq. ammonium chloride solution (15 mL) and then diluted with water (50 mL). The mixture was extracted with ethyl acetate (3×100 mL). The combined organic layers were dried over anhydrous $Na_2SO_4$, filtered and concentrated reduced pressure. The residue was purified by silica gel column chromatography with 20-30% of ethyl acetate in petroleum ether to obtain the 1-(tert-butyl) 2-methyl (2R,4R)-2-(3-((tert-butyldimethylsilyl)oxy)propyl)-4-fluoropyrrolidine-1,2-dicarboxylate (7.23 g, 17.24 mmol, 85.0% yield) as colorless oil. $^1$H NMR (400 MHz, $CDCl_3$): δ 5.18-5.03 (m, 1H), 4.10-3.98 (m, 1H), 3.78 (s, 3H), 3.74-3.52 (m, 3H), 2.48-2.23 (m, 3H), 2.19-1.98 (m, 1H), 1.65 (s, 9H), 1.48-1.44 (m, 2H), 0.90 (s, 9H), 0.60 (s, 6H) ppm. $^{19}$F (376 MHz, $CD_3OD$): δ −172.47 to −172.96 (m) ppm. LCMS-ELSD (ESI) m/z: 320.2 [M+H-Boc]$^+$.

Preparation of Intermediate 9C: 1-(tert-butyl) 2-methyl (2R,4R)-4-fluoro-2-(3-hydroxypropyl)pyrrolidine-1,2-dicarboxylate

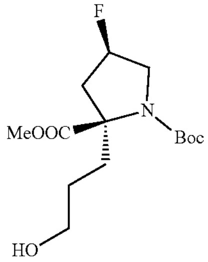 [SMILES: COC(=O)[C@@]1(CCCO)C[C@@H](F)CN1C(=O)OC(C)(C)C]

To a stirred solution of 1-(tert-butyl) 2-methyl (2R,4R)-2-(3-((tert-butyldimethylsilyl)oxy)propyl)-4-fluoropyrrolidine-1,2-dicarboxylate (7.00 g, 16.68 mmol) at 25° C. was added TBAF (1M in THF, 16.68 mL, 16.68 mmol) dropwise, and stirred at the same temperature for 4 h. Reaction mixture was quenched with saturated aq. ammonium chloride solution (90 mL) and diluted with ethyl acetate (100 mL). The mixture was extracted with ethyl acetate (3×150 mL). Combined organic layer was dried over anhydrous sodium sulphate, filtered, and concentrated reduced pressure to obtain the crude residue as colorless oil. The crude was purified by silica gel column chromatography using 50% ethyl acetate in petroleum ether to obtain 1-(tert-butyl) 2-methyl (2R,4R)-4-fluoro-2-(3-hydroxypropyl)pyrrolidine-1,2-dicarboxylate (4.97 g, 15.64 mmol, 94.0% yield) as colorless oil. LCMS-ELSD (ESI) m/z: 206.2 [M+H-Boc]$^+$.

Preparation of Intermediate 9D: 1-(tert-butyl) 2-methyl (2R,4R)-4-fluoro-2-(3-iodopropyl)pyrrolidine-1,2-dicarboxylate

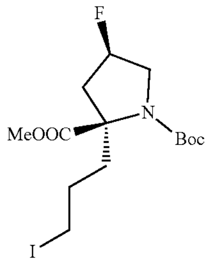 [SMILES: COC(=O)[C@@]1(CCCI)C[C@@H](F)CN1C(=O)OC(C)(C)C]

To a stirred solution of 1-(tert-butyl) 2-methyl (2R,4R)-4-fluoro-2-(3-hydroxypropyl)pyrrolidine-1,2-dicarboxylate (9.00 g, 29.5 mmol) in dichloromethane (100 mL) at 0° C. was added triphenylphosphine (15.50 g, 58.9 mmol), imidazole (6.02 g, 88 mmol) and the reaction mixture was stirred at same temperature for 10 min before addition of iodine (29.9 g, 118 mmol). The reaction mixture was stirred at room temperature for 12 h. The reaction mixture was then quenched with sat. aq. sodium thiosulfate solution (30 mL) and the suspension was extracted with dichloromethane (2×200 mL). The combined organic layers were dried over anhydrous sodium sulphate, filtered, and concentrated reduced pressure to obtain the crude residue. This crude was purified by silica gel column chromatography using 10-20% ethyl acetate in petroleum ether to obtain 1-(tert-butyl) 2-methyl (2R,4R)-4-fluoro-2-(3-iodopropyl)pyrrolidine-1,2-dicarboxylate (10.10 g, 24.32 mmol, 83.0% yield) as colourless oil. LCMS-ELSD (ESI) m/z: 361.2 $[M+H-Boc]^+$.

Preparation of Intermediate 9E: tert-butyl 3-(6-chloro-8-fluoro-7-(3-hydroxynaphthalen-1-yl)-2-(((R)-1-(piperidin-1-yl)propan-2-yl)oxy)quinazolin-4-yl)-3,8-diazabicyclo[3.2.1]octane-8-carboxylate

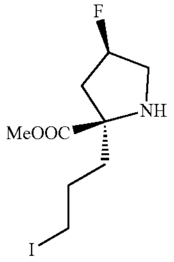 [SMILES: COC(=O)[C@@]1(CCCI)C[C@@H](F)CN1]

To a stirred solution of 1-(tert-butyl) 2-methyl (2R,4R)-4-fluoro-2-(3-iodopropyl)pyrrolidine-1,2-dicarboxylate (10.0 g, 24.08 mmol) in dichloromethane (20 mL) at 25° C. was added HCl in dioxane (8.03 mL, 24.08 mmol) and reaction mixture was stirred for 6h at same temperature. On complete consumption of starting material, the reaction mixture was concentrated reduced pressure at room temperature to obtain the crude residue of methyl (2R,4R)-4-fluoro-2-(3-iodopropyl)pyrrolidine-2-carboxylate·HCl (6.5 g, 20.63 mmol, 86.0% yield), which was used as such for the next step without any further purification. LCMS-ELSD (ESI) m/z: 188.2 $[M+H]^+$.

Preparation of Intermediate 9F: methyl (2R,7aR)-2-fluorotetrahydro-1H-pyrrolizine-7a(5H)-carboxylate

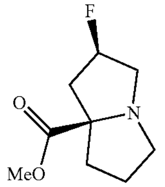 [SMILES: COC(=O)[C@]12CCCN1C[C@H](F)C2]

To a stirred solution of methyl (2R,4R)-4-fluoro-2-(3-iodopropyl)pyrrolidine-2-carboxylate (6.5 g, 20.63 mmol) in anhydrous acetonitrile (30 mL) was added triethylamine (10 mL) at room temperature. Reaction mixture was stirred at 45° C. for 12 h. Reaction mixture was concentrated reduced pressure to obtain the crude residue. The residue was purified by column chromatography (alumina-neutral) using 40-50% ethyl acetate in petroleum ether to obtain the methyl (2R,7aR)-2-fluorotetrahydro-1H-pyrrolizine-7a(5H)-carboxylate (3.20 g, 83.0% yield) as pale-yellow oil. $^1H$ NMR (400 MHz, DMSO-$d_6$): δ 5.76-5.19 (m, 1H), 3.59 (s, 3H), 3.25-3.16 (m, 1H), 2.97-2.95 (m, 1H), 2.86-2.76 (m, 1H), 2.68-2.51 (m, 2H), 2.02-1.91 (m, 2H), 1.85-1.72 (m, 3H) ppm. LCMS-ELSD (ESI) m/z: 188.3 $[M+H]^+$.

Preparation of Intermediate 9G: ((2R,7aR)-2-fluorotetrahydro-1H-pyrrolizin-7a(5H)-yl)methanol

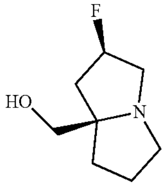 [SMILES: OC[C@]12CCCN1C[C@H](F)C2]

To a stirred solution of methyl (2R,7aR)-2-fluorotetrahydro-1H-pyrrolizine-7a(5H)-carboxylate (3.20 g, 17.09 mmol) under nitrogen at 0° C. was added $LiAlH_4$ (2M in THF, 17.09 mL, 34.2 mmol) dropwise over 10 min. After addition, the reaction mixture was warmed to room temperature in 30 min. The mixture was stirred at this temperature for 1 h prior to being quenched with saturated aq. ammonium chloride (5 mL) at 0° C. Once the effervescence was stopped, anhydrous sodium sulphate was added to the reaction mixture, followed by dichloromethane (20 mL). The reaction mixture was stirred for 20 min and filtered. The filtrate was collected, dried over anhydrous sodium sulphate, filtered, and concentrated reduced pressure to obtain the crude residue of ((2R,7aR)-2-fluorotetrahydro-1H-pyrrolizin-7a(5H)-yl)methanol (2.20 g, 13.68 mmol, 80.0% yield) as pale brown oil. $^1H$ NMR (400 MHz, $CD_3OD$): δ 5.34-5.10 (m, 1H), 3.51-3.29 (m, 3H), 3.25-3.10 (m, 1H), 3.04-2.93 (m, 1H), 2.90-2.73 (m, 1H), 2.71-2.59 (m, 1H), 2.28-2.12 (m, 1H), 1.95-1.73 (m, 4H), 1.68-1.66 (m, 1H) ppm. $^{19}F$ (376 MHz, $CD_3OD$): δ −175.69 to −176.04 (m) ppm. LCMS-ELSD (ESI) m/z: 160.0 $[M+H]^+$.

Preparation of Intermediate 9H: tert-butyl 3-(7-(6-(bis(4-methoxybenzyl)amino)-4-methylpyridin-2-yl)-6-chloro-2,8-difluoroquinazolin-4-yl)-3,8-diazabicyclo[3.2.1]octane-8-carboxylate

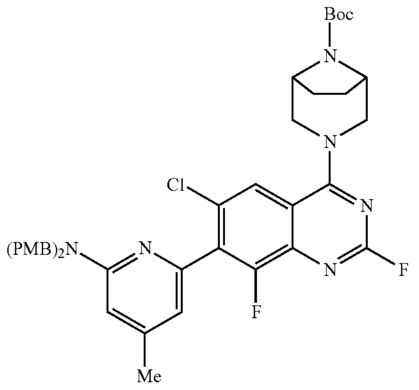

To a degassed solution of Example 8A (2.00 g, 4.08 mmol) in anhydrous 1,4-dioxane (20 mL) were added potassium phosphate (1.73 g, 8.17 mmol), N,N-bis(4-methoxybenzyl)-4-methyl-6-(4,4,5,5-tetramethyl-1,3,2-dioxaborolan-2-yl)pyridin-2-amine (5.8 g, 12.25 mmol), $PdCl_2(dppf)$ (149 mg, 0.204 mmol). The mixture was degassed again and heated at 80° C. for 48 h. Reaction progress was monitored by LCMS. The reaction vessel was allowed to cool to ambient temperature, diluted with ethyl acetate (40 mL), filtered through a bed of Celite and concentrated in vacuo to afford crude product. The residue was purified by silica gel column chromatography using 30% ethyl acetate in petroleum ether to obtain tert-butyl 3-(7-(6-(bis(4-methoxybenzyl)amino)-4-methylpyridin-2-yl)-6-chloro-2,8-difluoroquinazolin-4-yl)-3,8-diazabicyclo[3.2.1]octane-8-carboxylate (1.5 g, 1.74 mmol, 42% yield). $^1H$ NMR (400 MHz, $CDCl_3$): δ 7.76 (d, J=1.6 Hz, 1H), 7.20-7.18 (d, J=8.8 Hz, 4H), 6.86 (dt, J=9.6 Hz, 4H), 6.60 (s, 1H), 6.38 (s, 1H), 4.60 (s, 3H), 4.39-4.21 (m, 4H), 3.63 (s, 6H), 2.29 (s, 3H), 1.98-1.96 (m, 6H), 1.76-1.63 (m, 2H), 1.49 (s, 9H) ppm. LCMS (ESI) m/z: 757.2 $[M+H]^+$.

Preparation of Intermediate 91: tert-butyl 3-(7-(6-(bis(4-methoxybenzyl)amino)-3-iodo-4-methylpyridin-2-yl)-6-chloro-2,8-difluoroquinazolin-4-yl)-3,8 diazabicyclo[3.2.1]octane-8-carboxylate

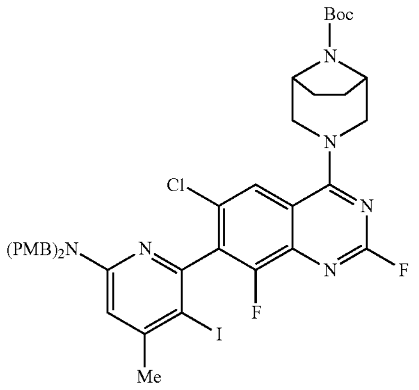

To a stirred solution of tert-butyl 3-(7-(6-(bis(4-methoxybenzyl)amino)-4-methylpyridin-2-yl)-6-chloro-2,8-difluoroquinazolin-4-yl)-3,8-diazabicyclo[3.2.1]octane-8-carboxylate (1.40 g, 1.849 mmol) in anhydrous acetonitrile (15 mL) under nitrogen at 0° C. were added N-iodosuccinimide (0.42 g, 1.849 mmol) and trifluoroacetic acid (0.028 mL, 0.370 mmol). The reaction mixture was allowed to reach room temperature over one hour. The reaction mixture was then quenched with saturated aq. sodium thiosulphate (5 mL) and saturated aq. sodium bicarbonate (4 mL). The mixture was extracted with ethyl acetate (3×20 mL). Combined organic layers were dried over anhydrous sodium sulphate, filtered, and concentrated reduced pressure to obtain the crude residue. The crude residue was purified by silica gel column chromatography using 30% ethyl acetate in petroleum ether to obtain tert-butyl 3-(7-(6-(bis(4-methoxybenzyl)amino)-3-iodo-4-methylpyridin-2-yl)-6-chloro-2,8-difluoroquinazolin-4-yl)-3,8 diazabicyclo[3.2.1]octane-8-carboxylate (1.42 g, 1.560 mmol, 84% yield) as pale yellow fluffy solid. LCMS (ESI) m/z: 883.3 $[M+H]^+$.

Preparation of Intermediate 9J: tert-butyl 3-(7-(6-(bis(4-methoxybenzyl)amino)-4-methyl-3-(trifluoromethyl)pyridin-2-yl)-6-chloro-2,8-difluoroquinazolin-4-yl)-3,8-diazabicyclo[3.2.1]octane-8-carboxylate

9J

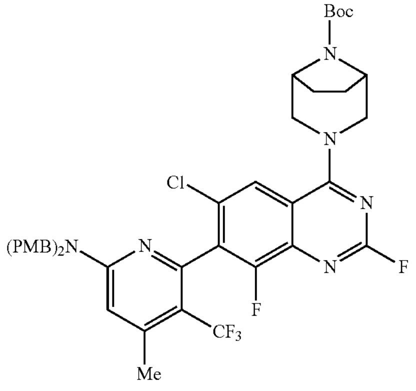

To a stirred solution of tert-butyl 3-(7-(6-(bis(4-methoxybenzyl)amino)-3-iodo-4-methylpyridin-2-yl)-6-chloro-2,8-difluoroquinazolin-4-yl)-3,8-diazabicyclo[3.2.1]octane-8-carboxylate (1.40 g, 1.585 mmol) in anhydrous DMA (10 mL) in a sealed tube under nitrogen atmosphere was added copper(I) iodide (0.60 g, 3.17 mmol). The reaction mixture was degassed 10 min before the addition of methyl 2,2-difluoro-2-(fluorosulfonyl)acetate (0.91 g, 4.76 mmol) and reaction mixture was heated to 90° C. for 12 h. Reaction progress was monitored by LCMS. Reaction mixture was diluted with diethyl ether (20 mL) and water (10 mL). Layers were separated and aqueous layer was extracted with diethyl ether (3×20 mL). Combined organic layers were dried over anhydrous sodium sulphate, filtered, and concentrated reduced pressure to obtain the crude residue. The crude was purified by silica gel column chromatography using 30% ethyl acetate in petroleum ether to obtain tert-butyl 3-(7-(6-(bis(4-methoxybenzyl)amino)-4-methyl-3-(trifluoromethyl)pyridin-2-yl)-6-chloro-2,8-difluoroquinazolin-4-yl)-3,8-diazabicyclo[3.2.1]octane-8-carboxylate (0.85 g, 0.630 mmol, 40% yield) as a pale yellow solid.

$^1H$ NMR (400 MHz, $CDCl_3$): δ 7.77 (s, 1H), 7.16 (d, J=8.8 Hz, 4H), 6.87 (dt, J=9.6 and 2.8 Hz, 4H), 6.43 (s, 1H), 4.76-4.72 (m, 2H), 4.59-4.55 (m, 2H), 3.81 (s, 6H), 2.43 (s, 3H), 1.97-1.82 (m, 4H), 1.97-1.82 (m, 4H), 1.53 (s, 9H) ppm. LCMS (ESI) m/z: 825.2 $[M+H]^+$.

Preparation of intermediate 9K: tert-butyl 3-(7-(6-(bis(4-methoxybenzyl)amino)-4-methyl-3-(trifluoromethyl)pyridin-2-yl)-6-chloro-8-fluoro-2-(((2R,7aR)-2-fluorotetrahydro-1H-pyrrolizin-7a(5H)-yl)methoxy)quinazolin-4-yl)-3,8-diazabicyclo[3.2.1]octane-8-carboxylate

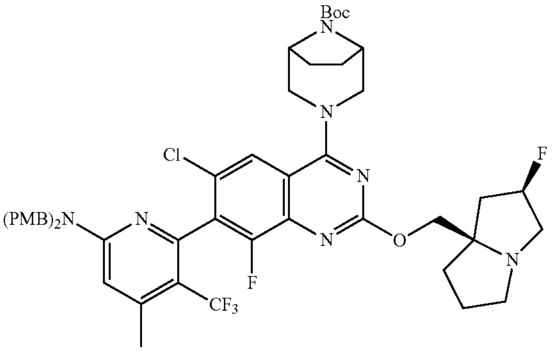

To a stirred solution of ((2R,7aR)-2-fluorotetrahydro-1H-pyrrolizin-7a(5H)-yl)methanol (0.23 g, 1.454 mmol) in anhydrous THF (2.1 mL) at 0° C. was added sodium hydride (43.6 mg, 1.091 mmol) and the reaction mixture was stirred at the same temperature for 30 min. After 30 min tert-butyl 3-(7-(6-(bis(4-methoxybenzyl)amino)-4-methyl-3-(trifluoromethyl)pyridin-2-yl)-6-chloro-2,8-difluoroquinazolin-4-yl)-3,8-diazabicyclo[3.2.1]octane-8-carboxylate (0.60 g, 0.727 mmol) dissolved in anhydrous THF (10 mL) was added to the reaction mixture dropwise while maintaining the temperature 0° C. The reaction mixture was stirred for the next 2 h while warming the reaction mixture to room temperature. The reaction mixture was quenched with saturated aq. ammonium chloride solution (1 mL) and diluted with ethyl acetate (5 mL). The mixture was extracted with ethyl acetate (3×5 mL). Combined organic layers were dried over anhydrous sodium sulphate, filtered, and concentrated under a vacuum to obtain the crude residue of the product. Crude residue was purified over neutral alumina using 30% ethyl acetate in petroleum ether to obtain tert-butyl 3-(7-(6-(bis(4-methoxybenzyl)amino)-4-methyl-3-(trifluoromethyl)pyridin-2-yl)-6-chloro-8-fluoro-2-(((2R,7aR)-2-fluorotetrahydro-1H-pyrrolizin-7a(5H)-yl)methoxy)quinazolin-4-yl)-3,8-diazabicyclo[3.2.1]octane-8-carboxylate (657 mg, 0.703 mmol, 97.0% yield) obtained as pale yellow solid. LCMS (ESI) m/z: 964.3 $[M+H]^+$.

Examples 9-1 and 9-2

6-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine

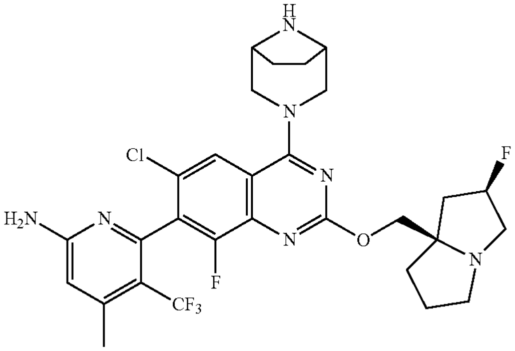

9-1 (isomer 1)
9-2 (isomer 2)

To a stirred solution of TFA (200 μl, 2.59 mmol) and triethyl silane (83 μl, 0.518 mmol) was added tert-butyl 3-(7-(6-(bis(4-methoxybenzyl)amino)-4-methyl-3-(trifluoromethyl)pyridin-2-yl)-6-chloro-8-fluoro-2-(((2R,7aR)-2-fluorotetrahydro-1H-pyrrolizin-7a(5H)-yl)methoxy)quinazolin-4-yl)-3,8-diazabicyclo[3.2.1]octane-8-carboxylate (0.50 g, 0.518 mmol) at room temperature. Then reaction mixture was stirred at 35° C. for 12 h. The progress of the reaction was monitored by LCMS. After completion, the reaction mixture was concentrated to remove most of the TFA reduced pressure and below 35° C. The residue was co-evaporated with methanol (3×1 mL) to remove any residual TFA. The residue was neutralized with DIPEA and concentrated reduced pressure to obtain a free base. The crude was then purified by silica gel (previously neutralized with DIPEA) column chromatography using a mixture of MeOH, dichloromethane and DIPEA (15:80:2.5) to obtain 6-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine. Atropisomers were separated by chiral SFC (Column: OD 25×5 mm I.D., 5 um. Mobile phase: Phase A for $CO_2$, and Phase B for MeOH (0.1% $NH_4OH$); Gradient elution: 40% MeOH (0.1% $NH_4OH$) in $CO_2$. Flow rate: 350 mL/min; Detector: UV 220 nm; Column Temp: 30° C.; Back Pressure: 100 Bar) to obtain two product peaks: peak 1 (Example 9-1) and peak 2 (Example 9-2).

Peak 1, isomer 1: Example 9-1 (66 mg, 33% yield). MS (ESI) m/z 624.3 $[M+1]^+$. $^1H$ NMR (499 MHz, DMSO-$d_6$) δ 7.88-7.76 (m, 1H), 6.94-6.75 (m, 2H), 6.57-6.42 (m, 1H), 5.49-5.24 (m, 1H), 4.36-4.27 (m, 1H), 4.22-4.16 (m, 1H), 4.11 (s, 1H), 4.07-4.01 (m, 1H), 3.58-3.49 (m, 3H), 3.48-3.42 (m, 1H), 3.01-2.92 (m, 1H), 2.89-2.74 (m, 1H), 2.58-2.54 (m, 1H), 2.40-2.36 (m, 3H), 2.35-2.26 (m, 1H), 1.87-1.87 (m, 1H), 1.96-1.78 (m, 3H), 1.71-1.57 (m, 5H).

Peak 2, isomer 2: Example 9-2 (58.8 mg, 29% yield). MS (ESI) m/z 624.3 $[M+1]^+$. $^1H$ NMR (499 MHz, DMSO-$d_6$) δ 7.92-7.72 (m, 1H), 6.96-6.76 (m, 2H), 6.60-6.41 (m, 1H), 5.52-5.23 (m, 1H), 4.40-4.31 (m, 1H), 4.27-4.18 (m, 1H), 4.15-4.04 (m, 2H), 3.68-3.61 (m, 2H), 3.60-3.54 (m, 1H), 3.53-3.46 (m, 1H), 3.00-2.92 (m, 1H), 2.90-2.75 (m, 1H), 2.60-2.53 (m, 1H), 2.37 (d, J=1.4 Hz, 3H), 2.36-2.27 (m, 1H), 1.96-1.77 (m, 4H), 1.74-1.61 (m, 5H).

Examples 10-1 and 10-2

4-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol

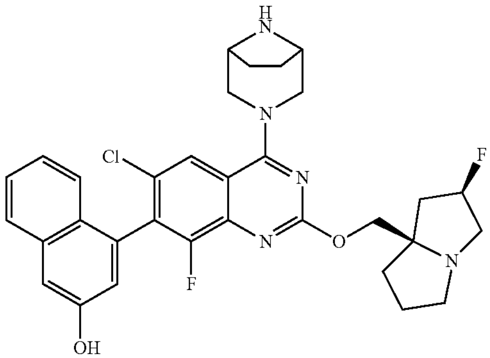

10-1 (Isomer 1)
10-2 (Isomer 2)

Preparation of Intermediate 10A: tert-butyl 3-(7-bromo-6-chloro-8-fluoro-2-(((2R,7aR)-2-fluorotetrahydro-1H-pyrrolizin-7a(5H)-yl)methoxy)quinazolin-4-yl)-3,8-diazabicyclo[3.2.1]octane-8-carboxylate

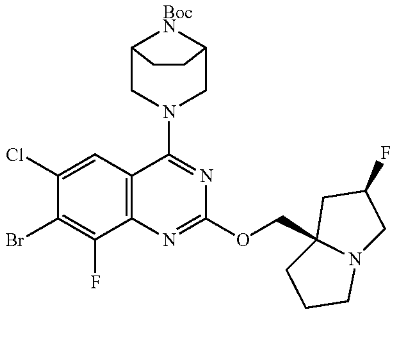 [SMILES: CC(C)(C)OC(=O)N1C2CCC1CN(c1nc(OC[C@]34CCCN3C[C@H](F)C4)nc3c(F)c(Br)c(Cl)cc13)C2]

To a stirred solution of ((2R,7aR)-2-fluorotetrahydro-1H-pyrrolizin-7a(5H)-yl)methanol (0.390 g, 2.450 mmol) in THE (20 mL) was added NaH (60% in mineral oil, 0.074 g, 3.06 mmol) at 0° C. and reaction mixture was stirred for 30 min. tert-butyl 3-(7-bromo-6-chloro-2,8-difluoroquinazolin-4-yl)-3,8 diazabicyclo[3.2.1]octane-8-carboxylate (1.0 g, 2.042 mmol) in THE (20 mL) was added to above reaction mixture at 0° C. The reaction mixture was stirred at ambient temperature for 16 h. Reaction progress was monitored by LCMS confirming desired product formation. The reaction mixture was quenched with saturated ammonium chloride solution (10 mL) and extracted with ethyl acetate (2×20 mL). Combined organic layer was washed with water and saturated brine solution, dried over anhydrous $Na_2SO_4$, filtered and concentrated under reduced pressure to afford crude product. The crude product obtained was purified by column chromatography (Grace, 50 g snap, dry pack) over neutral alumina by eluting with 50-100% ethyl acetate in petroleum ether. The desired fractions were pooled and concentrated under reduced pressure to obtain tert-butyl 3-(7-bromo-6-chloro-8-fluoro-2-(((2R,7aR)-2-fluorotetrahydro-1H-pyrrolizin-7a(5H)-yl)methoxy)quinazolin-4-yl)-3,8-diazabicyclo[3.2.1]octane-8-carboxylate (650 mg, 1.002 mmol, 49.1% yield) as a pale brown solid. LCMS (ESI) m/z: 629.0 $[M+H]^+$.

Preparation of Intermediate 10B: tert-butyl 3-(6-chloro-8-fluoro-2-(((2R,7aR)-2-fluorotetrahydro-1H-pyrrolizin-7a(5H)yl)methoxy)-7-(3-hydroxynaphthalen-1-yl)quinazolin-4-yl)-3,8-diazabicyclo[3.2.1]octane-8-carboxylate

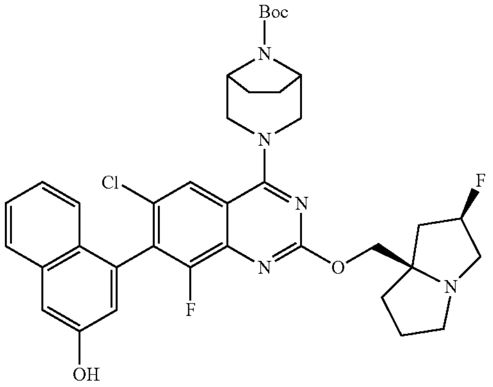 [SMILES: CC(C)(C)OC(=O)N1C2CCC1CN(c1nc(OC[C@]34CCCN3C[C@H](F)C4)nc3c(F)c(-c4cc(O)cc5ccccc45)c(Cl)cc13)C2]

To a degassed solution of tert-butyl 3-(7-bromo-6-chloro-8-fluoro-2-(((2R,7aR)-2-fluorotetrahydro-1H-pyrrolizin-7a(5H)-yl)methoxy)quinazolin-4-yl)-3,8 diazabicyclo[3.2.1]octane-8-carboxylate (650 mg, 1.033 mmol) in water (0.5 mL), DMF (1.5 mL) and 1,4-dioxane (5.0 mL), 4-(4,4,5,5-tetramethyl-1,3,2-dioxaborolan-2-yl)naphthalen-2-ol (698 mg, 2.58 mmol), sodium carbonate (274 mg, 2.58 mmol) and palladium(II)bis(triphenylphosphine) dichloride (76 mg, 0.103 mmol) were added. The mixture was degassed again and heated in a pressure vial at 100° C. for 16 h. Reaction was monitored by LCMS; analysis shows desired product formation. The reaction vessel was allowed to cool to ambient temperature, diluted with ethyl acetate, filtered through a bed of Celite and concentrated in vacuo to afford crude product. The residue was purified by preparative HPLC (Ammonium acetate as additive, Instrument: Agilent; Column: XBridge C8 250*19*5 um; Mobile phase: A (10 Mm aq. ammonium acetate) and B: Acetonitrile; Gradient: B 4%-80% in 15 min linearly; Flow rate: 15 mL/min; Wavelength: 220 nm.254 nm) to afford the desired product tert-butyl 3-(6-chloro-8-fluoro-2-(((2R,7aR)-2-fluorotetrahydro-1H-pyrrolizin-7a(5H)-yl)methoxy)-7-(3-hydroxynaphthalen-1-yl)quinazolin-4-yl)-3,8-diazabicyclo[3.2.1]octane-8-carboxylate (0.15 g, 0.204 mmol, 19.70%) as off white solid. LCMS (ESI) m/z: 692.2 [M+H].

Examples 10-1 and 10-2

4-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol

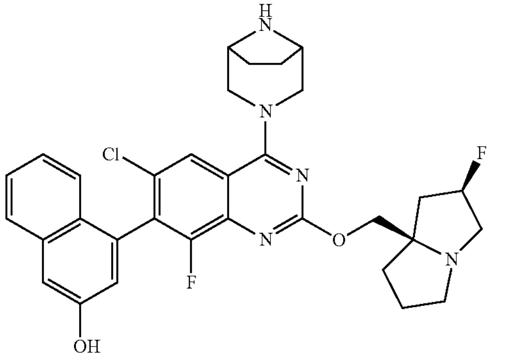

10-1 (Isomer 1)
10-2 (Isomer 2)

To a stirred solution of tert-butyl 3-(6-chloro-8-fluoro-2-(((2R,7aR)-2-fluorotetrahydro-1Hpyrrolizin-7a(5H)-yl)methoxy)-7-(3-hydroxynaphthalen-1-yl)quinazolin-4-yl)-3,8-diazabicyclo[3.2.1]octane-8-carboxylate (0.15 mg, 0.217 μmol) in dichloromethane (10 mL) and hydrogen chloride in dioxane (4M, 0.054 μl, 0.217 μmol) was added at 0° C. The reaction mixture was stirred at 25° C. for 5 h. Reaction progress was monitored by LCMS confirming the formation of desired product. The reaction mixture was concentrated under reduced pressure to afford the desired product 4-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol. HCl as a yellow solid (0.12 g, 0.202 mmol, 88.2%). LCMS (ESI) m/z: 592.1 $[M+H]^+$. 1H NMR (400 MHz, $CD_3OD$) δ 8.22 (s, 1H), 7.80 (d, J=8.4 Hz, 1H), 7.80 (d, J=8.4 Hz, 1H), 7.46 (t, J=6.8 Hz, 1H), 7.33-7.22 (m, 3H), 7.10 (d, J=2.4 Hz, 1H), 5.62-5.50 (m, 1H), 5.11-4.93 (m, 3H), 4.35-4.14 (m, 3H), 3.76-3.74 (m, 2H), 3.71-3.61 (m, 1H), 3.49-3.36 (m, 1H), 3.32-3.24 (m, 1H), 2.56 (t, J=5.6 Hz, 1H), 2.34-2.32 (m, 1H), 2.24-2.19 (m, 2H), 2.19-2.01 (m, 4H), 1.41-1.37 (m, 4H) ppm. Atropisomers were separated by chiral SFC (Column: Cellulose-4 25×3 mm I.D., 5 um. Mobile phase: Phase A for $CO_2$, and Phase B for MeOH (0.2% $NH_4OH$); Elution: 40% MeOH (0.2% $NH_4OH$) in $CO_2$. Flow rate: 180 mL/min; Detector: UV 220 nm; Column Temp: 28° C.; Back Pressure: 100 Bar) to obtain two product peaks: peak 1 (Example 10-1) and peak 2 (Example 10-2).

Peak 1, isomer 1: Example 10-1 (29 mg). MS (ESI) m/z 592.5 $[M+1]^+$. $^1H$ NMR (499 MHz, METHANOL-$d_4$) δ 8.02-7.93 (m, 1H), 7.81-7.74 (m, 1H), 7.47-7.38 (m, 1H), 7.30-7.24 (m, 2H), 7.24-7.18 (m, 1H), 7.08-7.01 (m, 1H), 5.54-5.20 (m, 1H), 4.65-4.51 (m, 2H), 4.49-4.43 (m, 1H), 4.40-4.29 (m, 1H), 3.79-3.61 (m, 4H), 3.54-3.41 (m, 1H), 3.21-3.07 (m, 1H), 3.04-2.88 (m, 1H), 2.85-2.72 (m, 1H), 2.64-2.44 (m, 1H), 2.23-2.12 (m, 1H), 2.09-1.93 (m, 4H), 1.88 (br s, 4H), 1.45-1.14 (m, 2H).

Peak 2, isomer 2: Example 10-2 (29 mg). MS (ESI) m/z 592.5 $[M+1]^+$. $^1H$ NMR (499 MHz, METHANOL-$d_4$) δ 8.01-7.94 (m, 1H), 7.81-7.73 (m, 1H), 7.47-7.39 (m, 1H), 7.30-7.18 (m, 3H), 7.08-7.01 (m, 1H), 5.49-5.23 (m, 1H), 4.65-4.51 (m, 2H), 4.49-4.41 (m, 1H), 4.40-4.31 (m, 1H), 3.80-3.63 (m, 5H), 3.55-3.42 (m, 1H), 3.20-3.10 (m, 1H), 3.04-2.88 (m, 1H), 2.85-2.72 (m, 1H), 2.63-2.46 (m, 1H), 2.22-2.11 (m, 1H), 2.09-1.93 (m, 4H), 1.92-1.81 (m, 5H).

Examples 11-1 and 11-2

6-(2-{[(2R,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine

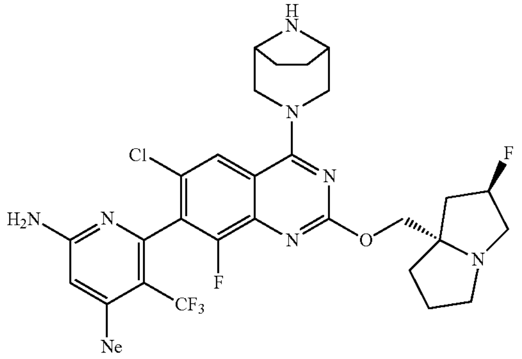

11-1 (Isomer 1)
11-2 (Isomer 2)

Preparation of Intermediate 11A: tert-butyl 3-(7-(6-(bis(4-methoxybenzyl)amino)-4-methyl-3-(trifluoromethyl)pyridin-2-yl)-6-chloro-8-fluoro-2-(((2R,7aS)-2-fluorotetrahydro-1H-pyrrolizin-7a(5H)-yl)methoxy)quinazolin-4-yl)-3,8-diazabicyclo[3.2.1]octane-8-carboxylate

11A

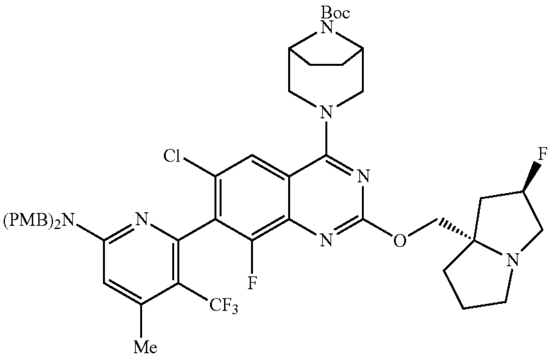

To a stirred solution of ((2R,7aS)-2-fluorotetrahydro-1H-pyrrolizin-7a(5H)-yl)methanol (251 mg, 1.575 mmol) in THF (5 mL) at 0° C. was added NaH (28.4 mg, 1.181 mmol) and the mixture was stirred for an additional 30 minutes. Then, a solution of tert-butyl 3-(7-(6-(bis(4-methoxybenzyl)amino)-4-methyl-3-(trifluoromethyl)pyridin-2-yl)-6-chloro-2,8-difluoroquinazolin-4-yl)-3,8-diazabicyclo[3.2.1]octane-8-carboxylate (650 mg, 0.788 mmol) in THF (2 mL) was added and gradually warmed to room temperature over a period of 2 h. The reaction mixture was quenched with saturated aq. ammonium chloride solution and extracted with ethyl acetate. The combined organic layers were washed with water, then brine, and then dried over $Na_2SO_4$ and concentrated under reduced pressure to provide a crude residue, which was purified by silica gel column chromatography using CombiFlash instrument (40 g RediSep® column, 50 to 60% EtOAc—pet ether) to afford tert-butyl 3-(7-(6-(bis(4-methoxybenzyl)amino)-4-methyl-3-(trifluoromethyl)pyridin-2-yl)-6-chloro-8-fluoro-2-(((2R,7aS)-2-fluorotetrahydro-1H-pyrrolizin-7a(5H)-yl)methoxy)quinazolin-4-yl)-3,8-diazabicyclo[3.2.1]octane-8-carboxylate (475 mg, 0.492 mmol, 62.5% yield) as a brown solid. MS(ESI) m/z: 964.2 (M+H)+.

Examples 11-1 and 11-2

6-(2-{[(2R,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine

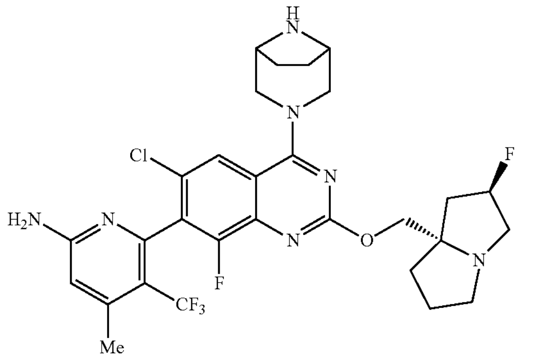

11-1 (Isomer 1)
11-2 (Isomer 2)

A stirred solution of TFA (190 μL, 2.462 mmol) and triethylsilane (79 μL, 0.492 mmol) was added to tert-butyl 3-(7-(6-(bis(4-methoxybenzyl)amino)-4-methyl-3-(trifluoromethyl)pyridin-2-yl)-6-chloro-8-fluoro-2-(((2R,7aS)-2-fluorotetrahydro-1H-pyrrolizin-7a(5H)-yl)methoxy)quinazolin-4-yl)-3,8-diazabicyclo[3.2.1]octane-8-carboxylate (475 mg, 0.492 mmol) at room temperature and the resulting reaction mixture was heated to 35° C. for 24 h. Then, the reaction mixture was concentrated under reduced pressure, co-distilled with toluene (twice), neutralised with DIPEA and concentrated under reduced pressure to provide the crude residue, which was purified by achiral SFC followed by chiral SFC to afford 6-(2-{[(2R,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine (11-1, isomer 1) (9 mg, 0.014 mmol, 2.93% yield) and (11-2, isomer 2) (8 mg, 0.013 mmol, 2.60% yield).

11-1 (Isomer 1): MS(ESI) m/z: 624.2, $[M+H]^+$. $^1H$ NMR (400 MHz, DMSO-$d_6$) δ =7.82 (s, 1H), 6.84 (s, 2H), 6.49 (s, 1H), 5.27 (d, J=45.2 Hz, 1H), 4.35 (d, J=9.4 Hz, 1H), 4.27 (d, J=9.4 Hz, 1H), 4.08 (ABq, J=8.4 Hz, 2H), 3.76-3.68 (m, 2H), 3.59 (d, J=10.1 Hz, 1H), 3.51 (d, J=10.1 Hz, 1H), 3.10-3.00 (m, 3H), 2.87-2.80 (m, 1H), 2.35 (s, 3H), 2.14-2.10 (m, 1H), 2.05-2.03 (m, 1H), 2.02-1.95 (m, 1H), 1.80-1.70 (m, 7H).

11-2 (Isomer 2): MS(ESI) m/z: 624.2, $[M+H]^+$. $^1H$ NMR (400 MHz, DMSO-$d_6$) δ =7.80 (s, 1H), 6.84 (s, 2H), 6.49 (s, 1H), 5.27 (d, J=45.2 Hz, 1H), 4.29 (d, J=9.4 Hz, 1H), 4.16 (d, J=9.4 Hz, 1H), 4.01 (ABq, J=8.4 Hz, 2H), 3.66-3.49 (m, 3H), 3.42 (d, J=10.1 Hz, 1H), 3.10-3.00 (m, 3H), 2.87-2.80 (m, 1H), 2.35 (s, 3H), 2.13-2.10 (m, 1H), 2.05-2.03 (m, 1H), 2.02-1.98 (m, 1H), 1.88-1.70 (m, 3H), 1.65-1.55 (m, 4H).

Preparative achiral SFC Conditions: column/dimensions: Princeton SFC Diol (250×4.6) mm, 5u; $CO_2$%: 30%; Co-solvent %: 70% of (0.2% $NH_3$ in methanol); Flow rate: 3 mL/min; Back Pressure: 100 bar; Retention time=6.129 min.

Preparative Chiral SFC Conditions: Column/dimensions: Chiralcel ODH (250×4.6) mm, 5u; $CO_2$%: 30%; Co-solvent %: 70% of (5 mM $NH_{40}$Ac in CAN: methanol (1:1)); Flow rate: 4 mL/min; Back Pressure: 100 bar; Retention time of Peak-01=3.234 min & Retention time of Peak-02=6.862 min.

Examples 12-1 and 12-2

4-(2-{[(2R,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol

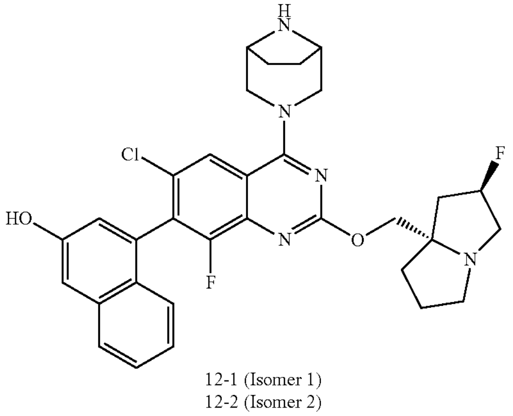 [SMILES: Oc1cc(-c2c(Cl)cc3c(N4CC5CCC(C4)N5)nc(OC[C@@]45CCCN4C[C@H](F)C5)nc3c2F)c2ccccc2c1]

12-1 (Isomer 1)
12-2 (Isomer 2)

Preparation of Intermediate 12A: tert-butyl 3-(7-bromo-6-chloro-8-fluoro-2-(((2R,7aS)-2-fluorotetrahydro-1H-pyrrolizin-7a(5H)-yl)methoxy)quinazolin-4-yl)-3,8-diazabicyclo[3.2.1]octane-8-carboxylate

12A

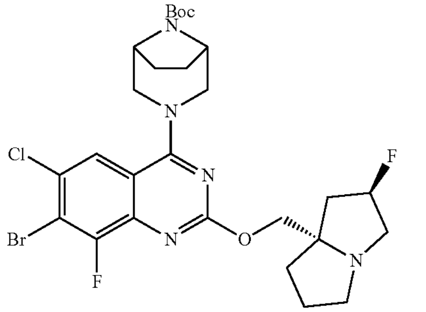

To a stirred solution of ((2R,7aS)-2-fluorotetrahydro-1H-pyrrolizin-7a(5H)-yl)methanol (195 mg, 1.225 mmol) in THE (8 mL) at 0° C. was added NaH (61.3 mg, 1.531 mmol) and the resulting reaction mixture was stirred for an additional 30 minutes. Then, a solution of Example 8A (500 mg, 1.021 mmol) in THE (2 mL) was added and gradually warmed to room temperature over a period of 1 h. The reaction mixture was quenched with saturated aq. ammonium chloride solution and extracted with ethyl acetate. The combined organic layers were washed with water, then brine, and dried over $Na_2SO_4$ and concentrated to provide the crude residue, which was purified by silica gel column chromatography using CombiFlash instrument (40 g RediSep® column, 70 to 80% EtOAc-pet. ether) to afford tert-butyl 3-(7-bromo-6-chloro-8-fluoro-2-(((2R,7aS)-2-fluorotetrahydro-1H-pyrrolizin-7a(5H)-yl)methoxy)quinazolin-4-yl)-3,8-diazabicyclo[3.2.1]octane-8-carboxylate (400 mg, 0.636 mmol, 62.3% yield). MS(ESI) m/z: 628.2 $[M+H]^-$.

Preparation of Intermediate 12B: tert-butyl 3-(6-chloro-8-fluoro-2-(((2R,7aS)-2-fluorotetrahydro-1H-pyrrolizin-7a(5H)-yl)methoxy)-7-(3-hydroxynaphthalen-1-yl)quinazolin-4-yl)-3,8-diazabicyclo[3.2.1]octane-8-carboxylate

12B

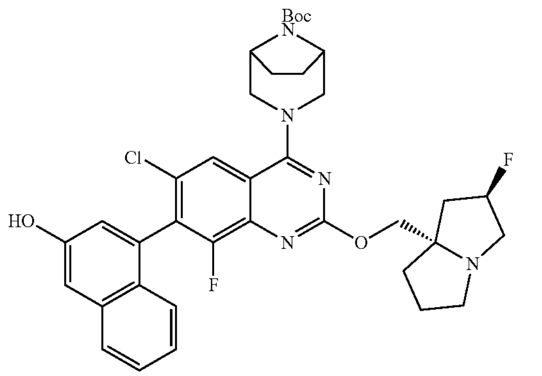

To a stirred solution of tert-butyl 3-(7-bromo-6-chloro-8-fluoro-2-(((2R,7aS)-2-fluorotetrahydro-1H-pyrrolizin-7a(5H)-yl)methoxy)quinazolin-4-yl)-3,8-diazabicyclo[3.2.1]octane-8-carboxylate (320 mg, 0.509 mmol) in 1,4-dioxane (5 mL) at room temperature, was added 4-(4,4,5,5-tetramethyl-1,3,2-dioxaborolan-2-yl)naphthalen-2-ol (165 mg, 0.611 mmol), and $K_2CO_3$ (aqueous solution) (0.509 mL, 1.526 mmol). The reaction mixture was purged with nitrogen for 5 minutes and charged with $Pd(Ph_3P)_4$ (58.8 mg, 0.051 mmol). The reaction mixture was again purged with nitrogen for 3 minutes and heated at 85° C. for 16 h. The reaction mixture was then cooled to room temperature, filtered through Celite and the filtrate was concentrated under reduced pressure to afford the crude compound which was purified by silica gel column chromatography using a CombiFlash instrument (24 g RediSep® column; pet. ether-ethyl acetate as eluent). The desired product was eluted at 60-70% ethyl acetate in pet. ether. The pure fractions were evaporated under reduced pressure to afford tert-butyl 3-(6-chloro-8-fluoro-2-(((2R,7aS)-2-fluorotetrahydro-1H-pyrrolizin-7a(5H)-yl)methoxy)-7-(3-hydroxynaphthalen-1-yl)quinazolin-4-yl)-3,8-diazabicyclo[3.2.1]octane-8-carboxylate (170 mg, 0.246 mmol, 48.3% yield) as a pale yellow solid. MS(ESI) m/z: 692.7 $[M+H]^+$.

Examples 12-1 and 12-2

4-(2-{[(2R,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol

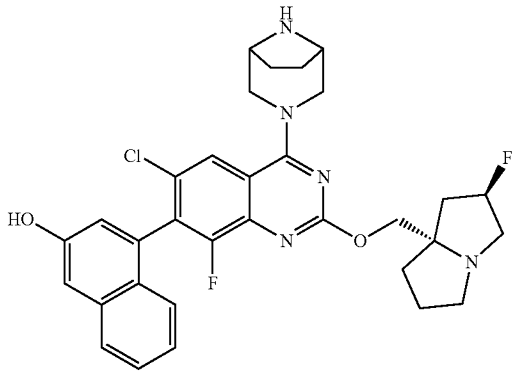

12-1 (Isomer 1)
12-2 (Isomer 2)

To a stirred solution of tert-butyl 3-(6-chloro-8-fluoro-2-(((2R,7aS)-2-fluorotetrahydro-1H-pyrrolizin-7a(5H)-yl)methoxy)-7-(3-hydroxynaphthalen-1-yl)quinazolin-4-yl)-3,8-diazabicyclo[3.2.1]octane-8-carboxylate (150 mg, 0.217 mmol) in DCM (1 mL) at 0° C., was added TFA (0.083 mL, 1.083 mmol) and the resulting reaction mixture was stirred at room temperature for 1 h. Then, the reaction mixture was concentrated under reduced pressure at 30° C., co-distilled with 1,4-dioxane, neutralized using $Et_3N$, again co-distilled with 1,4-dioxane and MeOH to afford the crude compound as a pale yellow solid, which was purified by chiral SFC to afford 4-(2-{[(2R,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol (12-1, isomer 1) (13 mg, 0.022 mmol, 9.93% yield) and (12-2, isomer 2) (20 mg, 0.032 mmol, 14.81% yield).

12-1 (Isomer 1): MS(ESI) m/z: 592.2. $^1H$ NMR (400 MHz, DMSO-$d_6$) δ=9.98-9.55 (brs, 1H), 7.93 (s, 1H), 7.80 (d, J=8.3 Hz, 1H), 7.47-7.40 (m, 1H), 7.28 (d, J=2.3 Hz, 1H), 7.22 (d, J=3.9 Hz, 2H), 7.06 (d, J=2.3 Hz, 1H), 5.27 (d, J=45.2 Hz, 1H), 4.37-4.28 (m, 2H), 3.95 (ABq, J=9.6 Hz, 2H), 3.57-3.49 (m, 4H), 3.12-3.05 (m, 2H), 3.03-2.98 (m, 1H), 2.87-2.78 (m, 1H), 2.16-2.11 (m, 1H), 2.07-2.03 (m, 1H), 2.03-1.98 (m, 1H), 1.90-1.72 (m, 3H), 1.70-1.60 (m, 4H).

12-2 (Isomer 2): MS(ESI) m/z: 592.2. $^1H$ NMR (400 MHz, DMSO-$d_6$) δ=9.98-9.55 (brs, 1H), 7.93 (s, 1H), 7.79 (d, J=8.4 Hz, 1H), 7.47-7.41 (m, 1H), 7.27 (d, J=2.3 Hz, 1H), 7.21 (d, J=3.8 Hz, 2H), 7.07-7.04 (m, 1H), 5.27 (d, J=45.2 Hz, 1H), 4.36-4.28 (m, 2H), 3.98 (ABq, J=9.6 Hz, 2H), 3.57-3.49 (m, 4H), 3.12-3.06 (m, 2H), 3.02-2.99 (m, 1H), 2.87-2.77 (m, 1H), 2.15-2.10 (m, 1H), 2.07-2.03 (m, 1H), 2.02-1.97 (m, 1H), 1.88-1.72 (m, 3H), 1.68-1.62 (m, 4H).

Preparative Chiral SFC Conditions: Column/dimensions: Column Name: Lux Cellulose C2 (250×4.6) mm. 5μ; Co-Solvent Name: 5 mM Ammonium acetate in ACN:Methanol (1:1). Flow Rate: 4 mL/min; Co-Solvent Percentage: 50%;

Back Pressure: 100 Bar. Retention time of Peak-01=4.380 min & Retention time of Peak-02=7.016 min.

Examples 13-1 and 13-2

4-(2-{[(2S,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol

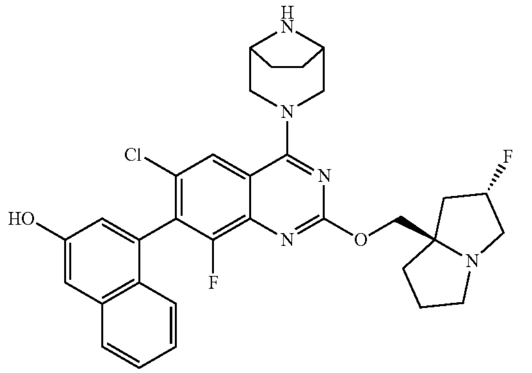

13-1 (Isomer 1)
13-2 (Isomer 2)

Preparation of Intermediate 13A: tert-butyl 3-(2-{[(2S,7aR)-2-fluoro-hexahydro-1H-pyrrolizin-7a-yl]methoxy}-7-bromo-6-chloro-8-fluoroquinazolin-4-yl)-3,8-diazabicyclo[3.2.1]octane-8-carboxylate

13A

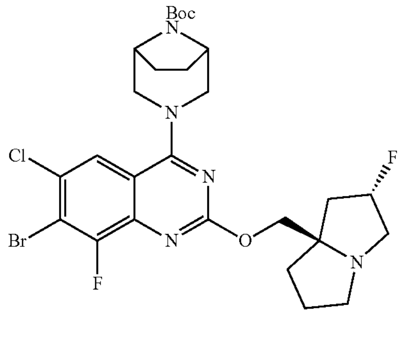

To a stirred solution of Example 8A (200 mg, 0.408 mmol) and ((2S,7aR)-2-fluorotetrahydro-1H-pyrrolizin-7a(5H)-yl)methanol. HCl (120 mg, 0.613 mmol) in 1,4-dioxane (2 mL) was added $Cs_2CO_3$ (532 mg, 1.634 mmol) and the resulting reaction mixture was heated at 80° C. for 16 h. The reaction mixture was filtered and concentrated to provide the crude residue, which was purified by silica gel column chromatography using CombiFlash instrument (24 g RediSep® column, 100% EtOAc-pet. ether) to afford tert-butyl 3-(2-{[(2S,7aR)-2-fluoro-hexahydro-1H-pyrrolizin-7a-yl]methoxy}-7-bromo-6-chloro-8-fluoroquinazolin-4-yl)-3,8-diazabicyclo[3.2.1]octane-8-carboxylate (140 mg, 0.223 mmol, 54.5% yield). MS(ESI) m/z: 628.5 $[M+H]^+$.

Preparation of Intermediate 13B: tert-butyl 3-(2-{[(2S,7aR)-2-fluoro-hexahydro-1H-pyrrolizin-7a-yl]methoxy}-6-chloro-8-fluoro-7-(3-hydroxynaphthalen-1-yl)quinazolin-4-yl)-3,8-diazabicyclo[3.2.1]octane-8-carboxylate

13B

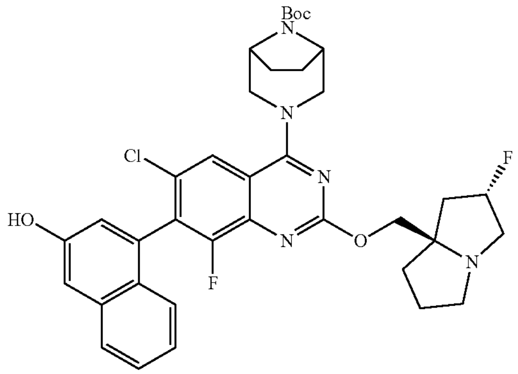

To a stirred solution of Example 13A (320 mg, 0.509 mmol) in 1,4-dioxane (2 mL) and water (0.2 mL) at room temperature, were added 4-(4,4,5,5-tetramethyl-1,3,2-dioxaborolan-2-yl)naphthalen-2-ol (72.2 mg, 0.267 mmol) and $K_2CO_3$ (92 mg, 0.668 mmol). The reaction mixture was purged with nitrogen for 5 minutes and charged with $Pd(Ph_3P)_4$ (12.86 mg, 0.011 mmol). The reaction mixture was again purged with nitrogen for 3 minutes and heated at 85° C. for 16 h. The reaction mixture was then cooled to room temperature, filtered through Celite and the filtrate was concentrated under reduced pressure to afford the crude tert-butyl 3-(2-{[(2S,7aR)-2-fluoro-hexahydro-1H-pyrrolizin-7a-yl]methoxy}-6-chloro-8-fluoro-7-(3-hydroxynaphthalen-1-yl)quinazolin-4-yl)-3,8-diazabicyclo[3.2.1]octane-8-carboxylate (140 mg) as a brown solid, which was taken for the next step without further purification. MS(ESI) m/z: 692.3 $[M+H]^+$.

Examples 13-1 and 13-2

4-(2-{[(2S,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol

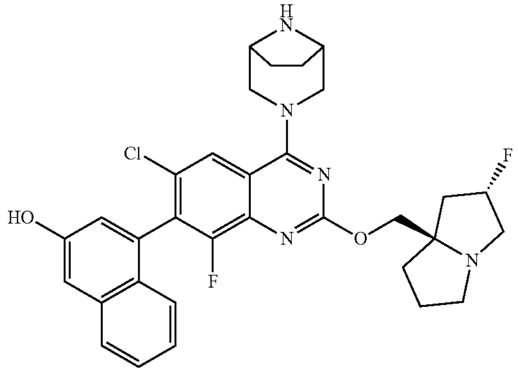

13-1 (Isomer 1)
13-2 (Isomer 2)

To a stirred solution of tert-butyl 3-(2-{[(2S,7aR)-2-fluoro-hexahydro-1H-pyrrolizin-7a-yl]methoxy}-6-chloro-8-fluoro-7-(3-hydroxynaphthalen-1-yl)quinazolin-4-yl)-3,8-diazabicyclo[3.2.1]octane-8-carboxylate (120 mg, 0.173 mmol) in DCM (2 mL) at 0° C., was added TFA (1 mL, 12.98 mmol) and the resulting reaction mixture was stirred at room temperature for 1 h. Then, the reaction mixture was concentrated under reduced pressure at 30° C., co-distilled with 1,4-dioxane, neutralized using $Et_3N$, again co-distilled with 1,4-dioxane and MeOH to afford crude compound as a pale yellow solid, which was purified by preparative HPLC followed by chiral SFC to afford 4-(2-{[(2S,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl) naphthalen-2-ol (13-1, isomer 1) (5 mg, 8.44 μmol, 4.87% yield) and (13-2, isomer 2) (3.7 mg, 6.12 μmol, 3.53% yield).

13-1 (Isomer 1): MS(ESI) m/z: 592.2. $^1$H NMR (400 MHz, DMSO-$d_6$) δ=10.04 (br s, 1H), 7.94 (s, 1H), 7.81 (d, J=8.4 Hz, 1H), 7.44 (ddd, J=2.8, 5.2, 8.3 Hz, 1H), 7.29 (d, J=2.3 Hz, 1H), 7.26-7.17 (m, 2H), 7.06 (d, J=2.4 Hz, 1H), 5.25 (d, J=53.6 Hz, 1H), 4.42-4.27 (m, 2H), 4.05 (ABq, J=10.3 Hz, 2H), 3.64-2.84 (m, 7H), 2.16-2.11 (m, 2H), 2.07-1.97 (m, 2H), 1.86-1.71 (m, 7H).

13-2 (Isomer 2): MS(ESI) m/z: 592.2. $^1$H NMR (400 MHz, DMSO-$d_6$) δ=10.04 (br s, 1H), 7.96 (s, 1H), 7.81 (d, J=8.4 Hz, 1H), 7.45 (ddd, J=1.8, 6.2, 8.2 Hz, 1H), 7.29 (d, J=2.3 Hz, 1H), 7.25-7.16 (m, 2H), 7.06 (d, J=2.4 Hz, 1H), 5.28 (d, J=54.3 Hz, 1H), 4.45-4.40 (m, 2H), 4.08 (ABq, J=10.7 Hz, 2H), 3.90 (br s, 2H), 3.70-3.00 (m, 5H), 2.87-2.81 (m, 1H), 2.17-2.11 (m, 1H), 2.07-1.96 (m, 2H), 1.89-1.85 (m, 3H), 1.81-1.70 (m, 4H).

Preparative HPLC Conditions: Column/dimensions: Column Name: Kinetex EVO (250 mm×21.2 mm ID, 5μ); Mobile phase A=10 mM Ammonium Bicarbonate in water pH 9.5, Mobile phase B=Acetonitrile:MeOH(1:1), Flow Rate: 19 mL/min; Retention time=11.66 min. Preparative Chiral SFC Conditions: Column/dimensions: Column Name: Lux Cellulose $C_4$ (250*4.6)mm. 5μ; Co-Solvent Name: 5 mM Ammonium acetate in ACN:Methanol (1:1). Flow Rate: 4 mL/min; Co-Solvent Percentage: 50%; Back Pressure: 100 Bar. Retention time of Peak-01=5.11 min & Retention time of Peak-02=6.86 min.

Example 14

6-(2-{[(2S,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine

14

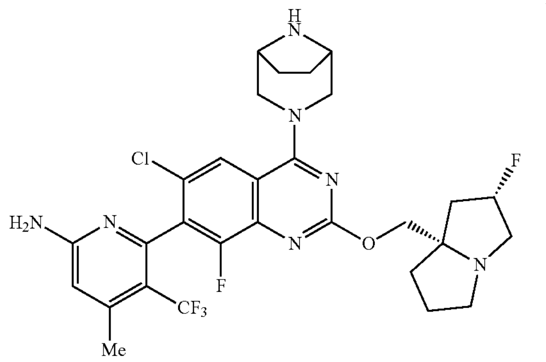

Preparation of Intermediate 14A: 1-(tert-butyl) 2-methyl (2S,4S)-4-fluoropyrrolidine-1,2-dicarboxylate

14A

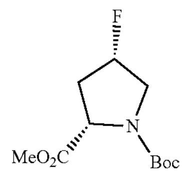

To a stirred solution of 1-(tert-butyl) 2-methyl (2S,4R)-4-hydroxypyrrolidine-1,2-dicarboxylate (60.0 g, 245 mmol) in dichloromethane (900 mL) was added diethylaminosulfur trifluoride (64.6 mL, 489 mmol) at 0° C. The reaction mixture was stirred at room temperature for 16 h. The reaction mixture was quenched with ice and extracted with dichloromethane (3×500 mL). The combined organic layers were dried over anhydrous sodium sulphate, filtered and concentrated under reduced pressure to provide a pale-yellow oil. The residue was purified by silica gel column chromatography with 0-20% ethyl acetate in petroleum ether to obtain 1-(tert-butyl) 2-methyl (2S,4S)-4-fluoropyrrolidine-1,2-dicarboxylate (53.0 g, 206 mmol, 84% yield) as a pale yellow oil. LCMS-ELSD (ESI) m/z: 148.2 [M+H-Boc]$^+$.

Preparation of Intermediate 14B: 1-(tert-butyl) 2-methyl (2S,4S)-2-(3-((tert-butyldimethylsilyl)oxy)propyl)-4-fluoropyrrolidine-1,2-dicarboxylate

14B

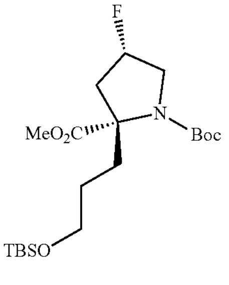

To a stirred solution of 1-(tert-butyl) 2-methyl (2S,4S)-4-fluoropyrrolidine-1,2-dicarboxylate (20.0 g, 81 mmol) in anhydrous THE (200 mL) under a nitrogen atmosphere at −25° C. was added LiHMDS (1M in THF, 121.0 mL, 121 mmol), dropwise. The reaction mixture was stirred at the same temperature for 30 minutes, followed by the dropwise addition of (3-bromopropoxy)(tert-butyl)dimethylsilane (24.6 g, 97 mmol). After stirring at −25° C. for 30 minutes, the reaction mixture was slowly warmed to room temperature. The reaction was quenched with a saturated aq. ammonium chloride solution (100 mL) and then diluted with water (100 mL). The mixture was extracted with ethyl acetate (2×500 mL). The combined organic layers were dried over anhydrous sodium sulphate, filtered and concentrated under reduced pressure. The residue was purified by silica gel column chromatography with 20-30% ethyl acetate in petroleum ether to obtain 1-(tert-butyl) 2-methyl (2S,4S)-2-(3-((tert-butyldimethylsilyl)oxy)propyl)-4-fluoropyrrolidine-1, 2-dicarboxylate (28.0 g, 66.1 mmol, 82% yield) as colorless oil. $^1$H NMR (400 MHz, $CDCl_3$): δ 5.18-5.03 (m, 1H), 4.10-3.98 (m, 1H), 3.78 (s, 3H), 3.74-3.52 (m, 3H), 2.48-2.23 (m, 3H), 2.19-1.98 (m, 1H), 1.65 (s, 9H), 1.48-1.44 (m, 2H), 0.90 (s, 9H), 0.06 (s, 6H) ppm. $^{19}$F (376 MHz, $CD_3OD$): δ −172.47 to −172.96 (m) ppm. LCMS-ELSD (ESI) m/z: 320.2 $[M+H-Boc]^+$.

Preparation of Intermediate 14C: 1-(tert-butyl) 2-methyl (2S,4S)-4-fluoro-2-(3-hydroxypropyl)pyrrolidine-1,2-dicarboxylate

14C

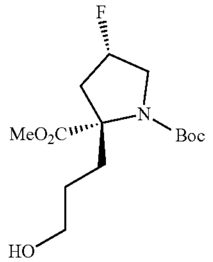

To a stirred solution of 1-(tert-butyl) 2-methyl (2S,4S)-2-(3-((tert-butyldimethylsilyl)oxy)propyl)-4-fluoropyrrolidine-1,2-dicarboxylate (28 g, 66.7 mmol) at 25° C. was added TBAF (1M in THF, 100 mL, 100 mmol) dropwise, and the mixture was stirred at the same temperature for 4 h. The reaction was then quenched with saturated aq. ammonium chloride solution (200 mL) and diluted with ethyl acetate (300 mL). The mixture was extracted with ethyl acetate (3×600 mL). The combined organic layers were dried over anhydrous sodium sulphate, filtered, and then concentrated reduced pressure to obtain the crude residue as a colorless oil. The crude material was purified by silica gel column chromatography using 50% ethyl acetate in petroleum ether to obtain 1-(tert-butyl) 2-methyl (2S,4S)-4-fluoro-2-(3-hydroxypropyl)pyrrolidine-1,2-dicarboxylate (15 g, 49.0 mmol, 74% yield) as a colorless oil. LCMS-ELSD (ESI) m/z: 206.2 $[M+H-Boc]^+$.

Preparation of Intermediate 14D: 1-(tert-butyl) 2-methyl (2S,4S)-4-fluoro-2-(3-iodopropyl)pyrrolidine-1,2-dicarboxylate

14D

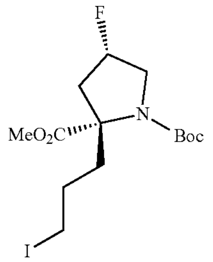

To a stirred solution of 1-(tert-butyl) 2-methyl (2S,4S)-4-fluoro-2-(3-hydroxypropyl)pyrrolidine-1,2-dicarboxylate (22.0 g, 72.0 mmol) in dichloromethane (500 mL) at 0° C. was added triphenylphosphine (76.0 g, 288 mmol) and imidazole (9.81 g, 144 mmol), and the mixture was stirred for 10 min. Iodine (73.1 g, 288 mmol) was added and the mixture was warmed to room temperature and stirred for 12 h. The reaction was then quenched with sat. aq. sodium thiosulfate solution (70 mL) and the suspension was extracted with dichloromethane (3×200 mL). The combined organic layers were dried over anhydrous sodium sulphate, filtered, and concentrated reduced pressure to obtain the crude residue. This crude was purified by silica gel column chromatography using 10-20% ethyl acetate in petroleum ether to obtain 1-(tert-butyl) 2-methyl (2S,4S)-4-fluoro-2-(3-iodopropyl)pyrrolidine-1,2-dicarboxylate (16.5 g, 39.5 mmol, 55% yield) as a pale yellow oil. LCMS-ELSD (ESI) m/z: 361.0 $[M+H-Boc]^+$.

Preparation of Intermediate 14E: Methyl (2S,4S)-4-fluoro-2-(3-iodopropyl)pyrrolidine-2-carboxylate

14E

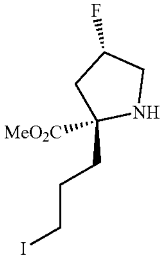

To a stirred solution of 1-(tert-butyl) 2-methyl (2S,4S)-4-fluoro-2-(3-iodopropyl)pyrrolidine-1,2-dicarboxylate (16.5 g, 39.7 mmol) in dichloromethane (200 mL) at 25° C. was added HCl in dioxane (4M, 160 mL, 640 mmol) and the reaction mixture was stirred for 6 h. The reaction mixture was then concentrated under reduced pressure at room temperature to obtain the crude residue of methyl (2S,4S)-4-fluoro-2-(3-iodopropyl)pyrrolidine-2-carboxylate, HCl (12 g, 33.7 mmol, 85% yield), which was used in the next step without any further purification. LCMS-ELSD (ESI) m/z: 188.2 $[M+H]^+$.

Preparation of Intermediate 14F: methyl (2S,7aS)-2-fluorotetrahydro-1H-pyrrolizine-7a(5H)-carboxylate

14F

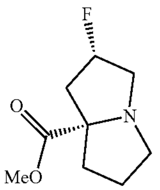

To a stirred solution of methyl (2S,4S)-4-fluoro-2-(3-iodopropyl)pyrrolidine-2-carboxylate (12.0 g, 38.1 mmol) in anhydrous acetonitrile (120 mL) was added triethylamine (26.5 mL, 190 mmol) at room temperature. The reaction mixture was stirred at 45° C. for 12 h. The reaction mixture was then concentrated to dryness under reduced pressure. The residue was purified by column chromatography (alumina-neutral) using 40-50% ethyl acetate in petroleum ether to obtain methyl (2S,7aS)-2-fluorotetrahydro-1H-pyrrolizine-7a(5H)-carboxylate (6.2 g, 15.57 mmol, 41% yield) as pale-brown oil. 1H NMR (400 MHz, $CDCl_3$): δ 5.32-5.19 (m, 1H), 3.78 (s, 3H), 3.64-3.55 (m, 1H), 3.31-3.29 (m, 1H), 2.97-2.73 (m, 1H), 2.89-2.81 (m, 1H), 2.73-2.71 (m, 1H), 2.19-2.16 (m, 1H), 1.96-1.77 (m, 4H) ppm. LCMS-ELSD (ESI) m/z: 188.3 $[M+H]^+$.

Preparation of Intermediate 14G: ((2S,7aS)-2-fluorotetrahydro-1H-pyrrolizin-7a(5H)-yl)methanol

14G

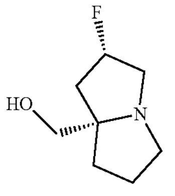

To a stirred solution of methyl (2S,7aS)-2-fluorotetrahydro-1H-pyrrolizine-7a(5H)-carboxylate (7.00 g, 37.4 mmol) in anhydrous THE (100 mL) under nitrogen at 0° C. was added $LiAlH_4$ (2M in THF, 37.4 mL, 74.8 mmol) dropwise over 10 minutes. After the addition was complete, the reaction mixture was warmed to room temperature over 30 minutes. The mixture was stirred at this temperature for 1 h before quenching with saturated aq. ammonium chloride (5 mL) at 0° C. Anhydrous sodium sulphate was added to the reaction mixture, followed by dichloromethane (50 mL). The reaction mixture was stirred for 20 minutes and filtered. The filtrate was collected, dried over anhydrous sodium sulfate, and concentrated reduced pressure to obtain ((2S,7aS)-2-fluorotetrahydro-1H-pyrrolizin-7a(5H)-yl)methanol (4.7 g, 29.2 mmol, 78% yield) as a colourless oil. $^1$HNMR (400 MHz, DMSO-$d_6$): δ 5.32-5.38 (m, 1H), 5.18-5.25 (m, 1H), 4.48-4.55 (m, 2H), 3.60-3.65 (m, 1H), 3.13-3.21 (m, 6H), 2.83-2.87 (m, 4H), 2.50 (s, 1H), 2.16-2.25 (m, 2H), 1.76-1.87 (m, 2H), 1.67-1.73 (m, 7H), 1.36-1.46 (m, 2H). $^{19}$F (376 MHz, $CD_3OD$): δ −175.69 to −176.04 (m) ppm. LCMS-ELSD (ESI) m/z: 160.2 $[M+H]^+$.

Intermediates 14H and 141: tert-butyl 3-(7-(6-(bis(4-methoxybenzyl)amino)-4-methyl-3-(trifluoromethyl)pyridin-2-yl)-6-chloro-2,8-difluoroquinazolin-4-yl)-3,8-diazabicyclo[3.2.1]octane-8-carboxylate

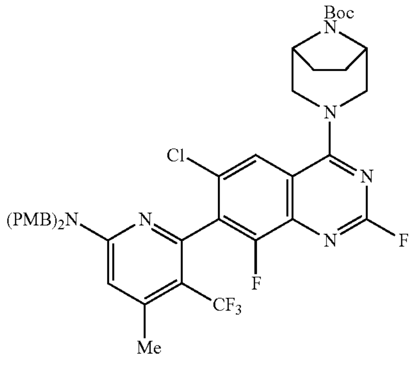

14H (Isomer 1)
14I (Isomer 2)

Example 9J (5.0 g, 6.06 mmol) was subjected to SFC separation (Column: Chiralpak IH (250 mm×4.6×5u), mobile phase-0.25% Isopropanol), where Peak-1 eluted at 5.85 RT (2.4 g, 2.90 mmol, 40% yield) and Peak-2 at 9.53 retention time (2.4 g, 2.90 mmol, 40% yield).

Peak-1 (14H): $^1$H NMR (400 MHz, $CDCl_3$): δ 7.78 (s, 1H), 7.16 (d, J=8.8 Hz, 4H), 6.87 (dt, J=9.6 and 2.8 Hz, 4H), 6.43 (s, 1H), 4.76-4.72 (m, 2H), 4.59-4.55 (m, 2H), 3.81 (s, 6H), 2.43 (s, 3H), 1.97-1.82 (m, 4H), 1.97-1.82 (m, 4H), 1.53 (s, 9H) ppm. LCMS (ESI) m/z: 825.2 $[M+H]^+$. LCMS (ESI) m/z: 825.2 $[M+H]^+$. $[\alpha]^{23.5}$ (MeOH=0.10)=+96.00

Peak-2: (14I)$^1$H NMR (400 MHz, $CDCl_3$): δ 7.78 (s, 1H), 7.16 (d, J=8.8 Hz, 4H), 6.87 (dt, J=9.6 and 2.8 Hz, 4H), 6.43 (s, 1H), 4.76-4.72 (m, 2H), 4.59-4.55 (m, 2H), 3.81 (s, 6H), 2.43 (s, 3H), 1.97-1.82 (m, 4H), 1.97-1.82 (m, 4H), 1.53 (s, 9H) ppm. LCMS (ESI) m/z: 825.2 $[M+H]^+$. $[\alpha]^{23.3}$ (MeOH=0.10)=−110.00.

Preparation of intermediate 14J: tert-butyl-3-(7-(6-(bis(4-methoxybenzyl)amino)-4-methyl-3-(trifluoromethyl)pyridin-2-yl)-6-chloro-8-fluoro-2-(((2S,7aS)-2-fluorotetrahydro-1H-pyrrolizin-7a(5H)-yl)methoxy)quinazolin-4-yl)-3,8-diazabicyclo[3.2.1]octane-8-carboxylate

14J

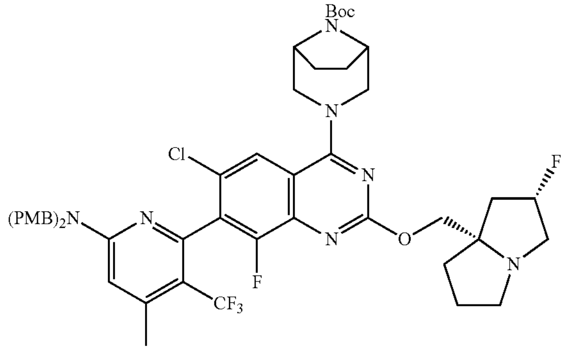

To a stirred solution of ((2S,7aS)-2-fluorotetrahydro-1H-pyrrolizin-7a(5H)-yl)methanol (109 mg, 0.685 mmol) in anhydrous THE (2.1 mL) at 0° C. was added sodium hydride (60% in mineral oil, 43.6 mg, 1.091 mmol) and the reaction mixture was stirred for 30 minutes. A solution of Intermediate 141 (300 mg, 0.364 mmol) in anhydrous THE (10 mL) was added dropwise to the reaction mixture while maintaining the temperature at 0° C. The reaction mixture was allowed to reach room temperature over 2 h. The reaction was then quenched with saturated aq. ammonium chloride solution (1 mL) and diluted with ethyl acetate (5 mL). The mixture was extracted with ethyl acetate (3×5 mL). The combined organic layers were dried over anhydrous sodium sulfate and concentrated under reduced pressure to obtain the crude product. The crude residue was purified by column chromatography over neutral alumina using 30% ethyl acetate in petroleum ether to obtain tert-butyl 3-(7-(6-(bis(4-methoxybenzyl)amino)-4-methyl-3-(trifluoromethyl)pyridin-2-yl)-6-chloro-8-fluoro-2-(((2S,7aS)-2-fluorotetrahydro-1H-pyrrolizin-7a(5H)-yl)methoxy)quinazolin-4-yl)-3,8-diazabicyclo[3.2.1]octane-8-carboxylate (250 mg, 0.251 mmol, 69% yield) as a pale yellow solid. LCMS (ESI) m/z: 964.2 $[M+H]^+$.

Example 14

6-(2-{[(2S,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine

14

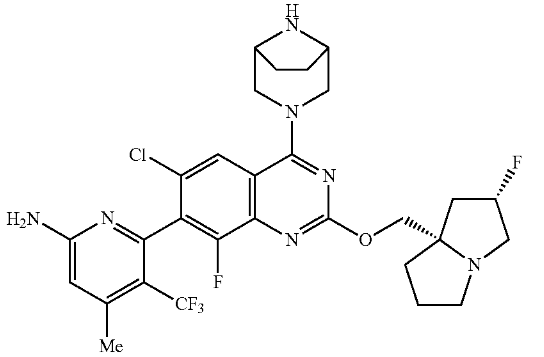

To a stirred solution of TFA (2 mL, 26.0 mmol) and triethyl silane (0.2 mL, 1.252 mmol) was added tert-butyl 3-(7-(6-(bis(4-methoxybenzyl)amino)-4-methyl-3-(trifluoromethyl)pyridin-2-yl)-6-chloro-8-fluoro-2-(((2S,7aS)-2-fluorotetrahydro-1H-pyrrolizin-7a(5H)-yl)methoxy)quinazolin-4-yl)-3,8-diazabicyclo[3.2.1]octane-8-carboxylate (250 mg, 0.259 mmol) at room temperature. Then reaction mixture was stirred at 35° C. for 12 h. The reaction mixture was then concentrated to remove most of the TFA reduced pressure at a temperature below 35° C. The residue was then co-evaporated with methanol (3×2 mL) to remove residual TFA. The residue was then neutralized with DIPEA and concentrated reduced pressure to obtain a free base. The crude was then purified by silica gel (previously neutralized with DIPEA) column chromatography using a mixture of MeOH, dichloromethane and DIPEA (15:80:2.5) to obtain 6-(4-(3,8-diazabicyclo[3.2.1]octan-3-yl)-6-chloro-8-fluoro-2-(((2S,7aS)-2-fluorotetrahydro-1H-pyrrolizin-7a(5H)-yl)methoxy)quinazolin-7-yl)-4-methyl-5-(trifluoromethyl)pyridin-2-amine (56 mg, 0.089 mmol, 34% yield) as a white solid. MS (ESI) m/z: 624.3 $[M+H]^+$. $^1H$ NMR (400 MHz, DMSO-$d_6$) δ 77.85 (s, 1H), 6.62 (s, 1H), 5.28 (m, 1H), 4.54-4.41 (m, 3H), 4.31 (d, J=10.40 Hz, 1H), 3.85-3.61 (m, 4H), 3.49-3.46 (m, 1H), 3.15-3.11 (m, 1H), 2.77 (t, J=5.20 Hz, 1H), 2.54 (m, 3H), 2.16-2.11 (m, 3H), 1.37-1.31 (m, 2H) ppm.

Example 15

6-(2-{[(2S,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine

15

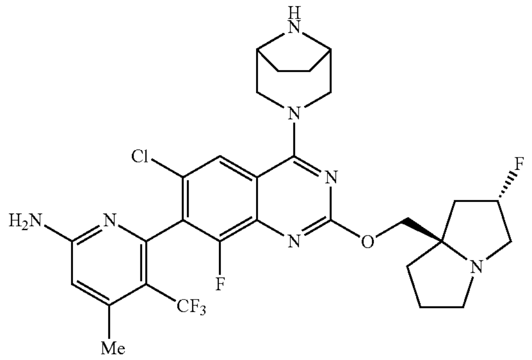 [SMILES: Cc1cc(N)nc(-c2c(Cl)cc3c(N4CC5CCC(C4)N5)nc(OC[C@]45CCCN4C[C@@H](F)C5)nc3c2F)c1C(F)(F)F]

Preparation of Intermediate 15A: tert-butyl-3-(2-{[(2S,7aR)-2-fluoro-hexahydro-1H-pyrrolizin-7a-yl]methoxy}-7-(6-{bis[(4-methoxyphenyl)methyl]amino}-4-methyl-3-(trifluoromethyl)pyridin-2-yl)-6-chloro-8-fluoroquinazolin-4-yl)-3,8-diazabicyclo[3.2.1]octane-8-carboxylate

15A

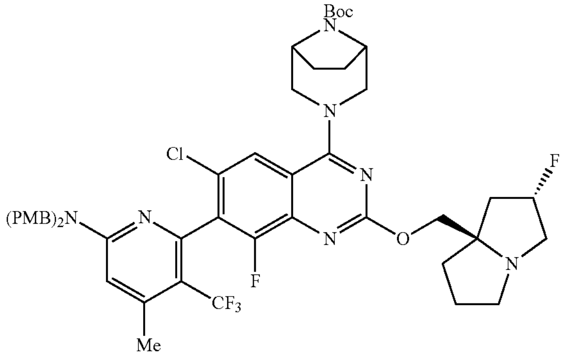

To a solution of ((2S,7aR)-2-fluorotetrahydro-1H-pyrrolizin-7a(5H)-yl)methanol HCl (427 mg, 2.181 mmol) in DCM (10 mL) was added approximately 1 g of $Na_2CO_3$ and the reaction mixture was stirred at room temperature for 30 minutes. The solid was filtered and the filtrate was evaporated at 20° C. with a minimum vacuum to obtain the free amine. The free base was dissolved in THE (10 mL) and cooled to 0° C. Then, NaH (87 mg, 2.181 mmol) was added and stirred for additional 30 minutes. Then, a solution of Intermediate 141 (900 mg, 1.091 mmol) in THE (2 mL) was added and the mixture was gradually warmed to room temperature over a period of 2 h. The reaction mixture was quenched with saturated aq. ammonium chloride solution and extracted with ethyl acetate. The combined organic layers were washed with water and brine, and then dried over $Na_2SO_4$. The mixture was filtered and concentrated under reduced pressure to provide crude product, which was purified by silica gel column chromatography using CombiFlash instrument (40 g RediSep® column, 50 to 60% EtOAc—pet ether) to afford tert-butyl-3-(2-{[(2S,7aR)-2-fluoro-hexahydro-1H-pyrrolizin-7a-yl]methoxy}-7-(6-{bis[(4-methoxyphenyl)methyl]amino}-4-methyl-3-(trifluoromethyl)pyridin-2-yl)-6-chloro-8-fluoroquinazolin-4-yl)-3,8-diazabicyclo[3.2.1]octane-8-carboxylate (1 g, 1.037 mmol, 95% yield) as a pale brown solid. MS(ESI) m/z: 964.3 (M+H)+.

Examples 15

6-(2-{[(2S,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine

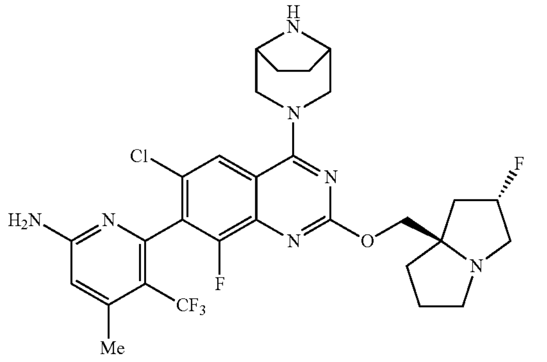

A stirred solution of TFA (5 mL, 64.9 mmol) and triethylsilane (2 mL, 12.52 mmol) was added to tert-butyl-3-(2-{[(2S,7aR)-2-fluoro-hexahydro-1H-pyrrolizin-7a-yl]methoxy}-7-(6-{bis[(4-methoxyphenyl)methyl]amino}-4-methyl-3-(trifluoromethyl)pyridin-2-yl)-6-chloro-8-fluoroquinazolin-4-yl)-3,8-diazabicyclo[3.2.1]octane-8-carboxylate (1 g, 1.037 mmol) at room temperature and the resulting reaction mixture was heated to 35° C. for 24 h. Then, the reaction mixture was concentrated under reduced pressure, co-distilled with toluene (twice), neutralised with DIPEA and concentrated under reduced pressure to provide the crude residue, which was purified by achiral SFC to afford 6-(2-{[(2S,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine (320 mg, 0.513 mmol, 49.5% yield). MS(ESI) m/z: 624.2, $[M+H]^+$. $^1$H NMR (400 MHz, DMSO-$d_6$) δ=7.81 (s, 1H), 6.83 (s, 2H), 6.48 (s, 1H), 5.26 (d, J=52 Hz, 1H), 4.30 (d, J=12 Hz, 1H), 4.17 (d, J=12 Hz, 1H), 4.02 (ABq, J=10.4 Hz, 2H), 3.54-3.40 (m, 3H), 3.44 (d, J=12 Hz, 1H), 3.08-2.98 (m, 3H), 2.88-2.78 (m, 1H), 2.36 (s, 3H), 2.12-2.0 (m, 3H), 1.84-1.76 (m, 3H), 1.62-1.60 (m, 4H).

Preparative achiral SFC Conditions: column/dimensions: Princeton SFC Diol (250×4.6) mm, 5u; $CO_2$%: 70%; Co-solvent %: 30% of (0.2% $NH_3$ in methanol); Flow rate: 3 mL/min; Back Pressure: 100 bar; Retention time=6.289 min.

Examples 16-1 and 16-2

4-(2-{[(2S,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol

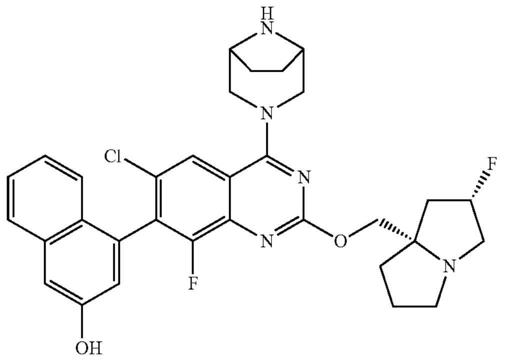

16-1 (Isomer 1)
16-2 (Isomer 2)

Preparation of Intermediate 16A: tert-butyl 3-(6-chloro-2,8-difluoro-7-(3-(methoxymethoxy)naphthalen-1-yl)quinazolin-4-yl)-3,8-diazabicyclo[3.2.1]octane-8-carboxylate

16A

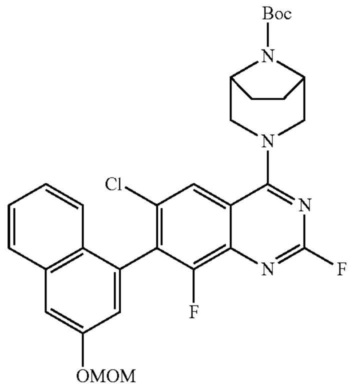

To a degassed solution of Example 8A (1000 mg, 2.042 mmol)) in 1,4-dioxane (60 mL) was added 2-(3-(methoxymethoxy)naphthalen-1-yl)-4,4,5,5-tetramethyl-1,3,2-dioxaborolane (1283 mg, 4.08 mmol), $Pd_2(dba)_3$ (93 mg, 0.102 mmol) and pentaphenyl(di-tert-butylphosphino)ferrocene (72.5 mg, 0.102 mmol, QPhos, Cas No: 312959-24-3). The mixture was degassed again and heated in a pressure vial at 70° C. for 12 hours. The reaction mixture was concentrated reduced pressure to obtain the crude residue. The crude material was purified by silica gel column chromatography using 30% ethyl acetate in petroleum ether to obtain tert-butyl 3-(6-chloro-2,8-difluoro-7-(3-(methoxymethoxy)naphthalen-1-yl)quinazolin-4-yl)-3,8-diazabicyclo[3.2.1]octane-8-carboxylate (1.0 g, 1.591 mmol, 78% yield) as a pale brown solid. LCMS (ESI) m/z: 597.2 $[M+H]^+$.

Preparation of Intermediate 16B: tert-butyl 3-(6-chloro-8-fluoro-2-(((2S,7aS)-2-fluorotetrahydro-1H-pyrrolizin-7a(5H)-yl)methoxy)-7-(3-(methoxymethoxy)naphthalen-1-yl)quinazolin-4-yl)-3,8-diazabicyclo[3.2.1]octane-8-carboxylate

16B

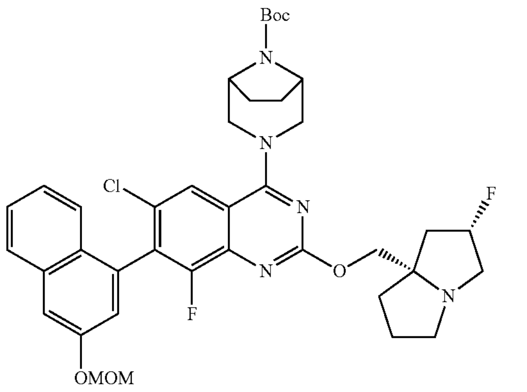

To a stirred solution of ((2S,7aS)-2-fluorotetrahydro-1H-pyrrolizin-7a(5H)-yl)methanol (192 mg, 1.206 mmol), in THE (20 mL) was added NaH (40.2 mg, 1.005 mmol) at 0° C. and the suspension was stirred for 30 minutes. tert-Butyl 3-(6-chloro-2,8-difluoro-7-(3-(methoxymethoxy)naphthalen-1-yl)quinazolin-4-yl)-3,8-diazabicyclo[3.2.1]octane-8-carboxylate (400 mg, 0.670 mmol) in THE (20 mL) was added to the reaction mixture at 0° C. The reaction mixture was then stirred at ambient temperature for 16 h. The reaction was then quenched with saturated ammonium chloride solution (10 mL) and extracted with ethyl acetate (2×20 mL). The combined organic layers were washed with water (20 mL) and brine solution (10 mL), and then dried over anhydrous $Na_2SO_4$ The mixture was filtered and concentrated under reduced pressure to afford crude product. The residue was purified by column chromatography over neutral alumina by eluting with 50-100% ethyl acetate in petroleum ether. The desired fractions were pooled and concentrated under reduced pressure to obtain tert-butyl 3-(6-chloro-8-fluoro-2-(((2S,7aS)-2-fluorotetrahydro-1H-pyrrolizin-7a(5H)-yl)methoxy)-7-(3-(methoxymethoxy)naphthalen-1-yl)quinazolin-4-yl)-3,8-diazabicyclo[3.2.1]octane-8-carboxylate (406 mg, 0.540 mmol, 81% yield as a pale brown solid. LCMS (ESI) m/z: 629.0 $[M+H]^+$.

Examples 16-1 and 16-2

4-(2-{[(2S,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol

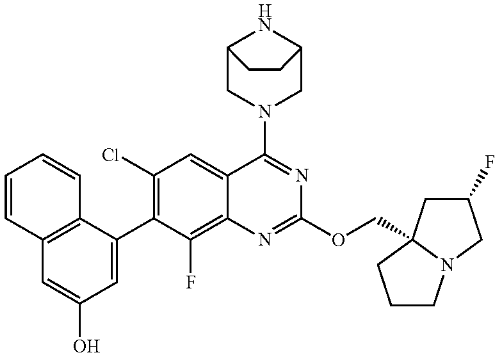

16-1 (Isomer 1)
16-2 (Isomer 2)

To a stirred solution of tert-butyl 3-(6-chloro-8-fluoro-2-(((2S,7aS)-2-fluorotetrahydro-1H-pyrrolizin-7a(5H)-yl)methoxy)-7-(3-(methoxymethoxy)naphthalen-1-yl)quinazolin-4-yl)-3,8-diazabicyclo[3.2.1]octane-8-carboxylate (350 mg, 0.475 mmol) in methanol (2 mL) was added hydrogen chloride in dioxane (4 M, 2.377 mL, 9.51 mmol) at 0° C. The reaction mixture was stirred at 25° C. for 8 h. The reaction mixture was then concentrated under reduced pressure to afford the crude product, which was purified by column chromatography (Biotage, $SiO_2$, eluted with 3-5% methanol in dichloromethane) to afford 4-(4-(3,8-diazabicyclo[3.2.1]octan-3-yl)-6-chloro-8-fluoro-2-(((2S,7aS)-2-fluorotetrahydro-1H-pyrrolizin-7a(5H)-yl)methoxy)quinazolin-7-yl)naphthalen-2-ol (130 mg, 0.24 mmol, 25% yield). The desired compound was subjected to SFC separation (Column: Cellulose-4 (250 mm×4.6×5u), mobile phase-0.5% Isopropylamine in MeOH), to afford two isomers of 4-(2-{[(2S,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol (16-1, isomer 1, 50 mg, 0.079 mmol, 17% yield) and (16-2, isomer 2, 54 mg, 0.085 mmol, 19% yield).

16-1, isomer 1: $^1$H NMR (400 MHz, DMSO-$d_6$) δ 7.97 (d, J=1.60 Hz, 1H), 7.76 (d, J=8.40 Hz, 1H), 7.44-7.42 (m, 1H), 7.27-7.21 (m, 3H), 7.05 (d, J=2.40 Hz, 1H), 5.28-5.41 (m, 1H), 4.55 (t, J=14.80 Hz, 2H), 4.43 (d, J=10.00 Hz, 1H), 4.31 (d, J=10.00 Hz, 1H), 3.69-3.64 (m, 3H), 3.45-3.43 (m, 1H), 3.12-3.10 (m, 1H), 2.90 (dd, J=, Hz, 1H), 2.76-2.73 (m, 1H), 2.50 (m, 1H), 2.15-2.10 (m, 1H), 2.00 (m, 3H), 1.97-1.86 (m, 5H), 1.22 (d, J=6.40 Hz, 2H) ppm. LCMS (ESI) m/z: 592.2 $[M+H]^+$.

16-2, isomer 2: $^1$H NMR (400 MHz, DMSO-$d_6$) δ 7.97 (d, J=1.60 Hz, 1H), 7.76 (d, J=8.40 Hz, 1H), 7.44-7.42 (m, 1H), 7.27-7.21 (m, 3H), 7.05 (d, J=2.40 Hz, 1H), 5.28-5.41 (m, 1H), 4.55 (t, J=14.80 Hz, 2H), 4.43 (d, J=10.00 Hz, 1H), 4.31 (d, J=10.00 Hz, 1H), 3.69-3.64 (m, 3H), 3.45-3.43 (m, 1H), 3.12-3.10 (m, 1H), 2.90 (dd, J=, Hz, 1H), 2.76-2.73 (m, 1H), 2.50 (m, 1H), 2.15-2.10 (m, 1H), 2.00 (m, 3H), 1.97-1.86 (m, 5H), 1.22 (d, J=6.40 Hz, 2H) ppm. LCMS (ESI) m/z: 592.2 $[M+H]^+$.

Example 17-1

4-(2-{[(2R,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol 17-1

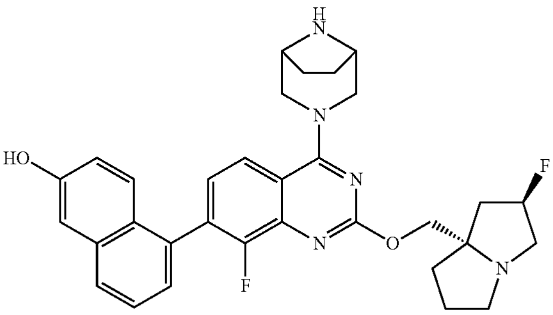

Preparation of Intermediate 17A: 7-bromo-8-fluoroquinazoline-2,4-diol

17A

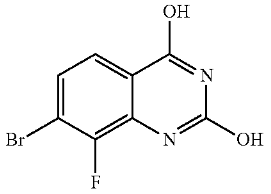

A mixture of 2-amino-4-bromo-3-fluorobenzoic acid (1.5 g, 6.41 mmol) and urea (11.55 g, 192 mmol) was stirred at 200° C. for 2 h. The reaction mixture was cooled to 80° C., and water (30 mL) was added with stirring and continued for 1h at the same temperature. After filtration, the solid was collected and washed with hot water (30 mL×2), dried under reduced pressure and co-evaporated with toluene (50 mL×2) to afford 7-bromo-8-fluoroquinazoline-2,4-diol (1.338 g, 5.17 mmol, 81% yield). MS(ESI) m/z: 258.9, $[M+H]^+$.

Preparation of Intermediate 17B: 7-bromo-2,4-dichloro-8-fluoroquinazoline

17B

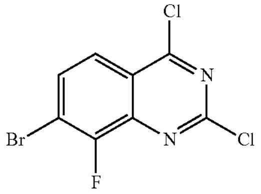

To a stirred suspension of 7-bromo-8-fluoroquinazoline-2,4-diol (1.4 g, 5.40 mmol) in $POCl_3$ (10.1 mL, 108 mmol), was added DMF (0.021 mL, 0.270 mmol) and the reaction mixture was refluxed (115° C.) for 16 h. The volatiles from the reaction mixture were removed under reduced pressure to afford a crude solid residue, which was dissolved in dry dichloromethane (100 mL) and filtered. The filtrate was concentrated under reduced pressure to provide 7-bromo-2,4-dichloro-8-fluoroquinazoline (1.213 g, 4.10 mmol, 76% yield). MS(ESI) m/z: 294.9, $[M+H]^+$.

Preparation of Intermediate 17C: tert-butyl 3-(7-bromo-2-chloro-8-fluoroquinazolin-4-yl)-3,8-diazabicyclo[3.2.1]octane-8-carboxylate

17C

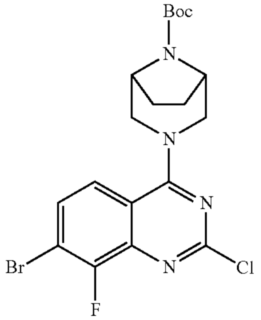

To a stirred solution of 7-bromo-2,4-dichloro-8-fluoroquinazoline (1.0 g, 3.38 mmol) in 1,4-dioxane (15 mL) at room temperature was added DIPEA (1.77 mL, 10.14 mmol) and 8-Boc-3,8-diaza-bicyclo[3.2.1]octane (1.076 g, 5.07 mmol). The reaction mixture was stirred at room temperature for 2h. The volatiles from the reaction mixture were evaporated under reduced pressure and the crude residue was dissolved in ethyl acetate (100 mL). The organic layer was washed with water. The aqueous layer was back extracted with ethyl acetate (30 mL×2). The combined organic layers were washed with brine, dried over anhydrous sodium sulfate, filtered, and evaporated under reduced pressure to provide the crude product. The crude compound was purified by ISCO (using 40 g silicagel column, pre-treated with 5% triethyl amine in pet ether; using 50 to 100% ethyl acetate/pet ether) to afford tert-butyl 3-(7-bromo-2-chloro-8-fluoroquinazolin-4-yl)-3,8-diazabicyclo[3.2.1]octane-8-carboxylate (1.105 g, 2.342 mmol, 69.3% yield). MS(ESI) m/z: 473. 1, $[M+H]^+$.

Preparation of Intermediate 17D: tert-butyl 3-(2-{[(2R,7aS)-2-fluoro-hexahydro-1H-pyrrolizin-7a-yl]methoxy}-7-bromo-8-fluoroquinazolin-4-yl)-3,8-diazabicyclo[3.2.1]octane-8-carboxylate

17D

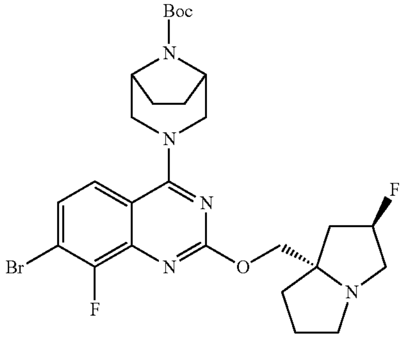

To a stirred solution of ((2R,7aS)-2-fluorotetrahydro-1H-pyrrolizin-7a(5H)-yl)methanol (0.157 g, 0.988 mmol) in tetrahydrofuran (10 mL) at 0° C. was added sodium hydride, 60% dispersion in mineral oil (0.079 g, 1.977 mmol) and the reaction was stirred at room temperature for 30 min. The reaction mixture was cooled back to 0° C. and tert-butyl 3-(7-bromo-2,8-difluoroquinazolin-4-yl)-3,8-diazabicyclo[3.2.1]octane-8-carboxylate (0.3 g, 0.659 mmol) (in 0.5 mL THF) was added. The reaction mixture was stirred at the same temperature for 2 h. To the reaction mixture was then added a few pieces of ice to quench excess NaH. The volatiles from the reaction mixture were removed under reduced pressure and the crude residue was dissolved in ethyl acetate (50 mL). The organic layer was washed with water. The aqueous layer was back extracted with ethyl acetate (20 mL×2). The combined organic layers were washed with brine, dried over anhydrous sodium sulfate, filtered and evaporated under reduced pressure to provide the crude product. The crude compound was purified by ISCO (using 40 g silicagel column, pre-treated with 5% triethylamine in pet ether; using 3 to 5% DCM/Methanol) to afford tert-butyl-3-(7-bromo-8-fluoro-2-(((2R,7aS)-2-fluorotetrahydro-1H-pyrrolizin-7a(5H)-yl)methoxy)quinazolin-4-yl)-3,8-diazabicyclo[3.2.1]octane-8-carboxylate (312 mg, 0.525 mmol, 80% yield). MS(ESI) m/z: 596.3, $[M+H]^+$.

Preparation of Intermediate 17E: tert-butyl 3-(2-{[(2R,7aS)-2-fluoro-hexahydro-1H-pyrrolizin-7a-yl]methoxy}-8-fluoro-7-[3-(methoxymethoxy)naphthalen-1-yl]quinazolin-4-yl)-3,8-diazabicyclo[3.2.1]octane-8-carboxylate

17E

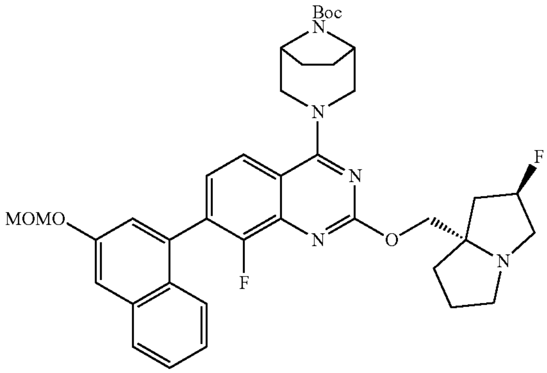

To a stirred solution of tert-butyl-3-(7-bromo-8-fluoro-2-(((2R,7aS)-2-fluorotetrahydro-1H-pyrrolizin-7a(5H)-yl)methoxy)quinazolin-4-yl)-3,8-diazabicyclo[3.2.1]octane-8-carboxylate (0.4 g, 0.673 mmol) in 1,4-dioxane (5 mL) was added 2-(3-(methoxymethoxy)naphthalen-1-yl)-4,4,5,5-tetramethyl-1,3,2-dioxaborolane (0.254 g, 0.807 mmol), aqueous sodium carbonate (1.0 mL, 2.018 mmol), followed by bis(triphenylphosphine)palladium(II) dichloride (0.047 g, 0.067 mmol). The reaction mixture was purged with $N_2$ for 5 min and heated at 100° C. for 16 h. The reaction mixture was concentrated under reduced pressure to afford a crude residue, which was dissolved in ethyl acetate and filtered through Celite. The filtrate was concentrated under reduced pressure to afford the crude product, which was purified by ISCO (using 40 g silicagel column, pre-treated with 5% triethyl amine in pet ether; using 50 to 100% ethyl acetate/pet ether) to afford tert-butyl-3-(8-fluoro-2-(((2R,7aS)-2-fluorotetrahydro-1H-pyrrolizin-7a(5H)-yl)methoxy)-7-(3-(methoxymethoxy)naphthalen-1-yl)quinazolin-4-yl)-3,8-diazabicyclo[3.2.1]octane-8-carboxylate (355 mg, 0.506 mmol, 75% yield). MS(ESI) m/z: 702.3, $[M+H]^+$.

Example 17-1

4-(2-{[(2R,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol 17-1

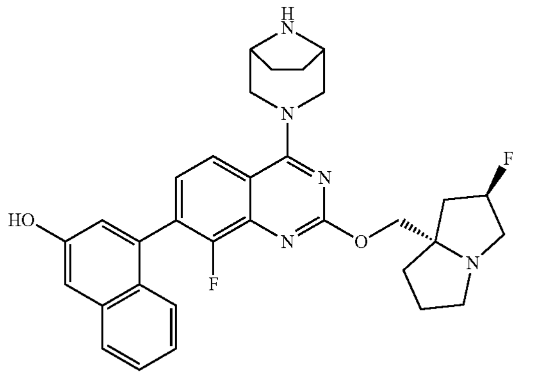

To a stirred solution of tert-butyl-3-(8-fluoro-2-(((2R,7aS)-2-fluorotetrahydro-1H-pyrrolizin-7a(5H)-yl)methoxy)-7-(3-(methoxymethoxy)naphthalen-1-yl)quinazolin-4-yl)-3,8-diazabicyclo[3.2.1]octane-8-carboxylate (0.06 g, 0.085 mmol) at 0° C. was added 4N HCl (0.214 mL, 0.855 mmol, in 1,4-dioxane) and the reaction mixture was stirred at room temperature for 5 h. The volatiles from the reaction mixture were removed under reduced pressure (at lower temperature, −30° C.) and the crude residue was co-evaporated with 1,4-dioxane. Then the crude residue was dissolved in 1,4-dioxane and triethylamine was added and evaporated under reduced pressure to provide an off-white solid. The crude compound was purified by Prep-HPLC [HPLC Method: Preparative column: YMC EXRS (250×20×5), Mobile phase A: 10 mM Ammonium bicarbonate in water-9.5; Mobile phase B: acetonitrile: methanol; Gradient=60-80% B over 13 minutes; Temperature: 27° C.; Flow rate: 20.0 mL/min; Detection: UV at 220 nm.] to afford 4-(3,8-diazabicyclo[3.2.1]octan-3-yl)-8-fluoro-2-(((2R,7aS)-2-fluorotetrahydro-1H-pyrrolizin-7a(5H)-yl)methoxy)quinazolin-7-yl)naphthalen-2-ol (7.0 mg, 0.012 mmol, 14.4% yield) MS(ESI) m/z: 558.4, $[M+H]^+$. $^1H$ NMR (400 MHz, DMSO-$d_6$) δ ppm 9.99-9.94 (m, 1H), 7.87 (d, J=8.3 Hz, 1H), 7.80 (d, J=8.5 Hz, 1H), 7.47-7.38 (m, 2H), 7.28-7.21 (m, 3H), 7.10-7.08 (m, 1H), 5.38-5.19 (m, 1H), 4.37-4.25 (m, 2H), 4.13-3.98 (m, 2H), 3.51-3.50 (m, 4H), 3.44-3.43 (m, 1H), 3.14-3.07 (m, 2H), 3.02-3.00 (m, 1H), 2.88-2.79 (m, 1H), 2.17-2.12 (m, 1H), 2.07-2.00 (m, 2H), 1.86-1.75 (m, 3H), 1.71-1.64 (m, 4H).

Examples in Table 6 were prepared according to procedures described for Example 17-1 from appropriate starting materials.

TABLE 6

| Example Number | Structure | Name | LCMS $(M + H)^+$ | $^1H$ NMR |
|---|---|---|---|---|
| 17-2 | 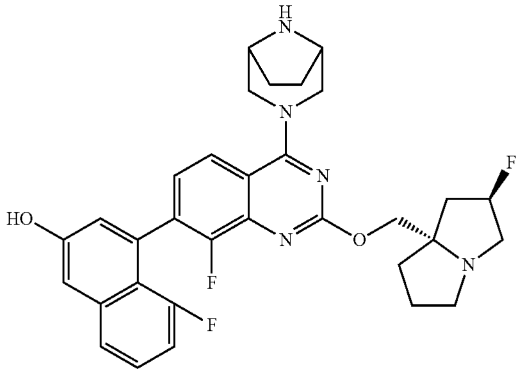 [SMILES: Oc1cc(-c2ccc3c(N4CC5CCC(C4)N5)nc(OC[C@@]45CCCN4C[C@H](F)C5)nc3c2F)c2c(F)cccc2c1] | 4-(2-{[(2R,7aS)-2-fluoro-hexahydro-1H-pyrrolizin-7a-yl]methoxy}-4-{3,8-diazabicyclo[3.2.1]octan-3-yl}-8-fluoroquinazolin-7-yl)-5-fluoronaphthalen-2-ol | 576.4 | (400 MHz, DMSO-$d_6$) δ ppm 7.77 (d, J = 9.0 Hz, 1H), 7.59-7.56 (m, 1H), 7.40-7.32 (m, 1H), 7.26-7.18 (m, 2H), 7.00-6.96 (m, 1H), 6.94-6.86 (m, 1H), 5.37-5.18 (m, 1H), 4.30-4.22 (m, 2H), 4.11-4.06 (m, 1H), 4.00 (br d, J = 2.6 Hz, 1H), 3.52-3.46 (m, 5H), 3.10-3.07 (m, 2H), 3.02-3.00 (m, 1H), 2.85-2.79 (m, 1H), 2.16-2.10 (m, 1H), 2.05-1.99 (m, 2H), 1.85-1.76 (m, 3H), 1.70-1.63 (m, 4H). |
| 17-3 | 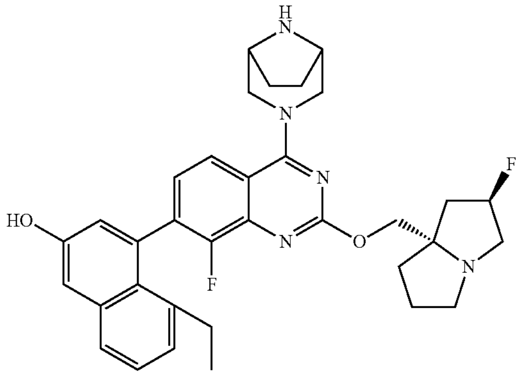 [SMILES: CCc1cccc2cc(O)cc(-c3ccc4c(N5CC6CCC(C5)N6)nc(OC[C@@]56CCCN5C[C@H](F)C6)nc4c3F)c12] | 4-(2-{[(2R,7aS)-2-fluoro-hexahydro-1H-pyrrolizin-7a-yl]methoxy}-4-{3,8-diazabicyclo[3.2.1]octan-3-yl}-8-fluoroquinazolin-7-yl)-5-ethylnaphthalen-2-ol | 586.30 | $^1H$ NMR (400 MHz, DMSO-$d_6$) δ ppm: 9.87 (s, 1H), 7.80 (d, J = 9.0 Hz, 1H), 7.66 (d, J = 7.0 Hz, 1H), 7.36 (t, J = 7.6 Hz, 1H), 7.28-7.18 (m, 2H), 7.12 (d, J = 6.8 Hz, 1H), 6.88 (d, J = 2.8 Hz, 1H), 5.35-5.21 (m, 1H), 4.36-4.24 (m, 2H), 4.15-4.07 (m, 1H), 4.04-3.96 (m, 1H), 3.56-3.48 (m, 4H), 3.13-3.08 (m, 3H), 2.85-2.78 (m, 1H), 2.35-2.28 (m, 2H), 2.17-1.97 (m, 3H), 1.88-1.75 (m, 3H), 1.70-1.65 (m, 4H), 0.80 (t, J = 7.4 Hz, 3H). |

TABLE 6-continued

| Example Number | Structure | Name | LCMS $(M + H)^+$ | $^1H$ NMR |
|---|---|---|---|---|
| 17-4 | 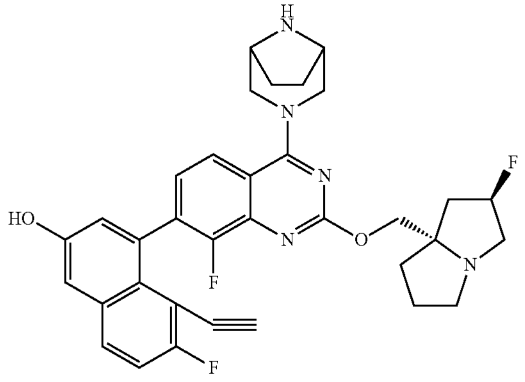 [SMILES: C#Cc1c(F)ccc2cc(O)cc(-c3ccc4c(N5CC6CCC(C5)N6)nc(OC[C@@]56CCCN5C[C@H](F)C6)nc4c3F)c12] | 4-(2-{[(2R,7aS)-2-fluoro-hexahydro-1H-pyrrolizin-7a-yl]methoxy}-4-{3,8-diazabicyclo[3.2.1]octan-3-yl}-8-fluoroquinazolin-7-yl)-5-ethynyl-6-fluoronaphthalen-2-ol | 600.3 | $^1H$ NMR (400 MHz, DMSO-$d_6$) δ ppm: 7.98 (dd, J = 9.3, 5.9 Hz, 1H), 7.83 (d, J = 8.8 Hz, 1H), 7.51-7.44 (m, 1H), 7.40-7.31 (m, 2H), 7.07 (d, J = 2.4 Hz, 1H), 5.66-5.47 (m, 1H), 4.62-4.54 (m, 2H), 4.53-4.38 (m, 2H), 4.21 (br d, J = 4.3 Hz, 2H), 3.92-3.70 (m, 7H), 2.58-2.53 (m, 1H), 2.36-2.32 (m, 1H), 2.25-2.12 (m, 3H), 2.00 (br s, 6H). |

Examples 18-1

6-(6-chloro-4-{3,8-diazabicyclo[3.2.1]octan-3-yl}-2-({1-[(dimethylamino)methyl]cyclopropyl}methoxy)-8-fluoroquinazolin-7-yl)-4-methyl-5-(trifluoromethyl)pyridin-2-amine 18-1

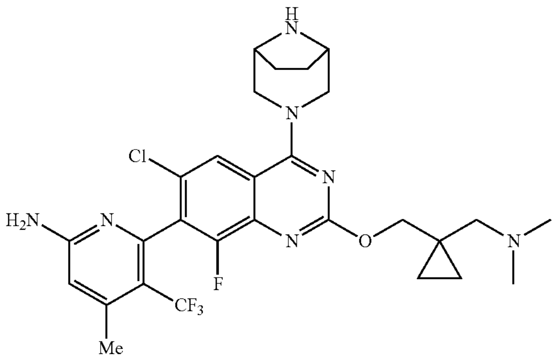

Preparation of Intermediate 18A: methyl 1-(dimethylcarbamoyl)cyclopropane-1-carboxylate

18A

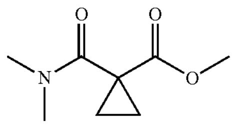

To a solution of 1-(methoxycarbonyl)cyclopropane-1-carboxylic acid (10 g, 69.4 mmol), dimethylamine hydrochloride (11.32 g, 139 mmol) and DIPEA (48.5 mL, 278 mmol) in DCM (100 mL) was added HOBt (15.94 g, 104 mmol) and EDC (19.95 g, 104 mmol) at 0° C. and the reaction mixture was stirred at room temperature for 16 h. The reaction was quenched with water and extracted with DCM. The combined organic layers were washed with water, brine, dried over $Na_2SO_4$ and concentrated under reduced pressure to provide crude residue, which was purified by silica gel column chromatography using CombiFlash instrument (80 g RediSep® column, 60 to 80% EtOAc—pet ether, uv inactive, slightly $KMnO_4$ active) to afford methyl 1-(dimethylcarbamoyl)cyclopropane-1-carboxylate (8 g, 46.7 mmol, 67.4% yield) as a pale yellow liquid. $^1H$ NMR (300 MHz, CHLOROFORM-d) δ ppm=3.73 (s, 3H), 3.04 (s, 3H), 2.99 (s, 3H), 1.54-1.47 (m, 2H), 1.38-1.31 (m, 2H).

Preparation of Intermediate 18B: {1-[(dimethylamino)methyl]cyclopropyl}methanol

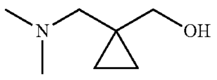

18B

To a solution of methyl 1-(dimethylcarbamoyl)cyclopropane-1-carboxylate (8 g, 46.7 mmol) in THE (150 mL) was added $LiAlH_4$ (2.4M solution in THF) (38.9 mL, 93 mmol) slowly at 0° C. and the reaction mixture was stirred at room temperature for 4 h. The reaction was cooled and quenched with water (20 mL), 10% NaOH solution (40 mL) and water (40 mL) and extracted with ethyl acetate. The organic layer was washed with water, brine, dried over $Na_2SO_4$ and concentrated to provide the {1-[(dimethylamino)methyl]cyclopropyl}methanol (3.7 g, 28.6 mmol, 61.3% yield) as a yellow liquid. $^1H$ NMR (300 MHz, CHLOROFORM-d) δ ppm=5.30-4.15 (m, 1H), 3.55 (s, 2H), 2.41 (s, 2H), 2.31 (s, 6H), 0.54-0.47 (m, 2H), 0.39-0.32 (m, 2H).

Preparation of Intermediate 18C: tert-butyl 3-[7-(6-{bis[(4-methoxyphenyl)methyl]amino}-4-methyl-3-(trifluoromethyl)pyridin-2-yl)-6-chloro-2-({1-[(dimethylamino)methyl]cyclopropyl}methoxy)-8-fluoroquinazolin-4-yl]-3,8-diazabicyclo[3.2.1]octane-8-carboxylate

18C

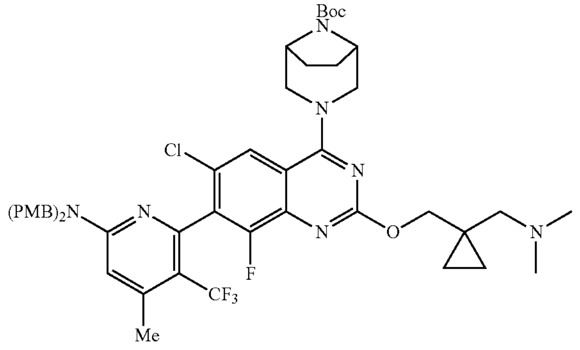

To a solution of {1-[(dimethylamino)methyl]cyclopropyl}methanol in THE (2 mL) at 0° C. was added NaH (29.1 mg, 0.727 mmol) and stirred for additional 30 min. Then, Intermediate 141 was added and gradually warmed up to room temperature over a period of 2 h. The reaction mixture was quenched with saturated aq. ammonium chloride solution and extracted with ethyl acetate. The combined organic layers were washed with water, brine, dried over $Na_2SO_4$ and concentrated under reduced pressure to provide crude residue, which was purified by silica gel column chromatography using CombiFlash instrument (40 g RediSep® column, 50 to 60% EtOAc—pet ether) to afford tert-butyl 3-[7-(6-{bis[(4-methoxyphenyl)-methyl]amino}-4-methyl-3-(trifluoromethyl)pyridin-2-yl)-6-chloro-2-({1-[(dimethylamino)methyl]cyclopropyl}-methoxy)-8-fluoroquinazolin-4-yl]-3,8-diazabicyclo[3.2.1]octane-8-carboxylate (250 mg, 0.268 mmol, 73.6% yield) as a pale yellow solid. MS(ESI) m/z: 934.3 $(M+H)^+$.

Examples 18-1

6-(6-chloro-4-{3,8-diazabicyclo[3.2.1]octan-3-yl}-2-({1-[(dimethylamino)methyl]cyclopropyl}methoxy)-8-fluoroquinazolin-7-yl)-4-methyl-5-(trifluoromethyl)pyridin-2-amine 18-1

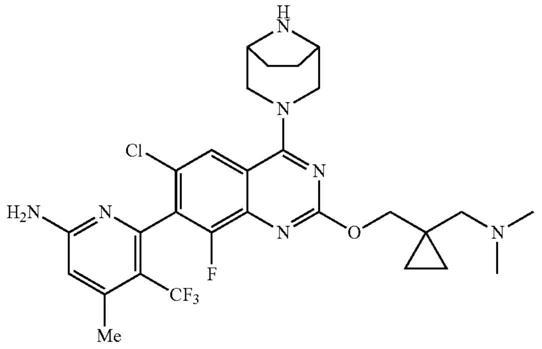

A stirred solution of TFA (3 mL, 38.9 mmol) and triethylsilane (1 mL, 6.26 mmol) was added to tert-butyl 3-[7-(6-{bis[(4-methoxyphenyl)methyl]amino}-4-methyl-3-(trifluoromethyl)pyridin-2-yl)-6-chloro-2-({1-[(dimethylamino)methyl]cyclopropyl}methoxy)-8-fluoroquinazolin-4-yl]-3,8-diazabicyclo[3.2.1]octane-8-carboxylate (280 mg, 0.300 mmol) at room temperature and the resulting reaction mixture was heated to 40° C. over a period of 24 h. Then, the reaction mixture was concentrated under reduced pressure, co-distilled with toluene (twice), neutralised with DIPEA and concentrated under reduced pressure to provide the crude residue, which was purified by preparative HPLC to afford 6-(6-chloro-4-{3,8-diazabicyclo[3.2.1]octan-3-yl}-2-({1-[(dimethylamino)methyl]cyclopropyl}methoxy)-8-fluoroquinazolin-7-yl)-4-methyl-5-(trifluoromethyl)pyridin-2-amine (45 mg, 0.076 mmol, 25.3% yield). MS(ESI) m/z: 594.4, $[M+H]^+$. $^1H$ NMR (400 MHz, DMSO-$d_6$) δ ppm=7.80 (s, 1H), 6.84 (s, 2H), 6.49 (s, 1H), 4.30 (br d, J=11.9 Hz, 1H), 4.24-4.12 (m, 3H), 3.58-3.39 (m, 5H), 2.37 (br d, J=1.4 Hz, 3H), 2.22 (s, 2H), 2.15 (s, 6H), 1.70-1.56 (m, 4H), 0.66-0.59 (m, 2H), 0.44-0.37 (m, 2H). Preparative HPLC Conditions: Column/dimensions: Kinetex EVO (250×4.6) mm, 5u; Mobile phase A: 10 mM Ammonium bicarbonate in water-9.5 pH, Mobile phase B: ACN:MeOH (1:1), Flow: 19 mL/min; Retention time=13.184 min.

Examples in Table 7 were prepared according to procedures described for Example 18-1 from appropriate starting materials.

TABLE 7

| Example Name | Structure | Name | LCMS (M + H)+ | 1H NMR |
|---|---|---|---|---|
| 18-2 | 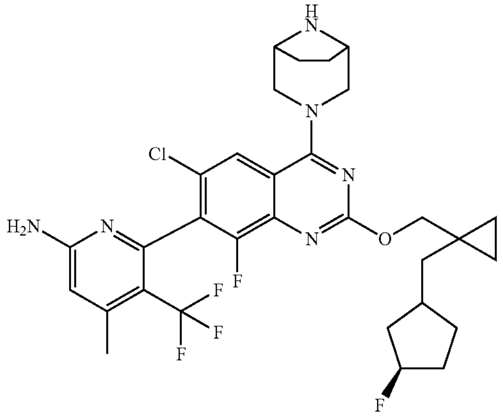 [SMILES: Cc1cc(N)nc(-c2c(Cl)cc3c(N4CC5CCC(C4)N5)nc(OCC4(CC5CC[C@@H](F)C5)CC4)nc3c2F)c1C(F)(F)F] | 6-(6-chloro-4-{3,8-diazabicyclo[3.2.1]octan-3-yl}-8-fluoro-2-[(1-{[(3R)-3-fluoropyrrolidin-1-yl]methyl}cyclopropyl)methoxy]quinazolin-7-yl)-4-methyl-5-(trifluoromethyl)pyridin-2-amine | 638.2 | $^1$H NMR (400 MHz, DMSO-$d_6$) δ ppm: 7.80 (s, 1H), 6.83 (s, 2H), 6.49 (s, 1H), 5.28-5.02 (m, 1H), 4.36-4.25 (m, 2H), 4.20-4.06 (m, 2H), 3.60-3.51 (m, 3H), 3.44-3.40 (m, 2H), 2.86-2.73 (m, 2H), 2.64-2.54 (m, 2H), 2.40-2.32 (m, 5H), 2.15-2.02 (m, 1H), 1.89-1.74 (m, 1H), 1.71-1.57 (m, 4H), 0.62 (br s, 2H), 0.43 (br s, 2H). |
| 18-3 | 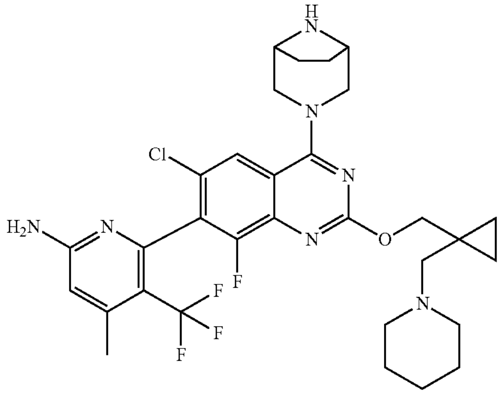 [SMILES: Cc1cc(N)nc(-c2c(Cl)cc3c(N4CC5CCC(C4)N5)nc(OCC4(CN5CCCCC5)CC4)nc3c2F)c1C(F)(F)F] | 6-(6-chloro-4-{3,8-diazabicyclo[3.2.1]octan-3-yl}-8-fluoro-2-({1-[(piperidin-1-yl)methyl]cyclopropyl}methoxy)quinazolin-7-yl)-4-methyl-5-(trifluoromethyl)pyridin-2-amine | 634.3 | $^1$H NMR (400 MHz, DMSO-$d_6$) δ ppm: 7.80 (d, J = 1.3 Hz, 1H), 6.84 (s, 2H), 6.49 (s, 1H), 4.35-4.13 (m, 5H), 3.57-3.40 (m, 4H), 2.42-2.29 (m, 7H), 2.28-2.21 (m, 2H), 1.70-1.56 (m, 4H), 1.49-1.38 (m, 4H), 1.37-1.29 (m, 2H), 0.64-0.58 (m, 2H), 0.41-0.35 (m, 2H) |
| 18-4 | 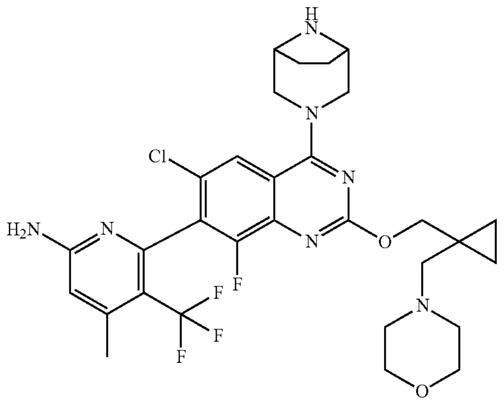 [SMILES: Cc1cc(N)nc(-c2c(Cl)cc3c(N4CC5CCC(C4)N5)nc(OCC4(CN5CCOCC5)CC4)nc3c2F)c1C(F)(F)F] | 6-(6-chloro-4-{3,8-diazabicyclo[3.2.1]octan-3-yl}-8-fluoro-2-({1-[(morpholin-4-yl)methyl]cyclopropyl}methoxy)quinazolin-7-yl)-4-methyl-5-(trifluoromethyl)pyridin-2-amine | 636.2 | $^1$H NMR (400 MHz, DMSO-$d_6$) δ ppm: 7.80 (d, J = 1.3 Hz, 1H), 6.83 (s, 2H), 6.49 (s, 1H), 4.31 (br d, J = 11.5 Hz, 1H), 4.28-4.22 (m, 2H), 4.21-4.13 (m, 1H), 3.59-3.49 (m, 7H), 3.44 (br d, J = 11.3 Hz, 1H), 2.37 (br d, J = 1.5 Hz, 6H), 2.29 (d, J = 4.0 Hz, 2H), 2.07 (s, 1H), 1.73-1.56 (m, 4H), 0.68-0.58 (m, 2H), 0.45-0.35 (m, 2H) |

TABLE 7-continued

| Example Name | Structure | Name | LCMS (M + H)+ | 1H NMR |
|---|---|---|---|---|
| 18-5 | 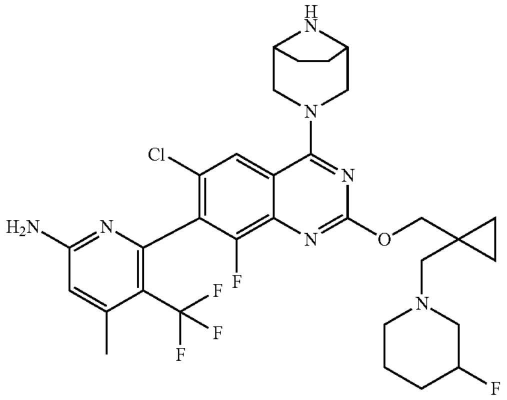 [SMILES: Cc1cc(N)nc(-c2c(Cl)cc3c(N4CC5CCC(C4)N5)nc(OCC4(CN5CCCC(F)C5)CC4)nc3c2F)c1C(F)(F)F] | 6-(6-chloro-4-{3,8-diazabicyclo[3.2.1]octan-3-yl}-8-fluoro-2-({1-[(3-fluoropiperidin-1-yl)methyl]cyclopropyl}methoxy)quinazolin-7-yl)-4-methyl-5-(trifluoromethyl)pyridin-2-amine | 652.2 | $^1$H NMR (400 MHz, DMSO-$d_6$) δ ppm: 7.80 (d, J = 1.1 Hz, 1H), 6.83 (s, 2H), 6.50 (s, 1H), 4.66-4.43 (m, 1H), 4.35-4.13 (m, 4H), 3.58-3.43 (m, 5H), 2.87-2.72 (m, 1H), 2.49-2.43 (m, 1H), 2.41-2.26 (m, 6H), 2.22-2.14 (m, 1H), 1.86-1.72 (m, 1H), 1.71-1.54 (m, 5H), 1.52-1.31 (m, 2H), 0.69-0.59 (m, 2H), 0.45-0.34 (m, 2H) |
| 18-6 | 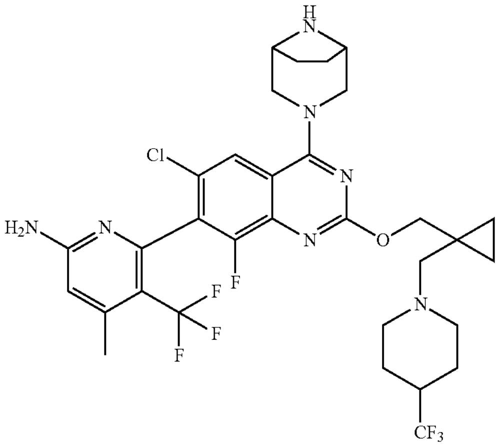 [SMILES: Cc1cc(N)nc(-c2c(Cl)cc3c(N4CC5CCC(C4)N5)nc(OCC4(CN5CCC(C(F)(F)F)CC5)CC4)nc3c2F)c1C(F)(F)F] | 6-(6-chloro-4-{3,8-diazabicyclo[3.2.1]octan-3-yl}-8-fluoro-2-[(1-{[4-(trifluoromethyl)piperidin-1-yl]methyl}cyclopropyl)methoxy]quinazolin-7-yl)-4-methyl-5-(trifluoromethyl)pyridin-2-amine | 702.25 | $^1$H NMR (400 MHz, DMSO-$d_6$) δ ppm: 7.78 (s, 1H), 6.82 (s, 2H), 6.48 (s, 1H), 4.33-4.13 (m, 4H), 3.54-3.40 (m, 4H), 3.06-2.95 (m, 2H), 2.38-2.34 (m, 4H), 2.33-2.28 (m, 4H), 2.24-2.17 (m, 1H), 1.90-1.81 (m, 2H), 1.73-1.59 (m, 5H), 1.40-1.34 (m, 1H), 0.71-0.53 (m, 2H), 0.46-0.27 (m, 2H). |
| 18-7 | 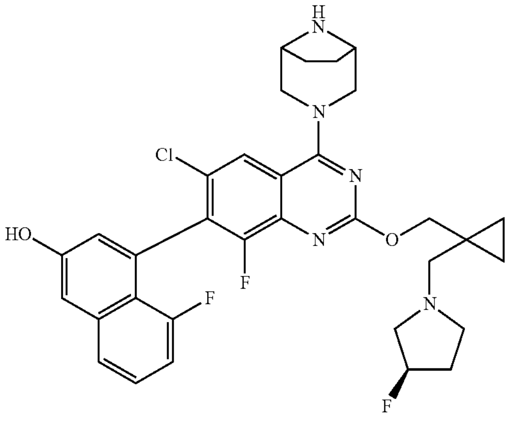 [SMILES: Oc1cc(-c2c(Cl)cc3c(N4CC5CCC(C4)N5)nc(OCC4(CN5CC[C@@H](F)C5)CC4)nc3c2F)c2c(F)cccc2c1] | 4-(6-chloro-4-{3,8-diazabicyclo[3.2.1]octan-3-yl}-8-fluoro-2-[(1-{[(3R)-3-fluoropyrrolidin-1-yl]methyl}cyclopropyl)methoxy]quinazolin-7-yl)-5-fluoronaphthalen-2-ol | 624.2 | $^1$H NMR (400 MHz, DMSO-$d_6$) δ ppm: 10.32 (s, 1H), 7.86 (s, 1H), 7.67 (d, J = 7.8 Hz, 1H), 7.42-7.39 (m, 1H), 7.35-7.34 (m, 1H), 7.04-6.91 (m, 2H), 5.27-5.02 (m, 1H), 4.35-4.15 (m, 4H), 3.60-3.51 (m, 3H), 3.44-3.40 (m, 2H), 2.86-2.73 (m, 2H), 2.64-2.54 (m, 2H), 2.40-2.32 (m, 2H), 2.15-2.02 (m, 1H), 1.89-1.74 (m, 1H), 1.71-1.57 (m, 4H), 0.62 (br s, 2H), 0.43 (br s, 2H). |

TABLE 7-continued

| Example Name | Structure | Name | LCMS $(M + H)^+$ | $^1H$ NMR |
|---|---|---|---|---|
| 18-8 | 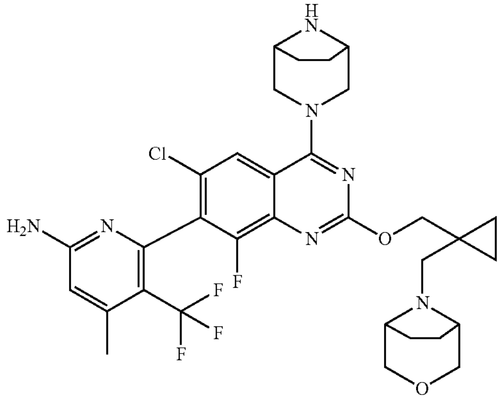 [SMILES: Cc1cc(N)nc(-c2c(Cl)cc3c(N4CC5CCC(C4)N5)nc(OCC4(CN5C6CCC5COC6)CC4)nc3c2F)c1C(F)(F)F] | 6-(6-chloro-4-{3,8-diazabicyclo[3.2.1]octan-3-yl}-8-fluoro-2-{[1-({3-oxa-8-azabicyclo[3.2.1]octan-8-yl}methyl)cyclopropyl]methoxy}quinazolin-7-yl)-4-methyl-5-(trifluoromethyl)pyridin-2-amine | 662.2 | $^1H$ NMR (400 MHz, DMSO-$d_6$) δ ppm: 7.80 (s, 1H), 6.82 (s, 2H), 6.49 (s, 1H), 4.38-4.27 (m, 3H), 4.20-4.13 (m, 1H), 3.56-3.41 (m, 7H), 3.38-3.34 (m, 2H), 3.08-3.04 (m, 2H), 2.39-2.35 (m, 3H), 2.31-2.27 (m, 2H), 1.82-1.76 (m, 2H), 1.69-1.57 (m, 6H), 0.60-0.53 (m, 2H), 0.46-0.40 (m, 2H) |
| 18-9 | 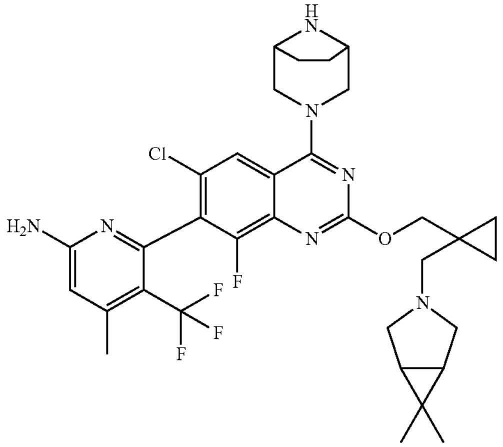 [SMILES: Cc1cc(N)nc(-c2c(Cl)cc3c(N4CC5CCC(C4)N5)nc(OCC4(CN5CC6C(C5)C6(C)C)CC4)nc3c2F)c1C(F)(F)F] | 6-(6-chloro-4-{3,8-diazabicyclo[3.2.1]octan-3-yl}-2-{[1-({6,6-dimethyl-3-azabicyclo[3.1.0]hexan-3-yl}methyl)cyclopropyl]methoxy}-8-fluoroquinazolin-7-yl)-4-methyl-5-(trifluoromethyl)pyridin-2-amine | 660.3 | $^1H$ NMR (400 MHz, DMSO-$d_6$) δ ppm: 7.79 (s, 1H), 6.81 (s, 2H), 6.51 (s, 1H), 4.35-4.11 (m, 5H), 3.55 (s, 4H), 2.85 (m, 2H), 2.56-2.53 (m, 2H), 2.44-2.31 (m, 5H), 1.67-1.53 (m, 4H), 1.15-1.12 (m, 2H), 1.09 (s, 3H), 0.90 (s, 3H), 0.59-0.52 (m, 2H), 0.41-0.34 (m, 2H) |
| 18-10 | 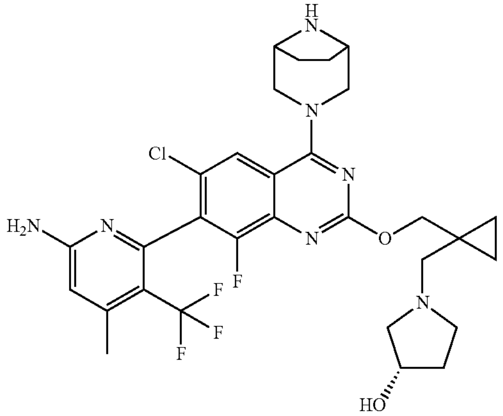 [SMILES: Cc1cc(N)nc(-c2c(Cl)cc3c(N4CC5CCC(C4)N5)nc(OCC4(CN5CC[C@H](O)C5)CC4)nc3c2F)c1C(F)(F)F] | (3S)-1-({1-[({7-[6-amino-4-methyl-3-(trifluoromethyl)pyridin-2-yl]-6-chloro-4-{3,8-diazabicyclo[3.2.1]octan-3-yl}-8-fluoroquinazolin-2-yl}oxy)methyl]cyclopropyl}methyl)pyrrolidin-3-ol | 636.3 | $^1H$ NMR (400 MHz, DMSO-$d_6$) δ ppm: 7.80 (d, J = 1.0 Hz, 1H), 6.83 (s, 2H), 6.49 (s, 1H), 4.35-4.11 (m, 7H), 3.57-3.54 (m, 3H), 3.45-3.42 (m, 1H), 2.76-2.65 (m, 1H), 2.59-2.53 (m, 1H), 2.43-2.34 (m, 5H), 2.33-2.26 (m, 2H), 1.99-1.92 (m, 1H), 1.71-1.59 (m, 4H), 1.54-1.45 (m, 1H), 0.66-0.53 (m, 2H), 0.46-0.35 (m, 2H). |

TABLE 7-continued

| Example Name | Structure | Name | LCMS (M + H)+ | $^1$H NMR |
|---|---|---|---|---|
| 18-11 | 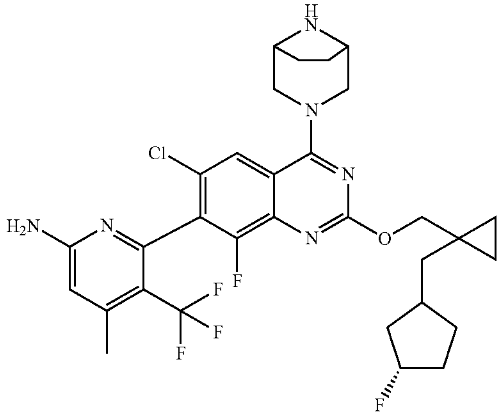 [SMILES: Cc1cc(N)nc(-c2c(Cl)cc3c(N4CC5CCC(C4)N5)nc(OCC4(CC5CC[C@H](F)C5)CC4)nc3c2F)c1C(F)(F)F] | 6-(6-chloro-4-{3,8-diazabicyclo[3.2.1]octan-3-yl}-8-fluoro-2-[(1-{[(3S)-3-fluoropyrrolidin-1-yl]methyl}cyclopropyl)methoxy]quinazolin-7-yl)-4-methyl-5-(trifluoromethyl)pyridin-2-amine | 638.2 | $^1$H NMR (400 MHz, DMSO-d$_6$) δ ppm: 7.80 (s, 1H), 6.84 (s, 2H), 6.49 (s, 1H), 5.29-5.02 (m, 1H), 4.34-4.22 (m, 2H), 4.21-4.11 (m, 2H), 3.56-3.47 (m, 3H), 3.44-3.41 (m, 2H), 2.90-2.73 (m, 2H), 2.66-2.56 (m, 2H), 2.46-2.32 (m, 5H), 2.15-1.99 (m, 1H), 1.92-1.75 (m, 1H), 1.69-1.48 (m, 4H), 0.62 (br s, 2H), 0.43 (br s, 2H). |
| 18-12 | 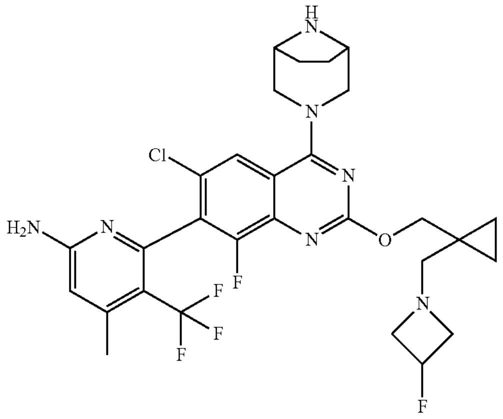 [SMILES: Cc1cc(N)nc(-c2c(Cl)cc3c(N4CC5CCC(C4)N5)nc(OCC4(CN5CC(F)C5)CC4)nc3c2F)c1C(F)(F)F] | 6-(6-chloro-4-{3,8-diazabicyclo[3.2.1]octan-3-yl}-8-fluoro-2-({1-[(3-fluoroazetidin-1-yl)methyl]cyclopropyl}methoxy)quinazolin-7-yl)-4-methyl-5-(trifluoromethyl)pyridin-2-amine | 624.1 | $^1$H NMR (400 MHz, DMSO-d$_6$) δ ppm: 7.80 (d, J = 1.1 Hz, 1H), 6.82 (s, 2H), 6.49 (s, 1H), 5.22-4.99 (m, 1H), 4.37-4.25 (m, 1H), 4.21-4.07 (m, 3H), 3.62-3.49 (m, 6H), 3.47-3.43 (m, 1H), 3.12-3.02 (m, 2H), 2.46 (s, 2H), 2.36 (br d, J = 1.4 Hz, 3H), 1.71-1.57 (m, 4H), 0.55-0.49 (m, 2H), 0.46-0.40 (m, 2H). |
| 18-13 | 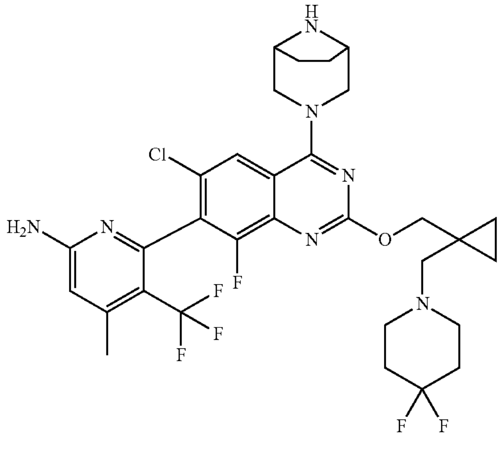 [SMILES: Cc1cc(N)nc(-c2c(Cl)cc3c(N4CC5CCC(C4)N5)nc(OCC4(CN5CCC(F)(F)CC5)CC4)nc3c2F)c1C(F)(F)F] | 6-(6-chloro-4-{3,8-diazabicyclo[3.2.1]octan-3-yl}-2-({1-[(4,4-difluoropiperidin-1-yl)methyl]cyclopropyl}methoxy)-8-fluoroquinazolin-7-yl)-4-methyl-5-(trifluoromethyl)pyridin-2-amine | 670.2 | $^1$H NMR (400 MHz, DMSO-d$_6$) δ ppm: 7.80 (d, J = 1.3 Hz, 1H), 6.83 (s, 2H), 6.49 (s, 1H), 4.35-4.13 (m, 4H), 3.60-3.39 (m, 6H), 2.57-2.51 (m, 3H), 2.39-2.34 (m, 5H), 1.95-1.91 (m, 1H), 1.89-1.81 (m, 3H), 1.69-1.56 (m, 4H), 0.67-0.61 (m, 2H), 0.46-0.35 (m, 2H). |

TABLE 7-continued

| Example Name | Structure | Name | LCMS (M + H)+ | $^1$H NMR |
|---|---|---|---|---|
| 18-14 | 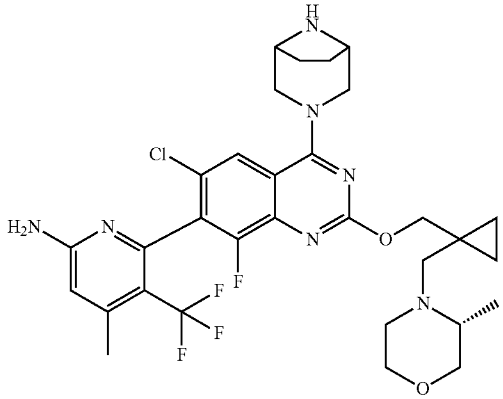 [SMILES: Cc1cc(N)nc(-c2c(Cl)cc3c(N4CC5CCC(C4)N5)nc(OCC4(CN5CCOC[C@H]5C)CC4)nc3c2F)c1C(F)(F)F] | 6-(6-chloro-4-{3,8-diazabicyclo[3.2.1]octan-3-yl}-8-fluoro-2-[(1-{[(3R)-3-methylmorpholin-4-yl]methyl}cyclopropyl)methoxy]quinazolin-7-yl)-4-methyl-5-(trifluoromethyl)pyridin-2-amine | 650.3 | $^1$H NMR (400 MHz, DMSO-$d_6$) δ ppm: 7.79 (s, 1H), 6.82 (s, 2H), 6.49 (s, 1H), 4.63-4.55 (m, 1H), 4.33-4.15 (m, 1H), 3.94-3.86 (m, 2H), 3.51-3.41 (m, 8H), 3.24-3.16 (m, 1H), 3.00-2.87 (m, 1H), 2.37 (d, J = 1.5 Hz, 2H), 2.28-2.18 (m, 1H), 2.14-2.04 (m, 1H), 1.89 (s, 3H), 1.66-1.54 (m, 4H), 0.79-0.77 (m, 3H), 0.69-0.61 (m, 1H), 0.56-0.45 (m, 2H), 0.35-0.28 (m, 1H). |
| 18-15 | 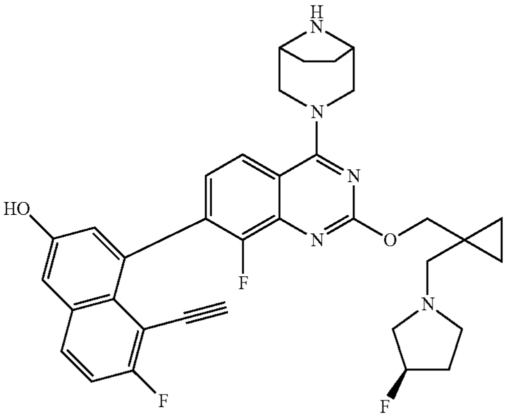 [SMILES: C#Cc1c(F)ccc2cc(O)cc(-c3ccc4c(N5CC6CCC(C5)N6)nc(OCC5(CN6CC[C@@H](F)C6)CC5)nc4c3F)c12] | 4-(4-{3,8-diazabicyclo[3.2.1]octan-3-yl}-8-fluoro-2-[(1-{[(3R)-3-fluoropyrrolidin-1-yl]methyl}cyclopropyl)methoxy]quinazolin-7-yl)-5-ethynyl-6-fluoronaphthalen-2-ol | 614.0 | $^1$H NMR (400 MHz, DMSO-$d_6$) δ ppm: 9.30 (s, 1H), 8.02-7.94 (m, 1H), 7.79 (s, 1H), 7.47(t, J = 9.0 Hz, 1H), 7.38 (d, J = 2.5 Hz, 1H), 7.34-7.27 (m, 1H), 7.06 (d, J = 2.8 Hz, 1H), 5.27-5.02 (m, 1H), 4.35-4.15 (m, 4H), 3.60-3.51 (m, 3H), 3.44-3.40 (m, 2H), 2.86-2.73 (m, 2H), 2.64-2.54 (m, 2H), 2.40-2.32 (m, 2H), 2.15-2.02 (m, 1H), 1.89-1.74 (m, 1H), 1.71-1.57 (m, 4H), 0.62 (br s, 2H), 0.43 (br s, 2H). |
| 18-16 | 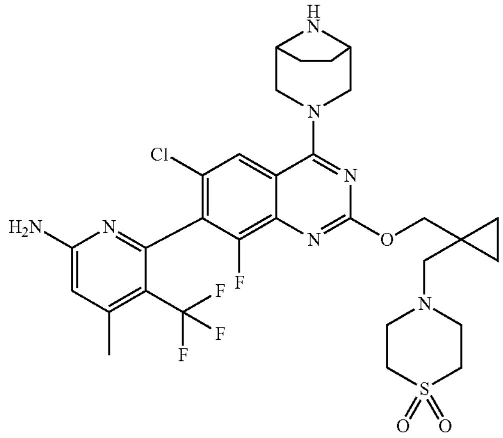 [SMILES: Cc1cc(N)nc(-c2c(Cl)cc3c(N4CC5CCC(C4)N5)nc(OCC4(CN5CCS(=O)(=O)CC5)CC4)nc3c2F)c1C(F)(F)F] | 4-({1-[{{7-[6-amino-4-methyl-3-(trifluoromethyl)pyridin-2-yl]-6-chloro-4-{3,8-diazabicyclo[3.2.1]octan-3-yl}-8-fluoroquinazolin-2-yl}oxy)methyl]cyclopropyl}methyl)-1lambda6-thiomorpholine-1,1-dione | 684.2 | $^1$H NMR (400 MHz, DMSO-$d_6$) δ ppm: 7.82 (s, 1H), 6.82 (s, 2H), 6.49 (s, 1H), 4.42-4.32 (m, 1H), 4.29-4.20 (m, 3H), 3.84-3.74 (m, 2H), 3.61 (br d, J = 13.3 Hz, 1H), 3.56-3.49 (m, 1H), 3.48-3.40 (m, 1H), 3.21-3.13 (m, 1H), 3.08-3.01 (m, 4H), 3.00-2.90 (m, 4H), 2.53-2.52 (m, 1H), 2.39-2.35 (m, 3H), 1.85-1.68 (m, 4H), 0.69-0.61 (m, 2H), 0.49-0.41 (m, 2H). |

TABLE 7-continued

| Example Name | Structure | Name | LCMS $(M + H)^+$ | $^1H$ NMR |
|---|---|---|---|---|
| 18-17 | 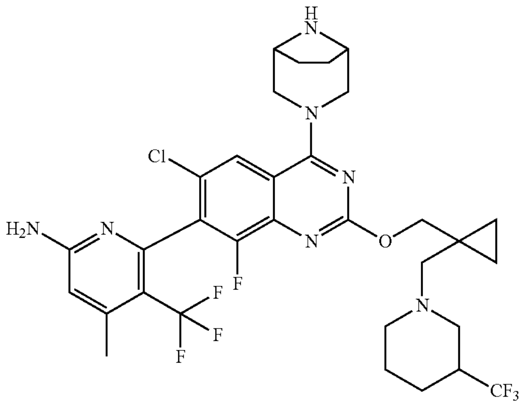 [SMILES: Cc1cc(N)nc(-c2c(Cl)cc3c(N4CC5CCC(C4)N5)nc(OCC4(CN5CCCC(C(F)(F)F)C5)CC4)nc3c2F)c1C(F)(F)F] | 6-(6-chloro-4-{3,8-diazabicyclo[3.2.1]octan-3-yl}-8-fluoro-2-[(1-{[3-(trifluoromethyl)piperidin-1-yl]methyl}cyclopropyl)methoxy]quinazolin-7-yl)-4-methyl-5-(trifluoromethyl)pyridin-2-amine | 702.4 | $^1H$ NMR (400 MHz, DMSO-$d_6$) δ ppm: 7.80 (s, 1H), 6.82 (s, 2H), 6.49 (s, 1H), 4.39-4.28 (m, 2H), 4.20-4.09 (m, 2H), 4.05-3.96 (m, 1H), 3.67-3.44 (m, 6H), 3.09-2.99 (m, 1H), 2.95-2.86 (m, 1H), 2.45-2.42 (m, 1H), 2.37 (br d, J = 1.3 Hz, 3H), 2.35-2.34 (m, 2H), 1.88-1.75 (m, 3H), 1.72-1.57 (m, 5H), 0.70-0.59 (m, 2H), 0.46-0.35 (m, 2H). |
| 18-18 | 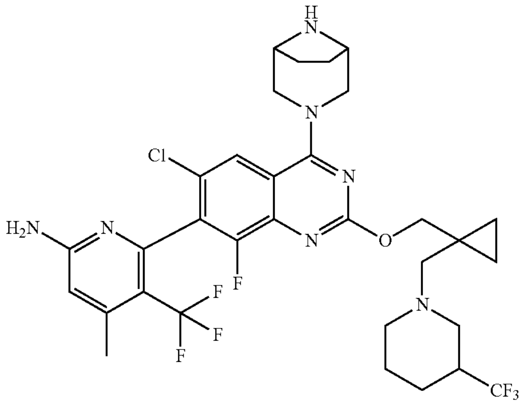 [SMILES: Cc1cc(N)nc(-c2c(Cl)cc3c(N4CC5CCC(C4)N5)nc(OCC4(CN5CCCC(C(F)(F)F)C5)CC4)nc3c2F)c1C(F)(F)F] | 6-(6-chloro-4-{3,8-diazabicyclo[3.2.1]octan-3-yl}-8-fluoro-2-[(1-{[3-(trifluoromethyl)piperidin-1-yl]methyl}cyclopropyl)methoxy]quinazolin-7-yl)-4-methyl-5-(trifluoromethyl)pyridin-2-amine | 702.4 | $^1H$ NMR (400 MHz, DMSO-$d_6$) δ ppm: 7.79 (d, J = 1.0 Hz, 1H), 6.82 (s, 2H), 6.49 (s, 1H), 4.35-4.12 (m, 5H), 3.56-3.42 (m, 6H), 3.14-3.06 (m, 1H), 2.89-2.82 (m, 1H), 2.43-2.39 (m, 2H), 2.37-2.35 (m, 3H), 2.30-2.25 (m, 1H), 1.87-1.76 (m, 3H), 1.62 (br d, J = 8.4 Hz, 3H), 1.66-1.56 (m, 2H), 0.69-0.61 (m, 2H), 0.44-0.37 (m, 2H). |
| 18-19 | 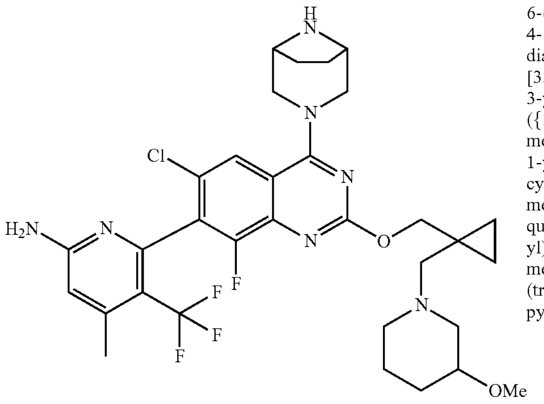 | 6-(6-chloro-4-{3,8-diazabicyclo[3.2.1]octan-3-yl}-8-fluoro-2-({1-[(3-methoxypiperidin-1-yl)methyl]cyclopropyl}methoxy)quinazolin-7-yl)-4-methyl-5-(trifluoromethyl)pyridin-2-amine | 664.5 | $^1H$ NMR (400 MHz, DMSO-$d_6$) δ ppm: 7.79 (s, 1H), 6.83 (s, 2H), 6.49 (s, 1H), 4.34-4.12 (m, 4H), 3.56-3.44 (m, 5H), 3.17 (br s, 4H), 3.14-3.07 (m, 2H), 3.02-2.95 (m, 1H), 2.39-2.35 (m, 4H), 2.31-2.27 (m, 2H), 1.64-1.57 (m, 4H), 1.06-0.98 (m, 4H), 0.67-0.58 (m, 2H), 0.43-0.35 (m, 2H) |

TABLE 7-continued

| Example Name | Structure | Name | LCMS (M + H)+ | 1H NMR |
|---|---|---|---|---|
| 18-20 | 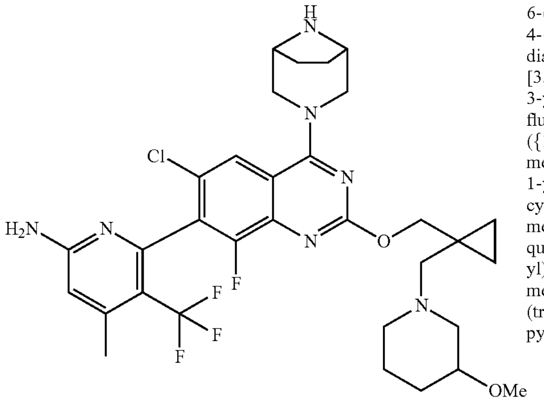 | 6-(6-chloro-4-{3,8-diazabicyclo[3.2.1]octan-3-yl}-8-fluoro-2-({1-[(3-methoxypiperidin-1-yl)methyl]cyclopropyl}methoxy)quinazolin-7-yl)-4-methyl-5-(trifluoromethyl)pyridin-2-amine | 664.5 | $^1$H NMR (400 MHz, DMSO-$d_6$) δ ppm: 7.79 (s, 1H), 6.83 (s, 2H), 6.49 (s, 1H), 4.33-4.25 (m, 2H), 4.22-4.12 (m, 2H), 3.55-3.41 (m, 6H), 3.18-3.16 (m, 4H), 3.10-3.04 (m, 1H), 2.98-2.94 (m, 1H), 2.38-2.34 (m, 4H), 2.30-2.24 (m, 2H), 1.87-1.83 (m, 1H), 1.61 (br d, J = 2.1 Hz, 3H), 1.26-1.21 (m, 1H), 1.17-1.14 (m, 1H), 1.11-1.04 (m, 2H), 0.66-0.57 (m, 2H), 0.42-0.33 (m, 2H). |
| 18-21 | 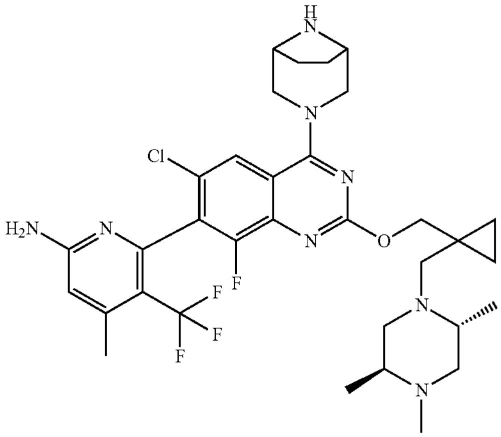 [SMILES: Cc1cc(N)nc(-c2c(Cl)cc3c(N4CC5CCC(C4)N5)nc(OCC4(CN5C[C@H](C)N(C)C[C@H]5C)CC4)nc3c2F)c1C(F)(F)F] | 6-(6-chloro-4-{3,8-diazabicyclo[3.2.1]octan-3-yl}-8-fluoro-2-[(1-{[(2R,5S)-2,4,5-trimethylpiperazin-1-yl]methyl}cyclopropyl)methoxy]quinazolin-7-yl)-4-methyl-5-(trifluoromethyl)pyridin-2-amine | 677.3 | $^1$H NMR (400 MHz, DMSO-$d_6$) δ ppm: 7.88-7.81 (m, 1H), 6.89 (br s, 2H), 6.49 (br s, 1H), 4.47-4.37 (m, 2H), 4.21-4.13 (m, 5H), 3.73-3.70 (m, 2H), 3.46-3.41 (m, 2H), 3.36-3.32 (m, 3H), 3.23-3.18 (m, 1H), 2.73-2.70 (m, 3H), 2.37-2.34 (m, 5H), 1.26-1.20 (m, 6H), 1.17-1.13 (m, 1H), 1.10-0.95 (m, 3H), 0.66-0.55 (m, 2H), 0.47-0.27 (m, 2H). |
| 18-22 | 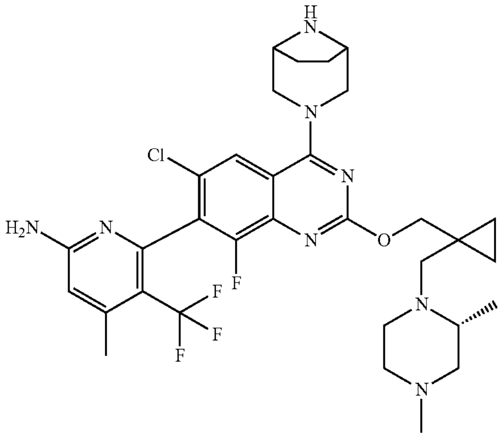 [SMILES: Cc1cc(N)nc(-c2c(Cl)cc3c(N4CC5CCC(C4)N5)nc(OCC4(CN5CCN(C)C[C@H]5C)CC4)nc3c2F)c1C(F)(F)F] | 6-(6-chloro-4-{3,8-diazabicyclo[3.2.1]octan-3-yl}-2-[(1-{[(2R)-2,4-dimethylpiperazin-1-yl]methyl}cyclopropyl)methoxy]-8-fluoroquinazolin-7-yl)-4-methyl-5-(trifluoromethyl)pyridin-2-amine | 663.3 | $^1$H NMR (400 MHz, DMSO-$d_6$) δ ppm: 7.78 (s, 1H), 6.82 (s, 2H), 6.49 (s, 1H), 4.57 (br d, J = 10.5 Hz, 1H), 4.28 (br d, J = 12.0 Hz, 1H), 4.19 (br d, J = 11.3 Hz, 1H), 3.88 (br d, J = 10.8 Hz, 1H), 3.54-3.42 (m, 5H), 3.23-3.13 (m, 1H), 3.00-2.90 (m, 1H), 2.54 (s, 3H), 2.53-2.51 (m, 1H), 2.48-2.43 (m, 1H), 2.42-2.33 (m, 5H), 2.31-2.22 (m, 1H), 2.14-2.06 (m, 2H), 1.64-1.57 (m, 4H), 0.85 (d, J = 6.3 Hz, 3H), 0.68-0.60 (m, 1H), 0.57-0.50 (m, 1H), 0.46 (s, 1H), 0.34-0.27 (m, 1H). |

TABLE 7-continued

| Example Name | Structure | Name | LCMS (M + H)$^+$ | $^1$H NMR |
|---|---|---|---|---|
| 18-23 | 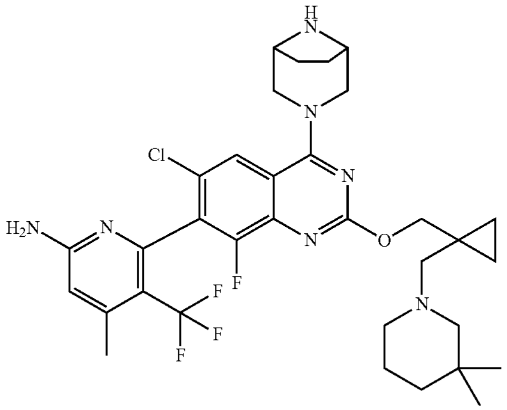 [SMILES: Cc1cc(N)nc(-c2c(Cl)cc3c(N4CC5CCC(C4)N5)nc(OCC4(CN5CCCC(C)(C)C5)CC4)nc3c2F)c1C(F)(F)F] | 6-(6-chloro-4-{3,8-diazabicyclo[3.2.1]octan-3-yl}-2-({1-[(3,3-dimethylpiperidin-1-yl)methyl]cyclopropyl}methoxy)-8-fluoroquinazolin-7-yl)-4-methyl-5-(trifluoromethyl)pyridin-2-amine | 662.3 | $^1$H NMR (400 MHz, DMSO-$d_6$) δ ppm: 7.80-7.77 (m, 1H), 6.82 (s, 2H), 6.49 (s, 1H), 4.36-4.27 (m, 3H), 4.25-4.21 (m, 1H), 4.18-4.14 (m, 1H), 3.58-3.47 (m, 4H), 3.46-3.41 (m, 1H), 2.38-2.35 (m, 1H), 2.40-2.35 (m, 2H), 2.32-2.20 (m, 4H), 1.67-1.56 (m, 4H), 1.48-1.41 (m, 2H), 1.16-1.10 (m, 2H), 0.82 (s, 6H), 0.64-0.58 (m, 2H), 0.40-0.33 (m, 2H). |

Example 19-1

6-(2-{[(4aS,7aR)-1-methyl-octahydro-1H-cyclopenta[b]pyridin-4a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine 19-1

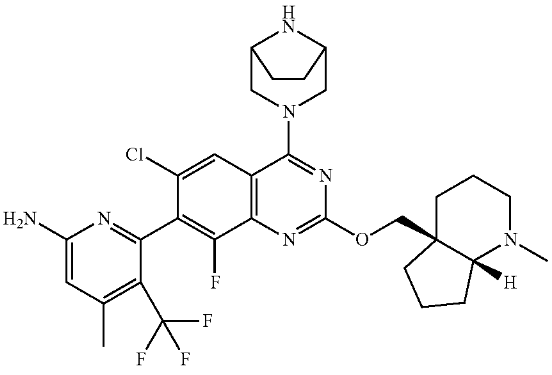

Preparation of Intermediate 19A: ethyl octahydro-4aH-cyclopenta[b]pyridine-4a-carboxylate

19A

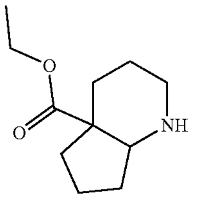

Intermediate 19A was prepared according to the procedure in Molecules 2017, 22:827, compound 25a.

Preparation of Intermediate 19B1, 19B2, 19B3, 19B4:1-benzyl 4a-ethyl (4aS,7aR)-hexahydro-1H-cyclopenta[b]pyridine-1,4a(2H)-dicarboxylate (peak 2)

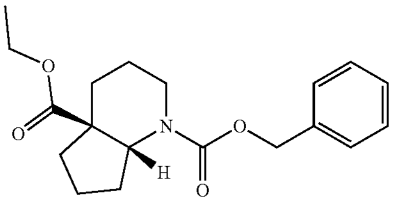

19B1, 19B2, 29B4, 19B4

To a solution of ethyl octahydro-4aH-cyclopenta[b]pyridine-4a-carboxylate (1.7 g, 8.62 mmol) and TEA (2.402 mL, 17.23 mmol) in THE (10 mL) was added N-(benzyloxycarbonyl)succinimide (1.718 g, 6.89 mmol) and the mixture was stirred at room temperature for 18 hours. The mixture was diluted with EtOAc (15 mL) and was washed with a solution of aqueous saturated sodium bicarbonate (2×15 mL). The ethyl acetate layer was dried over sodium sulfate, filtered and concentrated. The crude product was subjected to ISCO flash chromatography (silica gel/DCM-20% MeOH/DCM 100:0 to 50:50 gradient) to yield 1-benzyl 4a-ethyl hexahydro-1H-cyclopenta[b]pyridine-1,4a(2H)-dicarboxylate (2.20 g, 6.64 mmol, 77% yield). 1-Benzyl 4a-ethyl hexahydro-1H-cyclopenta[b]pyridine-1,4a(2H)-dicarboxylate (2.20 g) was subjected to SFC chiral separation. [column: Cellulose-4 (5×25 cm, 5 μm) method=$CO_2$/IPA: heptane (1:3) with 0.1% ammonia hydroxide. 320 mL/min.] to afford:

Peak 1 (19B1): 1-benzyl 4a-ethyl hexahydro-1H-cyclopenta[b]pyridine-1,4a(2H)-dicarboxylate (625 mg, 1.792 mmol, 20.79% yield). LCMS (ESI) m/z: 332.3 [M+H]$^+$ LC retention time: 1.05 min (Waters Acquity UPLC BEH C18, 2.1×50 mm, 1.7 □m particles; Mobile Phase A: water with 0.05% TFA; Mobile Phase B: ACN with 0.05% TFA; Gradient: 2-98% B over 1 minute, then a 0.5 minute hold at 98% B; Flow: 0.8 mL/min; Detection: MS and UV (220 nm).). $^1$H NMR (499 MHz, CHLOROFORM-d) δ 7.41-7.28

(m, 5H), 5.17 (br s, 2H), 4.13 (br d, J=6.4 Hz, 2H), 2.86 (br s, 1H), 2.15 (br d, J=10.8 Hz, 1H), 2.03-1.90 (m, 1H), 1.90-1.74 (m, 4H), 1.73-1.63 (m, 1H), 1.58-1.42 (m, 3H), 1.27-1.14 (m, 4H), 0.98-0.68 (m, 1H).

Peak 2 (19B2): 1-benzyl 4a-ethyl (4aS,7aR)-hexahydro-1H-cyclopenta[b]pyridine-1,4a(2H)-dicarboxylate (640 mg, 1.835 mmol, 21.29% yield). LCMS (ESI) m/z: 332.3 $[M+H]^+$ LC retention time: 1.05 min (Waters Acquity UPLC BEH C18, 2.1×50 mm, 1.7 □m particles; Mobile Phase A: water with 0.05% TFA; Mobile Phase B: ACN with 0.05% TFA; Gradient: 2-98% B over 1 minute, then a 0.5 minute hold at 98% B; Flow: 0.8 mL/min; Detection: MS and UV (220 nm).). $^1$H NMR (499 MHz, CHLOROFORM-d) δ 7.41-7.28 (m, 5H), 5.17 (br s, 2H), 4.13 (br d, J=6.4 Hz, 2H), 2.86 (br s, 1H), 2.15 (br d, J=10.8 Hz, 1H), 2.03-1.90 (m, 1H), 1.90-1.74 (m, 4H), 1.73-1.63 (m, 1H), 1.58-1.42 (m, 3H), 1.27-1.14 (m, 4H), 0.98-0.68 (m, 1H)

Peak 3 (19B3): 1-benzyl 4a-ethyl hexahydro-1H-cyclopenta[b]pyridine-1,4a(2H)-dicarboxylate (130 mg, 0.373 mmol, 4.32% yield). LCMS (ESI) m/z: 332.3 $[M+H]^+$ LC retention time: 1.05 min (Waters Acquity UPLC BEH C18, 2.1×50 mm, 1.7 □m particles; Mobile Phase A: water with 0.05% TFA; Mobile Phase B: ACN with 0.05% TFA; Gradient: 2-98% B over 1 minute, then a 0.5 minute hold at 98% B; Flow: 0.8 mL/min; Detection: MS and UV (220 nm).). $^1$H NMR (499 MHz, CHLOROFORM-d) δ 7.40-7.28 (m, 5H), 5.18-5.10 (m, 2H), 4.38 (ddd, J=13.4, 2.5, 1.4 Hz, 1H), 4.13-4.05 (m, 2H), 2.88 (dd, J=12.8, 7.0 Hz, 1H), 2.79-2.67 (m, 2H), 2.42 (dt, J=13.1, 2.7 Hz, 1H), 2.28-2.14 (m, 2H), 1.76-1.55 (m, 4H), 1.46-1.26 (m, 2H), 1.20 (t, J=7.2 Hz, 3H).

Peak 4 (19B4): 1-benzyl 4a-ethyl hexahydro-1H-cyclopenta[b]pyridine-1,4a(2H)-dicarboxylate (141 mg, 0.404 mmol, 4.69% yield). LCMS (ESI) m/z: 332.3 $[M+H]^+$ LC retention time: 1.05 min (Waters Acquity UPLC BEH C18, 2.1×50 mm, 1.7 □m particles; Mobile Phase A: water with 0.05% TFA; Mobile Phase B: ACN with 0.05% TFA; Gradient: 2-98% B over 1 minute, then a 0.5 minute hold at 98% B; Flow: 0.8 mL/min; Detection: MS and UV (220 nm).). $^1$H NMR (499 MHz, CHLOROFORM-d) δ 7.40-7.28 (m, 5H), 5.18-5.10 (m, 2H), 4.38 (ddd, J=13.4, 2.5, 1.4 Hz, 1H), 4.13-4.05 (m, 2H), 2.88 (dd, J=12.8, 7.0 Hz, 1H), 2.79-2.67 (m, 2H), 2.42 (dt, J=13.1, 2.7 Hz, 1H), 2.28-2.14 (m, 2H), 1.76-1.55 (m, 4H), 1.46-1.26 (m, 2H), 1.20 (t, J=7.2 Hz, 3H).

Preparation of Intermediate 19C—: ethyl (4aS,7aR)-octahydro-4aH-cyclopenta[b]pyridine-4a-carboxylate

19C

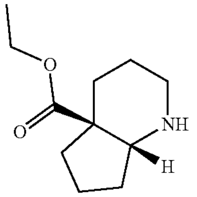

A mixture of 1-benzyl 4a-ethyl (4aS,7aR)-hexahydro-1H-cyclopenta[b]pyridine-1,4a(2H)-dicarboxylate-Intermediate 19B2 (640 mg, 1.931 mmol) and 10% Pd—C(103 mg, 0.097 mmol) in MeOH (10 mL) was hydrogenated under 1 atm of hydrogen for 18 hours. The Pd/C was filtered off and the filtrate was concentrated to provide crude ethyl (4aS,7aR)-octahydro-4aH-cyclopenta[b]pyridine-4a-carboxylate (385 mg, 1.854 mmol, 96% yield) as a clear oil. $^1$H NMR (499 MHz, CHLOROFORM-d) δ 4.17 (dtt, J=10.6, 7.1, 3.6 Hz, 2H), 3.57 (t, J=6.1 Hz, 1H), 2.90 (ddd, J=13.0, 7.7, 3.7 Hz, 1H), 2.71 (ddd, J=13.0, 7.0, 3.6 Hz, 1H), 2.01-1.92 (m, 2H), 1.84-1.62 (m, 7H), 1.60-1.40 (m, 2H), 1.28 (t, J=7.1 Hz, 3H).

Preparation of Intermediate 19D: ethyl (4aS,7aR)-1-methyloctahydro-4aH-cyclopenta[b]pyridine-4a-carboxylate

19D

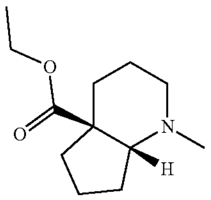

To a solution of ethyl (4aS,7aR)-octahydro-4aH-cyclopenta[b]pyridine-4a-carboxylate (385 mg, 1.952 mmol) and formaldehyde solution, 37 wt. % in $H_2O$ (176 mg, 5.85 mmol) in MeOH (5.0 mL) was added sodium cyanoborohydride (123 mg, 1.952 mmol) and the mixture was stirred at room temperature for 18 hours. The mixture was then concentrated. The mixture was diluted with EtOAc (5 mL) and was washed with a solution of aqueous saturated sodium carbonate (2×5 mL). The ethyl acetate layer was dried over sodium sulfate, filtered and concentrated to afford crude ethyl (4aS,7aR)-1-methyloctahydro-4aH-cyclopenta[b]pyridine-4a-carboxylate (380 mg, 1.798 mmol, 92% yield). $^1$H NMR (499 MHz, CHLOROFORM-d) δ 4.24-4.12 (m, 2H), 3.29 (t, J=6.4 Hz, 1H), 2.60-2.51 (m, 1H), 2.36-2.28 (m, 3H), 2.00-1.88 (m, 2H), 1.83-1.60 (m, 8H), 1.56-1.40 (m, 1H), 1.32-1.26 (m, 3H).

Preparation of Intermediate 19E: ((4aS,7aR)-1-methyloctahydro-4aH-cyclopenta[b]pyridin-4a-yl) methanol

19E

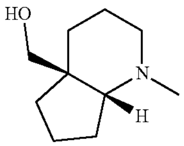

To a solution of ethyl (4aS,7aR)-1-methyloctahydro-4aH-cyclopenta[b]pyridine-4a-carboxylate (380 mg, 1.798 mmol) in anhydrous THE (2.0 mL) was added a solution of lithium aluminum hydride solution 1.0 M in THE (4496 µl, 4.50 mmol) and the mixture was stirred at room temperature for 18 hours. Brine (0.3 mL) was added dropwise to the mixture. EtOAc (5.0 mL) was added to the mixture. The precipitate was filtered off and the filtrate was concentrated to afford crude ((4aS,7aR)-1-methyloctahydro-4aH-cyclopenta[b]pyridin-4a-yl)methanol (327 mg, 1.739 mmol, 97% yield). $^1$H NMR (499 MHz, CHLOROFORM-d) δ 3.69-3.62 (m, 2H), 2.87 (t, J=7.6 Hz, 1H), 2.51 (td, J=11.1, 3.4 Hz, 1H), 2.43-2.35 (m, 1H), 2.30 (s, 3H), 2.01-1.85 (m, 2H), 1.82-1.74 (m, 1H), 1.68-1.52 (m, 6H), 1.47-1.42 (m, 1H), 1.39-1.33 (m, 1H).

Example 19-1

6-(2-{[(4aS,7aR)-1-methyl-octahydro-1H-cyclopenta[b]pyridin-4a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine 19-1

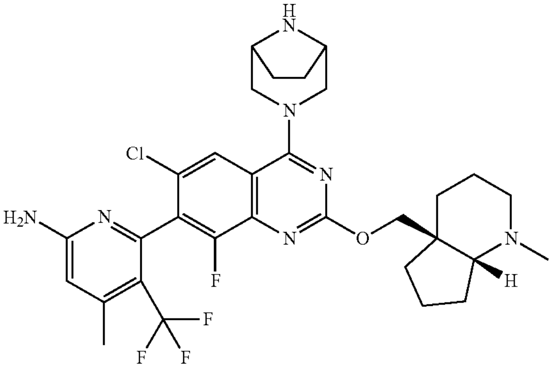

To a solution of tert-butyl 3-(7-(6-(bis(4-methoxybenzyl)amino)-4-methyl-3-(trifluoromethyl)pyridin-2-yl)-6-chloro-2,8-difluoroquinazolin-4-yl)-3,8-diazabicyclo[3.2.1]octane-8-carboxylate (Intermediate 141, 20 mg, 0.024 mmol) and ((4aS,7aR)-1-methyloctahydro-4aH-cyclopenta[b]pyridin-4a-yl)methanol (Intermediate 19E, 4.10 mg, 0.024 mmol) in anhydrous THE (1.0 mL) at room temperature under nitrogen was added a solution of 1.0 M LiHMDS in THE (36.4 μl, 0.036 mmol) and the mixture was stirred for 18 hours. The mixture was then diluted with DMF (1 mL) and the crude product was purified by prep-HPLC (Phenomenex, Luna 5 micron 30×250 mm, flow rate=30 mL/min., gradient=20% A to 100% B in 30 min., A=H2O/ACN/TFA(90:10:0.1), B=H2O/ACN/TFA(10:90:0.1)) to provide tert-butyl 3-(7-(6-(bis(4-methoxybenzyl)amino)-4-methyl-3-(trifluoromethyl)pyridin-2-yl)-6-chloro-8-fluoro-2-(((4aS,7aR)-1-methyloctahydro-4aH-cyclopenta[b]pyridin-4a-yl)methoxy)quinazolin-4-yl)-3,8-diazabicyclo[3.2.1]octane-8-carboxylate. A mixture of tert-butyl 3-(7-(6-(bis(4-methoxybenzyl)amino)-4-methyl-3-(trifluoromethyl)pyridin-2-yl)-6-chloro-8-fluoro-2-(((4aS,7aR)-1-methyloctahydro-4aH-cyclopenta[b]pyridin-4a-yl)methoxy)quinazolin-4-yl)-3,8-diazabicyclo[3.2.1]octane-8-carboxylate, water (1 drop), triethylsilane (1 drop) and TFA (1.5 mL) was stirred at 40° C. for 18 hours. The mixture was concentrated. The crude product was purified by prep-HPLC (Phenomenex, Luna 5 micron 30×250 mm, flow rate=30 mL/min., gradient=20% A to 100% B in 30 min., A=H2O/ACN/TFA(90:10:0.1), B=H2O/ACN/TFA(10:90:0.1)). The pure fractions were loaded onto an Oasis MCX cation mixed-mode polymer cartridge (150 mg), the cartridge was washed with methanol (30 mL) and the product was eluted with 0.1 N ammonia in methanol (5.0 mL). The ammonia eluent was concentrated. The pure product was lyopholized with ACN/$H_2O$ (1:1, 5 mL) to yield 6-(2-{[(4aS,7aR)-1-methyl-octahydro-1H-cyclopenta[b]pyridin-4a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine (8.67 mg, 0.013 mmol, 53.6% yield) as a white powder. LCMS (ESI) m/z: 635 $[M+H]^+$ LC retention time: 0.74 min (Waters Acquity UPLC BEH C18, 2.1×50 mm, 1.7 □m particles; Mobile Phase A: water with 0.05% TFA; Mobile Phase B: ACN with 0.05% TFA; Gradient: 2-98% B over 1 minute, then a 0.5 minute hold at 98% B; Flow: 0.8 mL/min; Detection: MS and UV (220 nm).). $^1H$ NMR (499 MHz, METHANOL-$d_4$) δ 7.85 (d, J=1.5 Hz, 1H), 6.62 (s, 1H), 4.55-4.43 (m, 3H), 4.24 (d, J=10.7 Hz, 1H), 3.69-3.58 (m, 4H), 2.89 (br d, J=4.9 Hz, 1H), 2.71-2.63 (m, 1H), 2.47 (d, J=1.3 Hz, 3H), 2.43-2.37 (m, 1H), 2.33 (s, 3H), 2.01-1.88 (m, 1H), 1.88-1.67 (m, 12H), 1.63-1.52 (m, 1H).

Compounds found in Table 8 may be prepared from Intermediate 19B according to the procedures found in Example 19-1.

TABLE 8

| Example Number | Structure | Name | MS m/z: [M + H]+ | $^1H$ NMR |
|---|---|---|---|---|
| 19-2 From-intermediate 19B1 | 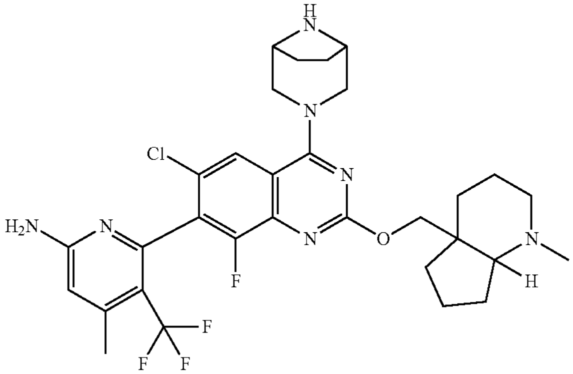 [SMILES: Cc1cc(N)nc(-c2c(Cl)cc3c(N4CC5CCC(C4)N5)nc(OCC45CCCC4N(C)CCC5)nc3c2F)c1C(F)(F)F] | 6-(6-chloro-4-{3,8-diazabicyclo[3.2.1]octan-3-yl}-8-fluoro-2-({1-methyl-octahydro-1H-cyclopenta[b]pyridin-4a-yl}methoxy)quinazolin-7-yl)-4-methyl-5-(trifluoromethyl)pyridin-2-amine | 635 | $^1H$ NMR (499 MHz, METHANOL-$d_4$) δ 7.85 (d, J = 1.5 Hz, 1H), 6.62 (s, 1H), 4.54-4.43 (m, 3H), 4.24 (d, J = 10.7 Hz, 1H), 3.67-3.59 (m, 4H), 2.90 (br s, 1H), 2.68 (br t, J = 7.7 Hz, 1H), 2.47 (d, J = 1.2 Hz, 3H), 2.44-2.38 (m, 1H), 2.34 (s, 3H), 2.00-1.91 |

TABLE 8-continued

| Example Number | Structure | Name | MS m/z: [M + H]+ | $^1$H NMR |
|---|---|---|---|---|
| | | | | (m, 1H), 1.88-1.67 (m, 12H), 1.63-1.51 (m, 1H) |
| 19-3 From-intermediate 19B3 | 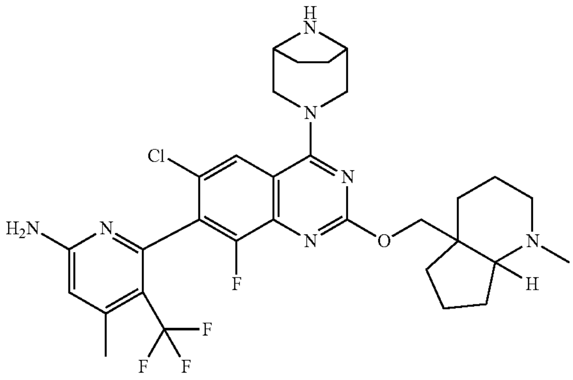 [SMILES: Cc1cc(N)nc(-c2c(Cl)cc3c(N4CC5CCC(C4)N5)nc(OCC45CCCC4N(C)CCC5)nc3c2F)c1C(F)(F)F] | 6-(6-chloro-4-{3,8-diazabicyclo[3.2.1]octan-3-yl}-8-fluoro-2-({1-methyl-octahydro-1H-cyclopenta[b]pyridin-4a-yl}methoxy)quinazolin-7-yl)-4-methyl-5-(trifluoromethyl)pyridin-2-amine | 635 | $^1$H NMR (499 MHz, METHANOL-$d_4$) δ 7.84 (d, J = 1.5 Hz, 1H), 6.62 (s, 1H), 4.82-4.76 (m, 1H), 4.53 (br d, J = 12.5 Hz, 1H), 4.47 (br d, J = 11.8 Hz, 1H), 4.23 (d, J = 11.8 Hz, 1H), 3.70-3.55 (m, 4H), 3.37-3.34 (m, 1H), 3.00 (br d, J = 8.9 Hz, 1H), 2.47 (d, J = 1.3 Hz, 3H), 2.37-2.26 (m, 1H), 2.22 (s, 2H), 2.15 (ddd, J = 12.6, 8.9, 1.8 Hz, 1H), 2.04-1.70 (m, 10H), 1.64-1.53 (m, 2H), 1.25 (br d, J = 9.5 Hz, 1H), 1.15-1.06 (m, 1H) |
| 19-4 From-intermediate 19B4 | 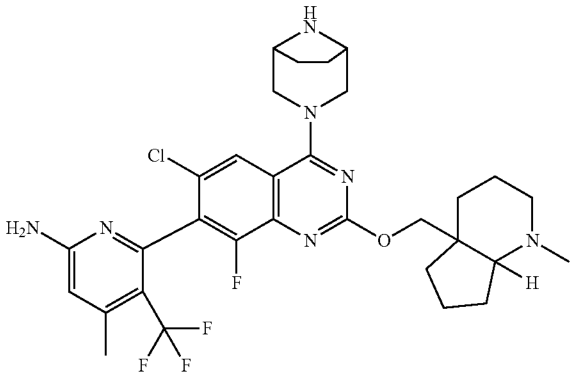 [SMILES: Cc1cc(N)nc(-c2c(Cl)cc3c(N4CC5CCC(C4)N5)nc(OCC45CCCC4N(C)CCC5)nc3c2F)c1C(F)(F)F] | 6-(6-chloro-4-{3,8-diazabicyclo[3.2.1]octan-3-yl}-8-fluoro-2-({1-methyl-octahydro-1H-cyclopenta[b]pyridin-4a-yl}methoxy)quinazolin-7-yl)-4-methyl-5-(trifluoromethyl)pyridin-2-amine | 635 | $^1$H NMR (499 MHz, METHANOL-$d_4$) δ 7.84 (s, 1H), 6.62 (s, 1H), 4.82-4.74 (m, 1H), 4.50 (br t, J = 11.1 Hz, 2H), 4.25 (d, J = 11.2 Hz, 1H), 3.69-3.57 (m, 4H), 3.48-3.34 (m, 1H), 3.03-2.98 (m, 1H), 2.47 (d, J = 1.3 Hz, 3H), 2.37-2.26 (m, 1H), 2.22 (s, 2H), 2.15 (ddd, J = 12.6, 9.0, 1.8 Hz, 1H), 2.01-1.80 (m, 8H), 1.77 (br dd, J = 8.5, 1.7 Hz, 1H), 1.63-1.53 (m, 2H), 1.25 (br d, J = 9.7 Hz, 1H), 1.15-1.07 (m, 1H) |

Example 20-1

4-(6-chloro-4-{3,8-diazabicyclo[3.2.1]octan-3-yl}-8-fluoro-2-({1-methyl-octahydro-1H-cyclopenta[b]pyridin-4a-yl}methoxy)quinazolin-7-yl)naphthalen-2-ol 20-1

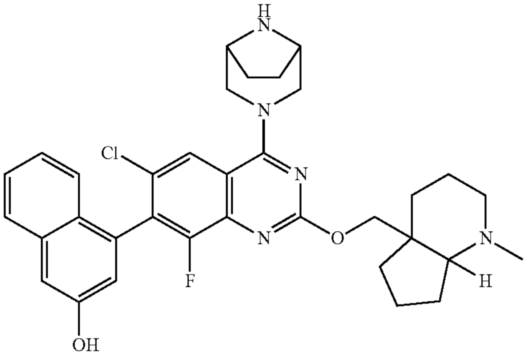

Preparation of intermediate 20A (Isomer 1) and 20B (Isomer 2): tert-butyl-3-(6-chloro-2,8-difluoro-7-(3-(methoxymethoxy)naphthalen-1-yl)quinazolin-4-yl)-3,8-diazabicyclo[3.2.1]octane-8-carboxylate

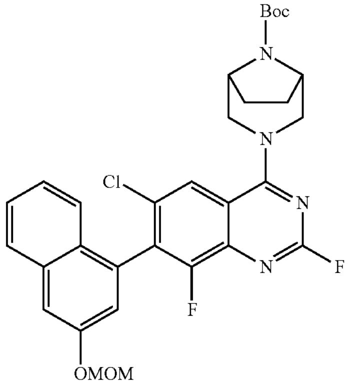

20A (Isomer 1)
20B (Isomer 2)

Intermediate 16A was subjected to SFC purification to separate the atropisomers (Column: Chiralpak ADH (250 mm×4.6×5p), mobile phase-30% Isopropanol), where Peak-1(Intermediate 20A) eluted at 2.72 min. (230 mg, 46%); LCMS (ESI) m/z: 597.2 $[M+H]^+$ and Peak-2 (Intermediate 20B) eluted at 5.47 min. (205 mg, 41%); LCMS (ESI) m/z: 597.2 $[M+H]^+$.

Example 20-1

4-(6-chloro-4-{3,8-diazabicyclo[3.2.1]octan-3-yl}-8-fluoro-2-({1-methyl-octahydro-1H-cyclopenta[b]pyridin-4a-yl}methoxy)quinazolin-7-yl)naphthalen-2-ol 20-1

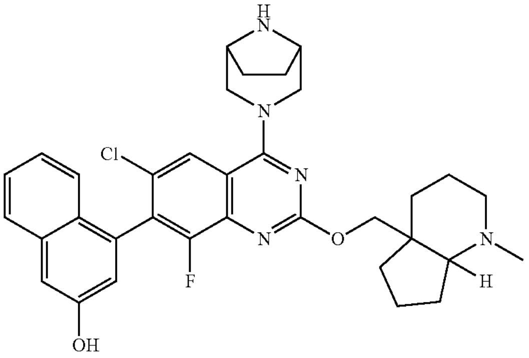

To a solution of tert-butyl 3-(6-chloro-2,8-difluoro-7-(3-(methoxymethoxy)naphthalen-1-yl)quinazolin-4-yl)-3,8-diazabicyclo[3.2.1]octane-8-carboxylate (Intermediate 20A, 20 mg, 0.033 mmol) and ((4aR,7aS)-1-methyloctahydro-4aH-cyclopenta[b]pyridin-4a-yl)methanol (Intermediate 19B1, 5.67 mg, 0.033 mmol) in anhydrous THE (1.0 mL) at room temperature under nitrogen was added a solution of 1.0 M LiHMDS in THE (50.2 µl, 0.050 mmol) and the mixture was stirred for 18 hours. The mixture was then diluted with DMF (1 mL) and the crude product was purified by prep-HPLC (Phenomenex, Luna 5 micron 30×250 mm, flow rate=30 mL/min., gradient=20% A to 100% B in 30 min., A=H2O/ACN/TFA(90:10:0.1), B=H2O/ACN/TFA(10:90:0.1)) to afford the desired product. A mixture of the compound prepared above, water (1 drop), triethylsilane (1 drop) and TFA (1.5 mL) was stirred at room temperature for 1 hour. The crude product was purified by prep-HPLC (Phenomenex, Luna 5 micron 30×250 mm, flow rate=30 mL/min., gradient=20% A to 100% B in 30 min., A=H2O/ACN/TFA(90:10:0.1), B=H2O/ACN/TFA(10:90:0.1)). The pure fractions were loaded onto an Oasis MCX cation mixed-mode polymer cartridge (150 mg), the cartridge was washed with methanol (30 mL) and the product was eluted with 0.1 N ammonia in methanol (5.0 mL). The ammonia eluent was concentrated. The pure product was lyopholized from ACN/$H_2O$ (1:1, 5 mL) to yield 4-(6-chloro-4-{3,8-diazabicyclo[3.2.1]octan-3-yl}-8-fluoro-2-({1-methyl-octahydro-1H-cyclopenta[b]pyridin-4a-yl}methoxy)quinazolin-7-yl)naphthalen-2-ol (3.33 mg, 5.25 µmol, 15.68% yield) as a white powder. LCMS (ESI) m/z: 603 $[M+H]^+$ LC retention time: 0.75 min (Waters Acquity UPLC BEH C18, 2.1×50 mm, 1.7 µm particles; Mobile Phase A: water with 0.05% TFA; Mobile Phase B: ACN with 0.05% TFA; Gradient: 2-98% B over 1 minute, then a 0.5 minute hold at 98% B; Flow: 0.8 mL/min; Detection: MS and UV (220 nm).). $^1H$ NMR (499 MHz, METHANOL-$d_4$) δ 7.97 (d, J=1.5 Hz, 1H), 7.77 (d, J=8.3 Hz, 1H), 7.43 (ddd, J=8.2, 6.6, 1.4 Hz, 111), 7.31-7.20 (in, 311), 7.05 (d, J=2.4 Hz, 111), 4.58-4.49 (in, 311), 4.30 (br d, J=11.0 Hz, 111), 3.72-3.63 (in, 411), 3.08-2.32 (in, 511), 2.04-1.56 (in, 1411), 0.12 (s, 111).

Compounds in Table 9 were prepared according to the procedures given for Example 20-1 and the corresponding Intermediate from 19B.

TABLE 9

| Example Number | Structure | Name | MS m/z: [M + H]+ | $^1$H NMR |
|---|---|---|---|---|
| 20-2 From-intermediate 19B2 | 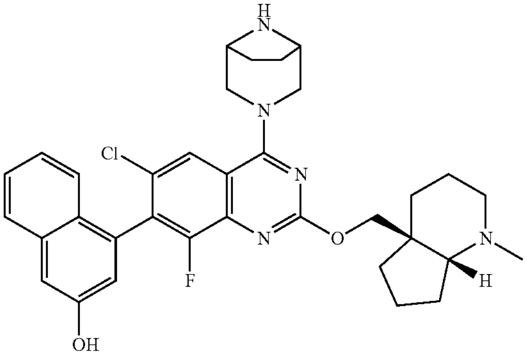 [SMILES: CN1CCC[C@@]2(COc3nc(N4CC5CCC(C4)N5)c4cc(Cl)c(-c5cc(O)cc6ccccc56)c(F)c4n3)CCC[C@@H]12] | 4-(2-{[(4aS,7aR)-1-methyl-octahydro-1H-cyclopenta[b]pyridin-4a-yl]methoxy}-6-chloro-4-{3,8-diazabicyclo[3.2.1]octan-3-yl}-8-fluoroquinazolin-7-yl)naphthalen-2-ol | 603 | $^1$H NMR (499 MHz, METHANOL-$d_4$) δ 7.96 (d, J = 1.5 Hz, 1H), 7.76 (d, J = 8.3 Hz, 1H), 7.42 (ddd, J = 8.2, 6.7, 1.3 Hz, 1H), 7.33-7.12 (m, 3H), 7.05 (d, J = 2.5 Hz, 1H), 4.54 (br d, J = 10.7 Hz, 3H), 4.24 (d, J = 10.7 Hz, 1H), 3.70-3.58 (m, 4H), 2.87 (br t, J=6.4 Hz, 1H), 2.72-2.51 (m, 1H), 2.39-2.29 (m, 4H), 2.05-1.89 (m, 2H), 1.88-1.66 (m, 12H), 1.57 (td, J = 8.7, 4.1 Hz, 1H) |
| 20-3 From-intermediate 19B3 | 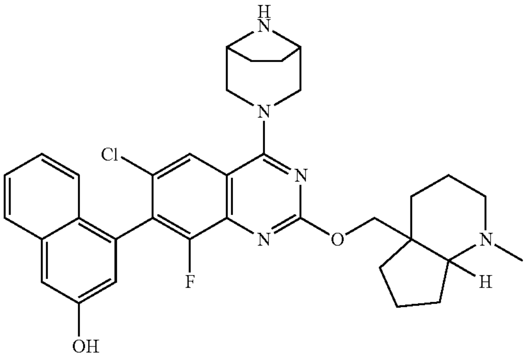 [SMILES: CN1CCCC2(COc3nc(N4CC5CCC(C4)N5)c4cc(Cl)c(-c5cc(O)cc6ccccc56)c(F)c4n3)CCCC12] | 4-(6-chloro-4-{3,8-diazabicyclo[3.2.1]octan-3-yl}-8-fluoro-2-({1-methyl-octahydro-1H-cyclopenta[b]pyridin-4a-yl}methoxy)quinazolin-7-yl)naphthalen-2-ol | 603 | $^1$H NMR (499 MHz, METHANOL-$d_4$) δ 7.96 (d, J = 1.5 Hz, 1H), 7.76 (d, J = 8.3 Hz, 1H), 7.42 (ddd, J = 8.2, 6.8, 1.1 Hz, 1H), 7.29-7.19 (m, 3H), 7.05 (d, J = 2.4 Hz, 1H), 4.82-4.77 (m, 1H), 4.62-4.51 (m, 2H), 4.24 (d, J = 11.1 Hz, 1H), 3.71-3.61 (m, 4H), 3.03-2.92 (m, 1H), 2.37-2.26 (m, 1H), 2.24-2.14 (m, 3H), 2.03-1.81 (m, 8H), 1.80-1.73 (m, 1H), 1.64-1.53 (m, 2H), 1.37-1.21 (m, 1H), 1.11 (td, J = 12.5, 3.6 Hz, 1H) |

TABLE 9-continued

| Example Number | Structure | Name | MS m/z: [M + H]+ | $^1$H NMR |
|---|---|---|---|---|
| 20-4 From-intermediate 19B4 | 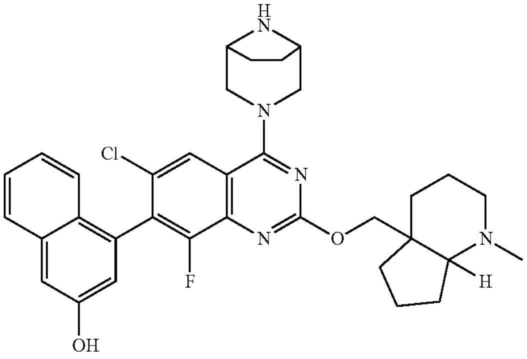 [SMILES: CN1CCCC2(COc3nc(N4CC5CCC(C4)N5)c4cc(Cl)c(-c5cc(O)cc6ccccc56)c(F)c4n3)CCCC12] | 4-(6-chloro-4-{3,8-diazabicyclo[3.2.1]octan-3-yl}-8-fluoro-2-({1-methyl-octahydro-1H-cyclopenta[b]pyridin-4a-yl}methoxy)quinazolin-7-yl)naphthalen-2-ol | 603 | $^1$H NMR (499 MHz, METHANOL-$d_4$) δ 7.96 (s, 1H), 7.76 (d, J = 8.2 Hz, 1H), 7.42 (ddd, J = 8.2, 6.8, 1.1 Hz, 1H), 7.29-7.18 (m, 3H), 7.05 (s, 1H), 4.81-4.73 (m, 1H), 4.61-4.50 (m, 2H), 4.25 (d, J = 11.0 Hz, 1H), 3.71-3.60 (m, 4H), 2.99 (br d, J = 8.8 Hz, 1H), 2.32 (br d, J = 13.1 Hz, 1H), 2.24-2.14 (m, 3H), 2.05-1.71 (m, 10H), 1.64-1.52 (m, 2H), 1.37-1.21 (m, 1H), 1.16-1.07 (m, 1H) |

Examples 21-1 and 21-2

4-(6-chloro-4-{3,8-diazabicyclo[3.2.1]octan-3-yl}-8-fluoro-2-{[(2S)-1-methylpyrrolidin-2-yl]methoxy}quinazolin-7-yl)-5-fluoronaphthalen-2-ol

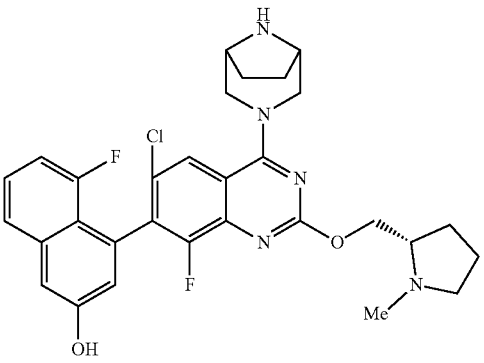

21-1 (isomer 1)
21-2 (Isomer 2)

Preparation of Intermediate 21A: N-(5-bromonaphthalen-1-yl)-1,1,1-trimethyl-N-(trimethylsilyl)silanamine

21A

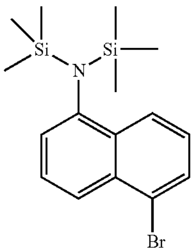

To a stirred solution of 5-bromonaphthalen-1-amine (40 g, 180 mmol) in anhydrous THE (650 mL) under a $N_2$ atmosphere at −78° C., was added LiHMDS (1M THE solution, 396 mL, 396 mmol) dropwise over 30 min. The reaction mixture was slowly warmed to 20° C. over 30 min and then again cooled back to −78° C. A solution of TMSCl (48.3 mL, 378 mmol) in anhydrous THE was added dropwise to the reaction mixture at −78° C. and it was slowly warmed to 20° C. over 1h. The reaction mixture was concentrated under reduced pressure to obtain the crude residue. The crude residue was dissolved in hexane (100 mL) and filtered through Celite, and the filtrate was concentrated under reduced pressure to obtain the crude product as a red oil, which was purified by flash column (Silica gel 100-200) chromatography using petroleum ether as an eluent. Pure fractions were concentrated under reduced pressure to provide N-(5-bromonaphthalen-1-yl)-1,1,1-trimethyl-N-(trimethylsilyl)silanamine (61 g, 166 mmol, 92% yield) as a brown liquid. LCMS (ESI) m/z: 366.45 $[M+H]^+$.

Preparation of Intermediate 21B: 5-fluoronaphthalen-1-amine

21B

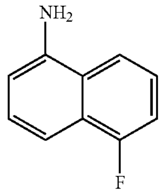

To a stirred solution of N-(5-bromonaphthalen-1-yl)-1,1,1-trimethyl-N-(trimethylsilyl)silanamine (100 g, 273 mmol) in anhydrous THE (1400 mL) under a $N_2$ atmosphere at −78° C. was added n-butyllithium (164 mL, 409 mmol) dropwise over 30 min. After complete addition, the reaction mixture was stirred for 10 min, and then a solution of N-fluorobenzenesulfonimide (138 g, 437 mmol) in anhydrous THE (400 mL) was added dropwise at −78° C. over 20 min. The resulting reaction mixture was slowly warmed to 20° C. for 1h, diluted with ice cold water (1000 mL) and extracted with ethyl acetate (3×800 mL). The extracted organic layers were combined, dried over anhydrous $Na_2SO_4$, filtered and concentrated under reduced pressure to obtain the crude residue. The residue was purified by flash column (Silica gel 100-200) chromatography using 10-20% ethyl acetate in petroleum ether as eluent. Pure fractions were concentrated under reduced pressure to obtain semi pure compound, which was further purified by reverse phase column chromatography using 80% acetonitrile in 0.01% ammonium formate in water. Pure fractions were concentrated under reduced pressure to obtain 5-fluoronaphthalen-1-amine (20 g, 115 mmol, 42.3% yield) as a brown solid. LCMS (ESI) m/z: 162.19 $[M+H]^+$.

Preparation of Intermediate 21C: 2,4-dibromo-5-fluoronaphthalen-1-amine

21C

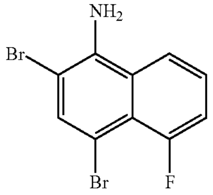

To a stirred solution of 5-fluoronaphthalen-1-amine (40 g, 228 mmol) in acetic acid (800 mL) at 0° C. was carefully added bromine (25.9 mL, 502 mmol) over 30 min and the resultant reaction mixture was stirred at 70° C. for 1 h. The reaction mixture was filtered, and the filter cake was washed with acetic acid (2×200 mL). The residue was suspended in 10% NaOH solution (600 mL) and filtered. The filter cake was washed with water (200 mL) and dried reduced pressure to obtain the crude 2,4-dibromo-5-fluoronaphthalen-1-amine (66 g, 170 mmol, 74.3% yield) as a pale-yellow solid. The crude compound was used in the next step without any further purification. LCMS (ESI) m/z: 319.98 $[M+H]^+$.

Preparation of Intermediate 21D: 5-bromo-6-fluoronaphtho[1,2-d][1,2,3]oxadiazole

21D

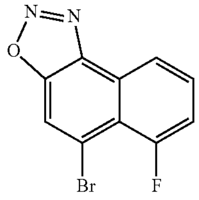

To a stirred solution of 2,4-dibromo-5-fluoronaphthalen-1-amine (66 g, 170 mmol) in acetic acid (1000 mL) was added propionic acid (136 mL, 1815 mmol) at 0° C. After 10 min, sodium nitrite (17.56 g, 255 mmol) was added portionwise to the reaction mixture at 0° C. The reaction mixture was stirred for 30 min at 0° C. and warmed to 25° C. over 1 h. The reaction mixture was diluted with cold water (2000 mL), stirred for 10 min, and filtered. The solid was washed with water (2×500 mL), and dried reduced pressure to obtain crude 5-bromo-6-fluoronaphtho[1,2-d][1,2,3]oxadiazole (40 g, 118 mmol, 69% yield) as a brown solid, which was used in the next step without any purification. LCMS (ESI) m/z: 265.9 $[M+H]^+$.

Preparation of Intermediate 21E: 4-bromo-5-fluoronaphthalen-2-ol

21E

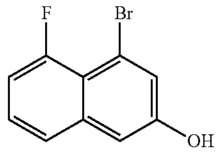

To a stirred solution of 5-bromo-6-fluoronaphtho[1,2-d][1,2,3]oxadiazole (40 g, 118 mmol)) in ethanol (500 mL) and tetrahydrofuran (250 mL) at 0° C. under nitrogen was added $NaBH_4$ (8.91 g, 235 mmol) portion-wise over 30 min. The reaction was stirred at the same temperature for 30 min and then warmed to 25° C. The reaction mixture was carefully quenched with aq. ammonium chloride (20 mL) and concentrated reduced pressure to remove the EtOH. The suspension was extracted with ethyl acetate (3×500 mL), combined organics were dried over anhydrous $Na_2SO_4$ filtered and concentrated under reduced pressure to obtain 4-bromo-5-fluoronaphthalen-2-ol (30 g, 86 mmol, 73% yield) which was used in the next step without further purification. LCMS (ESI) m/z: 241.08 $[M+H]^+$.

Preparation of Intermediate 21F: 1-bromo-8-fluoro-3-(methoxymethoxy)naphthalene

21F

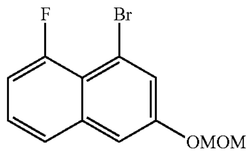

To a stirred solution of 4-bromo-5-fluoronaphthalen-2-ol (30 g, 86 mmol) and DIPEA (22.50 mL, 129 mmol) in anhydrous dichloromethane (300 mL) at 0° C. under a nitrogen atmosphere was dropwise added MOM-Cl (7.83 mL, 103 mmol) over 10 min. The resultant reaction mixture was allowed to warm to room temperature and stirred for 1h. The reaction mixture was diluted with cold water (500 mL) and extracted with DCM (2×500 mL). The combined organic layers were washed with brine (50 mL), dried over anhydrous $Na_2SO_4$ filtered and concentrated under reduced pressure to obtain a crude residue. The crude compound was purified by flash column (Silica gel 100-200) chromatography using 5-10% ethyl acetate in petroleum ether as eluent. Pure fractions were concentrated under reduced pressure to afford 1-bromo-8-fluoro-3-(methoxymethoxy)naphthalene (20.5 g, 68.3 mmol, 80% yield) as a brown solid. LCMS (ESI) m/z: 285.01 $[M+H]^+$.

Preparation of Intermediate 21G: 1-bromo-8-fluoro-3-(methoxymethoxy)naphthalene

21G

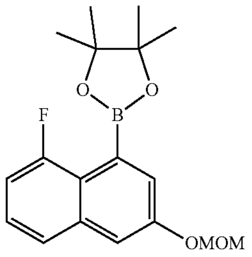

To a degassed solution of 1-bromo-8-fluoro-3-(methoxymethoxy)naphthalene (15 g, 50.0 mmol), bis-pinacolatodiboron (25.4 g, 100 mmol) and potassium acetate (14.72 g, 150 mmol) in anhydrous toluene (300 mL) was added $PdCl_2$(dppf) (3.66 g, 5.00 mmol) at room temperature under an inert atmosphere. The resultant reaction mixture was stirred at 110° C. for 3h. The reaction mixture was diluted with water (50 mL) and extracted with ethyl acetate (2×250 mL). The combined organic layers were washed with brine (50 mL), dried over anhydrous $Na_2SO_4$ filtered and concentrated under reduced pressure to obtain a crude residue. The crude material was purified by flash column (silica 100-200 mesh) chromatography by using 2-4% ethyl acetate in petroleum ether as eluent. Pure fractions were concentrated under reduced pressure to afford a brown gum which was further purified by reverse phase column chromatography using 80% acetonitrile in 0.01% of ammonium formate in water as eluent. Pure fractions were concentrated reduced pressure to obtain 2-(8-fluoro-3-(methoxymethoxy)naphthalen-1-yl)-4,4,5,5-tetramethyl-1,3,2-dioxaborolane (9 g, 26.6 mmol, 53.2% yield) as an off white solid. LCMS (ESI) m/z: 332.1 $[M+H]^+$. 1H-NMR (400 MHz, DMSO-$d_6$): δ 7.52 (d, J=0.80 Hz, 1H), 7.42-7.44 (m, 1H), 7.36-7.38 (m, 1H), 7.33-7.35 (m, 1H), 7.03 (dd, J=1.20, 7.60 Hz, 1H), 5.31 (s, 2H), 3.52 (s, 3H), 1.46 (s, 12H) ppm.

Preparation of Intermediate 21H: tert-butyl 3-(6-chloro-8-fluoro-7-(8-fluoro-3-(methoxymethoxy)naphthalen-1-yl)-2-(((S)-1-methylpyrrolidin-2-yl)methoxy)quinazolin-4-yl)-3,8-diazabicyclo[3.2.1]octane-8-carboxylate

21H

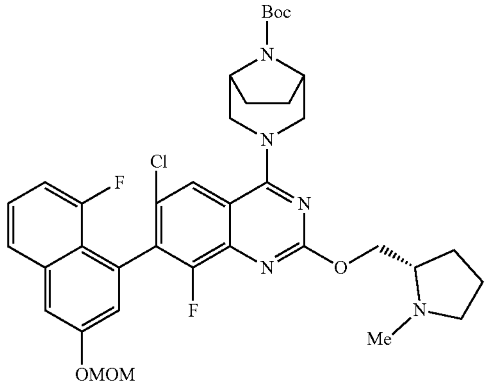

To a degassed solution of tert-butyl 3-(7-bromo-6-chloro-8-fluoro-2-(((S)-1-methylpyrrolidin-2-yl)methoxy)quinazolin-4-yl)-3,8-diazabicyclo[3.2.1]octane-8-carboxylate (Intermediate 6B, 588 mg, 1.005 mmol) in 1,4-dioxane (20 mL), and $H_2O$ (1 mL), were added 2-(8-fluoro-3-(methoxymethoxy)naphthalen-1-yl)-4,4,5,5-tetramethyl-1,3,2-dioxaborolane (668 mg, 2.011 mmol)l), cesium carbonate (655 mg, 2.011 mmol) and SPhos Pd-G3 (15.69 mg, 0.020 mmol). The mixture was degassed again and heated in a pressure vial at 70° C. for 16 hours. The reaction vessel was allowed to cool to ambient temperature, diluted with ethyl acetate, filtered through a bed of Celite and the filtrate was concentrated in vacuo to afford the crude product. The residue was purified by neutral alumina column chromatography in EtOAc to obtain the required product tert-butyl 3-(6-chloro-8-fluoro-7-(8-fluoro-3-(methoxymethoxy)naphthalen-1-yl)-2-(((S)-methylpyrrolidin-2-yl)methoxy)quinazolin-4-yl)-3,8-diazabicyclo[3.2.1]octane-8-carboxylate (321 mg, 41%) as pale yellow oil. LCMS (ESI) m/z: 710.2 $[M+H]^+$.

Examples 21-1 and 21-2

4-(6-chloro-4-{3,8-diazabicyclo[3.2.1]octan-3-yl}-8-fluoro-2-{[(2S)-1-methylpyrrolidin-2-yl]methoxy}quinazolin-7-yl)-5-fluoronaphthalen-2-ol

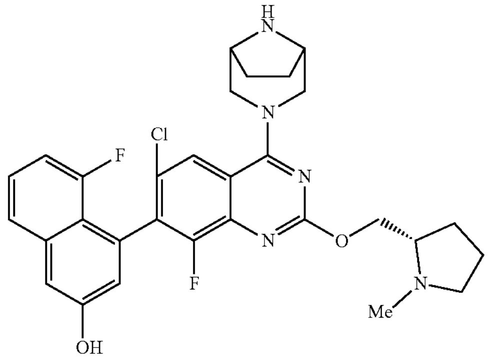

21-1 (isomer 1)
21-2 (Isomer 2)

To a stirred solution of tert-butyl 3-(6-chloro-8-fluoro-7-(8-fluoro-3-(methoxymethoxy)naphthalen-1-yl)-2-(((S)-1-methylpyrrolidin-2-yl)methoxy)quinazolin-4-yl)-3,8-diazabicyclo[3.2.1]octane-8-carboxylate (293 mg, 0.413 mmol) in MeOH (3 mL) was added HCl in 1,4-dioxane (1.031 mL, 4.13 mmol) at room temperature. The reaction mixture was stirred at the same temperature for the next 2h followed by concentration reduced pressure to obtain the crude residue. The residue was purified by column chromatography (Biotage, sfar KP-amino), eluted with 100% ethyl acetate in petroleum ether) to obtain 4-(4-(3,8-diazabicyclo[3.2.1]octan-3-yl)-6-chloro-8-fluoro-2-(((S)-1-methylpyrrolidin-2-yl)methoxy)quinazolin-7-yl)-5-fluoronaphthalen-2-ol (110 mg). The compound was subjected to SFC separation (Column: Cellulose-4(250 mm×4.6×5u), mobile phase-0.2% Ammonia in Methanol_40_5.1cd, Run Time: 25.00, Flow-rate: 3.0000 mL/min, Co-Solvent: 40.0%.), where Peak-1 (21-1), eluted at retention time=10.683 min. (13.0 mg, 0.02 mmol, 5.12% yield) LCMS (ESI) m/z: 566.2 $[M+H]^+$. $^1H$ NMR (400 MHz, $CD_3OD$): δ 7.88 (d, J=1.6 Hz, 1H), 7.58 (d, J=8.0 Hz, 1H), 7.40-7.35 (m, 1H), 7.30 (t, J=2.4 Hz, 1H), 6.98 (d, J=1.6 Hz, 1H), 6.90 (dd, J=13.2 and 7.6 Hz, 1H), 4.52-4.42 (m, 4H), 3.64-3.50 (m, 4H), 3.50-3.48 (m, 1H), 3.16-3.10 (m, 1H), 2.86-2.81 (m, 1H), 2.54 (s, 3H), 2.40-2.37 (m, 1H), 2.14-2.06 (m, 1H), 1.87-1.31 (m, 6H) ppm. Peak-2 (21-2) eluted at room temperature=11.79 (12 mg, 0.02 mmol, 4.78%) LCMS (ESI) m/z: 566.2 $[M+H]^+$. $^1H$ NMR (400 MHz, $CD_3OD$): δ 7.88 (d, J=1.6 Hz, 1H), 7.58 (d, J=8.0 Hz, 1H), 7.40-7.35 (m, 1H), 7.30 (t, J=2.4 Hz, 1H), 6.98 (d, J=1.6 Hz, 1H), 6.90 (dd, J=13.2 and 7.6 Hz, 1H), 4.52-4.42 (m, 4H), 3.64-3.50 (m, 4H), 3.50-3.48 (m, 1H), 3.16-3.10 (m, 1H), 2.86-2.81 (m, 1H), 2.54 (s, 3H), 2.40-2.37 (m, 1H), 2.14-2.06 (m, 1H), 1.87-1.31 (m, 6H) ppm.

Examples 22-1 and 22-2

4-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-ethylnaphthalen-2-ol

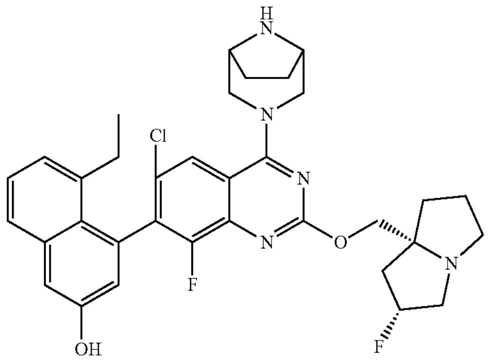

22-1 (Isomer 1)
22-2 (Isomer 2)

Preparation of Intermediate 22A: 8-((triisopropylsilyl)ethynyl)naphthalene-1,3-diol

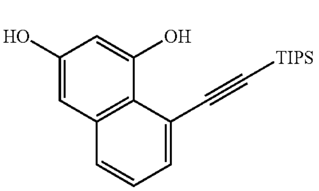

22A

To a stirred solution of naphthalene-1,3-diol (20 g, 125 mmol), bromoethynyl)triisopropylsilane (34.3 g, 131 mmol), and potassium acetate (24.51 g, 250 mmol) in anhydrous 1,4-dioxane (200 mL) was added dichloro(pcymene)ruthenium(II) dimer (7.65 g, 12.49 mmol) under a nitrogen atmosphere. The resulting mixture was stirred for 12h at 110° C. The reaction mixture was cooled to ambient temperature and was filtered through Celite. The Celite bed was washed with EtOAc (2×100 mL), the filtrate was combined and concentrated reduced pressure to obtain a crude residue. The crude material was purified by flash column (silica 100-200 mesh) chromatography using 12-15% ethyl acetate in petroleum ether as eluent. Pure fractions were concentrated under reduced pressure to obtain 8-((triisopropylsilyl)ethynyl)naphthalene-1,3-diol (30 g, 85 mmol, 67.7% yield). LCMS (ESI) m/z: 341.55 $[M+H]^+$.

Preparation of Intermediate 22B: 3-(methoxymethoxy)-8-((triisopropylsilyl)ethynyl) naphthalen-1-ol

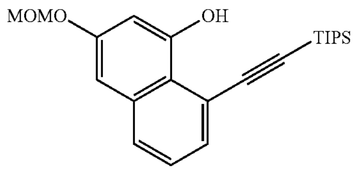

22B

To a stirred solution of 8-((triisopropylsilyl)ethynyl)naphthalene-1,3-diol (25 g, 73.4 mmol) in anhydrous DCM (300 mL) under nitrogen was added DIPEA (38.5 mL, 220 mmol) at −10° C. After 10 min, MOM-Cl (6.13 mL, 81 mmol) was added to the reaction mixture dropwise over 20 min under a nitrogen atmosphere. The resulting mixture was stirred for 2h at the same temperature. The reaction mixture was diluted with 100 mL of DCM and washed with 200 mL of brine. The combined organics were dried over anhydrous $Na_2SO_4$, filtered and concentrated reduced pressure to yield a crude residue. The crude material was purified by flash column (silica 100-200 mesh) chromatography using 5-10% ethyl acetate in petroleum ether as eluent. Pure fractions were concentrated under reduced pressure to obtain 3-(methoxymethoxy)-8-((triisopropylsilyl)ethynyl)naphthalen-1-ol (21 g, 53.5 mmol, 72.9% yield) as a pale yellow oil. LCMS (ESI) m/z: 385.60 $[M+H]^+$.

Preparation of Intermediate 22C: 3-(methoxymethoxy)-8-((triisopropylsilyl)ethynyl) naphthalen-1-yl pivalate

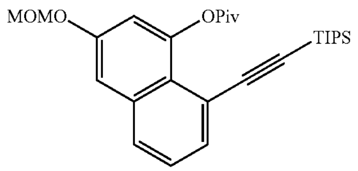

22C

To a stirred solution of 3-(methoxymethoxy)-8-((triisopropylsilyl)ethynyl)naphthalen-1-ol (20 g, 52.0 mmol), TEA (21.75 mL, 156 mmol), DMAP (1.271 g, 10.40 mmol) in anhydrous DCM (200 mL) at −10° C. under a nitrogen atmosphere was added pivaloyl chloride (12.80 mL, 104 mmol) dropwise for 10 min. The resulting mixture was stirred for 2 h at room temperature under nitrogen. The reaction mixture was then diluted with 200 mL of DCM and washed with brine (200 mL). The organics were dried over anhydrous $Na_2SO_4$, filtered and concentrated reduced pressure to yield a crude residue. The crude was purified by flash column (silica 100-200 mesh) chromatography using 10-15% ethyl acetate in petroleum ether as eluent. Pure fractions were concentrated under reduced pressure to obtain 3-(methoxymethoxy)-8-((triisopropylsilyl)ethynyl)naphthalen-1-yl pivalate (23 g, 49.1 mmol, 94% yield) as a pale yellow oil. LCMS (ESI) m/z: 469.2 $[M+H]^+$.

Preparation of Intermediate 22D: 8-ethynyl-3-(methoxymethoxy)naphthalen-1-yl pivalate

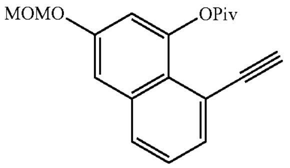

22D

To a stirred solution of 3-(methoxymethoxy)-8-((triisopropylsilyl)ethynyl)naphthalen-1-yl pivalate (12 g, 25.6 mmol) in anhydrous DMF (130 mL) at room temperature under a nitrogen atmosphere was added anhydrous CsF (27.2 g, 179 mmol). The reaction mixture was stirred for 2 h. The reaction mixture was diluted with DCM (200 mL) and washed with brine (200 mL). The organics were dried over anhydrous $Na_2SO_4$, filtered and concentrated reduced pressure to yield a crude residue. The crude was purified by flash column (silica 100-200 mesh) chromatography using 5-8% ethyl acetate in petroleum ether as eluent. Pure fractions were concentrated under reduced pressure to obtain 8-ethynyl-3-(methoxymethoxy)naphthalen-1-yl pivalate(7 g, 20.62 mmol, 81% yield). LCMS (ESI) m/z: 313.3 $[M+H]^+$.

Preparation of Intermediate 22E: 8-ethyl-3-methoxymethoxy)naphthalen-1-ylpivalate

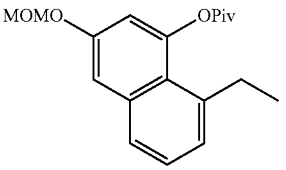

22E

To a stirred solution of 8-ethynyl-3-(methoxymethoxy) naphthalen-1-yl pivalate (7 g, 22.41 mmol) in anhydrous methanol (70 mL) was added Pd/C (1.4 g, 13.16 mmol) at 25° C. The suspension was degassed reduced pressure and purged with H2 several times. The mixture was stirred under H2 atmosphere (1 atm) at 25° C. for 5 hours. The reaction mixture was filtered and concentrated under reduced pressure to obtain a crude residue. The crude material was purified by flash column (silica 100-200 mesh) chromatography using 15-20% ethyl acetate in petroleum ether as eluent. Pure fractions were concentrated under reduced pressure to provide 8-ethyl-3-methoxymethoxy)naphthalen-1-ylpivalate (6.56 g, 17.83 mmol, 80% yield) as pale yellow oil. LCMS (ESI) m/z: 316.1 $[M+H]^+$.

Preparation of Intermediate 22F: 8-ethyl-3-methoxymethoxy)naphthalen-1-ol

22F

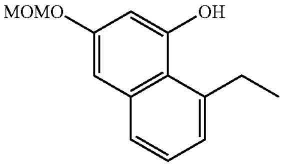

To a stirred solution of 8-ethyl-3-(methoxymethoxy) naphthalen-1-yl pivalate (10 g, 31.6 mmol) in THF:Water: MeOH (5:1:5) was added anhydrous LiOH (1.135 g, 47.4 mmol) at room temperature under nitrogen. The resulting mixture was stirred for 3 h at the same temperature. The reaction mixture was concentrated reduced pressure to remove the MeOH. The reaction mixture was diluted with EtOAc (150 mL) and washed with brine (200 mL). The organics were dried over anhydrous $Na_2SO_4$, filtered, and concentrated reduced pressure to yield a crude residue. The crude material was purified by flash column (silica 100-200 mesh) chromatography using 25-30% ethyl acetate in petroleum ether as eluent. Pure fractions were concentrated under reduced pressure to obtain 8-ethyl-3-methoxymethoxy) naphthalen-1-ol (6 g, 25.8 mmol, 82% yield). LCMS (ESI) m/z: 233.2 $[M+H]^+$.

Preparation of Intermediate 22G: 8-ethyl-3-(methoxymethoxy)naphthalen-1-yl trifluoromethanesulfonate

22G

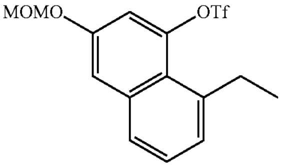

To a stirred solution of 8-ethyl-3-(methoxymethoxy) naphthalen-1-ol (3 g, 12.92 mmol) and DIPEA (22.50 mL, 129 mmol) in anhydrous dichloromethane (50 mL) at −40° C. under nitrogen was added $Tf_2O$ (2.182 mL, 12.92 mmol) dropwise. The resultant reaction mixture was allowed to warm to room temperature and stirred for 1h. The reaction mixture was diluted with cold water (500 mL) and extracted with DCM (2×500 mL). The combined organic layers were washed with brine (50 mL), dried over anhydrous $Na_2SO_4$, filtered, and concentrated under reduced pressure to obtain a crude residue. The crude compound was purified by flash column (Silicagel 100-200) chromatography using 5-10% ethyl acetate in petroleum ether as eluent. Pure fractions were concentrated under reduced pressure to afford 8-ethyl-3-(methoxymethoxy)naphthalen-1-yl trifluoromethanesulfonate (3.5 g, 9.03 mmol, 69.9% yield) as a pale yellow oil. LCMS (ESI) m/z: 365.3 $[M+H]^+$.

Preparation of Intermediate 22H: 2-(8-ethyl-3-(methoxymethoxy)naphthalen-1-yl)-4,4,5,5-tetramethyl-1,3,2-dioxaborolane

22H

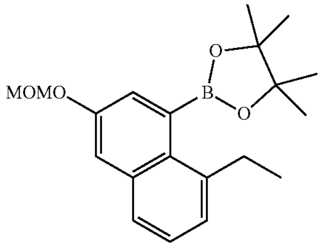

To a stirred solution of 8-ethyl-3-(methoxymethoxy) naphthalen-1-yl trifluoromethanesulfonate (7.4 g, 20.31 mmol) in 1,4-dioxane (80 mL) was added bispinacalatoborane (12.89 g, 50.8 mmol) and potassium acetate (5.98 g, 60.9 mmol). The mixture was degassed and purged with nitrogen for 5 min and $PdCl_2$(dppf) (1.659 g, 2.031 mmol) was added. The resulting mixture was stirred for 3 h at 100° C. temperature under nitrogen. The reaction mixture was diluted with water (50 mL) and extracted with ethyl acetate (250 mL). The combined organic layers were washed with brine (50 mL) dried over anhydrous $Na_2SO_4$ and concentrated under reduced pressure to obtain a crude residue. The crude was purified by flash column (silica 100-200 mesh) chromatography by using 2-4% ethyl acetate in petroleum ether as eluent. Pure fractions were concentrated under reduced pressure to afford a brown gum which was again purified by reverse phase column chromatography using 80% Acetonitrile in 0.01% of Ammonium formate in water as eluent. Pure fractions were concentrated reduced pressure to obtain 2-(8-ethyl-3-(methoxymethoxy)naphthalen-1-yl)-4,4,5,5-tetramethyl-1,3,2-dioxaborolane (4.5 g, 13.10 mmol, 64.5% yield). LCMS (ESI) m/z: 344.2 $[M+H]^+$. $^1$H-NMR (400 MHz, $CDCl_3$): δ 7.62 (dd, J=0.80, 8.00 Hz, 1H), 7.36-7.44 (m, 3H), 7.27 (t, J=0.40 Hz, 1H), 5.31 (s, 2H), 3.53 (s, 3H), 3.21 (q, J=7.20 Hz, 2H), 1.46 (s, 12H), 1.38 (t, J=7.60 Hz, 3H) ppm.

Preparation of Intermediate 221: tert-butyl-3-(7-bromo-6-chloro-8-fluoro-2-(((2R,7aR)-2-fluorotetrahydro-1H-pyrrolizin-7a(5H)-yl)methoxy)quinazolin-4-yl)-3,8 diazabicyclo[3.2.1]octane-8-carboxylate

22I

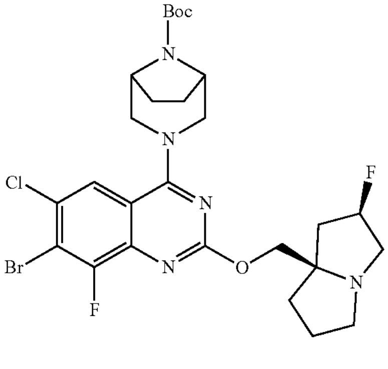

To a stirred solution of ((2R,7aR)-2-fluorotetrahydro-1H-pyrrolizin-7a(5H)-yl)methanol (500 mg, 3.14 mmol) in anhydrous THF (20 mL) at 0° C. under nitrogen was added sodium hydride (60% dispersion in mineral oil, 75 mg, 3.14 mmol) and the reaction mixture was stirred for 30 min at the same temperature. After 30 min, a solution of tert-butyl 3-(7-bromo-6-chloro-2,8-difluoroquinazolin-4-yl)-3,8-diazabicyclo[3.2.1]octane-8-carboxylate (Intermediate 8A, 1.0 g, 2.09 mmol) in THE (2 mL) was added dropwise to the reaction mixture at 0° C. The reaction mixture was stirred at ambient temperature for 3 h. The reaction mixture was quenched with saturated ammonium chloride solution (10 mL) and extracted with ethyl acetate (2×20 mL). The combined organic layers were washed with water and saturated brine solution, dried over anhydrous $Na_2SO_4$, filtered and concentrated under reduced pressure to afford crude product. The crude was purified by column chromatography (Grace, 50 g snap, dry pack) over neutral alumina using 50-100% ethyl acetate in petroleum ether. The desired fractions were pooled and concentrated under reduced pressure to obtain tert-butyl-3-(7-bromo-6-chloro-8-fluoro-2-(((2R,7aR)-2-fluorotetrahydro-1H-pyrrolizin-7a(5H)-yl)methoxy)quinazolin-4-yl)-3,8-diazabicyclo[3.2.1]octane-8-carboxylate (1200 mg, 1.91 mmol, 91.0% yield) as pale yellow solid. LCMS (ESI) m/z: 629.5 $[M+H]^+$.

Preparation of Intermediate 22J: tert-butyl-3-(6-chloro-7-(8-ethyl-3-(methoxymethoxy)naphthalen-1-yl)-8-fluoro-2-(((2R,7aR)-2-fluorotetrahydro-1H-pyrrolizin-7a(5H)-yl)methoxy)quinazolin-4-yl)-3,8-diazabicyclo[3.2.1]octane-8-carboxylate

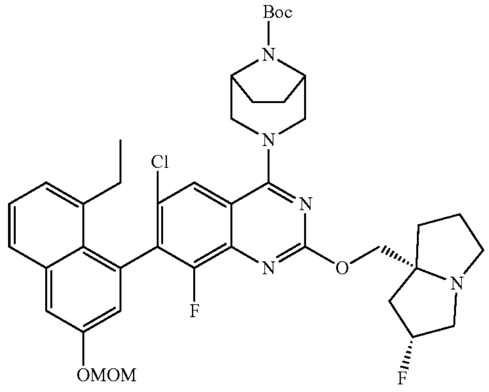

To a degassed solution of tert-butyl 3-(7-bromo-6-chloro-8-fluoro-2-(((2R,7aR)-2-fluorotetrahydro-1H-pyrrolizin-7a(5H)-yl)methoxy)quinazolin-4-yl)-3,8-diazabicyclo[3.2.1]octane-8-carboxylate (400 mg, 0.636 mmol) in 1,4-dioxane (7 mL), and $H_2O$ (0.5 mL), were added 2-(8-ethyl-3-(methoxymethoxy)naphthalen-1-yl)-4,4,5,5-tetramethyl-1,3,2-dioxaborolane (435 mg, 1.272 mmol), cesium carbonate (414 mg, 1.272 mmol) and S-phos-pd-g3 (24.81 mg, 0.032 mmol). The mixture was degassed again and heated in a pressure vial at 70° C. ° C. for 16 hours. The reaction vessel was allowed to cool to ambient temperature, diluted with ethyl acetate, filtered and concentrated reduced pressure to obtain the crude residue. Crude residue was purified by reverse phase HPLC [Column: Xselect C18 (150×19) mm, 5 micron, Mobile phase A: 10 mM Ammonium acetate in water, Phase B: Acetonitrile]. The fractions from reverse phase HPLC were pooled together and lyophilized to obtain the required product tert-butyl 3-(6-chloro-7-(8-ethyl-3-(methoxymethoxy)naphthalen-1-yl)-8-fluoro-2-(((2R,7aR)-2-fluorotetrahydro-1H-pyrrolizin-7a(5H)-yl)methoxy)quinazolin-4-yl)-3,8 diazabicyclo[3.2.1]octane-8-carboxylate (100 mg, 0.118 mmol, 18.52% yield) as off white solid. LCMS (ESI) m/z: 764.3 $[M+H]^+$.

Examples 22-1 and 22-2

4-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-ethylnaphthalen-2-ol

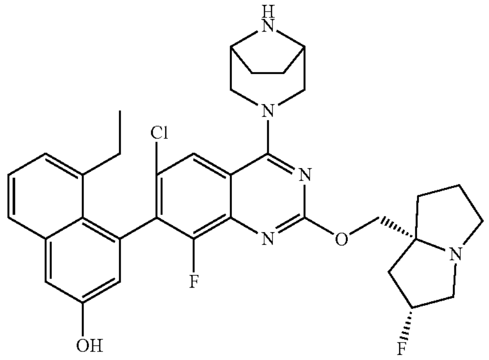

22-1 (Isomer 1)
22-2 (Isomer 2)

To a stirred solution of tert-butyl-3-(6-chloro-7-(8-ethyl-3-(methoxymethoxy)naphthalen-1-yl)-8-fluoro-2-(((2R,7aR)-2-fluorotetrahydro-1H-pyrrolizin-7a(5H)-yl)methoxy)quinazolin-4-yl)-3,8-diazabicyclo[3.2.1]octane-8-carboxylate (100 mg, 0.131 mmol) was added HCl (4.0 M in dioxane, 0.352 mL, 1.406 mmol) at ice cold temperature The reaction was allowed to warm to room temperature and then stirred for 2h. The reaction mixture was concentrated reduced pressure to obtain the crude residue. The residue was purified by column chromatography (Biotage, sfar KP-amino), eluted with 100% ethyl acetate in petroleum ether to obtain tert-butyl-3-(6-chloro-7-(8-ethyl-3-(methoxymethoxy)naphthalen-1-yl)-8-fluoro-2-(((2R,7aR)-2-fluorotetrahydro-1H-pyrrolizin-7a(5H)-yl)methoxy)quinazolin-4-yl)-3,8-diazabicyclo[3.2.1]octane-8-carboxylate (123 mg). The obtained compound was subjected to SFC separation (Column: Cellulose-4(250 mm×4.6×5u), mobile phase-0.2% Ammonia in Methanol_40_5.1cd, Run Time: 25.00, Flowrate: 3.0000 mL/min, Co-Solvent: 40.0%.), where Peak-1 (22-1), eluted at retention time=12.16 min. (45 mg, 52.8% yield); LCMS (ESI) m/z: 621.2 $[M+H]^+$; $^1H$ NMR (400 MHz, $CD_3OD$, 298 K) δ: 8.03-7.96 (m, 1H), 7.65 (d, J=7.6 Hz, 1H), 7.41-7.34 (m, 1H), 7.30 (d, J=2.6 Hz, 1H), 7.16 (d, J=6.9 Hz, 1H), 6.87 (d, J=2.6 Hz, 1H), 5.65-5.41 (m, 1H), 4.83-4.67 (m, 4H), 4.28 (br d, J=10.1 Hz, 2H), 4.12-4.00 (m, 1H), 3.99-3.83 (m, 2H), 3.76-3.65 (m, 1H), 3.60-3.45 (m, 2H), 2.74 (br s, 1H), 2.56-2.38 (m, 4H), 2.29 (td, J=4.8, 9.0 Hz, 2H), 2.23-2.08 (m, 3H), 0.94 (t, J=7.4 Hz, 3H) ppm. Peak-2 (22-2) is eluted at retention time=17.95 min. (40 mg, 57%); LCMS (ESI) m/z: 621.2 $[M+H]^+$; $^1H$ NMR (400 MHz, $CD_3OD$, 298 K) δ: 8.03-7.96 (m, 1H), 7.65 (d, J=7.6 Hz, 1H), 7.41-7.34 (m, 1H), 7.30 (d, J=2.6 Hz, 1H), 7.16 (d, J=6.9 Hz, 1H), 6.87 (d, J=2.6 Hz, 1H), 5.65-5.41 (m, 1H), 4.83-4.67 (m, 4H), 4.28 (br d, J=10.1 Hz, 2H), 4.12-4.00 (m, 1H), 3.99-3.83 (m, 2H), 3.76-3.65 (m, 1H), 3.60-3.45 (m, 2H), 2.74 (br s, 1H), 2.56-2.38 (m, 4H), 2.29 (td, J=4.8, 9.0 Hz, 2H), 2.23-2.08 (m, 3H), 0.94 (t, J=7.4 Hz, 3H) ppm.

Examples 23-1 and 23-2

4-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-ethyl-6-fluoronaphthalen-2-ol

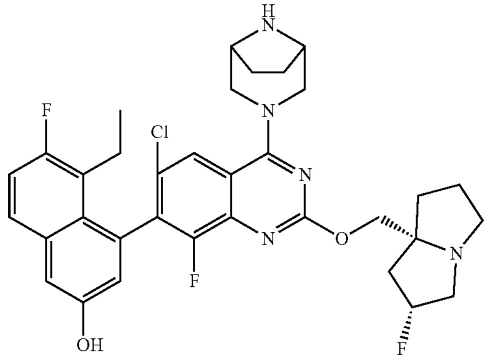

23-1 (Isomer 1)
23-2 (Isomer 2)

Preparation of Intermediate 23A: 7-fluoro-8-((triisopropylsilyl)ethynyl)naphthalene-1,3-diol

23A

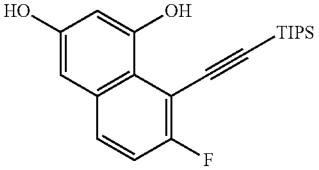

To a stirred solution of 7-fluoronaphthalene-1,3-diol (20 g, 112 mol), (bromoethynyl)triisopropylsilane (30.8 g, 118 mmol), and potassium acetate (22.03 g, 225 mmol) in anhydrous dioxane (200 mL) was added dichloro(p-cymene) ruthenium(II) dimer (6.87 g, 11.23 mmol) under a nitrogen atmosphere at room temperature. The resulting mixture was stirred for 12 h at 110° C. under a nitrogen atmosphere. The resulting reaction mixture was filtered through Celite and the Celite bed was washed with EtOAc (2×50 mL). The filtrate was collected and concentrated under a vacuum to obtain the crude residue. The crude material was purified by flash column (silica 100-200 mesh) chromatography using 5-10% ethyl acetate in petroleum ether as eluent. Pure fractions were concentrated under reduced pressure to obtain 7-fluoro-8-((triisopropylsilyl)ethynyl)naphthalene-1,3-diol (32 g, 88 mmol, 79% yield) as a pale yellow oil. LCMS (ESI) m/z: 359.1 $[M+H]^+$.

Preparation of Intermediate 23B: 7-fluoro-3-(methoxymethoxy)-8-((triisopropylsilyl)ethynyl)naphthalen-1-ol

23B

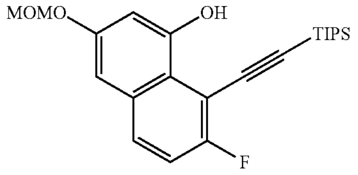

To a stirred solution of 7-fluoro-8-((triisopropylsilyl)ethynyl)naphthalene-1,3-diol (10 g, 27.9 mmol) in anhydrous DCM (100 mL) under nitrogen was added DIEA (14.61 mL, 84 mmol) at 0° C. The reaction mixture was stirred at the same temperature for 10 min before the dropwise addition of MOM-Cl (2.54 mL, 33.5 mmol) to the reaction mixture. The resulting mixture was stirred for 1 h at room temperature under nitrogen. The reaction mixture was diluted with cold water (50 mL) and extracted with DCM (2×100 mL). The combined organic layers were washed with brine (50 mL), dried over anhydrous $Na_2SO_4$ and concentrated under reduced pressure to obtain a crude residue. The crude material was purified by flash column (silica 100-200 mesh) chromatography using 5-10% ethyl acetate in petroleum ether as eluent. Pure fractions were concentrated under reduced pressure to obtain 7-fluoro-3-(methoxymethoxy)-8-((triisopropylsilyl)ethynyl)naphthalen-1-ol (10 g, 24.84 mmol, 89% yield). LCMS (ESI) m/z: 403.1 $[M+H]^+$.

Preparation of Intermediate 23C: 7-fluoro-3-(methoxymethoxy)-8-((triisopropylsilyl)ethynyl)naphthalen-1-yl pivalate

23C

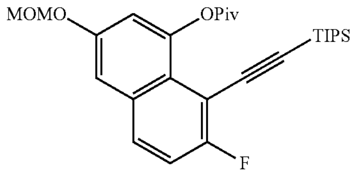

To a stirred solution of 7-fluoro-3-(methoxymethoxy)-8-((triisopropylsilyl)ethynyl)naphthalen-1-ol (17 g, 42.2 mmol) in anhydrous DCM (170 mL) at 0° C. under a nitrogen atmosphere were added TEA (17.66 mL, 127 mmol) and DMAP (1.032 g, 8.45 mmol). The reaction mixture was stirred at the same temperature for 10 min before the dropwise addition of pivaloyl chloride (6.23 mL, 50.7 mmol). The resulting reaction mixture was stirred at room temperature for 2 h. The reaction mixture was diluted with cold water (50 mL) and extracted with DCM (2×100 mL). The combined organic layers were washed with brine (200 mL), dried over anhydrous $Na_2SO_4$ and concentrated under reduced pressure to obtain a crude residue. The crude material was purified by flash column (silica 100-200 mesh) chromatography using 20-25% ethyl acetate in petroleum ether as eluent. Pure fractions were concentrated under reduced pressure to obtain 7-fluoro-3-(methoxymethoxy)-8-

((triisopropylsilyl)ethynyl)naphthalen-1-yl pivalate (19 g, 35.1 mmol, 83% yield). LCMS (ESI) m/z: 487.2 $[M+H]^+$.

Preparation of Intermediate 23D: 7-fluoro-3-(methoxymethoxy)-8-((triisopropylsilyl)ethynyl) naphthalen-1-yl pivalate

23D

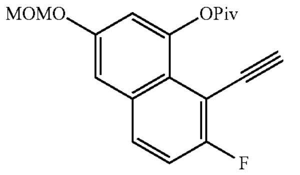

To a stirred solution of 7-fluoro-3-(methoxymethoxy)-8-((triisopropylsilyl)ethynyl)naphthalen-1-yl pivalate (20 g, 41.1 mmol) in anhydrous DMF (150 mL) under a nitrogen atmosphere was added CsF (43.7 g, 288 mmol) at room temperature. The resulting mixture was stirred for 5 h at room temperature. The reaction mixture was diluted with DCM (200 mL) and washed with brine (200 mL). The organics were dried over anhydrous $Na_2SO_4$, filtered and concentrated reduced pressure to yield a crude residue. The crude material was purified by flash column (silica 100-200 mesh) chromatography using 5-8% ethyl acetate in petroleum ether as eluent. Pure fractions were concentrated under reduced pressure to obtain 8-ethynyl-7-fluoro-3-(methoxymethoxy)naphthalen-1-yl pivalate (12 g, 32.7 mmol, 80% yield) as a pale yellow oil. LCMS (ESI) m/z: 331.2 $[M+H]^+$.

Preparation of Intermediate 23E: 8-ethyl-7-fluoro-3-(methoxymethoxy)naphthalen-1-yl pivalate

23E

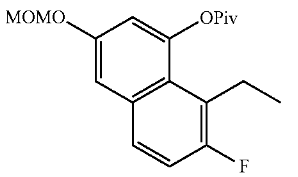

To a stirred solution of 8-ethynyl-7-fluoro-3-(methoxymethoxy)naphthalen-1-yl pivalate (15 g, 45.4 mmol) in ethanol (150 mL) was added 10% Pd/C (3 g, 28.2 mmol) at 25° C. The suspension was degassed reduced pressure and purged with H2 several times. The mixture was stirred under H2 atmosphere (1 Atm) at 25° C. for 5 hours. The reaction mixture was filtered and concentrated under reduced pressure to obtain a crude residue. The crude was purified by flash column (silica 100-200 mesh) chromatography using 15-20% ethyl acetate in petroleum ether as eluent. Pure fractions were concentrated under reduced pressure to provide 8-ethyl-7-fluoro-3-(methoxymethoxy) naphthalen-1-yl pivalate (14 g, 34.3 mmol, 76% yield) as a pale yellow oil. LCMS (ESI) m/z: 335.1 $[M+H]^+$.

Preparation of Intermediate 23F: 8-ethyl-7-fluoro-3-(methoxymethoxy)naphthalen-1-ol

23F

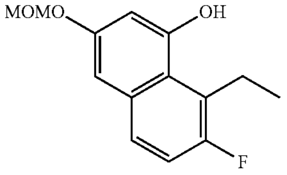

To a stirred solution of 8-ethyl-7-fluoro-3-(methoxymethoxy)naphthalen-1-yl pivalate (5 g, 14.95 mmol) in MeOH (50 mL) was added anhydrous LiOH (0.537 g, 22.43 mmol) at room temperature under nitrogen. The resulting mixture was stirred at the same temperature for 1 h. The reaction mixture was concentrated reduced pressure to remove the MeOH. The reaction mixture was diluted with EtOAc (150 mL) and washed with brine (200 mL). The organics were dried over anhydrous $Na_2SO_4$, filtered and concentrated reduced pressure to yield a crude residue. The crude material was purified by flash column (silica 100-200 mesh) chromatography using 25-30% ethyl acetate in petroleum ether as eluent. Pure fractions were concentrated under reduced pressure to obtain 8-ethyl-7-fluoro-3-(methoxymethoxy)naphthalen-1-ol (3.5 g, 12.59 mmol, 84% yield). LCMS (ESI) m/z: 251.2 $[M+H]^+$.

Preparation of Intermediate 23G: 8-ethyl-7-fluoro-3-(methoxymethoxy)naphthalen-1-yl trifluoromethanesulfonate

23G

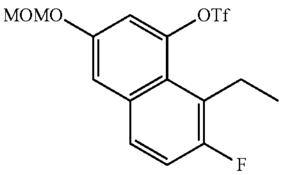

To a stirred solution of 8-ethyl-7-fluoro-3-(methoxymethoxy)naphthalen-1-ol (1.5 g, 5.99 mmol) and DIEA (3.66 mL, 20.98 mmol) in anhydrous dichloromethane (50 mL) at −10° C. was added $Tf_2O$ (1.215 mL, 7.19 mmol) dropwise. The resultant reaction mixture was allowed to warm to room temperature and stirred for 1 h. The reaction mixture was diluted with cold water (500 mL) and then extracted with DCM (2×500 mL). The combined organic layers were washed with brine (50 mL), dried over anhydrous $Na_2SO_4$, filtered and concentrated under reduced pressure to obtain a crude residue. The crude compound was purified by flash column (Silicagel 100-200) chromatography using 5-10% ethyl acetate in petroleum ether as eluent. Pure fractions were concentrated under reduced pressure to afford 8-ethyl-7-fluoro-3-(methoxymethoxy)naphthalen-1-yl-trifluoromethanesulfonate (1.8 g, 4.66 mmol, 78% yield) as a pale yellow oil. LCMS (ESI) m/z: 383.0 $[M+H]^+$.

Preparation of Intermediate 23H: 2-(8-ethyl-7-fluoro-3-(methoxymethoxy)naphthalen-1-yl)-4,4,5,5-tetramethyl-1,3,2-dioxaborolane

23H

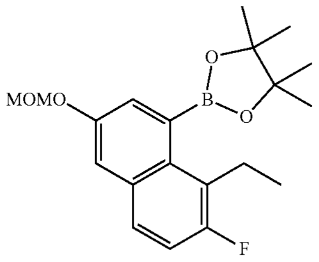

To a stirred solution of 8-ethyl-7-fluoro-3-(methoxymethoxy)naphthalen-1-yl trifluoromethanesulfonate (2.5 g, 6.54 mmol) in anhydrous 1,4-dioxane (80 mL) were added bispinacolatodiborane (4.15 g, 16.35 mmol) and potassium acetate (1.925 g, 19.62 mmol) and the resulting mixture was degassed and purged with nitrogen for 5 min. Then, $PdCl_2$(dppf) (0.534 g, 0.654 mmol) was added to the reaction mixture. The resulting mixture was stirred for 2 h at 100° C. under a nitrogen atmosphere. The reaction mixture was then diluted with water (50 mL) and extracted with ethyl acetate (250 mL). The combined organic layers were washed with brine (50 mL) dried over anhydrous $Na_2SO_4$, filtered and concentrated under reduced pressure to obtain a crude residue. The crude material was purified by flash column (silica 100-200 mesh) chromatography using 2-4% ethyl acetate in petroleum ether as eluent. Pure fractions were concentrated under reduced pressure to afford a brown gum which was again purified by reverse phase column chromatography using 80% acetonitrile in 0.01% of ammonium formate in water as eluent. Pure fractions were concentrated reduced pressure to obtain 22-(8-ethyl-7-fluoro-3-(methoxymethoxy)naphthalen-1-yl)-4,4,5,5-tetramethyl-1,3,2-dioxaborolane (1.8 g, 4.99 mmol, 76% yield). LCMS (ESI) m/z: 329 $[M-OCH_3]^+$. $^1$H-NMR (400 MHz, $CDCl_3$): δ 7.77 (t, J=8.40 Hz, 1H), 7.54 (s, 1H), 7.37 (t, J=9.60 Hz, 1H), 7.28 (s, 1H), 5.31 (s, 2H), 3.42 (s, 3H), 3.03 (d, J=6.80 Hz, 2H), 1.39 (s, 12H), 1.19 (t, J=7.20 Hz, 3H) ppm.

Preparation of Intermediate 23I: tert-butyl-3-(6-chloro-7-(8-ethyl-7-fluoro-3-(methoxymethoxy)naphthalen-1-yl)-8-fluoro-2-(((2R,7aR)-2-fluorotetrahydro-1H-pyrrolizin-7a(5H)-yl)methoxy)quinazolin-4-yl)-3,8-diazabicyclo[3.2.1]octane-8-carboxylate

23I

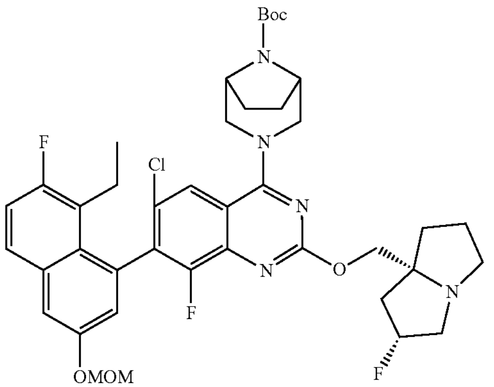

To a degassed solution of tert-butyl 3-(7-bromo-6-chloro-8-fluoro-2-(((2R,7aR)-2-fluorotetrahydro-1H-pyrrolizin-7a(5H)-yl)methoxy)quinazolin-4-yl)-3,8-diazabicyclo[3.2.1]octane-8-carboxylate (400 mg, 0.636 mmol) was added 2-(8-ethyl-7-fluoro-3-(methoxymethoxy)naphthalen-1-yl)-4,4,5,5-tetramethyl-1,3,2-dioxaborolane (458 mg, 1.272 mmol) and SPhosPd-G3 (24.81 mg, 0.032 mmol. The mixture was degassed again and heated in a pressure vial at 70° C. for 16 hours. The reaction vessel was allowed to cool to ambient temperature, diluted with ethyl acetate, filtered and concentrated under vacuum to obtain the crude residue. The crude residue was purified by reverse phase HPLC purification [Column: Xselect C18 (150×19) mm, 5 micron, Mobile phase A: 10 mM ammonium acetate in water, Phase B: acetonitrile]. The fractions from reverse phase HPLC were pooled together and lyophilized to obtain the required product tert-butyl-3-(6-chloro-7-(8-ethyl-7-fluoro-3-(methoxymethoxy)naphthalen-1-yl)-8-fluoro-2-(((2R,7aR)-2-fluorotetrahydro-1H-pyrrolizin-7a(5H)-yl)methoxy)quinazolin-4-yl)-3,8-diazabicyclo[3.2.1]octane-8-carboxylate (100 mg, 0.128 mmol, 20.10% yield) as off white solid. LCMS (ESI) m/z: 782.2 [M+H].

Examples 23-1 and 23-2

4-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-ethyl-6-fluoronaphthalen-2-ol

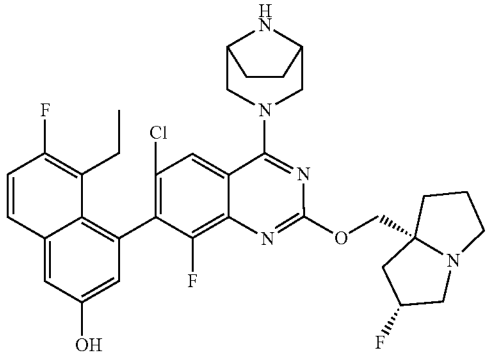

23-1 (Isomer 1)
23-2 (Isomer 2)

To a stirred solution of tert-butyl-3-(6-chloro-7-(8-ethyl-7-fluoro-3-(methoxymethoxy)naphthalen-1-yl)-8-fluoro-2-(((2R,7aR)-2-fluorotetrahydro-1H-pyrrolizin-7a(5H)-yl)methoxy)quinazolin-4-yl)-3,8-diazabicyclo[3.2.1]octane-8-carboxylate (110 mg, 0.141 mmol) in MeOH (5 mL was added HCl (4.0 M in dioxane, 0.352 mL, 1.406 mmol) at ice cold temperature. The reaction was allowed to warm to room temperature and then stirred for 2h. The reaction mixture was concentrated reduced pressure to obtain the crude residue. The residue was purified by column chromatography (Biotage, sfar KP-amino), eluted with 100% ethyl acetate in petroleum ether to obtain 4-(4-((3,8-diazabicyclo[3.2.1]octan-3-yl)-6-chloro-8-fluoro-2-(((2R,7aR)-2-fluorotetrahydro-1H-pyrrolizin-7a(5H)-yl)methoxy)quinazolin-7-yl)-5-ethyl-6-fluoronaphthalen-2-ol (110 mg). The obtained compound was subjected to SFC separation (Column: Cellulose-4 (250 mm×4.6×5u), mobile phase-0.2% ammonia in methanol, Run Time: 25.00, Flowrate: 3.0000 mL/min, Co-Solvent: 40.0%.), where Peak-1 (23-1), eluted at retention time=9.216 min. (40 mg, 42% yield) LCMS (ESI) m/z: 639.2 $[M+H]^+$; $^1H$ NMR (400 MHz, $CD_3OD$, 298 K) δ: 8.05-7.97 (m, 1H), 7.71 (dd, J=5.9, 9.1 Hz, 1H), 7.36-7.19 (m, 2H), 6.92 (d, J=2.6 Hz, 1H), 5.61-5.39 (m, 1H), 4.82-4.63 (m, 3H), 4.35-4.17 (m, 2H), 4.00-3.83 (m, 3H), 3.73-3.60 (m, 1H), 3.55-3.40 (m, 2H), 3.15 (td, J=1.6, 3.2 Hz, 1H), 2.77-2.62 (m, 2H), 2.51-2.35 (m, 2H), 2.33-2.23 (m, 3H), 2.21-2.06 (m, 5H), 0.81 (t, J=7.4 Hz, 3H) ppm. Peak-2 (23-2) eluted at retention time=14.51 min. (41, 43.4% yield); LCMS (ESI) m/z: 639.2 $[M+H]^+$; $^1H$ NMR (400 MHz, $CD_3OD$, 298 K) δ: 8.05-7.97 (m, 1H), 7.71 (dd, J=5.9, 9.1 Hz, 1H), 7.36-7.19 (m, 2H), 6.92 (d, J=2.6 Hz, 1H), 5.61-5.39 (m, 1H), 4.82-4.63 (m, 3H), 4.35-4.17 (m, 2H), 4.00-3.83 (m, 3H), 3.73-3.60 (m, 1H), 3.55-3.40 (m, 2H), 3.15 (td, J=1.6, 3.2 Hz, 1H), 2.77-2.62 (m, 2H), 2.51-2.35 (m, 2H), 2.33-2.23 (m, 3H), 2.21-2.06 (m, 5H), 0.81 (t, J=7.4 Hz, 3H) ppm.

Examples 24-1 and 24-2

4-(2-{[(2R,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-fluoronaphthalen-2-ol

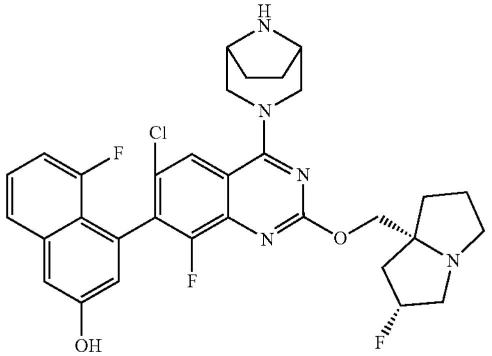

24-1 (Isomer 1)
24-2 (Isomer 2)

Preparation of Intermediate 24A: tert-butyl-3-(6-chloro-8-fluoro-7-(8-fluoro-3-(methoxymethoxy)naphthalen-1-yl)-2-(((2R,7aR)-2-fluorotetrahydro-1H-pyrrolizin-7a(5H)-yl)methoxy)quinazolin-4-yl)-3,8-diazabicyclo[3.2.1]octane-8-carboxylate

24A

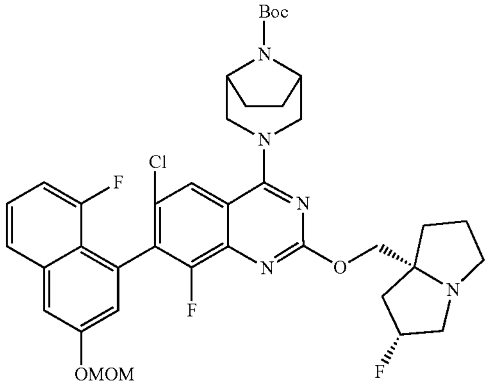

To a degassed solution of tert-butyl-3-(7-bromo-6-chloro-8-fluoro-2-(((2R,7aR)-2-fluorotetrahydro-1H-pyrrolizin-7a(5H)-yl)methoxy)quinazolin-4-yl)-3,8-diazabicyclo[3.2.1]octane-8-carboxylate (400 mg, 0.636 mmol) in 1,4-dioxane (7 mL) was added 2-(8-fluoro-3-(methoxymethoxy)naphthalen-1-yl)-4,4,5,5-tetramethyl-1,3,2-dioxaborolane (423 mg, 1.272 mmol), cesium carbonate (414 mg, 1.272 mmol) and SPhosPd-G3 (49.6 mg, 0.064 mmol). The mixture was degassed again and heated in a pressure vial at 70° C. for 16 hours. The reaction vessel was allowed to cool to ambient temperature, diluted with ethyl acetate, filtered and concentrated under vacuum to obtain the crude residue. The crude residue was by purified by reverse phase HPLC purification [Column: YMC C18 Phenyl (250×21) mm, 5 micron, Mobile Phase A=10 mM Ammonium acetate in water, Mobile Phase B=Acetonitrile, Flow:/15 min, mobile phase-A=grade-70-30%, mobile phase-B grade-30-70% 20 min]. The fractions from reverse phase HPLC were pooled together and lyophilized to obtain the tert-butyl-3-(6-chloro-8-fluoro-7-(8-fluoro-3-(methoxymethoxy)naphthalen-1-yl)-2-(((2R,7aR)-2-fluorotetrahydro-1H-pyrrolizin-7a(5H)-yl)methoxy)quinazolin-4-yl)-3,8-diazabicyclo[3.2.1]octane-8-carboxylate (120 mg, 0.107 mmol, 16.84% yield) as a pale brown solid. LCMS (ESI) m/z: 754.2 $[M+H]^+$.

Examples 25-1 and 25-2

6-(2-{[(7aR)-2,2-difluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine

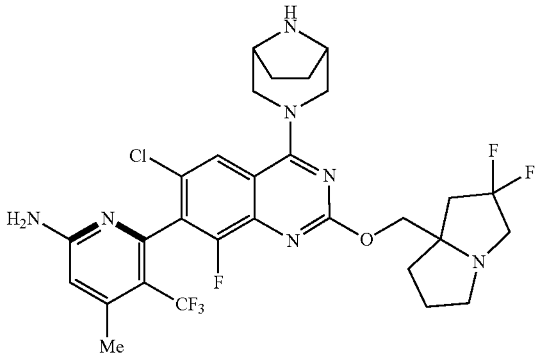

25-1 (Isomer 1)
25-2 (Isomer 2)

Preparation of Intermediate 25A: 1-(tert-butyl) 2-methyl-(S)-4,4-difluoropyrrolidine-1,2-dicarboxylate

25A

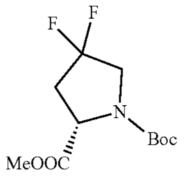

To a stirred solution of 1-(tert-butyl) 2-methyl (S)-4-oxopyrrolidine-1,2-dicarboxylate (30.0 g, 123 mmol) in DCM (20.0 mL) was added DAST (81 mL, 617 mmol) at 0° C. The reaction mixture was stirred at ambient temperature for 16 h. The reaction mixture was quenched with water and extracted with dichloromethane. The combined organic layers were washed with water and saturated brine solution, dried over anhydrous $Na_2SO_4$, filtered, and concentrated under reduced pressure to afford the crude product. The crude product obtained was purified by column chromatography (Grace, 340 g snap, dry pack) over silica (230-400 mesh) eluting with 20-50% ethyl acetate in petroleum ether. The desired fractions were pooled and concentrated under reduced pressure to obtain 1-(tert-butyl) 2-methyl (S)-4,4-difluoropyrrolidine-1,2-dicarboxylate (28 g, 90 mmol, 73.4% yield) as a pale brown liquid. LCMS-ELSD (ESI) m/z: 166.2 $[M+H-Boc]^+$.

Preparation of Intermediate 25B: 1-(tert-butyl) 2-methyl-2-(3-((tert-butyldimethylsilyl)oxy)propyl)-4,4-difluoropyrrolidine-1,2-dicarboxylate

25B

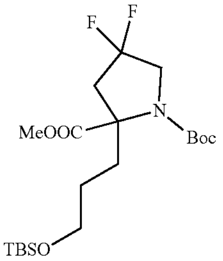

To a stirred solution of 1-(tert-butyl)-2-methyl (S)-4,4-difluoropyrrolidine-1,2-dicarboxylate (28 g, 106 mmol) in THF (300.0 mL) was added LiHMDS (158 mL, 158 mmol) at −45° C. dropwise. The reaction mixture was stirred at the same temperature for 30 min prior to the dropwise addition of 3-bromopropoxy)(tert-butyl)dimethylsilane (40.1 g, 158 mmol). The reaction mixture was stirred at the same temperature for 30 min and then slowly warmed to room temperature. The reaction mixture was quenched with saturated aq. ammonium chloride solution (15 mL) and then diluted with water (50 mL). The mixture was extracted with ethyl acetate (3×100 mL). The combined organic layers were dried over anhydrous $Na_2SO_4$, filtered and concentrated reduced pressure. The residue was purified by silica gel column chromatography with 20-30% of ethyl acetate in petroleum ether to obtain the 1-(tert-butyl) 2-methyl-2-(3-((tert-butyldimethylsilyl)oxy)propyl)-4,4-difluoropyrrolidine-1,2-dicarboxylate (35 g, 80 mmol, 76% yield) as a pale brown liquid. LCMS-ELSD (ESI) m/z: 388.2 $[M+H-Boc]^+$.

Preparation of Intermediate 25C: 1-(tert-butyl) 2-methyl-4,4-difluoro-2-(3-hydroxypropyl)pyrrolidine-1,2-dicarboxylate

25C

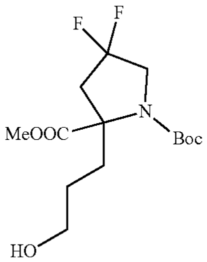

To a stirred solution of 1-(tert-butyl) 2-methyl-2-(3-((tert-butyldimethylsilyl)oxy)propyl)-4,4-difluoropyrrolidine-1,2-dicarboxylate (35.0 g, 80 mmol) in THE (50 mL) at 25° C. was added TBAF (1M in THF, 80 mL, 80 mmol) dropwise, and stirred at the same temperature for 4 h. The reaction mixture was quenched with saturated aq. ammonium chloride solution (90 mL) and diluted with ethyl acetate (100 mL). The mixture was extracted with ethyl acetate (3×150 mL). The combined organic layers were dried over anhydrous sodium sulphate, filtered, and concentrated reduced pressure to obtain the crude residue as a colorless oil. The crude was purified by silica gel column chromatography using 50% ethyl acetate in petroleum ether to obtain 1-(tert-butyl) 2-methyl-4,4-difluoro-2-(3-hydroxypropyl)pyrrolidine-1,2-dicarboxylate (20 g, 57.9 mmol, 72.4% yield) as a pale brown liquid. LCMS-ELSD (ESI) m/z: 224.2 [M+H-Boc]$^+$.

Preparation of Intermediate 25D: 1-(tert-butyl) 2-methyl-4,4-difluoro-2-(3-iodopropyl)pyrrolidine-1,2-dicarboxylate

25D

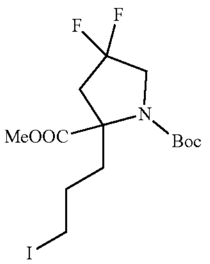

To a stirred solution of 1-(tert-butyl) 2-methyl-4,4-difluoro-2-(3-hydroxypropyl)pyrrolidine-1,2-dicarboxylate (20 g, 61.9 mmol) in DCM (100 mL) at 0° C. was added triphenylphosphine (48.7 g, 186 mmol), and imidazole (8.42 g, 124 mmol) and reaction mixture was stirred for 10 min before the addition of iodine (62.8 g, 247 mmol). The reaction mixture was stirred at room temperature for 12 h and then quenched with sat. aq. sodium thiosulfate solution (30 mL). The suspension was extracted with dichloromethane (2×200 mL). The combined organic layers were dried over anhydrous sodium sulphate, filtered, and concentrated reduced pressure to obtain the crude residue. This crude was purified by silica gel column chromatography using 10-20% ethyl acetate in petroleum ether to obtain 1-(tert-butyl) 2-methyl-4,4-difluoro-2-(3-iodopropyl)pyrrolidine-1,2-dicarboxylate (20 g, 46.1 mmol, 75% yield) as colourless oil. LCMS-ELSD (ESI) m/z: 333.0 [M+H-Boc]$^+$.

Preparation of Intermediate 25E: methyl-4,4-difluoro-2-(3-iodopropyl)pyrrolidine-2-carboxylate

25E

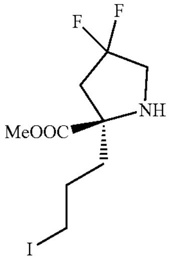

To a stirred solution of 1-(tert-butyl) 2-methyl-4,4-difluoro-2-(3-iodopropyl)pyrrolidine-1,2-dicarboxylate (15 g, 34.6 mmol) in DCM (100 mL) was added HCl in 1,4-dioxane (4M, 8.66 mL, 34.6 mmol) at 0° C. The reaction mixture was stirred at ambient temperature for 16 h. The reaction mixture was then concentrated reduced pressure at room temperature to obtain the crude residue of methyl (S)-4,4-difluoro-2-(3-iodopropyl)pyrrolidine-2-carboxylate·HCl (11.5 g, 31.1 mmol, 90% yield), which was used in the next step without any further purification. LCMS-ELSD (ESI) m/z: 334.1 [M+H]$^+$.

Preparation of Intermediate 25F: methyl 2,2-difluorotetrahydro-1H-pyrrolizine-7a(5H)-carboxylate

25F

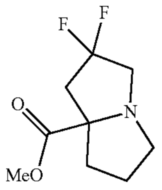

To a stirred solution of methyl-4,4-difluoro-2-(3-hydroxypropyl)pyrrolidine-2-carboxylate·HCl (11.5 g, 51.5 mmol) in THE (120.0 mL) was added TEA (35.9 mL, 258 mmol) at 0° C. followed by heating at 45° C. for 16 h. The reaction mixture was concentrated reduced pressure to obtain the crude residue which was purified by column chromatography (alumina-neutral) using 40-50% ethyl acetate in petroleum ether to obtain the methyl 2,2-difluorotetrahydro-1H-pyrrolizine-7a(5H)-carboxylate (6 g, 43.5 mmol, 81% yield) as a brown liquid.

Preparation of Intermediate 25G: (2,2-difluorotetrahydro-1H-pyrrolizin-7a(5H)-yl)methanol

25G

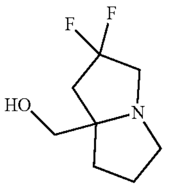

To a stirred solution of methyl 2,2-difluorotetrahydro-1H-pyrrolizine-7a(5H)-carboxylate (12.0 g, 58.5 mmol) in anhydrous THE (20.0 mL) under nitrogen at 0° C. was added $LiAlH_4$ (117 mL, 117 mmol) dropwise over 10 min. The mixture was stirred at this temperature for 1 h before quenching with saturated aq. ammonium chloride (5 mL) at 0° C. Once the effervescence had ceased, anhydrous sodium sulphate was added to the reaction mixture, followed by dichloromethane (20 mL). The reaction mixture was stirred for 20 min and filtered. The filtrate was dried over anhydrous sodium sulphate, filtered, and concentrated reduced pressure to obtain the crude residue of (2,2-difluorotetrahydro-1H-pyrrolizin-7a(5H)-yl)methanol (4.1 g, 23.02 mmol, 39.4% yield) as a pale yellow liquid. LCMS-ELSD (ESI) m/z: 178.1 [M+H]$^+$.

Preparation of Intermediate 25H: tert-butyl 3-(7-(6-(bis(4-methoxybenzyl)amino)-4-methyl-3-(trifluoromethyl)pyridin-2-yl)-6-chloro-2-((2,2-difluorotetrahydro-1H-pyrrolizin-7a(5H)-yl)methoxy)-8-fluoroquinazolin-4-yl)-3,8-diazabicyclo[3.2.1]octane-8-carboxylate

25H

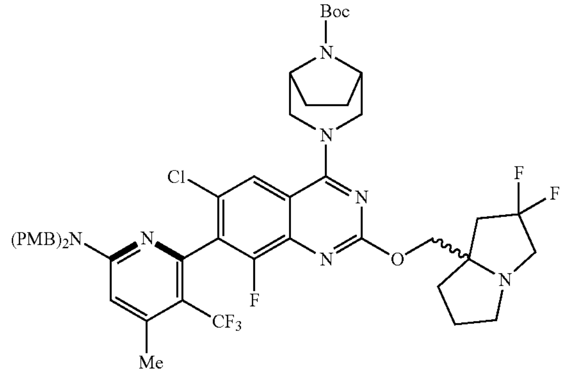

To a stirred solution (2,2-difluorotetrahydro-1H-pyrrolizin-7a(5H)-yl)methanol (rac) (129 mg, 0.727 mmol) in THE (10 mL) at 0° C. was added NaH (60% dispersion in mineral oil, 29.1 mg, 0.727 mmol) and the reaction mixture was stirred for 30 min. and then tert-butyl-3-(7-(6-(bis(4-methoxybenzyl)amino)-4-methyl-3-(trifluoromethyl)pyridin-2-yl)-6-chloro-2,8-difluoroquinazolin-4-yl)-3,8-diazabicyclo[3.2.1]octane-8-carboxylate (Intermediate 141, 300 mg, 0.364 mmol) dissolved in THE was added dropwise. The reaction mixture was stirred at ambient temperature for 3 h. The reaction mixture was quenched with saturated ammonium chloride solution (10 mL) and extracted with ethyl acetate (2×20 mL). The combined organic layers were washed with water and saturated brine solution, dried over anhydrous $Na_2SO_4$, filtered and concentrated under reduced pressure to afford the crude product. The crude was purified by column chromatography (Grace, 50 g snap, dry pack) over neutral alumina using 50-100% of ethyl acetate in petroleum ether. The desired fractions were pooled and concentrated under reduced pressure to obtain tert-butyl 3-(7-(6-(bis(4-methoxybenzyl)amino)-4-methyl-3-(trifluoromethyl)pyridin-2-yl)-6-chloro-2-((2,2-difluorotetrahydro-1H-pyrrolizin-7a(5H)-yl)methoxy)-8-fluoroquinazolin-4-yl)-3,8-diazabicyclo[3.2.1]octane-8-carboxylate (300 mg, 0.305 mmol, 84% yield) as a pale yellow solid. LCMS (ESI) m/z: 982.2 [M+H].

Examples 25-1 and 25-2

6-(2-{[(7aR)-2,2-difluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine

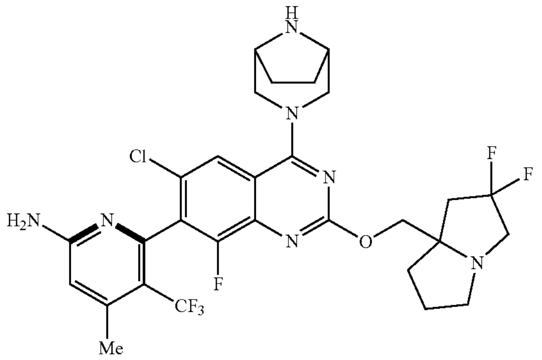

25-1 (Isomer 1)
25-2 (Isomer 2)

To a stirred solution of tert-butyl 3-(7-(6-(bis(4-methoxybenzyl)amino)-4-methyl-3-(trifluoromethyl)pyridin-2-yl)-6-chloro-2-((2,2-difluorotetrahydro-1H-pyrrolizin-7a(5H)-yl)methoxy)-8-fluoroquinazolin-4-yl)-3,8-diazabicyclo[3.2.1]octane-8-carboxylate (300 mg, 0.305 mmol) in TFA (1.5 mL) was added water (0.05 mL, 2.78 mmol) and triethylsilane (0.979 μl, 6.13 μmol). The reaction was allowed to stir at 40° C. for 16h. Then the reaction mixture was concentrated reduced pressure to obtain the crude residue which was purified by column chromatography (Biotage, sfar KP-amino), eluted with 100% ethyl acetate in petroleum ether to provide 6-(4-(3,8-diazabicyclo[3.2.1]octan-3-yl)-6-chloro-2-((2,2-difluorotetrahydro-1H-pyrrolizin-7a(5H)-yl)methoxy)-8-fluoroquinazolin-7-yl)-4-methyl-5-(trifluoromethyl)pyridin-2-amine (110 mg). The obtained product was subjected to SFC separation (Cellulose-4(250 mm×4.6×5u)_0.2% Ammonia in Methanol Run Time: 20.00 Flowrate: 3.0000 mL/min), where Peak-1, eluted at retention time=14.352 min (28 mg, 0.040 mmol, 13.00% yield); LCMS (ESI) m/z: 642.1 $[M+H]^+$; $^1H$ NMR (400 MHz, $CD_3OD$) δ: 7.85 (d, J=1.6 Hz, 1H), 6.69 (s, 1H), 4.50-4.43 (m, 2H), 4.27 (s, 2H), 3.65-3.60 (m, 4H), 3.50-3.59 (m, 2H), 3.33-3.32 (m, 2H), 3.18-3.12 (m, 1H), 2.87 (q, J=7.6 HZ, 1H), 2.46 (s, 3H), 2.35 (q, J=7.9 Hz, 1H), 2.35-2.32 (m, 1H), 1.92-1.79 (m, 7H) ppm. Peak-2 eluted at retention time=16.033 min. (27 mg, 0.039 mmol, 12.81% yield); LCMS (ESI) m/z: 642.1 $[M+H]^+$; $^1H$ NMR (400 MHz, $CD_3OD$) δ: 7.85 (d, J=1.6 Hz, 1H), 6.69 (s, 1H), 4.50-4.43 (m, 2H), 4.27 (s, 2H), 3.65-3.60 (m, 4H), 3.50-3.59 (m, 2H), 3.33-3.32 (m, 2H), 3.18-3.12 (m, 1H), 2.87 (q, J=7.6 HZ, 1H), 2.46 (s, 3H), 2.35 (q, J=7.9 Hz, 1H), 2.35-2.32 (m, 1H), 1.92-1.79 (m, 7H) ppm.

Examples 26-1 and 26-2

6-{2-[(1S)-1-[(2R,7aR)-2-fluoro-hexahydro-1H-pyrrolizin-7a-yl]ethoxy]-6-chloro-4-{3,8-diazabicyclo[3.2.1]octan-3-yl}-8-fluoroquinazolin-7-yl}-4-methyl-5-(trifluoromethyl)pyridin-2-amine

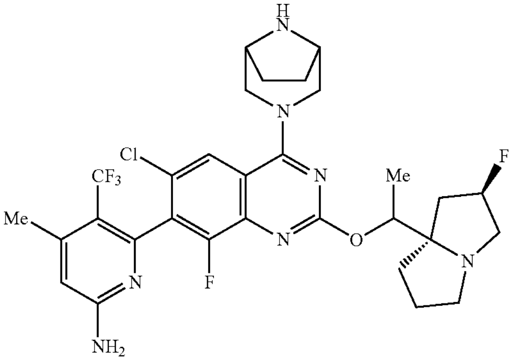

26-1 (Isomer 1)
26-2 (Isomer 2)

Preparation of Intermediate 26A: 1-(tert-butyl) 2-methyl (2R,4R)-2-(3-((tert-butyldimethylsilyl)oxy)propyl)-4-fluoropyrrolidine-1,2-dicarboxylate

26A

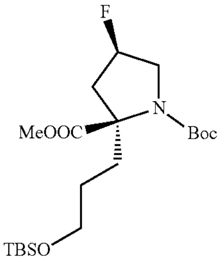

To a stirred solution of 1-(tert-butyl) 2-methyl (2S,4R)-4-fluoropyrrolidine-1,2-dicarboxylate (5.00 g, 20.22 mmol) in anhydrous THE (30 mL) under nitrogen atmosphere at −25° C. was added LiHMDS (1M in THF, 30.3 mL, 30.3 mmol) dropwise. The reaction mixture was stirred at the same temperature for the next 30 min prior to the dropwise addition of (3-bromopropoxy)(tert-butyl)dimethylsilane (7.68 g, 30.3 mmol). The mixture was then stirred at the same temperature for 30 min and then slowly warmed to room temperature. The reaction was quenched with saturated aq. ammonium chloride solution (15 mL) and then diluted with water (50 mL). The suspension was extracted with ethyl acetate (3×100 mL). The combined organic layers were dried over anhydrous $Na_2SO_4$, filtered and concentrated reduced pressure. The residue was purified by silica gel column chromatography with 20-30% of ethyl acetate in petroleum ether to obtain the 1-(tert-butyl) 2-methyl (2R, 4R)-2-(3-((tert-butyldimethylsilyl)oxy)propyl)-4-fluoropyrrolidine-1,2-dicarboxylate (7.23 g, 17.24 mmol, 85% yield) as colorless oil. $^1H$ NMR (400 MHz, $CDCl_3$): δ 5.18-5.03 (m, 1H), 4.10-3.98 (m, 1H), 3.78 (s, 3H), 3.74-3.52 (m, 3H), 2.48-2.23 (m, 3H), 2.19-1.98 (m, 1H), 1.65 (s, 9H), 1.48-1.44 (m, 2H), 0.90 (s, 9H), 0.60 (s, 6H) ppm. $^{19}F$ (376 MHz, $CD_3OD$): δ −172.47 to −172.96 (m) ppm. LCMS-ELSD (ESI) m/z: 320.2 $[M+H-Boc]^+$.

Preparation of Intermediate 26B: 1-(tert-butyl) 2-methyl (2R,4R)-4-fluoro-2-(3-hydroxypropyl) pyrrolidine-1,2-dicarboxylate

26B

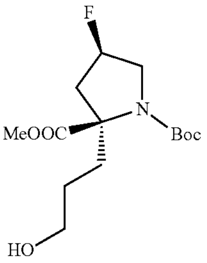

To a stirred solution of 1-(tert-butyl) 2-methyl (2R,4R)-2-(3-((tert-butyldimethylsilyl)oxy)propyl)-4-fluoropyrrolidine-1,2-dicarboxylate (7.00 g, 16.68 mmol) at 25° C. was added TBAF (1M in THF, 16.68 mL, 16.68 mmol) dropwise, and stirred at the same temperature for 4 h. The reaction mixture was quenched with saturated aq. ammonium chloride solution (90 mL) and diluted with ethyl acetate (100 mL). The mixture was extracted with ethyl acetate (3×150 mL). The combined organic layers were dried over anhydrous sodium sulphate, filtered, and concentrated under a vacuum to obtain the crude residue as colorless oil. The crude was purified by silica gel column chromatography using 50% ethyl acetate in petroleum ether to obtain 1-(tert-butyl) 2-methyl (2R,4R)-4-fluoro-2-(3-hydroxypropyl)pyrrolidine-1,2-dicarboxylate (4.97 g, 15.64 mmol, 94% yield) as colorless oil. LCMS-ELSD (ESI) m/z: 206.2 $[M+H-Boc]^+$.

Preparation of Intermediate 26C: 1-(tert-butyl) 2-methyl (2R,4R)-4-fluoro-2-(3-iodopropyl)pyrrolidine-1,2-dicarboxylate

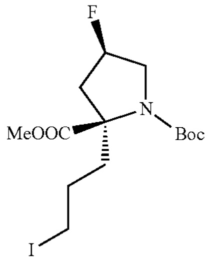

To a stirred solution of 1-(tert-butyl) 2-methyl (2R,4R)-4-fluoro-2-(3-hydroxypropyl)pyrrolidine-1,2-dicarboxylate (9.00 g, 29.5 mmol) at 0° C. was added triphenylphosphine (15.50 g, 58.9 mmol), and imidazole (6.02 g, 88 mmol) and reaction mixture was stirred at same temperature for 10 min before addition of iodine (29.9 g, 118 mmol). After stirring at room temperature for 12 h, the reaction mixture was quenched with sat. aq. sodium thiosulfate solution (30 mL) and the suspension was extracted with dichloromethane (2×200 mL). The combined organic layers were dried over anhydrous sodium sulphate, filtered, and concentrated reduced pressure to obtain the crude residue. This crude was purified by silica gel column chromatography using 10-20% ethyl acetate in petroleum ether to obtain 1-(tert-butyl) 2-methyl (2R,4R)-4-fluoro-2-(3-iodopropyl)pyrrolidine-1,2-dicarboxylate (10.10 g, 24.32 mmol, 83% yield) as colourless oil. LCMS-ELSD (ESI) m/z: 361.2 [M+H-Boc]$^+$.

Preparation of Intermediate 26D: tert-butyl 3-(6-chloro-8-fluoro-7-(3-hydroxynaphthalen-1-yl)-2-(((R)-1-(piperidin-1-yl)propan-2-yl)oxy)quinazolin-4-yl)-3,8-diazabicyclo[3.2.1]octane-8-carboxylate

26D

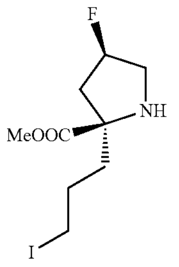

To a stirred solution of 1-(tert-butyl) 2-methyl (2R,4R)-4-fluoro-2-(3-iodopropyl)pyrrolidine-1,2-dicarboxylate (10.0 g, 24.08 mmol) in dichloromethane (20 mL) at 25° C. was added HCl in dioxane (8.03 mL, 24.08 mmol) and reaction mixture was stirred for 6 h at the same temperature. The reaction mixture was concentrated reduced pressure at room temperature to obtain the crude residue of methyl (2R,4R)-4-fluoro-2-(3-iodopropyl)pyrrolidine-2-carboxylate·HCl (6.5 g, 20.63 mmol, 86% yield) was used for the next step without any further purification. LCMS-ELSD (ESI) m/z: 188.2 [M+H]$^+$.

Preparation of Intermediate 26E: methyl (2R,7aR)-2-fluorotetrahydro-1H-pyrrolizine-7a(5H)-carboxylate

26E

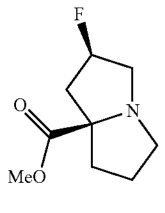

To a stirred solution of methyl (2R,4R)-4-fluoro-2-(3-iodopropyl)pyrrolidine-2-carboxylate (6.5 g, 20.63 mmol) in anhydrous acetonitrile (30 mL) was added triethylamine (10 mL) at room temperature. After stirring for 12 h at 45° C. the reaction mixture was concentrated reduced pressure to obtain the crude residue. The residue was purified by column chromatography (alumina-neutral) using 40-50% ethyl acetate in petroleum ether to obtain the methyl (2R,7aR)-2-fluorotetrahydro-1H-pyrrolizine-7a(5H)-carboxylate (3.20 g, 83% yield) as pale-yellow oil. 1H NMR (400 MHz, DMSO-$d_6$): δ 5.76-5.19 (m, 1H), 3.59 (s, 3H), 3.25-3.16 (m, 1H), 2.97-2.95 (m, 1H), 2.86-2.76 (m, 1H), 2.68-2.51 (m, 2H), 2.02-1.91 (m, 2H), 1.85-1.72 (m, 3H) ppm. LCMS-ELSD (ESI) m/z: 188.3 [M+H]$^+$.

Preparation of Intermediate 26F: ((2R,7aR)-2-fluorotetrahydro-1H-pyrrolizin-7a(5H)-yl)methanol

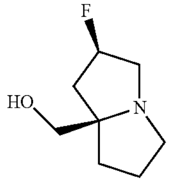 [SMILES: OC[C@]12CCCN1C[C@H](F)C2]

To a stirred solution of methyl (2R,7aR)-2-fluorotetrahydro-1H-pyrrolizine-7a(5H)-carboxylate (3.20 g, 17.09 mmol) under nitrogen at 0° C. was added $LiAlH_4$ (2M in THF, 17.09 mL, 34.2 mmol) dropwise over 10 min. After addition, the reaction mixture was warmed to room temperature in 30 min. The mixture was stirred at this temperature for 1 h before being quenched with saturated aq. ammonium chloride (5 mL) at 0° C. Once the effervescences were stopped, anhydrous sodium sulphate was added to the reaction mixture, followed by dichloromethane (20 mL). The reaction mixture was stirred for 20 min and filtered. The filtrate was collected, dried over anhydrous sodium sulphate, filtered, and concentrated reduced pressure to obtain the crude residue of ((2R,7aR)-2-fluorotetrahydro-1H-pyrrolizin-7a(5H)-yl)methanol (2.20 g, 13.68 mmol, 80% yield) as a pale brown oil. $^1$H NMR (400 MHz, $CD_3OD$): δ 5.34-5.10 (m, 1H), 3.51-3.29 (m, 3H), 3.25-3.10 (m, 1H), 3.04-2.93 (m, 1H), 2.90-2.73 (m, 1H), 2.71-2.59 (m, 1H), 2.28-2.12 (m, 1H), 1.95-1.73 (m, 4H), 1.68-1.66 (m, 1H) ppm. $^{19}$F (376 MHz, $CD_3OD$): δ −175.69 to −176.04 (m) ppm. LCMS-ELSD (ESI) m/z: 160.0 [M+H]$^+$.

Preparation of Intermediate 26G: (2R,7aR)-2-fluorotetrahydro-1H-pyrrolizine-7a(5H)-carbaldehyde

26G

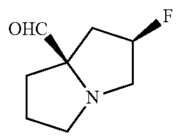

To a stirred solution of ((2R,7aR)-2-fluorotetrahydro-1H-pyrrolizin-7a(5H)-yl)methanol (100 mg, 0.628 mmol) in anhydrous DCM (3 mL) was added Dess-Martin periodinane (533 mg, 1.256 mmol) and reaction mixture was stirred at room temperature for 6 h. After 6 h, reaction mixture was carefully quenched with a saturated aqueous solution of $NaHCO_3$ and solid $Na_2S_2O_3$ followed by dilution with DCM (30 mL×3). The combined organic layers were washed with brine, dried over $MgSO_4$, filtered, and concentrated reduced pressure to obtain the crude residue. The crude residue was purified by neutral alumina column chromatography eluting with 100% ethyl acetate in petroleum ether to obtain the require product (2R,7aR)-2-fluorotetrahydro-1H-pyrrolizine-7a(5H)-carbaldehyde (50 mg, 0.318 mmol, 51% yield) as pale yellow oil.

Preparation of Intermediate 26H: 1-((2R,7aR)-2-fluorotetrahydro-1H-pyrrolizin-7a(5H)-yl)ethan-1-ol

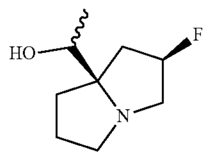

To a stirred solution of (2R,7aR)-2-fluorotetrahydro-1H-pyrrolizine-7a(5H)-carbaldehyde (250 mg, 1.590 mmol) in anhydrous THF (10 mL) was added methylmagnesium bromide (2M in THF, 2.386 mL, 4.77 mmol)dropwise at 0° C. The reaction mixture was stirred at the same temperature for 30 min and then at room temperature overnight. The reaction mixture was carefully quenched with aq. ammonium chloride (1 mL) and diluted with DCM (20 mL). Anhydrous sodium sulphate was added to the reaction mixture and stirred for 10 min. The suspension was filtered and concentrated reduced pressure to obtain the crude residue of 1-((2R,7aR)-2-fluorotetrahydro-1H-pyrrolizin-7a(5H)-yl)ethan-1-ol (256 mg, 1.478 mmol, 93% yield) which was used as such for the next step without any further purification.

Preparation of Intermediate 261: tert-butyl-3-(7-(6-(bis(4-methoxybenzyl)amino)-4-methyl-3-(trifluoromethyl)pyridin-2-yl)-6-chloro-8-fluoro-2-(1-((2R,7aR)-2-fluorotetrahydro-1H-pyrrolizin-7a(5H)-yl)ethoxy)quinazolin-4-yl)-3,8-diazabicyclo[3.2.1]octane-8-carboxylate

26I

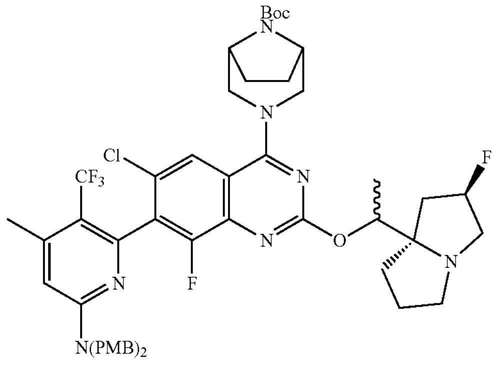

To a stirred solution 1-((2R,7aR)-2-fluorotetrahydro-1H-pyrrolizin-7a(5H)-yl)ethan-1-ol (31.5 mg, 0.182 mmol) in THE (5 mL) at 0° C. was added NaH (60% dispersion in mineral oil, 7.27 mg, 0.182 mmol) reaction mixture was stirred for 30 min. and then tert-butyl-3-(7-(6-(bis(4-methoxybenzyl)amino)-4-methyl-3-(trifluoromethyl)pyridin-2-yl)-6-chloro-2,8-difluoroquinazolin-4-yl)-3,8-diazabicyclo[3.2.1]octane-8-carboxylate (Intermediate 141, 100 mg, 0.121 mmol) dissolved in THE (2 mL) was added dropwise. The reaction mixture was stirred at ambient temperature for 3 h. The reaction mixture was quenched with saturated ammonium chloride solution (10 mL) and extracted with ethyl acetate (2×20 mL). The combined organic layers were washed with water and saturated brine solution, dried over anhydrous $Na_2SO_4$, filtered and concentrated under reduced pressure to afford crude product. The crude was purified by column chromatography (Grace, 50 g snap, dry pack) over neutral alumina using 50-100% of ethyl acetate in petroleum ether. The desired fractions were pooled and concentrated under reduced pressure to obtain tert-butyl-3-(7-(6-(bis(4-methoxybenzyl)amino)-4-methyl-3-(trifluoromethyl)pyridin-2-yl)-6-chloro-8-fluoro-2-(1-((2R,7aR)-2-fluorotetrahydro-1H-pyrrolizin-7a(5H)-yl)ethoxy)quinazolin-4-yl)-3,8-diazabicyclo[3.2.1]octane-8-carboxylate (65 mg, 0.066 mmol, 55% yield) as a pale yellow solid. LCMS (ESI) m/z: 978.0 $[M+H]^+$.

Examples 26-1 and 26-2

6-{2-[(1S)-1-[(2R,7aR)-2-fluoro-hexahydro-1H-pyrrolizin-7a-yl]ethoxy]-6-chloro-4-{3,8-diazabicyclo[3.2.1]octan-3-yl}-8-fluoroquinazolin-7-yl}-4-methyl-5-(trifluoromethyl)pyridin-2-amine

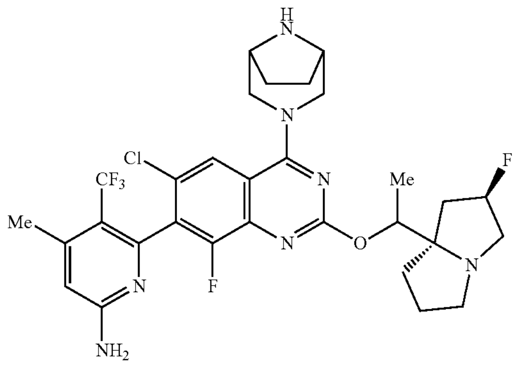

26-1 (Isomer 1)
26-2 (Isomer 2)

To a stirred solution of tert-butyl-3-(7-(6-(bis(4-methoxybenzyl)amino)-4-methyl-3-(trifluoromethyl)pyridin-2-yl)-6-chloro-8-fluoro-2-(1-(−2-fluorotetrahydro-1H-pyrrolizin-7a(5H)-yl)ethoxy)quinazolin-4-yl)-3,8-diazabicyclo[3.2.1]octane-8-carboxylate (76 mg, 0.078 mmol) in TFA (59.8 μl, 0.777 mmol) was added water (0.05 mL, 2.78 mmol) and triethylsilane (35.4 mg, 0.311 mmol). The reaction was allowed to stir at 40° C. for 16h. Then the reaction mixture was concentrated reduced pressure to obtain the crude residue which was purified by column chromatography (Biotage, sfar KP-amino), eluted with 100% ethyl acetate in petroleum ether to provide 6-(4-(3,8-diazabicyclo[3.2.1]octan-3-yl)-6-chloro-8-fluoro-2-(−1-((2R,7aR)-2-fluorotetrahydro-1H-pyrrolizin-7a(5H)-yl)ethoxy)quinazolin-7-yl)-4-methyl-5-(trifluoromethyl)pyridin-2-amine (87 mg). The obtained product was subjected to SFC separation (Cellulose-4(250 mm×4.6×5u)_0.2% Ammonia in Methanol Run Time: 20.00 Flowrate: 3.0000 mL/min), where Peak-1 (26-1), eluted at retention time=16.00 min. (12 mg, 0.015 mmol, 20% yield); LCMS (ESI) m/z: 638.1 $[M+H]^+$; $^1H$ NMR (400 MHz, $CD_3OD$) δ: 8.01-7.80 (m, 1H), 6.65 (s, 1H), 5.65-5.33 (m, 2H), 4.77-4.52 (m, 3H), 4.26 (br s, 2H), 4.06-3.95 (m, 1H), 3.93-3.81 (m, 2H), 3.64 (dt, J=6.1, 11.9 Hz, 1H), 3.57-3.40 (m, 2H), 3.15 (td, J=1.6, 3.3 Hz, 1H), 2.90-2.77 (m, 1H), 2.68 (s, 3H), 2.65-2.57 (m, 1H), 2.47 (d, J=1.3 Hz, 2H), 2.39-2.23 (m, 3H), 2.22-2.06 (m, 3H), 1.59 (d, J=6.1

Hz, 3H) ppm. Peak-2 (26-2) at eluted at retention time=9.262 min. (10 mg, 0.012 mmol, 15.58% yield); LCMS (ESI) m/z: 638.1 $[M+H]^+$; $^1H$ NMR (400 MHz, $CD_3OD$, 296 K) δ: 8.01-7.80 (m, 1H), 6.65 (s, 1H), 5.65-5.33 (m, 2H), 4.77-4.52 (m, 3H), 4.26 (br s, 2H), 4.06-3.95 (m, 1H), 3.93-3.81 (m, 2H), 3.64 (dt, J=6.1, 11.9 Hz, 1H), 3.57-3.40 (m, 2H), 3.15 (td, J=1.6, 3.3 Hz, 1H), 2.90-2.77 (m, 1H), 2.68 (s, 3H), 2.65-2.57 (m, 1H), 2.47 (d, J=1.3 Hz, 2H), 2.39-2.23 (m, 3H), 2.22-2.06 (m, 3H), 1.59 (d, J=6.1 Hz, 3H) ppm.

Example 27

6-(2-{[(2R,6R,7aR)-2-fluoro-6-methyl-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine

27

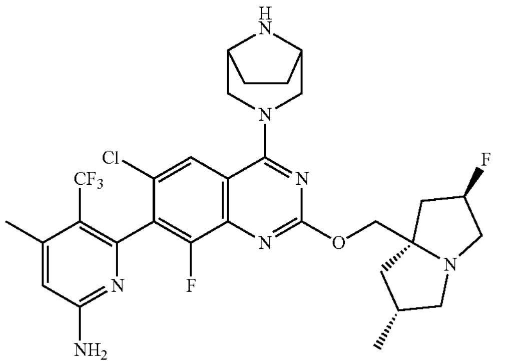

Preparation of Intermediate 27A: 1-(tert-butyl) 2-methyl (2R,4R)-2-(2-(chloromethyl)allyl)-4-fluoropyrrolidine-1,2-dicarboxylate

27A

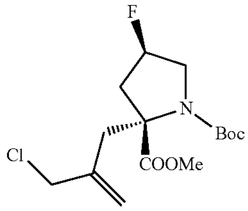

To a stirred solution of 1-(tert-butyl) 2-methyl (2S,4R)-4-fluoropyrrolidine-1,2-dicarboxylate (50 g, 202 mmol) in anhydrous THE (300.0 mL) at −45° C. under nitrogen atmosphere was added LiHMDS (1M THE solution, 303 mL, 303 mmol) dropwise over 30 min while maintaining the temperature at −45° C. After stirring at this temperature for 1h, a solution of 3-chloro-2-(chloromethyl)prop-1-ene (30.3 g, 243 mmol) in anhydrous THE (300.0 mL) was added dropwise. The reaction mixture was slowly warmed to room temperature over 2 h and stirred for 16 h. The reaction mixture was carefully quenched with saturated ammonium chloride solution (40 mL) and extracted with ethyl acetate (2×200 mL). The combined organic layers were washed with water and saturated brine solution, dried over anhydrous $Na_2SO_4$, filtered, and concentrated under reduced pressure to afford crude product. The crude residue was purified by column chromatography (Grace, 350 g snap, dry pack) over silica gel (230-400 mesh) by eluting with 10-30% ethyl acetate in petroleum ether. The desired fractions were pooled and concentrated under reduced pressure to obtain 1-(tert-butyl) 2-methyl (2R,4R)-2-(2-(chloromethyl)allyl)-4-fluoropyrrolidine-1,2-dicarboxylate (64 g, 91 mmol, 45% yield) as a colourless liquid. LCMS (ESI) m/z: 336.1 $[M+H]^+$.

Preparation of Intermediate 27B: methyl (2R,4R)-2-(2-(chloromethyl)allyl)-4-fluoropyrrolidine-2-carboxylate

27B

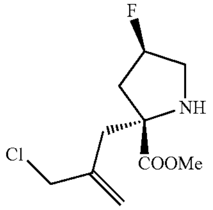

To a stirred solution of 1-(tert-butyl) 2-methyl (2R,4R)-2-(2-(chloromethyl)allyl)-4-fluoropyrrolidine-1,2-dicarboxylate (64 g, 191 mmol) in anhydrous DCM (600 mL) was added HCl solution (4.0 M in dioxane, 119 mL, 476 mmol) at 0° C. under nitrogen atmosphere. Reaction mixture was stirred at ambient temperature for 6 h followed by concentration under reduced pressure to obtain methyl (2R,4R)-2-(2-(chloromethyl)allyl)-4-fluoropyrrolidine-2-carboxylate, HCl (50 g, 180 mmol, 94% yield) as a pale brown solid. LCMS (ESI) m/z: 236.2 $[M+H]^+$.

Preparation of Intermediate 27C: methyl (2R,7aR)-2-fluoro-6-methylenetetrahydro-1H-pyrrolizine-7a(5H)-carboxylate

27C

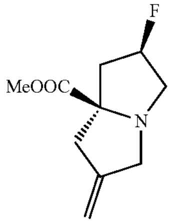

To a stirred solution of methyl (2R,4R)-2-(2-(chloromethyl)allyl)-4-fluoropyrrolidine-2-carboxylate (50 g, 212 mmol) in anhydrous acetonitrile (500 mL) was added. The reaction mixture was stirred at ambient temperature for 16 h. The reaction mixture was diluted with water (50 mL) and then basified with an aqueous bicarbonate solution (70 mL). The resulting solution was extracted with DCM (2×300 mL); combined organic layers were washed with saturated brine solution (50 mL), dried over anhydrous $Na_2SO_4$, filtered, and concentrated under reduced pressure to afford methyl (2R,7aR)-2-fluoro-6-methylenetetrahydro-1H-pyrrolizine-7a(5H)-carboxylate (35 g, 176 mmol, 83% yield) as a brown liquid. LCMS (ESI) m/z: 200.1 $[M+H]^+$.

Preparation of Intermediate 27E: methyl (2R,7aR)-2-fluoro-6-methyltetrahydro-1H-pyrrolizine-7a(5H)-carboxylate

27E

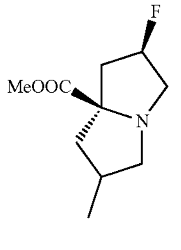

To a stirred solution of methyl (2R,7aR)-2-fluoro-6-methylenetetrahydro-1H-pyrrolizine-7a(5H)-carboxylate (2.0 g, 10.04 mmol) in methanol (10 mL) was added Pd/C (1.068 g, 10.04 mmol) at 25° C. The suspension was degassed reduced pressure and purged with H2 several times. The mixture was then stirred under H2 (1 Atm) at 25° C. for 5 hours. The suspension was filtered through Celite bed and washed with EtOAc (2×20 mL). The combined filtrate was concentrated under reduced pressure to afford methyl (2R,7aR)-2-fluoro-6-methyltetrahydro-1H-pyrrolizine-7a(5H)-carboxylate (2.0 g, 9.65 mmol, 96% yield) as a colorless liquid. LCMS (ESI) m/z: 202.2 $[M+H]^+$.

Preparation of Intermediate 27F: ((2R,7aR)-2-fluoro-6-methyltetrahydro-1H-pyrrolizin-7a(5H)-yl) methanol

27F

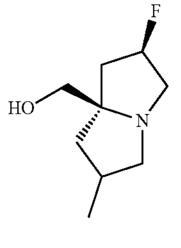

To a stirred solution of methyl ((2R,7aR)-2-fluoro-6-methyltetrahydro-1H-pyrrolizine-7a(5H)-carboxylate (2.0 g, 9.65 mmol) in anhydrous THE (20 mL) under nitrogen at 0° C. was added $LiAlH_4$ (2M in THF, 5.09 mL, 11.95 mmol) dropwise over 10 min. After addition, the reaction mixture was warmed to room temperature in 30 min. The mixture was stirred at this temperature for 1 h before being quenched with saturated aq. ammonium chloride (5 mL) at 0° C. Once the effervescence ceased, anhydrous sodium sulphate was added to the reaction mixture, followed by dichloromethane (20 mL). The suspension was stirred for 20 min and filtered. The filtrate was collected, dried over anhydrous sodium sulphate, filtered, and concentrated reduced pressure to obtain the crude residue of ((2R,7aR)-2-fluoro-6-methyltetrahydro-1H-pyrrolizin-7a(5H)-yl)methanol (1.3 g, 7.34 mmol, 76% yield) as pale brown oil. $^1H$ NMR (400 MHz, $CD_3OD$): δ 5.33-5.10 (m, 1H), 3.51-3.29 (m, 3H), 3.25-3.10 (m, 1H), 3.04-2.93 (m, 1H), 0.90-2.73 (m, 1H), 2.71-2.59 (m, 1H), 2.28-2.12 (m, 1H), 1.93-1.71 (m, 3H), 1.68-1.66 (m, 1H). 0.92 (d, J=6.4 Hz, 3H) ppm. LCMS-ELSD (ESI) m/z: 174.1 $[M+H]^+$.

Preparation of Intermediate 27G: tert-butyl-3-(7-(6-(bis(4-methoxybenzyl)amino)-4-methyl-3-(trifluoromethyl)pyridin-2-yl)-6-chloro-8-fluoro-2-(((2R,7aR)-2-fluoro-6-methyltetrahydro-1H-pyrrolizin-7a(5H)-yl)methoxy)quinazolin-4-yl)-3,8-diazabicyclo[3.2.1]octane-8-carboxylate

27G

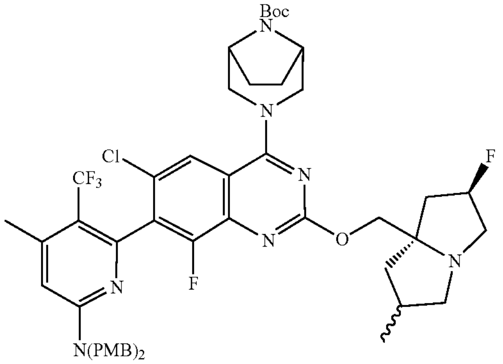

To a stirred solution of ((2R,7aR)-2-fluoro-6-methyltetrahydro-1H-pyrrolizin-7a(5H)-yl)methanol (63.0 mg, 0.364 mmol) in anhydrous THE (2.1 mL) at 0° C. was added sodium hydride (6.54 mg, 0.273 mmol) and the reaction mixture was stirred at the same temperature for min. After 30 min, tert-butyl-3-(7-(6-(bis(4-methoxybenzyl)amino)-4-methyl-3-(trifluoromethyl)pyridin-2-yl)-6-chloro-2,8-difluoroquinazolin-4-yl)-3,8-diazabicyclo[3.2.1]octane-8-carboxylate (150 mg, 0.182 mmol), dissolved in anhydrous THE (10 mL) was added to the reaction mixture dropwise while maintaining the temperature 0° C. The reaction mixture was stirred for the next 2 h while warming the reaction mixture to room temperature. The reaction mixture was then quenched with saturated aq. ammonium chloride solution (1 mL) and diluted with ethyl acetate (5 mL). The mixture was extracted with ethyl acetate (3×5 mL). The combined organic layers were dried over anhydrous sodium sulphate, filtered and concentrated reduced pressure to obtain the crude product. The crude product was purified by column chromatography (Grace, 50 g snap, dry pack) over neutral alumina using 50-100% of ethyl acetate in petroleum ether. The desired fractions were pooled and concentrated under reduced pressure to obtain tert-butyl-3-(7-(6-(bis(4-methoxybenzyl)amino)-4-methyl-3-(trifluoromethyl)pyridin-2-yl)-6-chloro-8-fluoro-2-(((2R,7aR)-2-fluoro-6-methyltetrahydro-1H-pyrrolizin-7a(5H)-yl)methoxy)quinazolin-4-yl)-3,8-diazabicyclo[3.2.1]octane-8-carboxylate (126 mg, 0.115 mmol, 63% yield) as pale yellow solid. LCMS (ESI) m/z: 978.5 $[M+H]^+$.

Example 27

6-(2-{[(2R,6R,7aR)-2-fluoro-6-methyl-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine

27

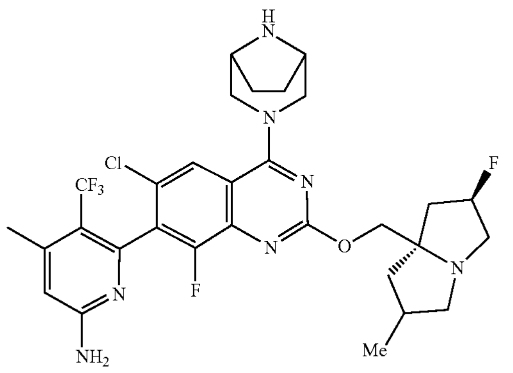

To a stirred solution of TFA (15.75 μl, 0.204 mmol) and triethylsilane (23.76 mg, 0.204 mmol) was added tert-butyl 3-(7-(6-(bis(4-methoxybenzyl)amino)-4-methyl-3-(trifluoromethyl)pyridin-2-yl)-6-chloro-8-fluoro-2-(((2R,7aR)-2-fluoro-6-methyltetrahydro-1H-pyrrolizin-7a(5H)-yl)methoxy)quinazolin-4-yl)-3,8-diazabicyclo[3.2.1]octane-8-carboxylate (200 mg, 0.204 mmol) at room temperature. Then reaction mixture was stirred at 35° C. for 12 h. The reaction mixture was concentrated to remove most of the TFA reduced pressure and below 35° C. The residue was co-evaporated with methanol (3×1 mL) to remove any residual TFA. The residue was neutralized with DIPEA and concentrated reduced pressure to obtain a free base. The crude was then purified by silica gel (previously neutralized with DIPEA) column chromatography using a mixture of MeOH, dichloromethane and DIPEA (15:80:2.5) to obtain 6-(4-(3,8-diazabicyclo[3.2.1]octan-3-yl)-6-chloro-8-fluoro-2-(((2R,6R,7aR)-2-fluoro-6-methyltetrahydro-1H-pyrrolizin-7a(5H)-yl)methoxy)quinazolin-7-yl)-4-methyl-5-(trifluoromethyl)pyridin-2-amine (60 mg, 0.089 mmol, 44% yield) as off white solid. LCMS: ESI m/z=638.2 $[M+H]^+$. $^1H$ NMR (400 MHz, $CD_3OD$, 297 K) δ: 8.27-8.06 (m, 1H), 6.65 (s, 1H), 5.62-5.47 (m, 1H), 4.77-4.69 (m, 3H), 4.53-4.30 (m, 4H), 4.18-3.91 (m, 1H), 3.74-3.63 (m, 1H), 3.61-3.43 (m, 5H), 2.86-2.68 (m, 1H), 2.61-2.39 (m, 5H), 2.37-2.25 (m, 3H), 2.21-2.14 (m, 1H), 2.12-2.03 (m, 2H), 2.02-1.93 (m, 1H), 1.91-1.78 (m, 1H) ppm.

Examples 28-1 and 28-2

4-(2-{[(6'R,7'aR)-6'-fluoro-hexahydrospiro[cyclopropane-1,2'-pyrrolizine]-7'a-yl]methoxy}-6-chloro-4-{3,8-diazabicyclo[3.2.1]octan-3-yl}-8-fluoroquinazolin-7-yl)naphthalen-2-ol

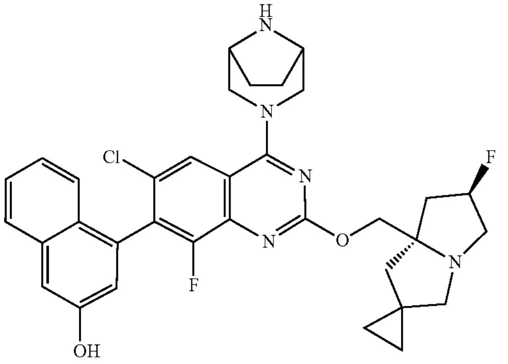

28-1 (Isomer 1)
28-2 (Isomer 2)

Preparation of Intermediate 28A: methyl (6'R,7a'R)-6'-fluorodihydro-1'H,3'H spiro[cyclopropane-1,2'-pyrrolizine]-7a'(5'H)-carboxylate

28A

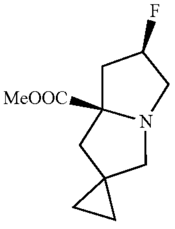

To a stirred solution of methyl (2R,7aR)-2-fluoro-6-methylenetetrahydro-1H-pyrrolizine-7a(5H)-carboxylate (2.0 g, 10.04 mmol) in anhydrous toluene (20 mL) under nitrogen atmosphere, diiodomethane (3.64 mL, 45.2 mmol) was added at 0° C. The reaction mixture was stirred at 0° C. for 30 min before the drop-wise addition of diethylzinc (50.2 mL, 50.2 mmol) (1M solution in Hexane). The reaction mixture was warmed to room temperature and stirred for 16 h before quenching with saturated aq. $NH_4Cl$ (5 mL). The suspension was extracted with ethyl acetate (2×20 mL). The combined organic layers were dried over anhydrous $Na_2SO_4$, filtered and concentrated reduced pressure to obtain a crude residue. The residue was purified by column chromatography (alumina-neutral) using 40-50% ethyl acetate in petroleum ether to obtain the methyl (6'R,7a'R)-6'-fluorodihydro-1'H,3'H-spiro[cyclopropane-1,2'-pyrrolizine]-7a'(5'H)-carboxylate (2.0 g, 8.05 mmol, 80% yield) as a colourless liquid. LCMS-ELSD (ESI) m/z: 204.1 $[M+H]^+$.

Preparation of Intermediate 28B: ((6'R,7a'R)-6'-fluorodihydro-1'H,3'H-spiro[cyclopropane-1,2'-pyrrolizin]-7a'(5'H)-yl)methanol

28B

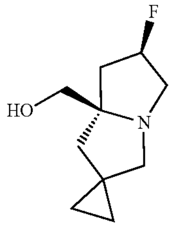

To a stirred solution of methyl (6'R,7a'R)-6'-fluorodihydro-1'H,3'H-spiro[cyclopropane-1,2'-pyrrolizine]-7a'(5'H)-carboxylate (2.0 g, 9.38 mmol) in THE (20 mL) was added $LiAlH_4$ (4.69 mL, 9.38 mmol, 2M in THF) at 0° C. The reaction mixture was stirred at ambient temperature for 3 h followed by quenching with saturated aq. ammonium chloride at 0° C. Once the effervescence ceased, anhydrous sodium sulphate was added to the reaction mixture, followed by DCM (20 mL). The reaction mixture was stirred for 20 minutes and then filtered. The filtrate was collected, dried over anhydrous sodium sulphate, filtered, and concentrated reduced pressure to obtain ((6'R,7a'R)-6'-fluorodihydro-1'H,3'H-spiro[cyclopropane-1,2'-pyrrolizin]-7a'(5'H)-yl)methanol (110 mg, 0.592 mmol, 6% yield) as a colourless liquid. LCMS-ELSD (ESI) m/z: 186.2 $[M+H]^+$.

Preparation of intermediate 28C: tert-butyl 3-(6-chloro-8-fluoro-2-(((6'R,7a'R)-6'-fluorodihydro-1'H,3'H-spiro[cyclopropane-1,2'-pyrrolizin]-7a'(5'H)-yl)methoxy)-7-(3-(methoxymethoxy)naphthalen-1-yl)quinazolin-4-yl)-3,8-diazabicyclo[3.2.1]octane-8-carboxylate

28C

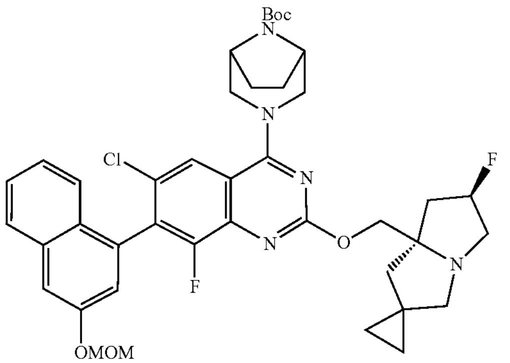

To a stirred solution of ((6'R,7a'R)-6'-fluorodihydro-1'H,3'H-spiro[cyclopropane-1,2'-pyrrolizin]-7a'(5'H)-yl)methanol (140 mg, 0.754 mmol) in anhydrous THE (2.1 mL) at 0° C. was added NaH (60% dispersion in mineral oil, 30.1 mg, 0.754 mmol) and the reaction mixture was stirred at the same temperature for 30 min. A solution of tert-butyl 3-(6-chloro-2,8-difluoro-7-(3-(methoxymethoxy)naphthalen-1-yl)quinazolin-4-yl)-3,8-diazabicyclo[3.2.1]octane-8-carboxylate (Intermediate 16A, 300 mg, 0.502 mmol) in anhydrous THE (10 mL) was added to the reaction mixture dropwise while maintaining the temperature below 0° C. The reaction mixture was warmed to room temperature over 2 h. The reaction mixture was quenched with saturated aq. ammonium chloride solution (1 mL) and extracted with ethyl acetate (3×5 mL). The combined organic layers were dried over anhydrous sodium sulphate, filtered, and concentrated under a vacuum to obtain the crude product. The crude was purified by column chromatography (Grace, 50 g snap, dry pack) over neutral alumina using 50-100% of ethyl acetate in petroleum ether. The desired fractions were pooled and concentrated under reduced pressure to obtain tert-butyl 3-(6-chloro-8-fluoro-2-(((6'R,7a'R)-6'-fluorodihydro-1'H,3'H-spiro[cyclopropane-1,2'-pyrrolizin]-7a'(5'H)-yl)methoxy)-7-(3(methoxymethoxy)naphthalen-1-yl)quinazolin-4-yl)-3,8-diazabicyclo[3.2.1]octane-8-carboxylate (289 mg, 0.379 mmol, 75% yield) as pale yellow solid. LCMS (ESI) m/z: 763.2 $[M+H]^+$.

Examples 28-1 and 28-2

4-(2-{[(6'R,7'aR)-6'-fluoro-hexahydrospiro[cyclopropane-1,2'-pyrrolizine]-7'a-yl]methoxy}-6-chloro-4-{3,8-diazabicyclo[3.2.1]octan-3-yl}-8-fluoroquinazolin-7-yl)naphthalen-2-ol

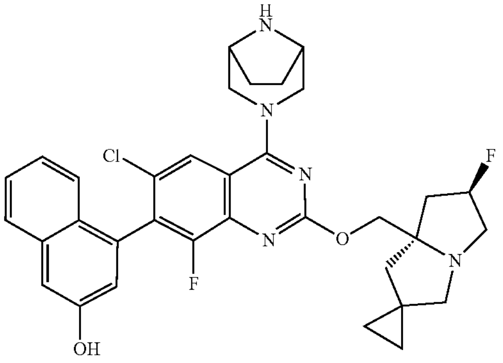

28-1 (Isomer 1)
28-2 (Isomer 2)

To a stirred solution of tert-butyl 3-(6-chloro-8-fluoro-2-(((6'R,7a'R)-6'-fluorodihydro-1'H,3'H-spiro[cyclopropane-1,2'-pyrrolizin]-7a'(5'H)-yl)methoxy)-7-(3-(methoxymethoxy)naphthalen-1-yl)quinazolin-4-yl)-3,8-diazabicyclo[3.2.1]octane-8-carboxylate (250 mg, 0.328 mmol) in MeOH (5 mL) was added HCl (4.0 M in dioxane, 0.410 mL, 1.640 mmol) at ice cold temperature The reaction was allowed to warm to room temperature and then stirred for 2h. The reaction mixture was concentrated reduced pressure to obtain the crude residue. The residue was purified by column chromatography (Biotage, sfar KP-amino), eluted with 100% ethyl acetate in petroleum ether to obtain 4-(4-(3,8-diazabicyclo[3.2.1]octan-3-yl)-6-chloro-8-fluoro-2-(((6'R,7a'R)-6'-fluorodihydro-1'H,3'H-spiro[cyclopropane-1,2'-pyrrolizin]-7a'(5'H)-yl)methoxy)quinazolin-7-yl)naphthalen-2-ol (130 mg). The obtained compound was subjected to reverse phase HPLC for the separation of atropisomers (Column: X SELECT C18 (4.6*150 mm) 3.5 um, Mobile phase: A: 0.05% TFA IN Water: CAN, Mobile phase: B: ACN:MEOH (50;50), Flowrate: 1.0 mL/min), where Peak-1 (28-1), eluted at retention time=6.396 min (17 mg, 0.022 mmol, 7% yield); LCMS (ESI) m/z: 618.2

$[M+H]^+$; $^1H$ NMR (400 MHz, $CD_3OD$, 298 K) δ: 8.14-8.01 (m, 1H), 7.79 (d, J=8.5 Hz, 1H), 7.45 (ddd, J=2.3, 5.8, 8.2 Hz, 1H), 7.36-7.30 (m, 1H), 7.24-7.20 (m, 2H), 7.06 (d, J=2.4 Hz, 1H), 5.70-5.39 (m, 1H), 4.35-4.15 (m, 2H), 4.05-3.82 (m, 3H), 3.76-3.62 (m, 1H), 2.91-2.59 (m, 3H), 3.22-2.57 (m, 3H), 2.21-2.13 (m, 4H), 1.98-1.66 (m, 3H), 1.02-0.73 (m, 3H), 0.82-0.50 (m, 3H) ppm. Peak-2 (28-2) eluted at retention time=6.529 min. (20 mg, 0.026 mmol, 8% yield); LCMS (ESI) m/z: 618.2 $[M+H]^+$; $^1H$ NMR (400 MHz, $CD_3OD$, 298 K) δ: 8.10-7.99 (m, 1H), 7.79 (d, J=8.4 Hz, 1H), 7.45 (ddd, J=1.9, 6.1, 8.2 Hz, 1H), 7.31-7.28 (m, 1H), 7.23 (d, J=0.9 Hz, 1H), 7.06 (d, J=2.4 Hz, 1H), 5.75-5.42 (m, 1H), 4.38-4.17 (m, 2H), 4.19-3.97 (m, 2H), 3.97-3.83 (m, 3H), 3.82-3.64 (m, 1H), 3.59-3.44 (m, 1H), 3.18-2.99 (m, 1H), 2.85-2.53 (m, 3H), 1.90 (d, J=13.6 Hz, 1H), 1.58-1.32 (m, 3H), 1.04-0.85 (m, 3H), 0.82-0.66 (m, 3H) ppm.

Example 30

6-(2-{[(2R,6S,7ar)-2,6-difluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine

30

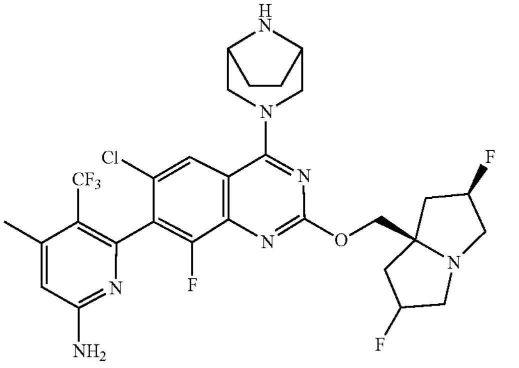

Preparation of intermediate 30A: Methyl (2R,7aR)-2-fluoro-6-oxotetrahydro-1H-pyrrolizine-7a(5H)-carboxylate

30A

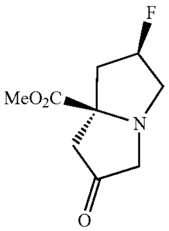

Ozone gas was bubbled through a solution of methyl (2R,7aR)-2-fluoro-6-methylenetetrahydro-1H-pyrrolizine-7a(5H)-carboxylate (10 g, 50.2 mmol) in 4:1 v/v DCM and MeOH (50 mL) at −78° C. for 45 min. Dimethyl sulfide (18.6 mL, 251 mmol) was added to the above solution at −78° C. and the reaction mixture was allowed to warm to room temperature over a period of 2 h. All the volatiles were removed under reduced pressure and the crude residue was purified by silica gel column chromatography by eluting with 2:1 petroleum ether and EtOAc to afford methyl (2R,7aR)-2-fluoro-6-oxotetrahydro-1H-pyrrolizine-7a(5H)-carboxylate (9.0 g, 78%) as a colorless oil. m/z [M+H] 202.2.

Preparation of intermediate 30B: Methyl (2R,7aR)-2-fluoro-6-hydroxytetrahydro-1H-pyrrolizine-7a(5H)-carboxylate

30B

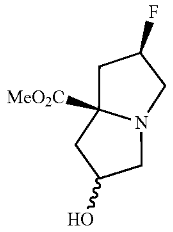

To a stirred solution of methyl (2R,7aR)-2-fluoro-6-oxo-tetrahydro-1H-pyrrolizine-7a(5H)-carboxylate (800 mg, 3.98 mmol) in MeOH (8 mL) at 0° C. was added sodium borohydride (150 mg, 3.98 mmol) in one portion and the resulting mixture was stirred at room temperature for 4 h. The reaction mixture was cooled to 0° C. and HCl (1.5 M aqueous solution) was added until the gas evolution subsided. The reaction mixture was evaporated under reduced pressure and the crude residue was diluted with 10:1 v/v DCM and MeOH and aqueous $NaHCO_3$. The two layers were separated and the organic layer was dried over $Na_2SO_4$, filtered and concentrated to afford (2R,7aR)-2-fluoro-6-hydroxytetrahydro-1H-pyrrolizine-7a(5H)-carboxylate (450 mg, 28%) as a 4:1 mixture of diastereomers. m/z [M+H] 204.1.

Preparation of intermediate 30C: Methyl (2R,7aR)-2,6-difluorotetrahydro-1H-pyrrolizine-7a(5H)-carboxylate

30C

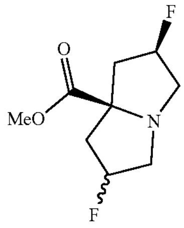

To a stirred solution of (2R,7aR)-2-fluoro-6-hydroxytetrahydro-1H-pyrrolizine-7a(5H)-carboxylate (50 mg, 0.25 mmol) in DCM (3 mL) at room temperature was added (diethylamino)sulfur trifluoride (79 mg, 0.49 mmol) at 0° C. and the reaction mixture was stirred at room temperature for 4 h. Saturated aqueous $NaHCO_3$(2 mL) was added and the reaction mixture was extracted with DCM (3×10 mL). The combined organic layers were dried over $Na_2SO_4$, filtered, and concentrated to provide methyl (2R,7aR)-2,6-difluorotetrahydro-1H-pyrrolizine-7a(5H)-carboxylate (50 mg, crude) as a mixture of diastereomers. The compound was taken to the next step without further purification. m/z [M+H] 206.1.

Preparation of intermediate 30D: ((2R,7aR)-2,6-difluorotetrahydro-1H-pyrrolizin-7a(5H)-yl)methanol

30D

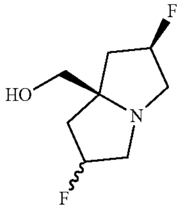

To (2R,7aR)-2,6-difluorotetrahydro-1H-pyrrolizine-7a(5H)-carboxylate (50 mg, 0.25 mmol) in THF (3 mL) at 0° C. was added $LiAlH_4$ (0.36 mL, 0.36 mmol, 1 M in THF) dropwise and the resulting mixture was stirred at room temperature for 2 h. The reaction mixture was cooled to 0° C. and saturated aq. $NH_4Cl$ was added dropwise until the gas evolution subsided. The reaction mixture was diluted with DCM (5 mL) and $Na_2SO_4$ was added. The reaction mixture was filtered through a cotton plug and the filtrate was evaporated under reduced pressure to afford ((2R,7aR)-2,6-difluorotetrahydro-1H-pyrrolizin-7a(5H)-yl)methanol (30 mg, 45%) as a brown oil. This compound was used in the next step without further purification. m/z [M+H] 178.1.

Preparation of Intermediate 30E: tert-butyl 3-(7-(6-(bis(4-methoxybenzyl)amino)-4-methyl-3-(trifluoromethyl)pyridin-2-yl)-6-chloro-2-(((2R)-2,6-difluorotetrahydro-1H-pyrrolizin-7a(5H)-yl)methoxy)-8-fluoroquinazolin-4-yl)-3,8-diazabicyclo[3.2.1]octane-8-carboxylate

30E

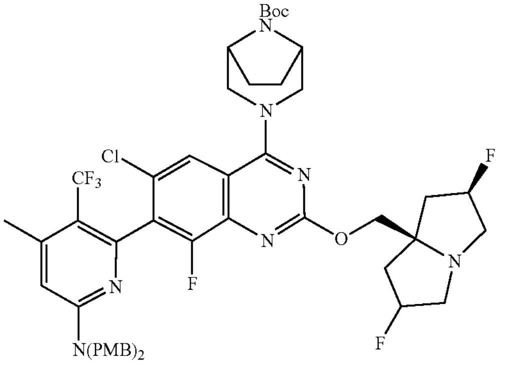

To a stirred solution of (((2R,7aR)-2,6-difluorotetrahydro-1H-pyrrolizin-7a(5H)-yl)methanol (32.2 mg, 0.182 mmol) (63.0 mg, 0.364 mmol) in anhydrous THF (2.1 mL) at 0° C. was added sodium hydride (60% dispersion in mineral oil, 6.54 mg, 0.273 mmol) and the reaction mixture was stirred at the same temperature for 30 min. A solution of tert-butyl 3-(7-(6-(bis(4-methoxybenzyl)amino)-4-methyl-3-(trifluoromethyl)pyridin-2-yl)-6-chloro-2,8-difluoroquinazolin-4-yl)-3,8-diazabicyclo[3.2.1]octane-8-carboxylate (Intermediate 141, 100 mg, 0.121 mmol) in THF (2 mL) was added dropwise while maintaining the temperature at 0° C. The reaction mixture was warmed to room temperature over 2 h. The reaction mixture was then quenched with saturated aq. ammonium chloride solution (1 mL) and extracted with ethyl acetate (3×5 mL). The combined organic layers were dried over anhydrous sodium sulphate, filtered and concentrated under a vacuum to obtain the crude product. The crude product was purified by column chromatography (Grace, 50 g snap, dry pack) over neutral alumina using 50-100% of ethyl acetate in petroleum ether. The desired fractions were pooled and concentrated under reduced pressure to obtain tert-butyl 3-(7-(6-(bis(4-methoxybenzyl)amino)-4-methyl-3-(trifluoromethyl)pyridin-2-yl)-6-chloro-2-(((2R)-2,6-difluorotetrahydro-1H-pyrrolizin-7a(5H)-yl)methoxy)-8-fluoroquinazolin-4-yl)-3,8-diazabicyclo[3.2.1]octane-8-carboxylate (145 mg, 0.120 mmol, 99% yield) as pale yellow solid. LCMS: ESI m/z=982.2 $[M+H]^+$.

Example 30

6-(2-{[(2R,6S,7ar)-2,6-difluoro-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine

30

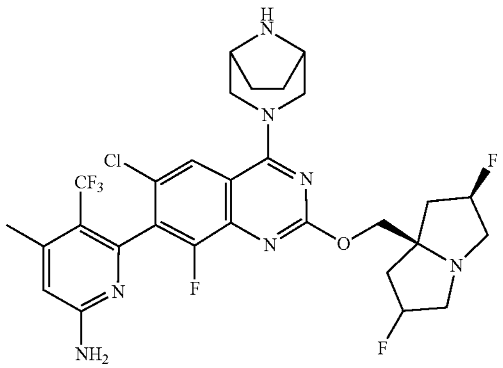

To a stirred solution of tert-butyl 3-(7-(6-(bis(4-methoxybenzyl)amino)-4-methyl-3-(trifluoromethyl)pyridin-2-yl)-6-chloro-2-(((2R)-2,6-difluorotetrahydro-1H-pyrrolizin-7a(5H)-yl)methoxy)-8-fluoroquinazolin-4-yl)-3,8-diazabicyclo[3.2.1]octane-8-carboxylate (120 mg, 0.122 mmol) in TFA (94 μl, 1.221 mmol) were added triethylsilane (0.244 mmol) and $H_2O$ (0.05 mL, 2.78 mmol) at room temperature. Then reaction mixture was stirred at 35° C. for 12 h. After completion, the reaction mixture was concentrated to remove most of the TFA reduced pressure and below 35° C. The residue was co-evaporated with methanol (3×1 mL) to remove any residual TFA. The residue was neutralized with DIPEA and concentrated reduced pressure to obtain a free base. The crude was then purified by silica gel (previously neutralized with DIPEA) column chromatography using a mixture of MeOH, dichloromethane and DIPEA (15:80:2.5) to obtain 6-(4-(3,8-diazabicyclo[3.2.1]octan-3-yl)-6-chloro-2-(((2R,6S,7ar)-2,6-difluorotetrahydro-1H-pyrrolizin-7a(5H)-yl)methoxy)-8-fluoroquinazolin-7-yl)-4-methyl-5-(trifluoromethyl)pyridin-2-amine (10 mg, 0.014 mmol, 12% yield) (10 mg, 0.015 mmol, 11.25% yield) as a pale-yellow solid. LCMS: ESI m/Z=642.3 $[M+H]^+$. 1H NMR (400 MHz, $CD_3OD$, 298 K) δ: 7.99-7.66 (m, 1H), 6.62 (s, 1H), 5.50-5.15 (m, 2H), 4.50 (br d, J=12.8 Hz, 2H), 4.42-4.28 (m, 2H), 3.78-3.61 (m, 4H), 3.59-3.49 (m, 1H), 3.31-3.10 (m, 5H), 2.57-2.53 (m, 1H), 2.51 (br d, J=4.6 Hz, 1H), 2.45-2.39 (m, 1H), 2.37-2.33 (m, 1H), 2.34-2.28 (m, 1H), 2.26-2.17 (m, 1H), 1.94-1.85 (m, 4H) ppm.

Examples 31-1 and 31-2

4-(2-{[(2R,6S,7ar)-2,6-difluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol

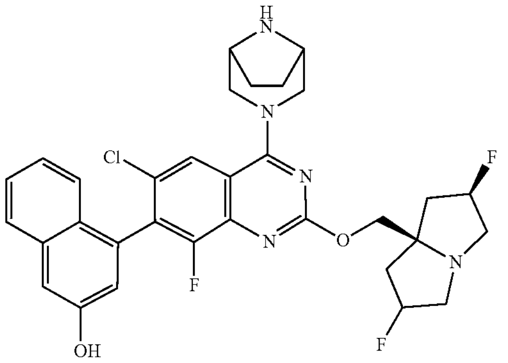

31-1 (Isomer 1)
31-2 (Isomer 2)

Preparation of intermediate 31A: tert-butyl-3-(6-chloro-2-(((2R)-2,6-difluorotetrahydro-1H-pyrrolizin-7a(5H)-yl)methoxy)-8-fluoro-7-(3-(methoxymethoxy)naphthalen-1-yl)quinazolin-4-yl)-3,8-diazabicyclo[3.2.1]octane-8-carboxylate

31A

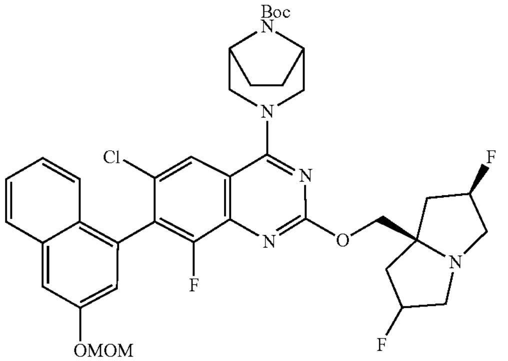

To a stirred solution of ((2R,7aR)-2,6-difluorotetrahydro-1H-pyrrolizin-7a(5H)-yl)methanol (134 mg, 0.754 mmol) in anhydrous THE (2.1 mL) at 0° C. was added NaH (60% dispersion in mineral oil, 30.1 mg, 0.754 mmol) and the reaction mixture was stirred at the same temperature for 30 min. A solution of tert-butyl-3-(6-chloro-2,8-difluoro-7-(3-(methoxymethoxy)naphthalen-1-yl)quinazolin-4-yl)-3,8-diazabicyclo[3.2.1]octane-8-carboxylate (Intermediate 16A, 300 mg, 0.502 mmol) in anhydrous THE (10 mL) was added to the reaction mixture dropwise while maintaining the temperature at 0° C. The reaction mixture was warmed to room temperature over 2 h. The reaction mixture was then quenched with saturated aq. ammonium chloride solution (1 mL) and extracted with ethyl acetate (3×5 mL). The combined organic layers were dried over anhydrous sodium sulphate, filtered and concentrated under a vacuum to obtain the crude product. The crude was purified by column chromatography (Grace, 50 g snap, dry pack) over neutral alumina using 50-100% ethyl acetate in petroleum ether. The desired fractions were pooled and concentrated under reduced pressure to obtain tert-butyl-3-(6-chloro-2-(((2R)-2,6-difluorotetrahydro-1H-pyrrolizin-7a(5H)-yl)methoxy)-8-fluoro-7-(3-(methoxymethoxy)naphthalen-1-yl)quinazolin-4-yl)-3,8-diazabicyclo[3.2.1]octane-8-carboxylate (145 mg, 0.108 mmol, 21% yield) as pale yellow solid. LCMS (ESI) m/z: 754.8 $[M+H]^+$.

Examples 31-1 and 31-2

4-(2-{[(2R,6S,7ar)-2,6-difluoro-hexahydro-1H-pyrrolizin-7a-yl]methoxy}-6-chloro-4-{3,8-diazabicyclo[3.2.1]octan-3-yl}-8-fluoroquinazolin-7-yl)naphthalen-2-ol

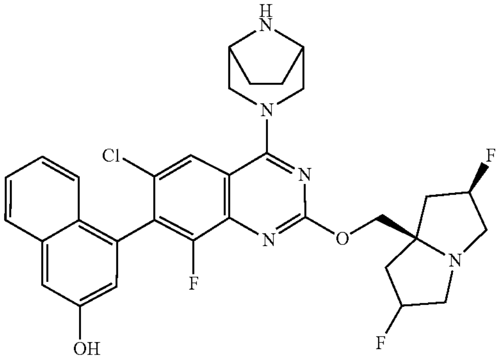

31-1 (Isomer 1)
31-2 (Isomer 2)

To a stirred solution of tert-butyl 3-(6-chloro-2-(((2R)-2,6-difluorotetrahydro-1H-pyrrolizin-7a(5H)-yl)methoxy)-8-fluoro-7-(3-(methoxymethoxy)naphthalen-1-yl)quinazolin-4-yl)-3,8-diazabicyclo[3.2.1]octane-8-carboxylate (140 mg, 0.186 mmol) was added HCl (4 M in dioxane, 0.056 mL, 1.856 mmol) at ice cold temperature. The reaction was allowed to warm to room temperature and stirred for 2h. The reaction mixture was concentrated reduced pressure to obtain the crude residue. The residue was purified by column chromatography (Biotage, sfar KP-amino), eluting with 100% ethyl acetate in petroleum ether to obtain 4-(4-(3,8-diazabicyclo[3.2.1]octan-3-yl)-6-chloro-2-(((2R,6S,7ar)-2,6-difluorotetrahydro-1H-pyrrolizin-7a(5H)-yl)methoxy)-8-fluoroquinazolin-7-yl)naphthalen-2-ol (80 mg). The obtained compound was subjected to SFC for the separation of atropisomers (Column: Cellulose-4(250 mm×4.6×5u), Mobile phase: 0.1% $NH_4OH$ in Methanol Flowrate: 3.0 mL/min), where Peak-1 (31-1), eluted at retention time=7.253 min. (14 mg, 11% yield) LCMS (ESI) m/z: 610.0 [M+H]$^+$; $^1$H NMR (400 MHz, $CD_3OD$, 298 K) δ: 7.79 (s, 1H), 7.75 (d, J=8.0 Hz, 1H), 7.42 (dt, J=6.8 and 1.6 Hz, 1H), 7.28-7.04 (m, 3H), 7.04 (d, J=1.6 Hz, 1H), 5.42-5.26 (m, 2H), 4.62-4.55 (m, 2H), 4.39 (q, J=10.4 Hz, 2H), 3.82-3.69 (m, 5H), 3.68-3.55 (m, 1H), 3.32-3.29 (m, 2H), 2.67-2.30 (m, 5H), 1.94 (s, 4H) ppm. Peak-2 (31-2) eluted at retention time=9.931 min. (9 mg, 7% yield) LCMS (ESI) m/z: 610.0 [M+H]$^+$; $^1$H NMR (400 MHz, $CD_3OD$, 298 K) δ: 7.97 (s, 1H), 7.75 (d, J=8.0 Hz, 1H), 7.42 (dt, J=6.8 and 1.6 Hz, 1H), 7.28-7.04 (m, 3H), 7.04 (d, J=1.6 Hz, 1H), 5.42-5.26 (m, 2H), 4.62-4.55 (m, 2H), 4.39 (q, J=10.4 Hz, 2H), 3.82-3.69 (m, 5H), 3.68-3.55 (m, 1H), 3.32-3.29 (m, 2H), 2.67-2.30 (m, 5H), 1.94 (s, 4H) ppm.

Example 32

6-(2-{[(6'R,7'aR)-3,3,6'-trifluoro-hexahydrospiro[cyclopropane-1,2'-pyrrolizine]-7'a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine

32

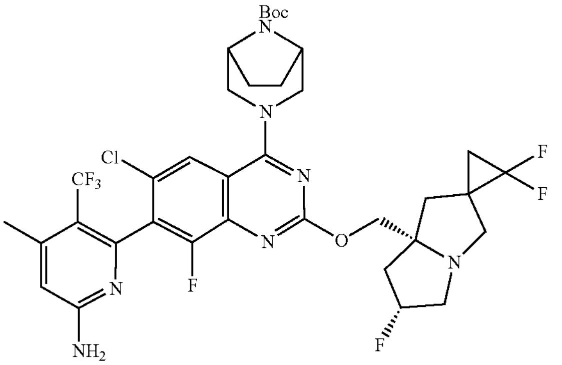

Preparation of intermediate 32A: methyl (6'R,7a'R)-2,2,6'-trifluorodihydro-1'H,3'H-spiro[cyclopropane-1,2'-pyrrolizine]-7a'(5'H)-carboxylate

32A

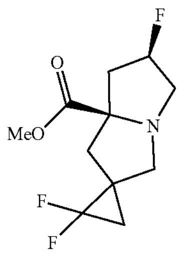

Trimethyl(trifluoromethyl)silane (1.112 mL, 7.53 mmol) and sodium iodide (226 mg, 1.506 mmol) were added in one portion to a solution containing methyl (2R,7aR)-2-fluoro-6-methylenetetrahydro-1H-pyrrolizine-7a(5H)-carboxylate (600 mg, 3.01 mmol) in dry THE (5 mL). After refluxing for 4 h reaction mixture was concentrated under vaccum to obtain the crude residue. The residue was purified by column chromatography (Biotage, Alumina-neutral) using 25% ethyl acetate in petroleum ether to provide methyl (6'R,7a'R)-2,2,6'-trifluorodihydro-1'H,3'H-spiro[cyclopropane-1,2'-pyrrolizine]-7a'(5'H)-carboxylate (237 mg, 0.190 mmol, 6% yield). LCMS (ESI) m/z: 250.1 [M+H]$^-$.

Preparation of intermediate 32B: ((6'R,7a'R)-2,2,6'-trifluorodihydro-1'H,3'H-spiro[cyclopropane-1,2'-pyrrolizin]-7a'(5'H)-yl)methanol

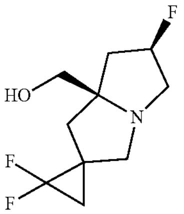 [SMILES: OC[C@@]12C[C@@H](F)CN1CC1(CC1(F)F)C2]

To a stirred solution of methyl (6'R,7a'R)-2,2,6'-trifluorodihydro-1'H,3'H-spiro[cyclopropane-1,2'-pyrrolizine]-7a'(5'H)-carboxylate (200 mg, 0.802 mmol) in anhydrous THE (5 mL)under nitrogen at 0° C. was added $LiALH_4$ (2M in THF, 0.8 mL, 1.605 mmol) dropwise over 10 min. After addition, the reaction mixture was warmed to room temperature over 30 min. The mixture was stirred at this temperature for 1 h before being quenched with saturated aq. ammonium chloride (5 mL) at 0° C. Once the effervescence ceased, anhydrous sodium sulphate was added to the reaction mixture, followed by dichloromethane (20 mL). The reaction mixture was stirred for 20 min and filtered. The filtrate was collected, dried over anhydrous sodium sulphate, filtered and concentrated reduced pressure to obtain the crude residue of ((6'R,7a'R)-2,2,6'-trifluorodihydro-1'H,3'H-spiro[cyclopropane-1,2'-pyrrolizin]-7a'(5'H)-yl)methanol (267 mg, 0.507 mmol, 63% yield) as a pale brown oil. LCMS (ESI) m/z: 222.1 [M+H]$^+$.

Preparation of Intermediate 32C: tert-butyl-3-(7-(6-(bis(4-methoxybenzyl)amino)-4-methyl-3-(trifluoromethyl)pyridin-2-yl)-6-chloro-8-fluoro-2-(((6'R,7a'R)-2,2,6'-trifluorodihydro-1'H,3'H-spiro[cyclopropane-1,2'-pyrrolizin]-7a'(5'H)-yl)methoxy)quinazolin-4-yl)-3,8-diazabicyclo[3.2.1]octane-8-carboxylate

32C

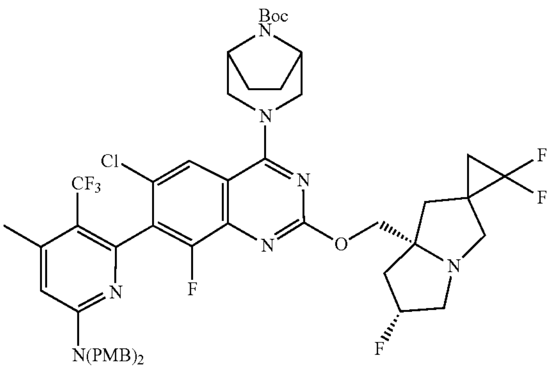

To a stirred solution of ((6'R,7a'R)-2,2,6'-trifluorodihydro-1'H,3'H-spiro[cyclopropane-1,2'-pyrrolizin]-7a'(5'H)-yl)methanol (121 mg, 0.545 mmol) in anhydrous THE (2.0 mL) at 0° C. was added sodium hydride (60% dispersion in mineral oil, 21.81 mg, 0.545 mmol) and the reaction mixture was stirred for 30 min. A solution of tert-butyl 3-(7-(6-(bis(4-methoxybenzyl)amino)-4-methyl-3-(trifluoromethyl)pyridin-2-yl)-6-chloro-2,8-difluoroquinazolin-4-yl)-3,8-diazabicyclo[3.2.1]octane-8-carboxylate (Intermediate 141, 150 mg, 0.182 mmol) in THE (2 mL) was added dropwise while maintaining the temperature 0° C. The reaction mixture was warmed to room temperature over 2 h. The reaction mixture was quenched with saturated aq. ammonium chloride solution (1 mL) and extracted with ethyl acetate (3×5 mL). The combined organic layers were dried over anhydrous sodium sulphate, filtered, and concentrated under a vacuum to obtain the crude product. The crude product was purified by column chromatography (Grace, 50 g snap, dry pack) over neutral alumina using 50-100% ethyl acetate in petroleum ether. The desired fractions were pooled and concentrated under reduced pressure to obtain tert-butyl-3-(7-(6-(bis(4-methoxybenzyl)amino)-4-methyl-3-(trifluoromethyl)pyridin-2-yl)-6-chloro-8-fluoro-2-(((6'R,7a'R)-2,2,6'-trifluorodihydro-1'H,3'H-spiro[cyclopropane-1,2'-pyrrolizin]-7a'(5'H)-yl)methoxy)quinazolin-4-yl)-3,8-diazabicyclo[3.2.1]octane-8-carboxylate (150 mg, 0.098 mmol, 54% yield) as a pale yellow solid. LCMS (ESI) m/z: 1025.384 $[M+H]^+$.

Example 32

6-(2-{[(6'R,7'aR)-3,3,6'-trifluoro-hexahydrospiro[cyclopropane-1,2'-pyrrolizine]-7'a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine

32

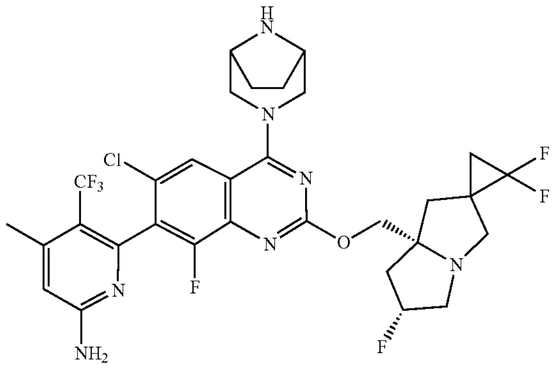

To a stirred solution of tert-butyl 3-(7-(6-(bis(4-methoxybenzyl)amino)-4-methyl-3-(trifluoromethyl)pyridin-2-yl)-6-chloro-8-fluoro-2-(((6'R,7a'R)-2,2,6'-trifluorodihydro-1'H,3'H-spiro[cyclopropane-1,2'-pyrrolizin]-7a'(5'H)-yl)methoxy)quinazolin-4-yl)-3,8-diazabicyclo[3.2.1]octane-8-carboxylate (130 mg, 0.127 mmol) in TFA (98 µl, 1.266 mmol) were added triethylsilane (29.5 mg, 0.253 mmol) and water (0.05 mL, 2.78 mmol) at room temperature. After stirring for 12 h at 35° C. the reaction mixture was concentrated reduced pressure to obtain the crude residue. The residue was purified by reverse phase preparative HPLC [Column: X bridge C18 (150×19)mm, 5 micron; Mobile phase A: 5 mM Ammonium formate in water; Mobile phase B: Acetonitrile; Retention time (min): 7.5]. The HPLC fractions were pooled together and lyophilized to yield 6-(4-(3,8-diazabicyclo[3.2.1]octan-3-yl)-6-chloro-8-fluoro-2-(((6'R,7a'R)-2,2,6'-trifluorodihydro-1'H,3'H-spiro[cyclopropane-1,2'-pyrrolizin]-7a'(5'H)-yl)methoxy)quinazolin-7-yl)-4-methyl-5-(trifluoromethyl)pyridin-2-amine (24 mg, 0.033 mmol, 26% yield) as an off white solid. LCMS (ESI) m/z: 686.2 $[M+H]^+$. $^1H$ NMR (400 MHz, $CD_3OD$, 303 K) δ: 8.56-8.35 (m, 1H), 7.87 (s, 1H), 6.63 (s, 1H), 5.51-5.16 (m, 2H), 4.61 (br dd, J=6.5, 14.0 Hz, 1H), 4.49 (q, J=1.0 Hz, 1H), 4.13 (br s, 2H), 3.79 (t, J=1.0 Hz, 4H), 3.51-3.36 (m, 2H), 2.98 (t, J=1.0 Hz, 1H), 2.91-2.81 (m, 1H), 2.56-2.53 (m, 1H), 2.51-2.43 (m, 3H), 2.39 (dd, J=6.3, 13.8 Hz, 1H), 2.20-2.00 (m, 3H), 2.21-2.00 (m, 1H), 1.58-1.41 (m, 4H) ppm.

Example 33-1

4-(2-{[(4aS,7aR)-1-methyl-octahydro-1H-cyclopenta[b]pyridin-4a-yl]methoxy}-4-{3,8-diazabicyclo[3.2.1]octan-3-yl}-8-fluoroquinazolin-7-yl)naphthalen-2-ol 33-1

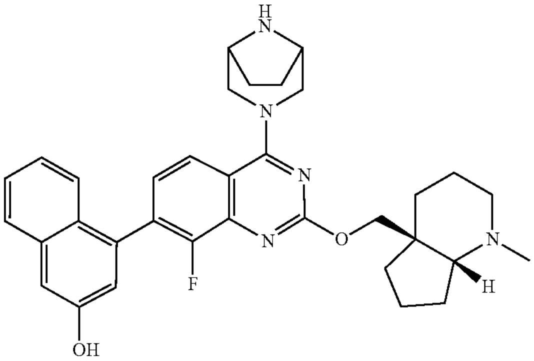

Preparation of Intermediate 33A: tert-butyl 3-(7-bromo-2-chloro-8-fluoroquinazolin-4-yl)-3,8-diazabicyclo[3.2.1]octane-8-carboxylate

33A

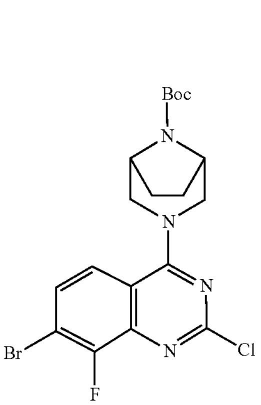

To a solution of 7-bromo-2,4-dichloro-8-fluoroquinazoline (1.0 g, 3.38 mmol) and DIEA (0.590 mL, 3.38 mmol) in THE (30 mL) at 0° C. under nitrogen was added 8-Boc-3, 8-diaza-bicyclo[3.2.1]octane (0.789 g, 3.72 mmol), and the mixture was stirred at 0° C. for 1 hour and room temperature for 18 hours. The mixture was then concentrated. The mixture was diluted with EtOAc (35 mL) and was washed with a solution of aqueous saturated sodium bicarbonate (2×35 mL). The ethyl acetate layer was dried over sodium sulfate and concentrated. The crude product was subjected to ISCO flash chromatography (silica gel/hexane-EtOAc 100:0 to 60:40 gradient) to yield tert-butyl 3-(7-bromo-2-chloro-8-fluoroquinazolin-4-yl)-3,8-diazabicyclo[3.2.1]octane-8-carboxylate (1.393 mg, 2.81 μmol, 0.083% yield) as a light yellow solid. LCMS (ESI) m/z: 472 $[M+H]^+$ LC retention time: 1.14 min (Method 3: Waters Acquity UPLC BEH C18, 2.1×50 mm, 1.7 □m particles; Mobile Phase A: water with 0.05% TFA; Mobile Phase B: ACN with 0.05% TFA; Gradient: 2-98% B over 1 minute, then a 0.5 minute hold at 98% B; Flow: 0.8 mL/min; Detection: MS and UV (220 nm)). $^1H$ NMR (499 MHz, CHLOROFORM-d) δ 7.51 (s, 2H), 4.51-4.30 (m, 4H), 3.78-3.51 (m, 2H), 2.02-1.91 (m, 2H), 1.75 (br s, 2H), 1.56-1.52 (m, 9H).

Preparation of Intermediate 33B: tert-butyl 3-(7-bromo-2,8-difluoroquinazolin-4-yl)-3,8-diazabicyclo[3.2.1]octane-8-carboxylate

33B

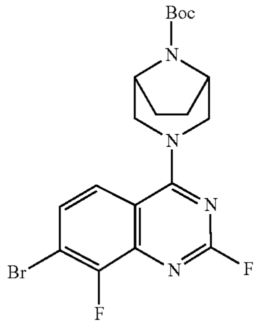

A solution of tert-butyl 3-(7-bromo-2-chloro-8-fluoroquinazolin-4-yl)-3,8-diazabicyclo[3.2.1]octane-8-carboxylate (1.14 g, 2.417 mmol) and potassium fluoride (0.281 g, 4.83 mmol) in DMSO (12 mL) was stirred at 100° C. for 2 days. The mixture was diluted with EtOAc (45 mL) and was washed with a solution of aqueous saturated sodium bicarbonate (2×45 mL). The ethyl acetate layer was dried over sodium sulfate and concentrated. The crude product was subjected to ISCO flash chromatography (silica gel/hexane-EtOAc 100:0 to 70:30 gradient) to yield tert-butyl 3-(7-bromo-2,8-difluoroquinazolin-4-yl)-3,8-diazabicyclo[3.2.1]octane-8-carboxylate (987 mg, 2.059 mmol, 85% yield) as off-white solid. LCMS (ESI) m/z: 456 $[M+H]^+$ LC retention time: 1.8 min (Waters Acquity UPLC BEH C18, 2.1×50 mm, 1.7 □m particles; Mobile Phase A: water with 0.05% TFA; Mobile Phase B: ACN with 0.05% TFA; Gradient: 2-98% B over 1 minute, then a 0.5 minute hold at 98% B; Flow: 0.8 mL/min; Detection: MS and UV (220 nm). $^1H$ NMR (499 MHz, CHLOROFORM-d) δ 7.56-7.47 (m, 2H), 4.53-4.31 (m, 4H), 3.78-3.56 (m, 2H), 2.02-1.92 (m, 2H), 1.76 (br s, 2H), 1.56-1.53 (m, 9H).

Preparation of Intermediate 33C: tert-butyl 3-(7-bromo-8-fluoro-2-(((4aS,7aR)-1-methyloctahydro-4aH-cyclopenta[b]pyridin-4a-yl)methoxy)quinazolin-4-yl)-3,8-diazabicyclo[3.2.1]octane-8-carboxylate

33C

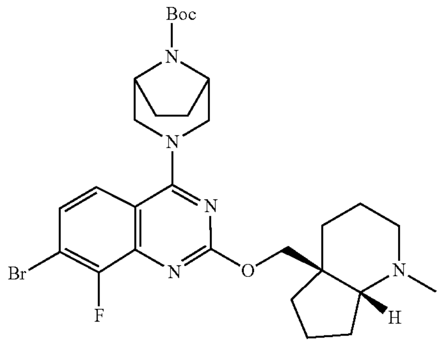

To a solution of tert-butyl 3-(7-bromo-2,8-difluoroquinazolin-4-yl)-3,8-diazabicyclo[3.2.1]octane-8-carboxylate (185 mg, 0.406 mmol), ((4aS,7aR)-1-methyloctahydro-4aH-cyclopenta[b]pyridin-4a-yl)methanol (68.8 mg, 0.406 mmol) in anhydrous THE (2.0 mL) was added lithium bis(trimethylsilyl)amide solution in THE (609 μl, 0.609 mmol) at 0° C. under nitrogen and the mixture was stirred at room temperature for 18 hours. The mixture was then concentrated. The crude product was purified by prep-HPLC (Phenomenex, Luna 5 micron 30×250 mm, flow rate=30 mL/min., gradient=20% A to 100% B in 12 min., A=H2O/ACN/TFA(90:10:0.1), B=H2O/ACN/TFA(10:90:0.1)) to yield tert-butyl 3-(7-bromo-8-fluoro-2-(((4aS,7aR)-1-methyloctahydro-4aH-cyclopenta[b]pyridin-4a-yl)methoxy)quinazolin-4-yl)-3,8-diazabicyclo[3.2.1]octane-8-carboxylate (172 mg, 0.270 mmol, 66.5% yield) as a white foam. LCMS (ESI) m/z: 605 $[M+H]^+$ LC retention time: 0.89 min (Waters Acquity UPLC BEH C18, 2.1×50 mm, 1.7 □m particles; Mobile Phase A: water with 0.05% TFA; Mobile Phase B: ACN with 0.05% TFA; Gradient: 2-98% B over 1 minute, then a 0.5 minute hold at 98% B; Flow: 0.8 mL/min; Detection: MS and UV (220 nm)). $^1H$ NMR (499 MHz, CHLOROFORM-d) δ 7.49-7.40 (m, 1H), 7.33-7.28 (m, 1H), 4.50-4.20 (m, 6H), 3.69-3.42 (m, 3H), 2.77-2.54 (m, 2H), 2.35-2.22 (m, 4H), 2.03-1.47 (m, 22H).

Example 33-1

4-(2-{[(4aS,7aR)-1-methyl-octahydro-1H-cyclopenta[b]pyridin-4a-yl]methoxy}-4-{3,8-diazabicyclo[3.2.1]octan-3-yl}-8-fluoroquinazolin-7-yl)naphthalen-2-ol 33-1

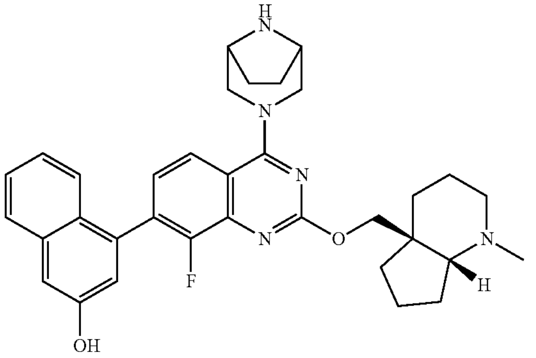

A mixture of tert-butyl 3-(7-bromo-8-fluoro-2-(((4aS,7aR)-1-methyloctahydro-4aH-cyclopenta[b]pyridin-4a-yl)methoxy)quinazolin-4-yl)-3,8-diazabicyclo[3.2.1]octane-8-carboxylate (20 mg, 0.033 mmol), 2-(3-(methoxymethoxy)naphthalen-1-yl)-4,4,5,5-tetramethyl-1,3,2-dioxaborolane (10.91 mg, 0.035 mmol), [1,1'-bis(di-tert-butylphosphino)ferrocene]dichloropalladium(II) (1.078 mg, 1.654 μmol) and 2.0 M Potassium phosphate tribasic (49.6 μl, 0.099 mmol) in dioxane (1 mL) under nitrogen was stirred at 50° C. for 18 hours. Then EtOAc (5 mL) was added to the mixture and the ethyl acetate layer was dried over sodium sulfate, filtered and concentrated to provide crude tert-butyl 3-(8-fluoro-7-(3-(methoxymethoxy)naphthalen-1-yl)-2-(((4aS,7aR)-1-methyloctahydro-4aH-cyclopenta[b]pyridin-4a-yl)methoxy)quinazolin-4-yl)-3,8-diazabicyclo[3.2.1]octane-8-carboxylate. LCMS (ESI) m/z: 712 $[M+H]^+$ LC retention time: 0.95 min (Waters Acquity UPLC BEH C18, 2.1×50 mm, 1.7 □m particles; Mobile Phase A: water with 0.05% TFA; Mobile Phase B: ACN with 0.05% TFA; Gradient: 2-98% B over 1 minute, then a 0.5 minute hold at 98% B; Flow: 0.8 mL/min; Detection: MS and UV (220 nm)). A solution of tert-butyl 3-(8-fluoro-7-(3-(methoxymethoxy)naphthalen-1-yl)-2-(((4aS,7aR)-1-methyloctahydro-4aH-cyclopenta[b]pyridin-4a-yl)methoxy)quinazolin-4-yl)-3,8-diazabicyclo[3.2.1]octane-8-carboxylate in DCM (0.6 mL), TES (1 drop) and TFA (0.4 mL) was stirred at room temperature for 30 min. The mixture was then concentrated. The crude product was purified by prep-HPLC (Phenomenex, Luna 5 micron 30×250 mm, flow rate=30 mL/min., gradient=20% A to 100% B in 12 min., A=H2O/ACN/TFA (90:10:0.1), B=H2O/ACN/TFA(10:90:0.1)). The pure fraction was loaded onto an Oasis MCX cation mixed-mode polymer cartridge (150 mg), the cartridge was washed with methanol (30 mL) and the product was eluted with 0.1 N ammonia in methanol (5.0 mL). The ammonia eluent was concentrated. The pure product was lyopholized with ACN/$H_2O$ (1:1, 5 mL) to yield 4-(2-{[(4aS,7aR)-1-methyl-octahydro-1H-cyclopenta[b]pyridin-4a-yl]methoxy}-4-{3,8-diazabicyclo[3.2.1]octan-3-yl}-8-fluoroquinazolin-7-yl)naphthalen-2-ol (10.83 mg, 0.019 mmol, 55.9% yield) as a white powder. LCMS (ESI) m/z: 568 $[M+H]^+$ LC retention time: 0.74 min (Waters Acquity UPLC BEH C18, 2.1×50 mm, 1.7 □m particles; Mobile Phase A: water with 0.05% TFA; Mobile Phase B: ACN with 0.05% TFA; Gradient: 2-98% B over 1 minute, then a 0.5 minute hold at 98% B; Flow: 0.8 mL/min; Detection: MS and UV (220 nm)). $^1H$ NMR (499 MHz, METHANOL-$d_4$) δ 7.87 (d, J=8.5 Hz, 1H), 7.75 (d, J=8.3 Hz, 1H), 7.48 (d, J=8.4 Hz, 1H), 7.42 (t, J=7.7 Hz, 1H), 7.28-7.21 (m, 3H), 7.11 (d, J=2.5 Hz, 1H), 4.61-4.50 (m, 3H), 4.29-4.24 (m, 1H), 3.68-3.58 (m, 4H), 2.90 (br t, J=6.2 Hz, 1H), 2.68 (ddd, J=11.6, 7.9, 4.1 Hz, 1H), 2.43-2.36 (m, 1H), 2.34 (s, 3H), 2.00-1.93 (m, 1H), 1.91-1.68 (m, 12H), 1.58 (td, J=8.9, 3.9 Hz, 1H).

Examples in Table 10 were prepared according to procedures in Example 33 using the appropriate starting materials

TABLE 10

| Example Number | Structure | Name | MS m/z: [M + H]+ | 1H NMR |
|---|---|---|---|---|
| 33-2 | 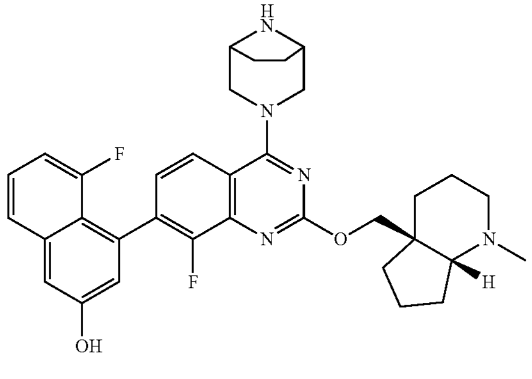 [SMILES: CN1CCC[C@@]2(COc3nc(N4CC5CCC(C4)N5)c4ccc(-c5cc(O)cc6cccc(F)c56)c(F)c4n3)CCC[C@@H]12] | 4-(2-{[(4aS,7aR)-1-methyl-octahydro-1H-cyclopenta[b]pyridin-4a-yl]methoxy}-4-{3,8-diazabicyclo[3.2.1]octan-3-yl}-8-fluoroquinazolin-7-yl)-5-fluoronaphthalen-2-ol | 586 | $^1H$ NMR (499 MHz, METHANOL-$d_4$) δ 7.82 (d, J = 8.7 Hz, 1H), 7.58 (d, J = 8.3 Hz, 1H), 7.38 (td, J = 7.9, 5.0 Hz, 1H), 7.30-7.25 (m, 2H), 7.04 (d, J = 2.3 Hz, 1H), 6.90 (dd, J = 13.1, 7.5 Hz, 1H), 4.59-4.48 (m, 3H), 4.31 (dd, J = 10.8, 3.9 Hz, 1H), 3.69-3.58 (m, 4H), 3.05-2.97 (m, 1H), 2.75 (br dd, J = 8.1, 3.5 Hz, 1H), 2.54- |

TABLE 10-continued

| Example Number | Structure | Name | MS m/z: [M + H]+ | 1H NMR |
|---|---|---|---|---|
| | | | | 2.45 (m, 1H), 2.40 (br d, J = 4.3 Hz, 3H), 2.04-1.94 (m, 1H), 1.92-1.86 (m, 6H), 1.86-1.69 (m, 7H), 1.6-1.57 (m, 1H) |
| 33-3 | 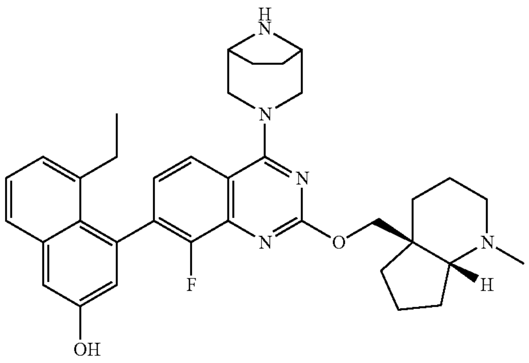 [SMILES: CCc1cccc2cc(O)cc(-c3ccc4c(N5CC6CCC(C5)N6)nc(OC[C@]56CCC[C@H]5N(C)CCC6)nc4c3F)c12] | 4-(2-{[(4aS,7aR)-1-methyl-octahydro-1H-cyclopenta[b]pyridin-4a-yl]methoxy}-4-{3,8-diazabicyclo [3.2.1]octan-3-yl}-8-fluoroquinazolin-7-yl)-5-ethylnaphthalen-2-ol | 596 | $^1$H NMR (499 MHz, METHANOL-$d_4$) δ 7.82 (d, J = 8.5 Hz, 1H), 7.62 (d, J = 8.1 Hz, 1H), 7.34 (dd, J = 8.0, 7.2 Hz, 1H), 7.27-7.20 (m, 2H), 7.14 (d, J = 6.8 Hz, 1H), 6.93 (d, J = 2.6 Hz, 1H), 4.58-4.49 (m, 3H), 4.26 (dd, J = 10.7, 6.2 Hz, 1H), 3.68-3.58 (m, 4H), 2.90 (br t, J = 6.1 Hz, 1H), 2.71-2.64 (m, 1H), 2.48-2.37 (m, 3H), 2.34 (s, 3H), 1.99-1.93 (m, 1H), 1.91-1.67 (m, 12H), 1.64-1.52 (m, 1H), 0.88 (td, J = 7.4, 2.1 Hz, 3H) |
| 33-4 | 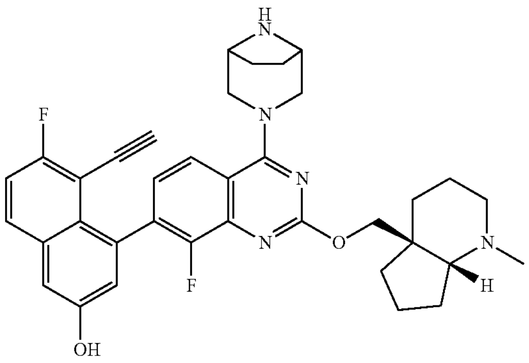 [SMILES: C#Cc1c(F)ccc2cc(O)cc(-c3ccc4c(N5CC6CCC(C5)N6)nc(OC[C@]56CCC[C@H]5N(C)CCC6)nc4c3F)c12] | 4-(2-{[(4aS,7aR)-1-methyl-octahydro-1H-cyclopenta[b]pyridin-4a-yl]methoxy}-4-{3,8-diazabicyclo[3.2.1] octan-3-yl}-8-fluoroquinazolin-7-yl)-5-ethynyl-6-fluoronaphthalen-2-ol | 610 | $^1$H NMR (499 MHz, METHANOL-$d_4$) δ 7.85 (t, J = 7.4 Hz, 1H), 7.79 (t, J = 6.7 Hz, 1H), 7.34-7.23 (m, 3H), 7.10 (d, J = 2.5 Hz, 1H), 4.58-4.44 (m, 3H), 4.40-4.28 (m, 1H), 3.69-3.59 (m, 4H), 3.24-3.20 (m, 1H), 3.15-3.03 (m, 1H), 2.86-2.75 (m, 1H), 2.64-2.51 (m, 1H), 2.51-2.39 (m, 3H), 2.06-1.97 (m, 1H), 1.95-1.72 (m, 12H), 1.71-1.59 (m, 1H) |

Preparation of Intermediate 34-1:7-fluoro-3-(methoxymethoxy)-8-{2-[tris(propan-2-yl)silyl]ethynyl}naphthalen-1-yl trifluoromethanesulfonate 34-1

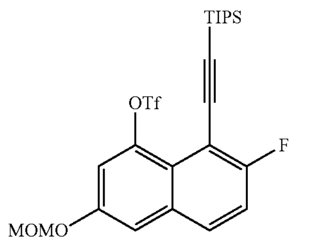

To a solution of 7-fluoro-3-(methoxymethoxy)-8-{2-[tris(propan-2-yl)silyl]ethynyl}naphthalen-1-ol (Intermediate 16-2)(8.6 g, 22.25 mmol) and DIPEA (11.66 mL, 66.7 mmol) in DCM (35 mL) was added triflic anhydride (5.64 mL, 33.4 mmol) dropwise at −40° C. and the reaction mixture was stirred for 30 min. The reaction mixture was diluted with water and extracted with DCM. The combined organic layers were washed with water, brine, dried over anhydrous $Na_2SO_4$ and concentrated under reduced pressure to provide the crude residue, which was purified by silica gel column chromatography using CombiFlash instrument (80 g RediSep® column, 5 to 10% EtOAc in petroleum ether to afford 7-fluoro-3-(methoxymethoxy)-8-{2-[tris(propan-2-yl)silyl]ethynyl}naphthalen-1-yl trifluoromethanesulfonate (8.5 g, 16.39 mmol, 73.7% yield) as a yellow oil. $^1$H NMR (400 MHz, DMSO-$d_6$) δ ppm 8.12 (dd, J=9.3, 5.8 Hz, 1H), 7.78 (d, J=2.5 Hz, 1H), 7.65 (t, J=9.0 Hz, 1H), 7.51 (d, J=2.0 Hz, 1H), 5.37 (s, 2H), 3.43 (s, 3H), 1.31-1.08 (m, 21H).

Preparation of Intermediate 34-2: {2-[2-fluoro-6-(methoxymethoxy)-8-(4,4,5,5-tetramethyl-1,3,2-dioxaborolan-2-yl)naphthalen-1-yl]ethynyl}tris(propan-2-yl)silane 34-2

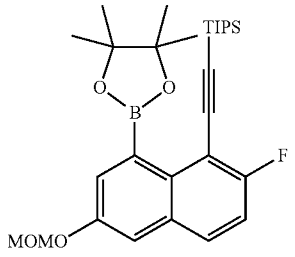

To a degassed solution of 7-fluoro-3-(methoxymethoxy)-8-{2-[tris(propan-2-yl)silyl]ethynyl}naphthalen-1-yl trifluoromethanesulfonate (4.0 g, 7.48 mmol), potassium acetate (2.203 g, 22.45 mmol) and bis(pinacolato)diboron (3.80 g, 14.96 mmol) in toluene (40 mL) was added 1,1-bis(diphenylphosphino)ferrocene]dichloropalladium(II) (0.547 g, 0.748 mmol) and the reaction mixture was heated at 120° C. for 3 h. The reaction mixture was cooled, filtered through a bed of Celite and washed with ethyl acetate. The filtrate was washed with water, brine, dried over anhydrous $Na_2SO_4$, filtered and concentrated under reduced pressure to provide the crude residue, which was purified by silica gel column chromatography using CombiFlash instrument (40 g RediSep® column, 10% EtOAc in petroleum ether to afford {2-[2-fluoro-6-(methoxymethoxy)-8-(4,4,5,5-tetramethyl-1,3,2-dioxaborolan-2-yl)naphthalen-1-yl]ethynyl}tris(propan-2-yl)silane (2.4 g, 4.68 mmol, 62.6% yield) as pale yellow solid. MS (ESI) m/z 513.4 [M+1]$^+$.

Examples in Table 11 were prepared according to the procedures described above from the appropriate starting materials

TABLE 11

| Example Number | Structure | Name | LCMS (M + H)$^+$ | $^1$H NMR |
|---|---|---|---|---|
| 34-1 | 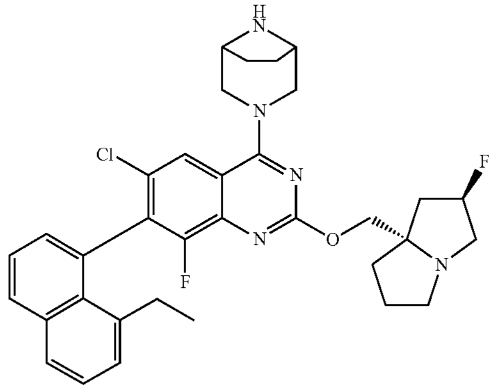 [SMILES: CCc1cccc2cccc(-c3c(Cl)cc4c(N5CC6CCC(C5)N6)nc(OC[C@@]56CCCN5C[C@H](F)C6)nc4c3F)c12] | 2-{[(2R,7aS)-2-fluoro-hexahydro-1H-pyrrolizin-7a-yl]methoxy}-6-chloro-4-{3,8-diazabicyclo[3.2.1]octan-3-yl}-7-(8-ethylnaphthalen-1-yl)-8-fluoroquinazoline | 604.2 | $^1$H NMR (400 MHz, DMSO-$d_6$) δ ppm: 8.09 (d, J = 8.1 Hz, 1H), 7.99-7.85 (m, 2H), 7.61 (t, J = 7.6 Hz, 1H), 7.52 (t, J = 7.6 Hz, 1H), 7.39 (d, J = 6.9Hz, 1H), 7.31 (dd, J = 1.2, 7.1 Hz, 1H), 5.40-5.14 (m, 1H), 4.41 (br d, J = 12.1 Hz, 1H), 4.33 (br d, J = 12.5 Hz, 1H), 4.15-4.07 (m, 1H), 4.05-3.99 (m, 1H), 3.89-3.76 (m, 2H), 3.67 (br d, J = 12.6 Hz, 1H), 3.59 (br d, J = 12.3 Hz, 1H), 3.14-3.06 (m, 2H), 3.02 (s, 1H), 2.88-2.79 (m, 1H), 2.41 (br dd, J = 7.4, 12.0 Hz, 1H), 2.20-2.10 (m, 1H), 2.09-1.94 (m, 2H), 1.90-1.72 (m, 6H), 1.24 (s, 3H), 0.90 (t, J = 7.4 Hz, 3H) |

TABLE 11-continued

| Example Number | Structure | Name | LCMS $(M + H)^+$ | $^1H$ NMR |
|---|---|---|---|---|
| 34-2 | 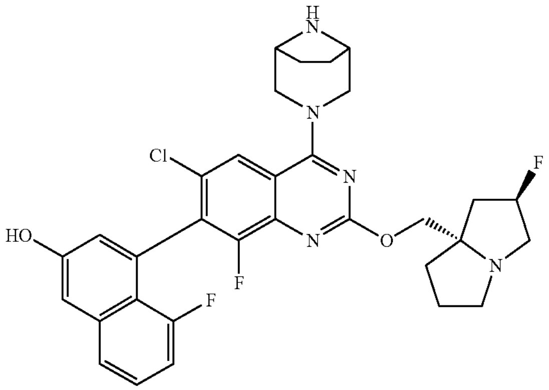 [SMILES: Oc1cc(-c2c(Cl)cc3c(N4CC5CCC(C4)N5)nc(OC[C@@]45CCCN4C[C@H](F)C5)nc3c2F)c2c(F)cccc2c1] | 4-(2-{[(2R, 7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-fluoronaphthalen-2-ol | 610.2 | $^1H$ NMR (400 MHz, DMSO-$d_6$) δ ppm: 7.86 (s, 1H), 7.62 (d, J = 8.3 Hz, 1H), 7.42-7.31 (m, 2H), 7.03 (d, J = 2.3 Hz, 1H), 6.94 (dd, J = 13.3, 7.3 Hz, 1H), 5.45-5.17 (m, 1H), 4.38-4.18 (m, 2H), 4.12-3.96 (m, 2H), 3.79-3.62 (m, 4H), 3.54 (br d, J = 8.3 Hz, 1H), 3.13-3.04 (m, 2H), 3.00 (br s, 1H), 2.82 (br d, J = 6.5 Hz, 1H), 2.19-1.97 (m, 4H), 1.77-1.60 (m, 6H). |
| 34-3 | 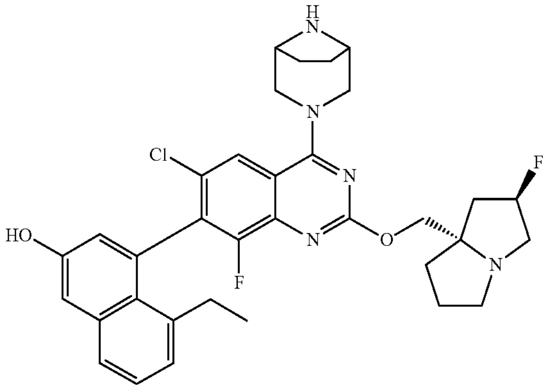<br>Isomer 1 | 4-(2-{[(2R, 7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-ethylnaphthalen-2-ol | 620.2 | $^1H$ NMR (400 MHz, DMSO-$d_6$) δ ppm: 7.89 (d, J = 1.5 Hz, 1H), 7.66 (d, J = 8.1 Hz, 1H), 7.36 (t, J = 7.7 Hz, 1H), 7.27 (d, J = 2.5 Hz, 1H), 7.11 (d, J = 7.0 Hz, 1H), 6.85 (d, J = 2.6 Hz, 1H), 5.37-5.18 (m, 1H), 4.37-4.22 (m, 2H), 4.13-3.96 (m, 2H), 3.91 (s, 1H), 3.59-3.48 (m, 4H), 3.12-3.05 (m, 2H), 3.00 (s, 1H), 2.86-2.79 (m, 1H), 2.40-2.24 (m, 2H), 2.16-1.95 (m, 3H), 1.89-1.72 (m, 3H), 1.64 (br d, J = 8.8 Hz, 4H), 0.86 (t, J = 7.4 Hz, 3H). |
| 34-4 | 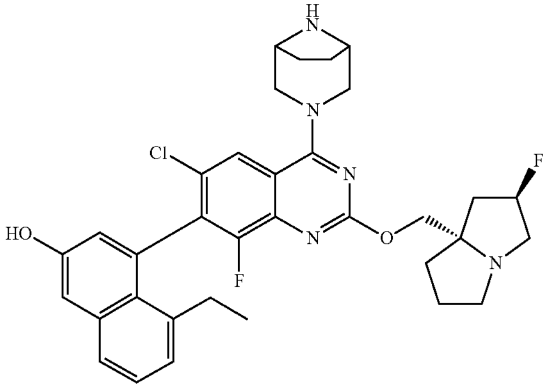<br>Isomer 2 | 4-(2-{[(2R, 7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-ethylnaphthalen-2-ol | 620.2 | $^1H$ NMR (400 MHz, DMSO-$d_6$) δ ppm = 7.89 (d, J = 1.0 Hz, 1H), 7.66 (d, J = 7.8 Hz, 1H), 7.36 (t, J = 7.6 Hz, 1H), 7.28 (d, J = 2.5 Hz, 1H), 7.11 (d, J = 6.8 Hz, 1H), 6.86 (d, J = 2.6 Hz, 1H), 5.37-5.18 (m, 1H), 4.36-4.23 (m, 2H), 4.12-3.98 (m, 2H), 3.91 (s, 1H), 3.60-3.46 (m, 4H), 3.14-2.99 (m, 3H), 2.82 (br d, J = 6.6 Hz, 1H), 2.39-2.25 (m, 2H), 2.20-1.96 (m, 3H), 1.90-1.72 (m, 3H), 1.65 (br d, J = 5.6 Hz, 4H), 0.86 (t, J = 7.4 Hz, 3H). |

TABLE 11-continued

| Example Number | Structure | Name | LCMS (M + H)+ | 1H NMR |
|---|---|---|---|---|
| 34-5 | 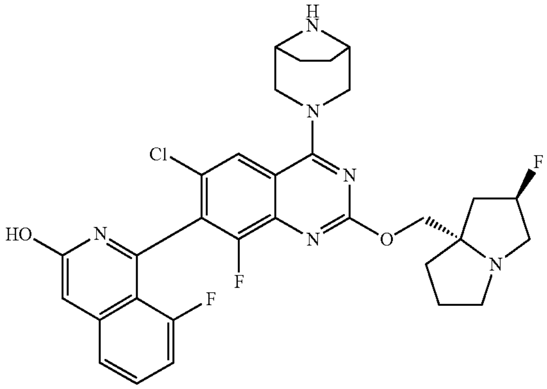 [SMILES: Oc1cc2cccc(F)c2c(-c2c(Cl)cc3c(N4CC5CCC(C4)N5)nc(OC[C@@]45CCCN4C[C@H](F)C5)nc3c2F)n1] | 1-(2-{[(2R,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-8-fluoroisoquinolin-3-amine | 610.2 | $^1$H NMR (400 MHz, DMSO-$d_6$) δ ppm: 7.85 (d, J = 0.8 Hz, 1H), 7.51-7.41 (m, 2H), 6.86-6.78 (m, 2H), 6.37 (s, 2H), 5.36-5.18 (m, 1H), 4.35 (br d, J = 12.0 Hz, 1H), 4.23-4.16 (m, 1H), 4.09 (d, J = 10.3 Hz, 1H), 3.97 (d, J = 10.4 Hz, 1H), 3.60-3.43 (m, 2H), 3.13-3.04 (m, 2H), 3.00 (s, 1H), 2.86-2.78 (m, 1H), 2.44-2.39 (m, 2H), 2.16-1.95 (m, 3H), 1.90-1.73 (m, 4H), 1.69-1.57 (m, 4H) |
| 34-6 | 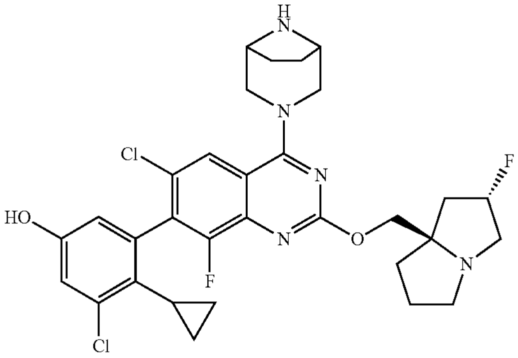 [SMILES: Oc1cc(Cl)c(C2CC2)c(-c2c(Cl)cc3c(N4CC5CCC(C4)N5)nc(OC[C@]45CCCN4C[C@@H](F)C5)nc3c2F)c1] | 3-(2-{[(2S,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-chloro-4-cyclopropylphenol | 616.2 | $^1$H NMR (400 MHz, DMSO-$d_6$) δ ppm: 7.87 (d, J = 1.3 Hz, 1H), 6.94 (d, J = 2.5 Hz, 1H), 6.56 (d, J = 2.5 Hz, 1H), 5.37-5.15 (m, 1H), 4.34 (br d, J = 11.5 Hz, 1H), 4.23 (br d, J = 9.8 Hz, 1H), 4.11-4.04 (m, 1H), 4.02-3.96 (m, 1H), 3.64-3.58 (m, 2H), 3.50-3.48 (m, 2H), 3.13-3.05 (m, 4H),2.85-2.77 (m, 1H), 2.16-1.95 (m, 3H), 1.87-1.53 (m, 8H), 0.63-0.46 (m, 2H), 0.21-0.06 (m, 2H). |
| 34-7 | 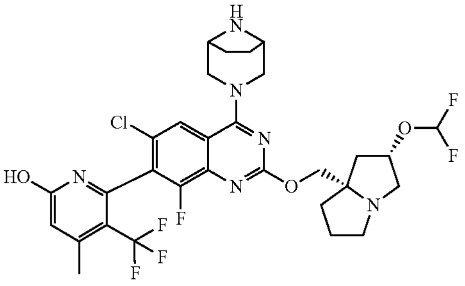 Isomer 1 | 6-(2-{[(2S,7aS)-2-(difluoromethoxy)-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine | 672.2 | $^1$H NMR (400 MHz, DMSO-$d_6$) δ ppm: 7.81 (d, J = 1.3 Hz, 1H), 6.92-6.79 (m, 2H), 6.60 (br t, J = 69.6 Hz, 1H), 6.50 (s, 1H), 4.83 (br t, J = 4.3 Hz, 1H), 4.30 (br d, J = 11.3 Hz, 1H), 4.19 (br d, J = 11.3 Hz, 1H), 4.15-4.02 (m, 2H), 3.54-3.47 (m, 4H), 3.05-3.0 (m, 1H), 3.00-2.93 (m, 1H), 2.90-2.88 (m, 1H), 2.85-2.80 (m, 1H), 2.59-2.55 (m, 1H), 2.37 (s, 3H), 2.14-2.08 (m, 1H), 2.03-1.88 (m, 2H), 1.86-1.72 (m, 3H), 1.67-1.53 (m, 4H). |
| 34-8 | 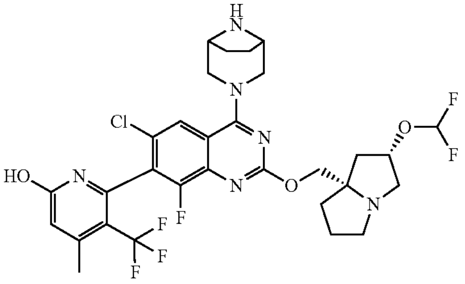 Isomer 2 | 6-(2-{[(2S,7aS)-2-(difluoromethoxy)-hexahydro-1H-pyrrolizin-7a-yl]methoxy}-6-chloro-4-{3,8-diazabicyclo[3.2.1]octan-3-yl}-8-fluoroquinazolin-7-yl)-4-methyl-5-(trifluoromethyl)pyridin-2-amine | 672.2 | $^1$H NMR (400 MHz, DMSO-$d_6$) δ ppm: 7.81 (d, J = 1.3 Hz, 1H), 6.92-6.79 (m, 2H), 6.60 (br t, J = 69.6 Hz, 1H), 6.50 (s, 1H), 4.83 (br t, J = 4.3 Hz, 1H), 4.30 (br d, J = 11.3 Hz, 1H), 4.19 (br d, J = 11.3 Hz, 1H), 4.15-4.02 (m, 2H), 3.54-3.47 (m, 4H), 3.05-3.0 (m, 1H), 3.00-2.93 (m, 1H), 2.90-2.88 (m, 1H), 2.85-2.80 (m, 1H), 2.59-2.55 (m, 1H), 2.37 (s, 3H), 2.14-2.08 (m, 1H), 2.03-1.88 (m, 2H), 1.86-1.72 (m, 3H), 1.67-1.53 (m, 4H). |

TABLE 11-continued

| Example Number | Structure | Name | LCMS (M + H)+ | 1H NMR |
|---|---|---|---|---|
| 34-9 | 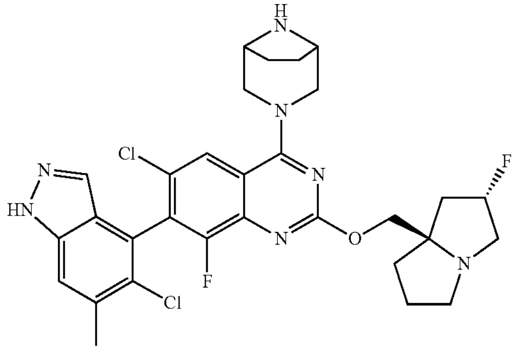 [SMILES: Cc1cc2[nH]ncc2c(-c2c(Cl)cc3c(N4CC5CCC(C4)N5)nc(OC[C@]45CCCN4C[C@@H](F)C5)nc3c2F)c1Cl] | 2-{[(2S,7aR)-2-fluoro-hexahydro-1H-pyrrolizin-7a-yl]methoxy}-6-chloro-7-(5-chloro-6-methyl-1H-indazol-4-yl)-4-{3,8-diazabicyclo[3.2.1]octan-3-yl}-8-fluoroquinazoline | 614.2 | $^1$H NMR (400 MHz, DMSO-$d_6$) δ ppm: 13.38 (br s, 1H), 7.96 (s, 1H), 7.70 (s, 1H), 7.64 (s, 1H), 5.38-5.15 (m, 1H), 4.31 (br d, J = 12.1 Hz, 2H), 4.12-4.07 (m, 1H), 4.00-3.90 (m, 1H), 3.13-2.98 (m, 4H), 2.82-2.75 (m, 1H), 2.54 (s, 3H), 2.14-1.98 (m, 4H), 1.94-1.74 (m, 6H), 1.67-1.62 (m, 4H). |
| 34-10 | 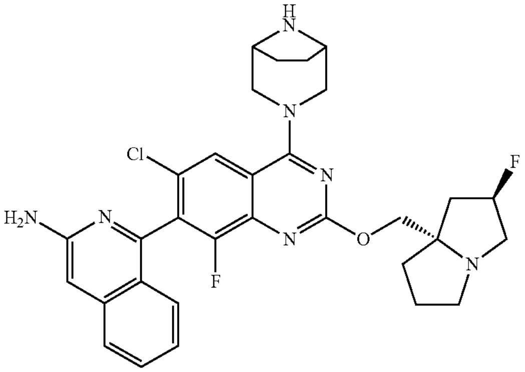 [SMILES: Nc1cc2ccccc2c(-c2c(Cl)cc3c(N4CC5CCC(C4)N5)nc(OC[C@@]45CCCN4C[C@H](F)C5)nc3c2F)n1] | 1-(2-{[(2R,7aS)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)isoquinolin-3-amine | 592.2 | $^1$H NMR (400 MHz, DMSO-$d_6$) δ ppm: 7.91 (d, J = 1.3 Hz, 1H), 7.64 (d, J = 8.5 Hz, 1H), 7.48 (ddd, J = 8.2, 6.8, 1.1 Hz, 1H), 7.25 (br d, J = 9.0 Hz, 1H), 7.12-7.05 (m, 1H), 6.77 (s, 1H), 6.12 (s, 2H), 5.38-5.19 (m, 1H), 4.33 (br dd, J = 10.1, 3.5 Hz, 2H), 4.10 (t, J = 10.9 Hz, 1H), 4.00 (t, J = 10.1 Hz, 1H), 3.60-3.50 (m, 3H), 3.14-2.99 (m, 4H), 2.88-2.77 (m, 1H), 2.56-2.52 (m, 1H), 2.16-2.10 (m, 1H), 2.09-1.94 (m, 3H), 1.89-1.73 (m, 3H), 1.66 (br s, 3H) |
| 34-11 | 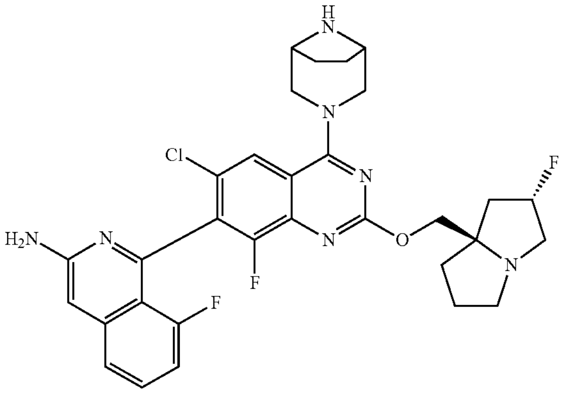 [SMILES: Nc1cc2cccc(F)c2c(-c2c(Cl)cc3c(N4CC5CCC(C4)N5)nc(OC[C@]45CCCN4C[C@@H](F)C5)nc3c2F)n1] | 1-(2-{[(2S,7aR)-2-fluoro-hexahydro-1H-pyrrolizin-7a-yl]methoxy }-6-chloro-4-{3,8-diazabicyclo[3.2.1]octan-3-yl}-8-fluoroquinazolin-7-yl)-8-fluoroisoquinolin-3-amine | 614.20 | $^1$H NMR (400 MHz, DMSO-$d_6$) δ ppm: 7.85 (d, J = 1.1 Hz, 1H), 7.54-7.35 (m, 2H), 6.88-6.70 (m, 2H), 6.37 (s, 2H), 5.41-5.12 (m, 1H), 4.36 (br d, J = 12.4 Hz, 1H), 4.20 (br d, J = 11.3 Hz, 1H), 4.13-4.05 (m, 1H), 4.03-3.95 (m, 1H), 3.56-3.50 (m, 3H), 3.12-3.05 (m, 2H), 3.01-2.98 (m, 1H), 2.87-2.77 (m, 1H), 2.15-1.98 (m, 3H), 1.95-1.74 (m, 5H), 1.65-1.60 (m, 4H). |
| 34-12 | 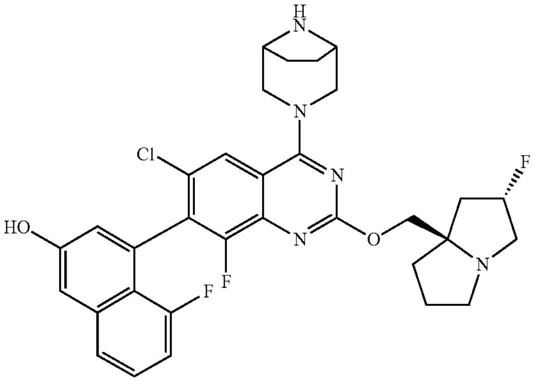 [SMILES: Oc1cc(-c2c(Cl)cc3c(N4CC5CCC(C4)N5)nc(OC[C@]45CCCN4C[C@@H](F)C5)nc3c2F)c2c(F)cccc2c1] | 4-(2-{[(2S,7aR)-2-fluoro-hexahydro-1H-pyrrolizin-7a-yl]methoxy}-6-chloro-4-{3,8-diazabicyclo[3.2.1]octan-3-yl}-8-fluoroquinazolin-7-yl)-5-fluoronaphthalen-2-ol | 610.20 | $^1$H NMR (400 MHz, DMSO-$d_6$) δ ppm: 7.87 (s, 1H), 7.66 (d, J = 8.3 Hz, 1H), 7.44-7.34 (m, 1H), 7.35 (s, 1H), 7.06-6.91 (m, 2H), 5.40-5.10 (m, 1H), 4.34 (br d, J = 12.3 Hz, 1H), 4.22 (br d, J = 11.3 Hz, 1H), 4.13-4.04 (m, 1H), 4.02-3.96 (m, 1H), 3.57-3.50 (m, 4H), 3.12-3.06 (m, 2H), 3.01-2.99 (m, 2H), 2.87-2.77 (m, 1H), 2.15-1.97 (m, 3H), 1.92-1.72 (m, 3H), 1.65-1.60 (m, 4H). |

BIOLOGICAL ACTIVITY

KRAS$^{G12D}$ RAF Disruption Assay

Recombinant GMPPNP-loaded KRAS G12D (5 nM) was treated with compound at room temperature for 20 minutes in assay buffer (50 mM Tris pH 7.5, 100 mM NaCl, 1 mM $MgCl_2$, 1 mM DTT, 100 ug/mL BSA). Recombinant GST-RAF1 RBD (9 nM) was added, followed by the addition of SA-Tb (0.25 nM), and the reaction mixture was incubated for 3 hours. HTRF signal was measured (PerkinElmer Envision), the signal ratio ($\lambda_{em}$ 520/$\lambda_{em}$ 495) was calculated, and IC50 values were calculated from the dose-response curve.

KRAS$^{G12D}$ Nucleotide Exchange Assay

Recombinant GDP-loaded KRAS G12D (20 nM) was treated with compound at room temperature for 20 minutes in assay buffer (10 mM Hepes pH 7.4, 150 mM NaCl, 5 mM $MgCl_2$, 0.0025% Igepal-CA630, 0.05% BSA, 1 mM DTT, 0.5 nM SA-Tb). BIODIPY-labeled GDP (400 nM) and recombinant SOS (10 nM) were added, and the reaction was incubated for 30 minutes. HTRF signal was measured (PerkinElmer Envision), the signal ratio ($\lambda_{em}$ 520/$\lambda_{em}$ 495) was calculated, and IC50 values were calculated from the dose-response curve.

The IC50 values for compounds described herein is shown in Table 12.

TABLE 12

| Example # | KRAS$^{G12D}$ RAF Disruption Assay ($IC_{50}$, □M) | KRAS$^{G12D}$ Nucleotide Exchange Assay ($IC_{50}$, □M) |
|---|---|---|
| 1-1 | 4.28 | 0.01 |
| 1-2 | >100 | 0.20 |
| 1-3 | 56.51 | 0.04 |
| 1-4 | 4.02 | 0.03 |
| 1-5 | 36.10 | — |
| 1-6 | 12.19 | 0.04 |
| 1-7 | >100 | 22.94 |
| 1-8 | 11.69 | 0.09 |
| 2-1 | 5.33 | 0.12 |
| 2-2 | 73.86 | 4.34 |
| 3-1 | 6.27 | 0.10 |
| 4-1 | >100 | 5.46 |
| 5-1 | 85.30 | 1.71 |
| 5-2 | >100 | 1.16 |
| 6-1 | 6.81 | 0.22 |
| 6-2 | 28.11 | 0.49 |
| 6-3 | 34.03 | 0.71 |
| 6-4 | >100 | 1.13 |
| 6-5 | >100 | 19.0 |
| 6-6 | >100 | 3.4 |
| 6-7 | >100 | 6.9 |
| 6-8 | 41.6 | 0.08 |
| 6-9 | >100 | 0.17 |
| 6-10 | >100 | 0.20 |
| 6-11 | >100 | 0.45 |
| 6-12 | >100 | 8.2 |
| 6-13 | >100 | 0.35 |
| 6-14 | >100 | 0.55 |
| 6-15 | >100 | 0.57 |
| 6-17 | >100 | 1.71 |
| 7-1 | >100 | 2.66 |
| 7-2 | 9.44 | 0.30 |
| 7-3 | 20.67 | 12.67 |
| 7-4 | >100 | 7.19 |
| 7-5 | >100 | 43.40 |
| 8-1 | 45.0 | 0.14 |
| 8-2 | >100 | 0.31 |
| 8-3 | 55.8 | 0.09 |
| 8-4 | 42.1 | 1.7 |
| 8-5 | 61.1 | 0.78 |
| 8-6 | 10.5 | 0.05 |
| 8-7 | 88.5 | 0.08 |
| 8-8 | 25.7 | 0.83 |
| 8-9 | 5.8 | 0.02 |
| 9-1 | 0.3 | 0.002 |
| 9-2 | 30.7 | 0.17 |
| 10-1 | 0.3 | 0.007 |
| 10-2 | 2.1 | 0.04 |
| 11-1 | 0.08 | 0.002 |
| 11-2 | 25.0 | 0.5 |
| 12-1 | 0.08 | 0.02 |
| 12-2 | 4.2 | 0.2 |
| 13-1 | 1.5 | 0.03 |
| 13-2 | 36.9 | 0.7 |
| 14 | 22.0 | 0.03 |
| 15 | 0.5 | 0.006 |
| 16-1 | 14.0 | 0.06 |
| 16-2 | 85.5 | 3.4 |
| 17-1 | 0.12 | 0.01 |
| 17-2 | 0.03 | 0.002 |
| 17-3 | 0.03 | 0.01 |
| 17-4 | 0.01 | 0.02 |
| 18-1 | 0.63 | 0.005 |
| 18-2 | 1.57 | 0.01 |
| 18-3 | 1.28 | 0.01 |
| 18-4 | 2.07 | 0.01 |
| 18-5 | 2.64 | 0.03 |
| 18-6 | 2.26 | 0.02 |
| 18-7 | 0.87 | 0.002 |
| 18-8 | 2.29 | 0.01 |
| 18-9 | 3.44 | 0.01 |
| 18-10 | 1.43 | 0.01 |
| 18-11 | 1.40 | 0.01 |
| 18-12 | 3.94 | 0.03 |
| 18-13 | 3.05 | 0.01 |
| 18-14 | 3.59 | 0.01 |
| 18-15 | 0.14 | 0.04 |
| 18-16 | >100 | 0.10 |
| 18-17 | 6.3 | 0.01 |
| 18-18 | 5.9 | 0.01 |
| 18-19 | 4.7 | 0.01 |
| 18-20 | 3.9 | 0.01 |
| 18-21 | 21.9 | 0.05 |
| 18-22 | 2.5 | 0.005 |
| 18-23 | 12.8 | 0.03 |
| 19-1 | 0.30 | 0.01 |
| 19-2 | 5.95 | 0.02 |
| 19-3 | 2.13 | 0.02 |
| 19-4 | 52.94 | 0.13 |
| 20-1 | 4.42 | 0.04 |
| 20-2 | 0.39 | 0.02 |
| 20-3 | 0.76 | 0.002 |
| 20-4 | 18.94 | 0.26 |
| 21-1 | 1.35 | 0.02 |
| 21-2 | 16.66 | 0.30 |
| 22-1 | 1.05 | 0.04 |
| 22-2 | 47.84 | 3.91 |
| 23-1 | 0.54 | 0.03 |
| 23-2 | 2.85 | 0.37 |
| 24-1 | 0.27 | 0.02 |
| 24-2 | 6.30 | 0.51 |
| 25-1 | 6.77 | 0.01 |
| 25-2 | 15.07 | 0.03 |
| 26-1 | 1.94 | 0.03 |
| 26-2 | 20.30 | 0.04 |
| 27 | 0.59 | 0.01 |
| 28-1 | 2.91 | 0.07 |
| 28-2 | 0.39 | 0.02 |
| 30 | 2.47 | 0.01 |
| 31-1 | 3.64 | 0.02 |
| 31-2 | 51.67 | 0.53 |
| 32 | 2.45 | 0.01 |
| 33-1 | 0.22 | 0.02 |
| 33-2 | 0.002 | 0.002 |
| 33-3 | 0.08 | 0.02 |
| 33-4 | 0.002 | 0.01 |

TABLE 12-continued

| Example # | $KRAS^{G12D}$ RAF Disruption Assay ($IC_{50}$, □M) | $KRAS^{G12D}$ Nucleotide Exchange Assay ($IC_{50}$, □M) |
|---|---|---|
| 34-1 | 9.02 | 0.01 |
| 34-2 | 0.12 | 0.02 |
| 34-3 | 2.69 | 0.21 |
| 34-4 | 0.14 | 0.01 |
| 34-5 | 1.54 | 0.01 |
| 34-6 | 0.30 | 0.002 |
| 34-7 | 3.41 | 0.02 |
| 34-8 | 1.25 | 0.02 |
| 34-9 | 5.26 | 0.02 |
| 34-10 | 6.71 | 0.04 |
| 34-11 | 6.61 | 0.04 |
| 34-12 | 0.14 | 0.002 |

It is to be appreciated that the Detailed Description section, and not the Summary and Abstract sections, is intended to be used to interpret the claims. The Summary and Abstract sections can set forth one or more but not all exemplary aspects of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific aspects will so fully reveal the general nature of the disclosure that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

What is claimed is:

1. A compound of formula (I):

(I)

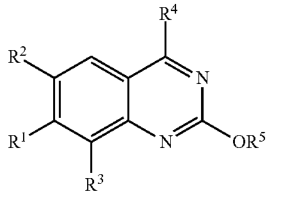

or a pharmaceutically acceptable salt thereof; wherein:

$R^1$ is aryl or heteroaryl, wherein the aryl and the heteroaryl are optionally substituted with one, two, three, four, or five substituents independently selected from $C_1$-$C_3$alkyl, $C_2$-$C_4$alkenyl, $C_2$-$C_4$alkynyl, amino, amino$C_1$-$C_3$alkyl, $C_3$-$C_4$cycloalkyl, halo, halo$C_1$-$C_3$alkyl, hydroxy, and hydroxy$C_1$-$C_3$alkyl;

$R^2$ and $R^3$ are independently selected from hydrogen, $C_1$-$C_3$alkoxy, $C_1$-$C_3$alkyl, cyano, halo, halo$C_1$-$C_3$alkyl, and hydroxy;

$R^4$ is selected from:

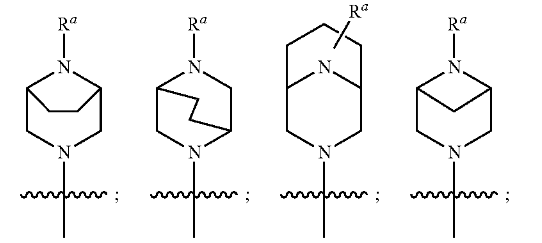

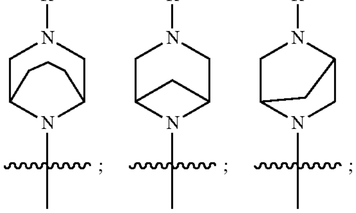

and

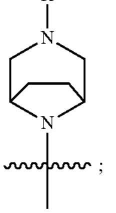

wherein $R^a$ is hydrogen or $C_1$-$C_3$alkyl; and

 denotes the point of attachment to the parent molecular moiety;

$R^5$ is selected from

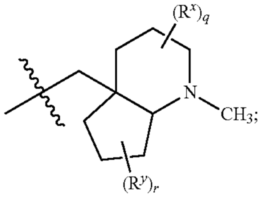

and

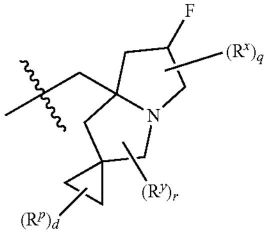

wherein q, r, and d are each independently 0 or 1; and wherein $R^x$, $R^y$, and $R^p$ are independently selected from $C_1$-$C_3$alkoxy, $C_1$-$C_3$alkyl, halo, halo$C_1$-$C_3$alkyl, and hydroxy.

2. The compound of claim 1, or a pharmaceutically acceptable salt thereof, wherein $R^2$ and $R^3$ are each halo.

3. The compound of claim 1, or a pharmaceutically acceptable salt thereof, wherein $R^1$ is naphthyl, wherein the naphthyl is optionally substituted with one, two, or three groups independently selected from $C_1$-$C_3$alkyl, $C_2$-$C_4$alkynyl, $C_3$cycloalkyl, halo, and hydroxy.

4. The compound of claim 1, or a pharmaceutically acceptable salt thereof, wherein $R^2$ is hydrogen;

$R^3$ is fluoro; and $R^1$ is selected from

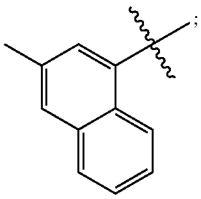
;
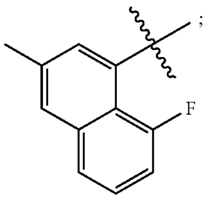
;
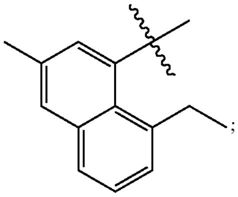
;
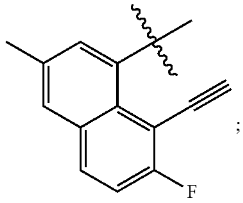
; and
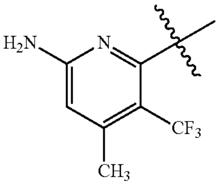
.

5. The compound of claim 1, or a pharmaceutically acceptable salt thereof, wherein $R^2$ is chloro;

$R^3$ is fluoro; and $R^1$ is selected from

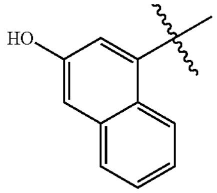
;
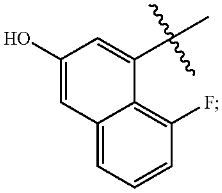
F;
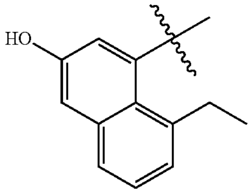
;
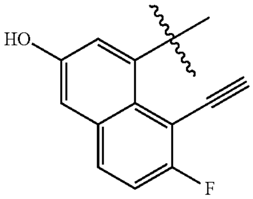
; and
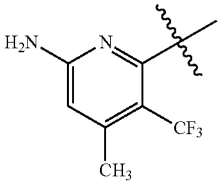
.

6. A pharmaceutical composition comprising a compound of claim 1, or a pharmaceutically acceptable salt thereof, and one or more pharmaceutically acceptable excipients.

7. A method for treating a cancer susceptible to KRAS G12D inhibition in a subject in need thereof, the method comprising administering to the subject a compound of claim 1, or a pharmaceutically acceptable salt thereof.

8. A method of treating cancer expressing KRAS G12D mutation in a subject in need thereof, the method comprising administering to the subject a compound of claim 1, or a pharmaceutically acceptable salt thereof.

9. A method for treating cancer in a subject in need thereof, the method comprising administering to the subject a compound of claim 1, or a pharmaceutically acceptable salt thereof, wherein the cancer is pancreatic cancer, colorectal cancer, lung cancer and/or gastric cancer.

10. A compound selected from:

isomer 1

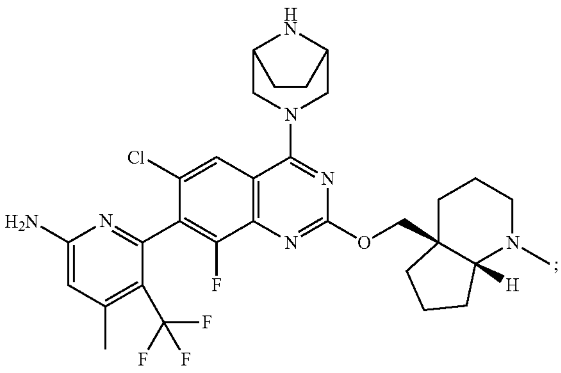
;

isomer 2

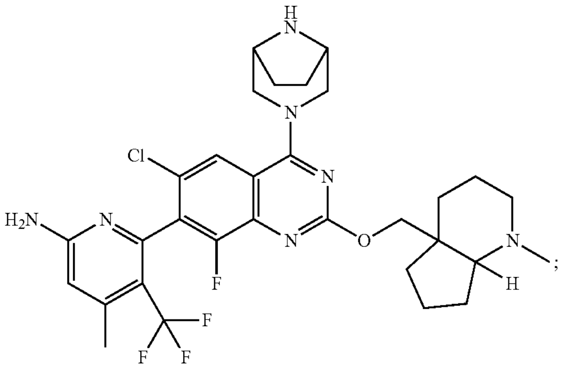
;

isomer 3

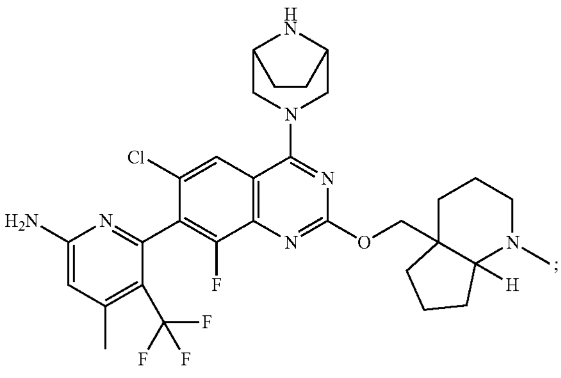
;

isomer 4
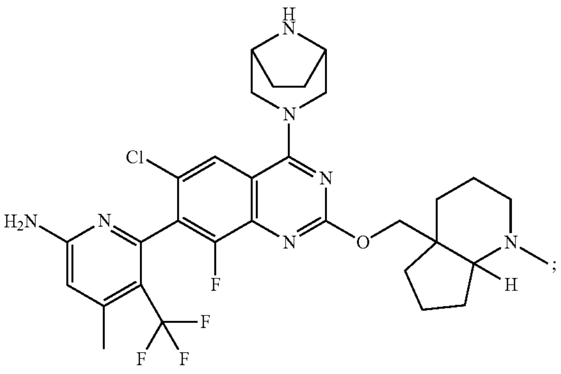
isomer 1
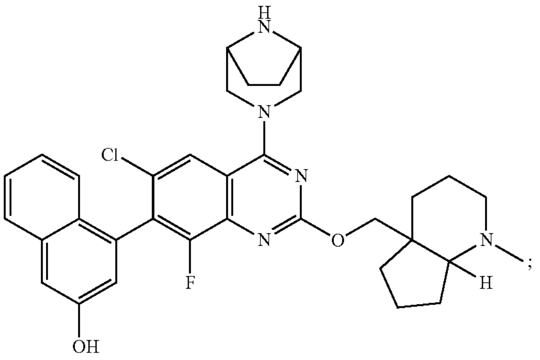
isomer 2
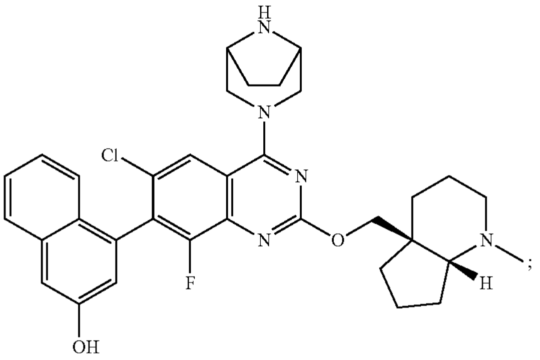
isomer 3
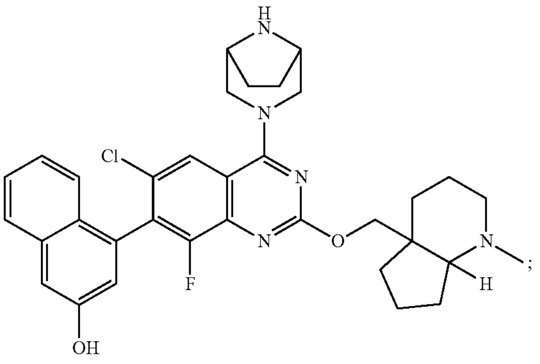
isomer 4
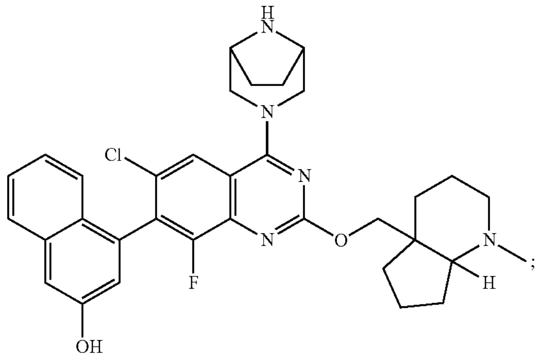
isomer 1
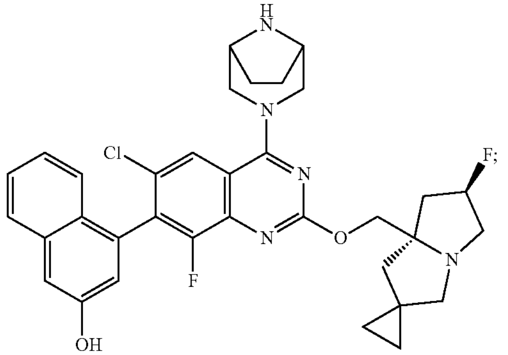
isomer 2
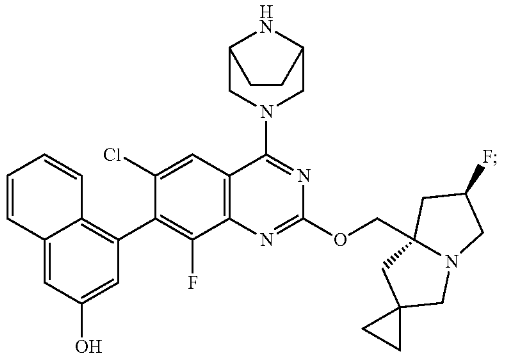
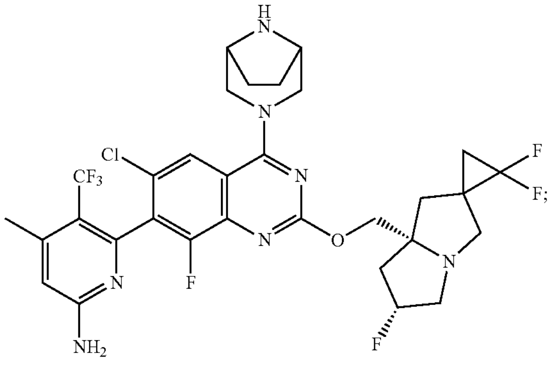

-continued
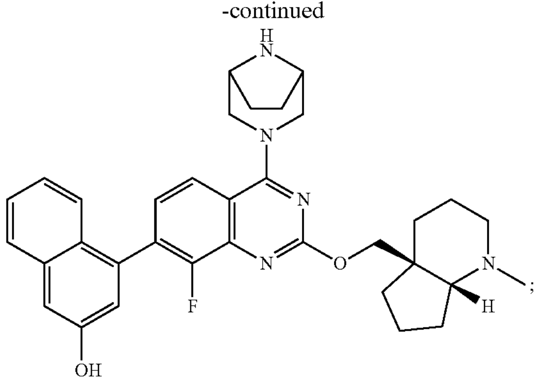
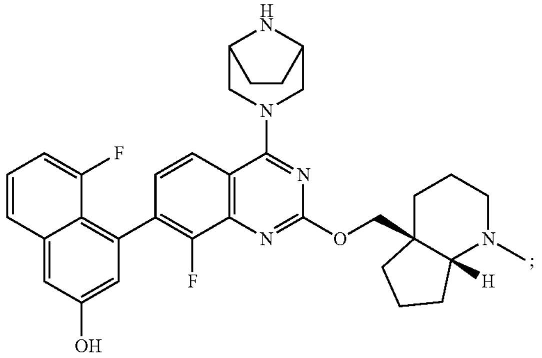
-continued
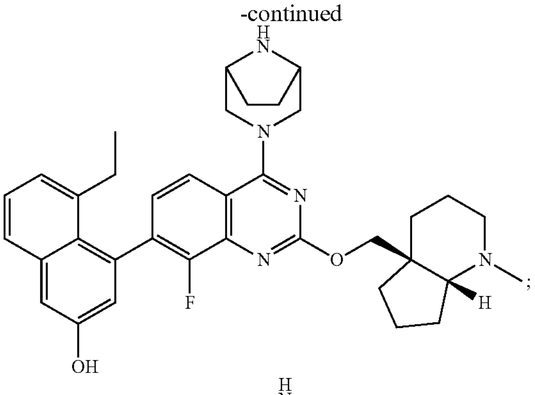
and
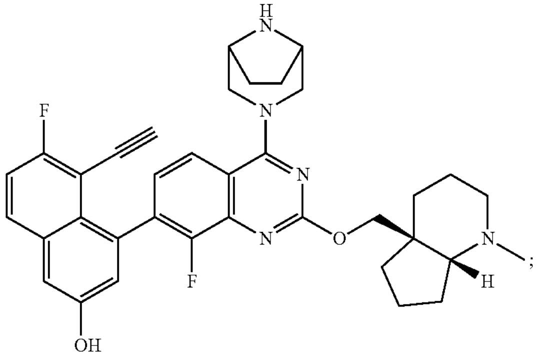
or a pharmaceutically acceptable salt thereof.
* * * * *